United States Patent
Lee et al.

(10) Patent No.: US 9,493,430 B2
(45) Date of Patent: Nov. 15, 2016

(54) BIARYL- OR HETEROCYCLIC BIARYL-SUBSTITUTED CYCLOHEXENE DERIVATIVE COMPOUNDS AS CETP INHIBITORS

(71) Applicant: CHONG KUN DANG PHARMACEUTICAL CORP., Seoul (KR)

(72) Inventors: Jae Kwang Lee, Gyeonggi-do (KR); Jung Taek Oh, Gyeonggi-do (KR); Jae Won Lee, Gyeonggi-do (KR); Seo Hee Lee, Gyeonggi-do (KR); Il-Hyang Kim, Gyeonggi-do (KR); Jae Young Lee, Gyeonggi-do (KR); Su Yeal Bae, Gyeonggi-do (KR); Se Ra Lee, Gyeonggi-do (KR); Yun Tae Kim, Gyeonggi-do (KR)

(73) Assignee: Chong Kun Dang Pharmaceutical Corp., Seoul (KR)

( * ) Notice: Subject to any disclaimer, the term of this patent is extended or adjusted under 35 U.S.C. 154(b) by 0 days.

(21) Appl. No.: 14/651,211

(22) PCT Filed: Jan. 29, 2014

(86) PCT No.: PCT/KR2014/000889
§ 371 (c)(1),
(2) Date: Jun. 10, 2015

(87) PCT Pub. No.: WO2014/119947
PCT Pub. Date: Aug. 7, 2014

(65) Prior Publication Data
US 2015/0322023 A1 Nov. 12, 2015
US 2016/0237046 A9 Aug. 18, 2016

(30) Foreign Application Priority Data
Jan. 31, 2013 (KR) .................. 10-2013-0011206
Jan. 29, 2014 (KR) .................. 10-2014-0011555

(51) Int. Cl.
| | |
|---|---|
| *A61P 9/00* | (2006.01) |
| *C07D 263/08* | (2006.01) |
| *C07D 413/10* | (2006.01) |
| *C07D 263/18* | (2006.01) |
| *A61K 31/421* | (2006.01) |
| *C07D 263/22* | (2006.01) |
| *C07D 413/08* | (2006.01) |

(52) U.S. Cl.
CPC ........... *C07D 263/22* (2013.01); *C07D 263/08* (2013.01); *C07D 413/08* (2013.01); *C07D 413/10* (2013.01)

(58) Field of Classification Search
CPC ............... C07D 413/10; C07D 263/22; C07D 413/08; A61P 9/00; A61K 31/421

USPC .................................................... 546/290
See application file for complete search history.

(56) References Cited

U.S. PATENT DOCUMENTS

| | | | |
|---|---|---|---|
| 6,426,365 B1 | 7/2002 | Shinkai et al. ............... 514/512 |
| 7,910,592 B2 * | 3/2011 | Ali et al. ............ C07D 413/06 |
| | | | 514/255.05 |
| 7,915,271 B2 * | 3/2011 | Ali et al. ............ C07D 263/20 |
| | | | 514/274 |
| 9,173,853 B2 | 11/2015 | Lee et al. ....................... 424/489 |
| 2010/0331309 A1 | 12/2010 | Chen et al. ............. 514/213.01 |
| 2014/0031335 A1* | 1/2014 | Lee et al. ............ C07D 263/16 |
| | | | 514/210.18 |
| 2014/0206616 A1 | 7/2014 | Ko et al. |
| 2015/0110876 A1 | 4/2015 | Lee et al. |
| 2015/0119376 A2* | 4/2015 | Lee et al. ............ C07D 263/16 |
| | | | 514/210.18 |
| 2015/0265535 A1 | 9/2015 | Yu et al. ........................ 424/400 |
| 2015/0290322 A1 | 10/2015 | Yoon et al. ............ A61K 47/24 |
| 2015/0290332 A1 | 10/2015 | Kim et al. |
| 2015/0297726 A1 | 10/2015 | Yoon et al. .................. 514/10.3 |
| 2015/0322023 A1 | 11/2015 | Lee et al. ...................... 546/290 |

FOREIGN PATENT DOCUMENTS

| | | |
|---|---|---|
| CN | 101365689 A | 2/2009 |
| WO | WO 98/35937 | 8/1998 |
| WO | WO 02/88085 | 11/2002 |
| WO | WO 2006/014357 | 2/2006 |
| WO | WO 2007/079186 | 7/2007 |
| WO | WO 2007/081569 | 7/2007 |
| WO | WO 2007/081571 | 4/2008 |
| WO | WO 2008/082567 | 7/2008 |
| WO | WO 2010/056849 | 5/2010 |
| WO | WO2012058187 | * 5/2012 |
| WO | WO 2012/141487 | 10/2012 |

(Continued)

OTHER PUBLICATIONS

Mantlo; J. Med. Chem. 2014, 57, 1-17.*

(Continued)

*Primary Examiner* — Noble Jarrell
*Assistant Examiner* — Daniel Carcanague
(74) *Attorney, Agent, or Firm* — Dentons US LLP; Stephanie Seidman

(57) ABSTRACT

The present invention provides biaryl- or heterocyclic biaryl-substituted cyclohexene derivative compounds, isomers thereof, or pharmaceutically acceptable salts. The compounds of the invention show a CETP inhibitory effect that increases HDL-cholesterol levels and reduces LDL-cholesterol levels. Pharmaceutical compositions comprising the compounds are useful for the prevention or treatment of dyslipidemia or dyslipidemia-related diseases.

10 Claims, No Drawings

(56) References Cited

FOREIGN PATENT DOCUMENTS

| WO | WO2013063217 | * | 5/2013 |
|---|---|---|---|
| WO | WO2013165854 | * | 11/2013 |
| WO | WO2014099836 | * | 6/2014 |

OTHER PUBLICATIONS

U.S. Appl. No. 14/440,058, filed Apr. 30, 2015.
U.S. Appl. No. 14/440,059, filed Apr. 30, 2015.
U.S. Appl. No. 14/440,060, filed Apr. 30, 2015.
U.S. Appl. No. 14/764,156, filed Jul. 28, 2015.
Letter/Written Disclosure of the Information Disclosure Statement for the above-referenced application, mailed on Sep. 10, 2015, 2 pages.
Banwell et al., "Synthesis of quinolines, 2-quinolones, phenanthridines, and 6(5h)-phenanthridinones via palladium[0]-mediated Ullmann cross-coupling of 1-bromo-2-nitroarenes with beta-halo-enals, -enones, or -esters," Org Lett. 6(16):2741-2744 (2004).
Barter et al., "Cholesteryl ester transfer protein: a novel target for raising HDL and inhibiting atherosclerosis," Arterioscler Thromb Vasc Biol. 23(2):160-167 (2003).
Cannon et al., "Safety of anacetrapib in patients with or at high risk for coronary heart disease," N Engl J Med. 363(25):2406-2415 (2010).
Forrest et al., "Torcetrapib-induced blood pressure elevation is independent of CETP inhibition and is accompanied by increased circulating levels of aldosterone," Br J. Pharmacol. 154(7):1465-1473 (2008).
Goldberg A. and Hegele R., "Cholesteryl ester transfer protein inhibitors for dyslipidemia:focus on dalcetrapib," Drug Des Devel Ther. 6:251-259 (2012).
Goldbourt et al., "Isolated low HDL cholesterol as a risk factor for coronary heart disease mortality. A 21-year follow-up of 8000 men," Arterioscler Thromb Vase Biol. 17(1):107-113 (1997).
Hu et al., "Torcetrapib induces aldosterone and cortisol production by an intracellular calcium-mediated mechanism independently of cholesteryl ester transfer protein inhibition," Endocrinology 150(5):2211-2219 (2009).
Liu et al., "Crystal structures of cholesteryl ester transfer protein in complex with inhibitors," J Biol Chem. 287(44):37321-37329 (2012).
Morris G. and Nguyen S., "A general route to pyridine-modified salicylaldehydes via Suzuki coupling," Tetrahedron Letters. 42(11):2093-2096 (2001).

Taylor et al., "Arterial Biology for the Investigation of the Treatment Effects of Reducing Cholesterol (ARBITER) 2: a double-blind, placebo-controlled study of extended-release niacin on atherosclerosis progression in secondary prevention patients treated with statins," Circulation 110(23)1512-3517 (2004).
Yin et al., "Highly diastereoselective catalytic Meerwein-Ponndorf-Verley reductions," J Org Chem. m 71(2):840-843 (2006).
International Search Report and Written Opinion, issued May 8, 2014, in connection with International Patent Application No. PCT/KR2014/000889, 9 pages.
International Search Report and Written Opinion, issued Aug. 4, 2015, in connection with International Patent Application No. PCT/KR2014/000889, 7 pages.
Letter/Written Disclosure of the Information Disclosure Statement for the above-referenced application, mailed on Dec. 15, 2015, 2 pages.
Clinicaltrials.gov, NCT01252953, "REVEAL: Randomized EValuation of the Effects of Anacetrapib Through Lipid-modification," first received Nov. 24, 2010, last updated May 29, 2015, accessed Dec. 11, 2015, available at: https://clinicaltrials.gov/ct2/show/NCT01252953?term—NCT01252953&rank=1, 4 pages.
Clinicaltrials.gov, NCT01687998, "A Study of Evacetrapib in High-Risk Vascular Disease (Accelerate)," first received Sep. 12, 2012, last updated Oct. 15, 2015, accessed Dec. 11, 2015, available at: https://clinicaltrials.gov/ct2/show/NCT01687998?term=NCT01687998&rank=1, 4 pages.
Examination Report, issued Nov. 3, 2015, in connection with New Zealand Patent Application No. 708079, 4 pages.
U.S. Appl. No. 14/785,812, filed Oct. 20, 2015.
Letter/Written Disclosure of the Supplemental Information Disclosure Statement for the above-referenced application, filed herewith on Jul. 6, 2016, 3 pages.
STN on the web, STN-Registry, RN. 1137446-82-2, published on Apr. 21, 2009, 5 pages.
Office Action, dated May 18, 2016, in connection with Chinese Patent Application No. 201480006696.7 [English translation and original document in Chinese], 10 pages.
Notice of Acceptance, issued May 18, 2016, in connection with Australian Patent Application No. 2014213125, 3 pages.
Letter/Written Disclosure of the Supplemental Information Disclosure Statement for the above-referenced application, filed herewith on Jun. 3, 2016, 2 pages.
Examination Report, issued Dec. 2, 2015, in connection with Australian Patent Application No. 2014213125, 4 pages.
Examination Report, issued Mar. 11, 2016, in connection with Canadian Patent Application No. 2,891,710, 4 pages.
Extended European Search Report, issued May 18, 2016, in connection with European Patent Application No. 14746389.7, 5 pages.

* cited by examiner

BIARYL- OR HETEROCYCLIC BIARYL-SUBSTITUTED CYCLOHEXENE DERIVATIVE COMPOUNDS AS CETP INHIBITORS

RELATED APPLICATIONS

This application is the U.S. National Stage of International Application. No. PCT/KR2014/000889, filed 29 Jan. 2014, which claims benefit of priority to Korean Patent Application KR 10-2014-0011555, filed 29 Jan. 2014, and to Korean Patent Application KR 10-2013-0011206, filed 31 Jan. 2013, the specification of each of which is incorporated by reference herein.

TECHNICAL FIELD

The present invention relates to novel biaryl- or heterocyclic biaryl-substituted cyclohexene derivative compounds, and more particularly to novel biaryl- or heterocyclic biaryl-substituted cyclohexene derivatives having CETP inhibitory activity, isomers thereof, pharmaceutically acceptable salts thereof, the use for preparing pharmaceutical compositions, pharmaceutical compositions comprising the same, methods of treating diseases using these compositions, and methods for preparing novel biaryl- or heterocyclic biaryl-substituted cyclohexene derivatives.

BACKGROUND ART

Dyslipidemia generally refers to high blood cholesterol levels and is asymptomatic. However, dyslipidemia is a very serious condition, because it causes angina pectoris, myocardial infarction and arteriosclerosis. Statins, drugs that are commonly used to treat hyperlipidemia, exhibit therapeutic effects mainly by lowering LDL-C, but their effects on the prevention of cardiovascular diseases are still very insufficient. A recent study reported that not only lowering low-density lipoprotein cholesterol (LDL-C) levels, but also increasing high-density lipoprotein cholesterol (HDL-C) levels is very effective in preventing cardiovascular diseases (Goldbourt et al., 1997, 17, 107-113). Among drugs that are used to increase HDL-C levels, the most effective drug is Niacin. However, this drug needs to be taken in relatively large doses and causes side effects such as facial flushing (Taylor et al., Circulation, 2004, 110, 3512-3517).

Meanwhile, cholesterol ester transfer protein (CETP) is a protein that participates in reverse cholesterol transport (the transport of cholesterol from peripheral tissue to the liver). When CETP is inhibited, HDL-C levels can be effectively increased, thus preventing cardiovascular diseases. Accordingly, the development of compounds capable of inhibiting CETP activity is very important (Barter et al., Arterioscler Thromb Vase Biol, 2003, 23, 160-167).

CETP inhibitors developed to date include Torcetrapib (International Patent Publication No. WO 02/088085), Anacetrapib (International Patent Publication No. WO 2006/014357) and Evacetrapib (US Patent Publication No. 2010/0331309), which are structurally similar to each other. In addition, Dalcetrapib (International Patent Publication No. WO 98/35937), a benzenethiol derivative, is known as a CETP inhibitor.

However, among these CETP inhibitors, Torcetrapib (Pfizer) causes an increase in blood pressure and an increase in mortality rate, and thus was stopped phase III clinical trial. It was reported that such side effects occur because Torcetrapib increases the levels of hormones, such as aldosterone and corticosterone, associated with an elevation in blood pressure, and increases the thickness of the vascular wall to cause inflammation, thus increasing mortality rate (Forrest et al, British Journal of Pharmacology, 2008, 1-9).

The other CETP inhibitor Dalcetrapib (Roche) was also stopped in phase III clinical trial, and it is known that Dalcetrapib does not have the side effects of Torcetrapib, but has insufficient effects (Alyse S Goldberg et al, Drug Design Development and Therapy, 2012, 6, 251-259).

Recently, the results of phase III DEFINE trial (Determining the Efficacy and Tolerability of CETP Inhibition with Anacetrapib)) for Anacetrapib (Merck) indicated that, in the case of patients administered with Anacetrapib, the HDL-c level increased by 138% and the LDL-c level decreased by 40% (Philip Barter et al, The New England Journal of Medicine, 2010, 363, 2406-2415). Based on such results, Merck has performed clinical trials on about 30,000 persons in order to examine whether administration of Anacetrapib ameliorate cardiovascular diseases (ClinicalTrials.gov, NCT01252953).

In addition, the results of phase II clinical trials for Evacetrapib (Lilly) showed that Evacetrapib increases HDL-c levels in a dose-dependent manner and does not cause side effects such blood pressure elevation. Recently, Evacetrapib entered phase III clinical trials on 10,000 persons (ClinicalTrials.gov, NCT01687998).

Efforts have been made to develop novel CETP inhibitors having more advantages over CETP inhibitors developed to date or CETP inhibitors being developed. Such advantages may include excellent efficacy, reduced off-target effects, increased bioavailability, reduced food effects, etc.

DISCLOSURE OF INVENTION

Technical Problem

It is an object of the present invention to provide novel biaryl- or heterocyclic biaryl-substituted cyclohexene derivative compounds, isomers thereof, or pharmaceutically acceptable salts thereof.

Another object of the present invention is to provide pharmaceutical compositions comprising novel biaryl- or heterocyclic biaryl-substituted cyclohexene derivatives, which have less side effects and can effectively inhibit CETP, isomers thereof, or pharmaceutically acceptable salts thereof.

Still another object of the present invention is to provide the use of the above compounds, isomers or pharmaceutically acceptable salts for preparing pharmaceutical compositions, and methods of treating diseases using the above compositions, and methods for preparing the above compounds, isomers or pharmaceutically acceptable salts.

Solution to Problem

Novel CETP Inhibitor Compounds

In accordance with a first embodiment of the present invention, there are provided novel biaryl- or heterocyclic biaryl-substituted cyclohexene derivative compounds of the following formula I, isomers thereof, or pharmaceutically acceptable salts thereof:

[Formula I]

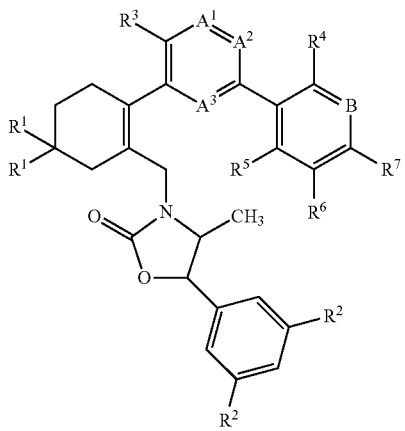

wherein
R¹ is —H or —C₁-C₃ alkyl;
R² is —H, halogen or —C₁-C₃ alkyl;
R³, R⁴, R⁵ and R⁶ are each independently —H, halogen, —NO₂, —C₁-C₃ alkyl, or —OC₁-C₃ alkyl;
R⁷ is —H, —(C═O)OR₈, or

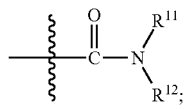

R⁸ is —H or —C₁-C₃ alkyl;
R¹¹ and R¹² are each independently —H or —C₁-C₃ alkyl or may form a 4- to 6-membered non-aromatic ring, wherein the non-aromatic ring may contain 0 to 2 N or O heteroatoms, and one or more —H in the non-aromatic ring may substituted with halogen or —OH;
A¹, A² and A³ are each independently N or CR⁹, wherein if A² or A³ is N, A¹ is CR⁹;
R⁹ is —H, halogen, —C₁-C₃ alkyl or —OC₁-C₃ alkyl;
B is N or CR¹⁰;
R¹⁰ is —H, halogen, —C₁-C₃ alkyl, —OC₁-C₃ alkyl, —(C═O)OR⁸, or

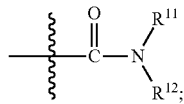

provided that one or more —H atoms in the —C₁-C₃ alkyl or the —OC₁-C₃ alkyl may be substituted with —F or —CH₃, and if R⁷ is —H, B is CR¹⁰, and R¹⁰ is —(C═O)OR⁸ or

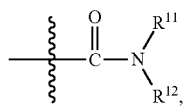

and if R⁷ is not —H, R¹⁰ cannot be —(C═O)OR⁸ or

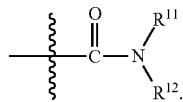

In accordance with a second embodiment of the present invention, there are provided compounds of formula I, isomers thereof, or pharmaceutically acceptable salts thereof, wherein
R¹ is —H or —CH₃;
R² is —F or —CF₃;
R³, R⁴, R⁵ and R⁶ are each independently —H, —F, —NO₂, —CH₃, —CH(CH₃)₂, —CF₃ or —OCH₃;
R⁷ is —H, —(C═O)OR⁸, or

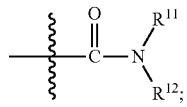

R⁸ is —H, —CH₃ or —CH₂CH₃;
R¹¹ and R¹² are each independently —H, —CH₃ or —CH₂CH₃ or may form 4- to 6-membered non-aromatic ring, wherein the non-aromatic ring may contain 0 to 2 N or O heteroatoms, and one or more —H atoms in the non-aromatic ring may be substituted with —F or —OH;
A¹, A² and A³ are each independently N or CR⁹, wherein if A² or A³ is N, A¹ is CR⁹;
R⁹ is —H, —F, —Cl, —CH₃, —CF₃ or —OCH₃;
B is N or CR¹⁰;
R¹⁰ is —H, —F, —Cl, —CH₃, —OCH₃, —CO₂H, —CO₂CH₃, —CO₂CH₂CH₃, or

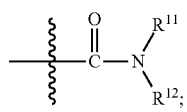

provided that if R⁷ is —H, B is CR¹⁰, and R¹⁰ is —CO₂H, —CO₂CH₃, —CO₂CH₂CH₃, or

and if R⁷ is not —H, R¹⁰ is not —CO₂H, —CO₂CH₃, —CO₂CH₂CH₃, or

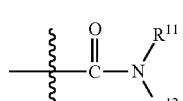

In accordance with a third embodiment of the present invention, there are provided compounds of formula I, isomers thereof, or pharmaceutically acceptable salts thereof, wherein
R¹ is —CH₃;
R² is —CF₃;

$R^3$ is —H, —F, —Cl or —OCH$_3$;
$R^4$ is —H, —F, —Cl, —CH$_3$, —CH(CH$_3$)$_2$, —CF$_3$ or —OCH$_3$;
$R^5$ is —H, —F or —Cl;
$R^6$ is —H;
$R^7$ is —H, —(C=O)OH,

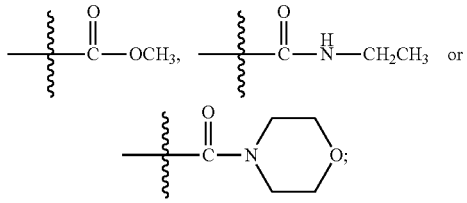

$A^1$, $A^2$ and $A^3$ are each independently N or CR$^9$, wherein if $A^2$ or $A^3$ is N, $A^1$ is CR$^9$;
$R^9$ is —H, —F, —CH$_3$, —CF$_3$ or —OCH$_3$;
B is CR$^{10}$;
$R^{10}$ is —H, —F or —CO$_2$CH$_3$;
provided that if $R^7$ is —H, B is CR$^{10}$, and $R^{10}$ is —CO$_2$CH$_3$, and if $R^7$ is not —H, $R^{10}$ is not —CO$_2$CH$_3$.

In accordance with a forth embodiment of the present invention, there are provided compounds of formula I, isomers thereof, or pharmaceutically acceptable salts thereof, wherein
$R^3$ is —H, —F or —OCH$_3$;
$R^4$ is —H, —F, —Cl, —CH$_3$ or —CF$_3$;
$R^5$ is —H or —F;
$R^7$ is —(C=O)OH;
$A^1$ is N or CR$^9$;
$A^2$ and $A^3$ are each independently CR$^9$;
$R^9$ is —H or —F; and
B is CH.

Preferred Examples of the compounds of formula I are as follows:

| No. | Name of compound |
|---|---|
| 553 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2-methylbiphenyl-4-carboxylate |
| 554 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2-methylbiphenyl-4-carboxylic acid |
| 555 | methyl 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-3-methylbenzoate |
| 556 | methyl 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)benzoate |
| 557 | 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-3-methylbenzoic acid |
| 558 | 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)benzoic acid |
| 559 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxybiphenyl-4-carboxylate |
| 560 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4'-methoxybiphenyl-4-carboxylate |
| 561 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4'-methoxybiphenyl-4-carboxylic acid |
| 564 | methyl 5-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)picolinate |
| 565 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxybiphenyl-4-carboxylic acid |
| 567 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxybiphenyl-3-carboxylate |
| 568 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxybiphenyl-3-carboxylic acid |
| 569 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2-nitrobiphenyl-4-carboxylate |
| 572 | methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-4'-methoxy-2-methylbiphenyl-4-carboxylate |
| 573 | methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-4'-methoxybiphenyl-4-carboxylate |
| 574 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-4'-methoxy-2-methylbiphenyl-4-carboxylic acid |
| 575 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-4'-methoxybiphenyl-4-carboxylic acid |
| 577 | methyl 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-3-isopropylbenzoate |
| 578 | 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-3-isopropylbenzoic acid |
| 579 | methyl 3'-(2-(((4S,5R)-5-(3,5-bis(trifluoromethyl)phenyl)-4-methyl-2-oxooxazolidin-3-yl)methyl)cyclohex-1-enyl)-4'-methoxy-2-methylbiphenyl-4-carboxylate |
| 580 | methyl 3'-(2-(((4S,5R)-5-(3,5-bis(trifluoromethyl)phenyl)-4-methyl-2-oxooxazolidin-3-yl)methyl)cyclohex-1-enyl)-2-fluoro-4'-methoxybiphenyl-4-carboxylate |
| 581 | 3'-(2-(((4S,5R)-5-(3,5-bis(trifluoromethyl)phenyl)-4-methyl-2-oxooxazolidin-3-yl)methyl)cyclohex-1-enyl)-4'-methoxy-2-methylbiphenyl-4-carboxylic acid |
| 582 | 3'-(2-(((4S,5R)-5-(3,5-bis(trifluoromethyl)phenyl)-4-methyl-2-oxooxazolidin-3-yl)methyl)cyclohex-1-enyl)-2-fluoro-4'-methoxybiphenyl-4-carboxylic acid |
| 583 | methyl 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-3-chlorobenzoate |
| 584 | 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-3-chlorobenzoic acid |
| 585 | methyl 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-3-fluorobenzoate |
| 586 | 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-3-fluorobenzoic acid |
| 587 | methyl 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)benzoate |
| 588 | 3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)benzoic acid |
| 590 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2,3-difluoro-4'-methoxybiphenyl-4-carboxylate |
| 591 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2,6-difluoro-4'-methoxybiphenyl-4-carboxylate |

| No. | Name of compound |
|---|---|
| 592 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2,3-difluoro-4'-methoxybiphenyl-4-carboxylic acid |
| 593 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2,6-difluoro-4'-methoxybiphenyl-4-carboxylic acid |
| 594 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2,4'-dimethoxybiphenyl-4-carboxylate |
| 595 | methyl 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-2,3-difluorobenzoate |
| 596 | 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-2,3-difluorobenzoic acid |
| 597 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2,4'-dimethoxybiphenyl-4-carboxylic acid |
| 599 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-3,4'-dimethoxybiphenyl-4-carboxylate |
| 600 | methyl 5-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3-methylpicolinate |
| 601 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-3,4'-dimethoxybiphenyl-4-carboxylic acid |
| 602 | 5-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3-methylpicolinic acid |
| 603 | methyl 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyrimidin-2-yl)-3-methylbenzoate |
| 604 | 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyrimidin-2-yl)-3-methylbenzoic acid |
| 605 | methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2'-(trifluoromethyl)biphenyl-4-carboxylate |
| 606 | methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4'-methoxy-2'-(trifluoromethyl)biphenyl-4-carboxylate |
| 607 | ethyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-3-fluoro-4'-methoxy-2'-(trifluoromethyl)biphenyl-4-carboxylate |
| 608 | methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2-chloro-4'-methoxy-2'-(trifluoromethyl)biphenyl-4-carboxylate |
| 609 | methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2-methyl-2'-(trifluoromethyl)biphenyl-4-carboxylate |
| 610 | methyl 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyrimidin-2-yl)-3-fluorobenzoate |
| 611 | 5-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)-3-fluoropicolinic acid |
| 612 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2'-(trifluoromethyl)biphenyl-4-carboxylic acid |
| 613 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4'-methoxy-2'-(trifluoromethyl)biphenyl-4-carboxylic acid |
| 614 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-3-fluoro-4'-methoxy-2'-(trifluoromethyl)biphenyl-4-carboxylic acid |
| 615 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2-chloro-4'-methoxy-2'-(trifluoromethyl)biphenyl-4-carboxylic acid |
| 616 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2-methyl-2'-(trifluoromethyl)biphenyl-4-carboxylic acid |
| 617 | 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyrimidin-2-yl)-3-fluorobenzoic acid |
| 618 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2-(trifluoromethyl)biphenyl-4-carboxylic acid |
| 619 | methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2'-methylbiphenyl-4-carboxylate |
| 620 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2'-methylbiphenyl-4-carboxylic acid |
| 621 | methyl 4-(2-(2-(((4S,5R)-5-(3,5-bis(trifluoromethyl)phenyl)-4-methyl-2-oxooxazolidin-3-yl)methyl)-4,4-dimethylcyclohex-1-enyl)-3-methoxypyridin-6-yl)-3-methylbenzoate |
| 622 | 4-(2-(2-(((4S,5R)-5-(3,5-bis(trifluoromethyl)phenyl)-4-methyl-2-oxooxazolidin-3-yl)methyl)-4,4-dimethylcyclohex-1-enyl)-3-methoxypyridin-6-yl)-3-methylbenzoic acid |
| 625 | methyl 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyrimidin-2-yl)benzoate |
| 626 | ethyl 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyrimidin-2-yl)-2-fluorobenzoate |
| 628 | 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyrimidin-2-yl)benzoic acid |
| 629 | 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyrimidin-2-yl)-2-fluorobenzoic acid |
| 630 | methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2-chloro-2'-fluoro-4'-methoxybiphenyl-4-carboxylate |
| 631 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2-chloro-2'-fluoro-4'-methoxybiphenyl-4-carboxylic acid |
| 632 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-3-chloro-4'-methoxy-2'-(trifluoromethyl)biphenyl-4-carboxylic acid |
| 633 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-3,4'-dimethoxy-2'-(trifluoromethyl)biphenyl-4-carboxylic acid |
| 636 | 4-(2-(2-(((4S,5R)-5-(3,5-bis(trifluoromethyl)phenyl)-4-methyl-2-oxooxazolidin-3-yl)methyl)-4,4-dimethylcyclohex-1-enyl)-3-methoxypyridin-6-yl)-3-chlorobenzoic acid |
| 637 | 4-(2-(2-(((4S,5R)-5-(3,5-bis(trifluoromethyl)phenyl)-4-methyl-2-oxooxazolidin-3-yl)methyl)-4,4-dimethylcyclohex-1-enyl)-3-methoxypyridin-6-yl)-3-fluorobenzoic acid |
| 638 | methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-3-chloro-4'-methoxy-2'-(trifluoromethyl)biphenyl-4-carboxylate |
| 639 | methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-3,4'-dimethoxy-2'-(trifluoromethyl)biphenyl-4-carboxylate |
| 642 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-chloro-4'-methoxybiphenyl-4-carboxylate |

| No. | Name of compound |
|---|---|
| 643 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-chloro-4'-methoxybiphenyl-4-carboxylic acid |
| 644 | 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyridin-2-yl)benzoic acid |
| 645 | 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyridin-2-yl)-3-methylbenzoic acid |
| 646 | 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyridin-2-yl)-3-fluorobenzoic acid |
| 647 | 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyridin-2-yl)-3-chlorobenzoic acid |
| 648 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-fluoro-2-methylbiphenyl-4-carboxylate |
| 649 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-methylbiphenyl-4-carboxylate |
| 650 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-fluoro-2-methylbiphenyl-4-carboxylic acid |
| 651 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-methylbiphenyl-4-carboxylic acid |
| 652 | methyl 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyridin-2-yl)benzoate |
| 653 | methyl 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyridin-2-yl)-3-methylbenzoate |
| 654 | methyl 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyridin-2-yl)-3-fluorobenzoate |
| 655 | methyl 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyridin-2-yl)-3-chlorobenzoate |
| 656 | methyl 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyridin-2-yl)-2,3-difluorobenzoate |
| 657 | methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2,2'-difluoro-4'-methoxybiphenyl-4-carboxylate |
| 658 | ethyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2',3-difluoro-4'-methoxybiphenyl-4-carboxylate |
| 659 | methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-3,4'-dimethoxybiphenyl-4-carboxylate |
| 660 | methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2,2',3-trifluoro-4'-methoxybiphenyl-4-carboxylate |
| 661 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2,2'-difluoro-4'-methoxybiphenyl-4-carboxylic acid |
| 662 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2',3-difluoro-4'-methoxybiphenyl-4-carboxylic acid |
| 663 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-3,4'-dimethoxybiphenyl-4-carboxylic acid |
| 664 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2,2',3-trifluoro-4'-methoxybiphenyl-4-carboxylic acid |
| 665 | methyl 5-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-6-methylpicolinate |
| 666 | 5-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-6-methylpicolinic acid |
| 667 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-fluoro-2-(trifluoromethyl)biphenyl-4-carboxylate |
| 668 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-fluoro-2-(trifluoromethyl)biphenyl-4-carboxylic acid |
| 670 | methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluorobiphenyl-4-carboxylate |
| 671 | methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2,2'-difluorobiphenyl-4-carboxylate |
| 672 | methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-2-methylbiphenyl-4-carboxylate |
| 673 | methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-methylbiphenyl-4-carboxylate |
| 674 | methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2,2'-dimethylbiphenyl-4-carboxylate |
| 675 | methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-2'-methylbiphenyl-4-carboxylate |
| 676 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-methylbiphenyl-4-carboxylic acid |
| 677 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2,2'-dimethylbiphenyl-4-carboxylic acid |
| 678 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-2'-methylbiphenyl-4-carboxylic acid |
| 679 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluorobiphenyl-4-carboxylic acid |
| 680 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2,2'-difluorobiphenyl-4-carboxylic acid |
| 681 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-2-methylbiphenyl-4-carboxylic acid |
| 682 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2-methylbiphenyl-4-carboxamide |
| 683 | methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2,2'-dimethylbiphenyl-4-carboxylate |
| 684 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2,2'-dimethylbiphenyl-4-carboxylic acid |
| 686 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-methoxybiphenyl-4-carboxylate |
| 687 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-methoxybiphenyl-4-carboxylic acid |
| 688 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-methoxy-2-methylbiphenyl-4-carboxylate |
| 689 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-methoxy-2-methylbiphenyl-4-carboxylic acid |
| 690 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-5'-methoxybiphenyl-4-carboxylate |
| 691 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-5'-methoxybiphenyl-4-carboxylic acid |
| 692 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-fluoro-2-methylbiphenyl-4-carboxylate |

| No. | Name of compound |
|---|---|
| 693 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-fluoro-2-(trifluoromethyl)biphenyl-4-carboxylate |
| 694 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-fluoro-2-methylbiphenyl-4-carboxylic acid |
| 695 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-fluoro-2-(trifluoromethyl)biphenyl-4-carboxylic acid |
| 696 | methyl 4-(2-(2-(((4S,5R)-5-(3,5-bis(trifluoromethyl)phenyl)-4-methyl-2-oxooxazolidin-3-yl)methyl)-4,4-dimethylcyclohex-1-enyl)-3-methoxypyridin-6-yl)-3-fluorobenzoate |
| 697 | methyl 4-(2-(2-(((4S,5R)-5-(3,5-bis(trifluoromethyl)phenyl)-4-methyl-2-oxooxazolidin-3-yl)methyl)-4,4-dimethylcyclohex-1-enyl)-3-methoxypyridin-6-yl)-3-chlorobenzoate |
| 699 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2,5'-difluorobiphenyl-4-carboxylate |
| 700 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-fluorobiphenyl-4-carboxylate |
| 701 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluorobiphenyl-4-carboxylate |
| 702 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2,5'-difluorobiphenyl-4-carboxylic acid |
| 703 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-fluorobiphenyl-4-carboxylic acid |
| 704 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluorobiphenyl-4-carboxylic acid |
| 705 | methyl 3'-(2-(((4S,5R)-5-(3,5-difluorophenyl)-4-methyl-2-oxooxazolidin-3-yl)methyl)-4,4-dimethylcyclohex-1-enyl)-4'-methoxy-2-methylbiphenyl-4-carboxylate |
| 706 | 3'-(2-(((4S,5R)-5-(3,5-difluorophenyl)-4-methyl-2-oxooxazolidin-3-yl)methyl)-4,4-dimethylcyclohex-1-enyl)-4'-methoxy-2-methylbiphenyl-4-carboxylic acid |
| 708 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-fluorobiphenyl-4-carboxylate |
| 709 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-fluorobiphenyl-4-carboxylic acid |
| 714 | methyl 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)pyridin-2-yl)-3-methylbenzoate |
| 716 | 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)pyridin-2-yl)-3-methylbenzoic acid |
| 718 | 3'-(2-(((4S,5S)-5-(3,5-bis(trifluoromethyl)phenyl)-4-methyl-2-oxooxazolidin-3-yl)methyl)-4,4-dimethylcyclohex-1-enyl)-4'-methoxy-2-methylbiphenyl-4-carboxylic acid |
| 719 | 3'-(2-(((4R,5S)-5-(3,5-bis(trifluoromethyl)phenyl)-4-methyl-2-oxooxazolidin-3-yl)methyl)-4,4-dimethylcyclohex-1-enyl)-4'-methoxy-2-methylbiphenyl-4-carboxylic acid |
| 720 | 3'-(2-(((4R,5R)-5-(3,5-bis(trifluoromethyl)phenyl)-4-methyl-2-oxooxazolidin-3-yl)methyl)-4,4-dimethylcyclohex-1-enyl)-4'-methoxy-2-methylbiphenyl-4-carboxylic acid |
| 722 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2,4'-difluorobiphenyl-4-carboxylic acid |
| 723 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-2-(trifluoromethyl)biphenyl-4-carboxylic acid |
| 724 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2,4'-difluorobiphenyl-4-carboxylate |
| 725 | methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-2-(trifluoromethyl)biphenyl-4-carboxylate |
| 726 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-chloro-2-methylbiphenyl-4-carboxylate |
| 727 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-chloro-2-methylbiphenyl-4-carboxylic acid |
| 728 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-chloro-2-(trifluoromethyl)biphenyl-4-carboxylate |
| 729 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-chloro-2-(trifluoromethyl)biphenyl-4-carboxylic acid |
| 738 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-chloro-4'-fluorobiphenyl-4-carboxylate |
| 739 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-chloro-4'-fluorobiphenyl-4-carboxylic acid |
| 740 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-chloro-4'-methoxybiphenyl-4-carboxamide |
| 741 | 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-2-methylbiphenyl-4-carboxamide |
| 742 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-fluoro-2-(trifluoromethyl)biphenyl-4-carboxamide |
| 743 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-methyl-5'-(trifluoromethyl)biphenyl-4-carboxylate |
| 744 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-methyl-5'-(trifluoromethyl)biphenyl-4-carboxylic acid |
| 745 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-(trifluoromethyl)biphenyl-4-carboxylate |
| 746 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-(trifluoromethyl)biphenyl-4-carboxylic acid |
| 747 | methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-5'-(trifluoromethyl)biphenyl-4-carboxylate |
| 748 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-5'-(trifluoromethyl)biphenyl-4-carboxylic acid |
| 754 | (4S,5R)-5-(3,5-bis(trifluoromethyl)phenyl)-3-((2-(4'-(3,3-difluoroazetidine-1-carbonyl)-4-fluoro-2'-(trifluoromethyl)biphenyl-3-yl)-4,4-dimethylcyclohex-1-enyl)methyl)-4-methyloxazolidin-2-one |
| 755 | (4S,5R)-5-(3,5-bis(trifluoromethyl)phenyl)-3-((2-(4-fluoro-4'-(3-hydroxyazetidine-1-carbonyl)-2'-(trifluoromethyl)biphenyl-3-yl)-4,4-dimethylcyclohex-1-enyl)methyl)-4-methyloxazolidin-2-one |
| 756 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-N-ethyl-4'-fluoro-2-(trifluoromethyl)biphenyl-4-carboxamide |
| 757 | 3'-(2-(((4S,5R)-5-(3,5-bis(trifluoromethyl)phenyl)-4-methyl-2-oxooxazolidin-3-yl)methyl)-4,4-dimethylcyclohex-1-enyl)-N-ethyl-4'-fluoro-N-methyl-2-(trifluoromethyl)biphenyl-4-carboxamide |
| 758 | (4S,5R)-5-(3,5-bis(trifluoromethyl)phenyl)-3-((2-(4-fluoro-4'-(morpholine-4-carbonyl)-2'-(trifluoromethyl)biphenyl-3-yl)-4,4-dimethylcyclohex-1-enyl)methyl)-4-methyloxazolidin-2-one |
| 763 | methyl 4-(2-(2-(((4S,5R)-5-(3,5-bis(trifluoromethyl)phenyl)-4-methyl-2-oxooxazolidin-3-yl)methyl)-4,4-dimethylcyclohex-1-enyl)-3-methoxypyridin-6-yl)-3-(trifluoromethyl)benzoate |
| 764 | 4-(2-(2-(((4S,5R)-5-(3,5-bis(trifluoromethyl)phenyl)-4-methyl-2-oxooxazolidin-3-yl)methyl)-4,4-dimethylcyclohex-1-enyl)-3-methoxypyridin-6-yl)-3-(trifluoromethyl)benzoic acid |

Pharmaceutical Compositions Comprising Novel CETP Inhibitor Compounds

The present invention provides pharmaceutical compositions comprising the compounds of formula I, isomers thereof, or pharmaceutically acceptable salts thereof, together with pharmaceutically acceptable carriers.

The carriers that are used in the present invention may be those that are conventionally used in the art, and Examples thereof include, but are not limited to, sugar, starch, microcrystalline cellulose, lactose (lactose hydrate), glucose, di-mannitol, alginate, alkaline earth metal salts, clay, polyethylene glycol, anhydrous dibasic calcium phosphate, or mixtures thereof.

Further, according to another embodiment of the present invention, the pharmaceutical compositions may contain additives such as binders, disintegrants, lubricants, pH-adjusting agents, antioxidants, and the like.

Examples of the binders that may be used in the present invention include, but are not limited to, starch, microcrystalline cellulose, highly dispersed silica, mannitol, di-mannitol, sucrose, lactose hydrate, polyethylene glycol, polyvinylpyrrolidone (povidone), polyvinylpyrrolidone copolymer (copovidone), hypromellose, hydroxypropyl cellulose, natural gum, synthetic gum, copovidone, gelatin, or mixtures thereof.

Examples of the disintegrants that may be used in the present invention include, but are not limited to, starches or modified starches such as sodium starch glyconate, maize starch, potato starch or pregelatinized starch; clays such as bentonite, montmorillonite, or veegum; celluloses such as microcrystalline cellulose, hydroxypropylcellulose or carboxymethylcellulose; algins such as sodium alginate or alginic acid; crosslinked celluloses such as croscarmellose sodium; gums such as guar gum or xanthan gum; crosslinked polymers such as crosslinked polyvinylpyrrolidone (crospovidone); effervescent formulations such as sodium bicarbonate or citric acid; or mixtures thereof.

Examples of the lubricants that may be used in the present invention include, but are not limited to, talc, stearic acid, magnesium stearate, calcium stearate, sodium lauryl sulfate, hydrogenated vegetable oil, sodium benzoate, sodium stearyl fumarate, glyceryl behenate, glyceryl monooleate, glyceryl monostearate, glyceryl palmitostearate, colloidal silicon dioxide, or mixtures thereof.

Examples of the pH-adjusting agents that may be used in the present invention include, but are not limited to, acidifying agents such as acetic acid, adipic acid, ascorbic acid, sodium ascorbate, sodium etherate, malic acid, succinic acid, tartaric acid, fumaric acid or citric acid, and basifying agents such as precipitated calcium carbonate, ammonia water, meglumine, sodium carbonate, magnesium oxide, magnesium carbonate, sodium citrate, or tribasic calcium phosphate.

Examples of the antioxidants that may be used in the present invention include, but are not limited to, dibutyl hydroxytoluene, butylated hydroxyanisole, tocopherol acetate, tocopherol, propyl gallate, sodium hydrogen sulfite, sodium pyrosulfite, and the like.

The compounds of formula I according to the present invention exhibit the effect of inhibiting CETP activity to increase high-density lipoprotein cholesterol (HDL-C) levels and reduce low-density lipoprotein cholesterol (LDL-C) levels. Thus, pharmaceutical compositions containing the compounds of formula I according to the present invention, isomers thereof, or pharmaceutically acceptable salts thereof, can be used for the prevention or treatment of dyslipidemia or dyslipidemia-related vascular diseases.

The dyslipidemia-related vascular diseases may include angina pectoris, myocardial infarction, and atherosclerosis.

Method for Prevention or Treatment of Dyslipidemia or Dyslipidemia-Related Vascular Diseases The present invention also provides a method for preventing or treating dyslipidemia or dyslipidemia-related vascular diseases, the method comprising administering a composition, which contains the compound of formula I as an active ingredient, to a subject in need thereof.

The composition that is used in the inventive method for preventing or treating dyslipidemia or dyslipidemia-related vascular diseases includes the pharmaceutical composition described in the specification.

In addition, the subject in the prevention or treatment method of the present invention includes mammals, particularly humans.

Methods for Preparing Novel CETP Inhibitor Compounds

The compounds of formula I according to the present invention can be prepared according to methods described in various literatures, but are not limited thereto.

Hereinafter, methods for preparing the compounds of formula I will be described in detail with reference to the following reaction schemes 1 and 2.

[Reaction scheme 1]

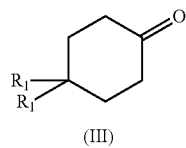

(III)

-continued

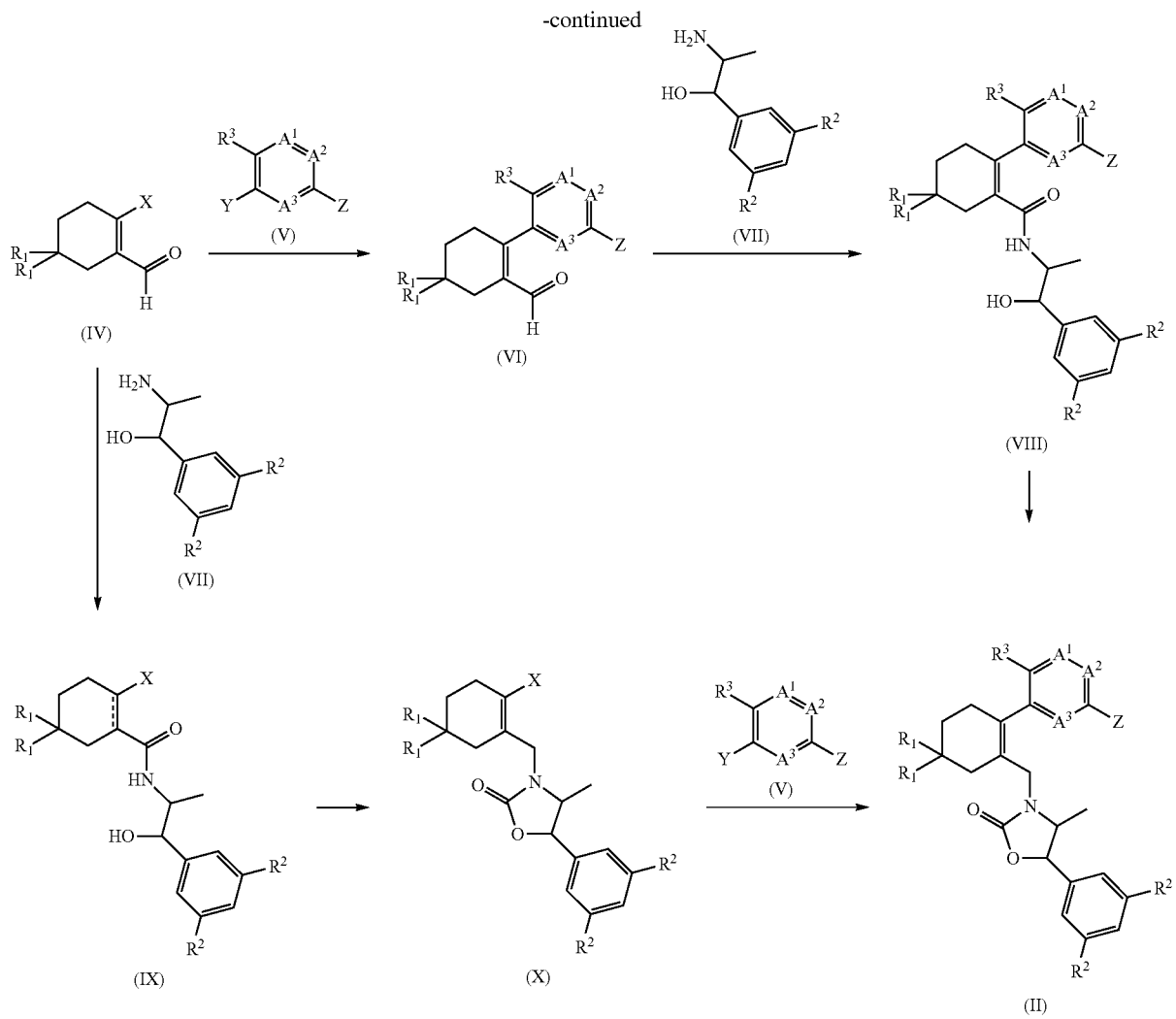

wherein $R^1$, $R^2$, $R^3$, $R^4$, $R^5$, $R^6$, $R^7$, $A^1$, $A^2$, $A^3$ and B are each as defined in formula I. In addition, X, Y, Z and Q may each independently be halogen,

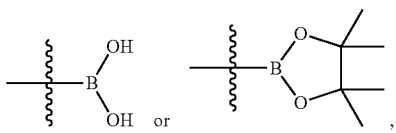

and the halogen is preferably chloride (—Cl) or bromide (—Br).

First, a compound of formula III as a starting material may be reacted with phosphorus tribromide ($PBr_3$) or phosphorous oxychloride ($POCl_3$) in dimethylformamide (DMF) [Vilsmeier reaction] to prepare a halogenated compound of formula IV.

In the Vilsmeier reaction, methylene chloride may be used as a solvent, and the reaction temperature is 0~70° C., and preferably 0~45° C.

The prepared compound of formula IV may be reacted with a compound of formula V according to the Suzuki reaction (Morris, G. A., et al., Tetrahedron Lett., 2001, 42, 2093) or the Ullman reaction (Martin G. Banwell et al. Org. Lett. 2004, 6, 2741) to prepare a compound of formula VI.

A solvent that is used in the Suzuki reaction or the Ullman reaction is dimethoxyethane (DME), dimethylsulfoxide (DMSO), water, or a mixture thereof, and the reaction temperature is 80~150° C., and preferably 80~100° C.

The prepared compound of formula VI may be subjected to reductive amination with a compound of formula VII to prepare a compound of formula VIII. The compound of formula VII that is used in the reductive amination reaction can be prepared with reference to the literature (International Patent Publication No. WO 2006/014357; Jingjun Yin et al., J. Org. Chem. 2006, 840).

The prepared compound of formula VIII may be subjected to cyclization with triphosgene to prepare a desired compound of formula II.

The Suzuki or Ullman reaction step and the reductive amination/cyclization reaction step are not limited to the above-described order and may be carried out in a reverse order.

The prepared compound of formula II may be subjected to the Suzuki reaction according to the following reaction scheme 2 to prepare a compound of formula I.

[Reaction scheme 2]
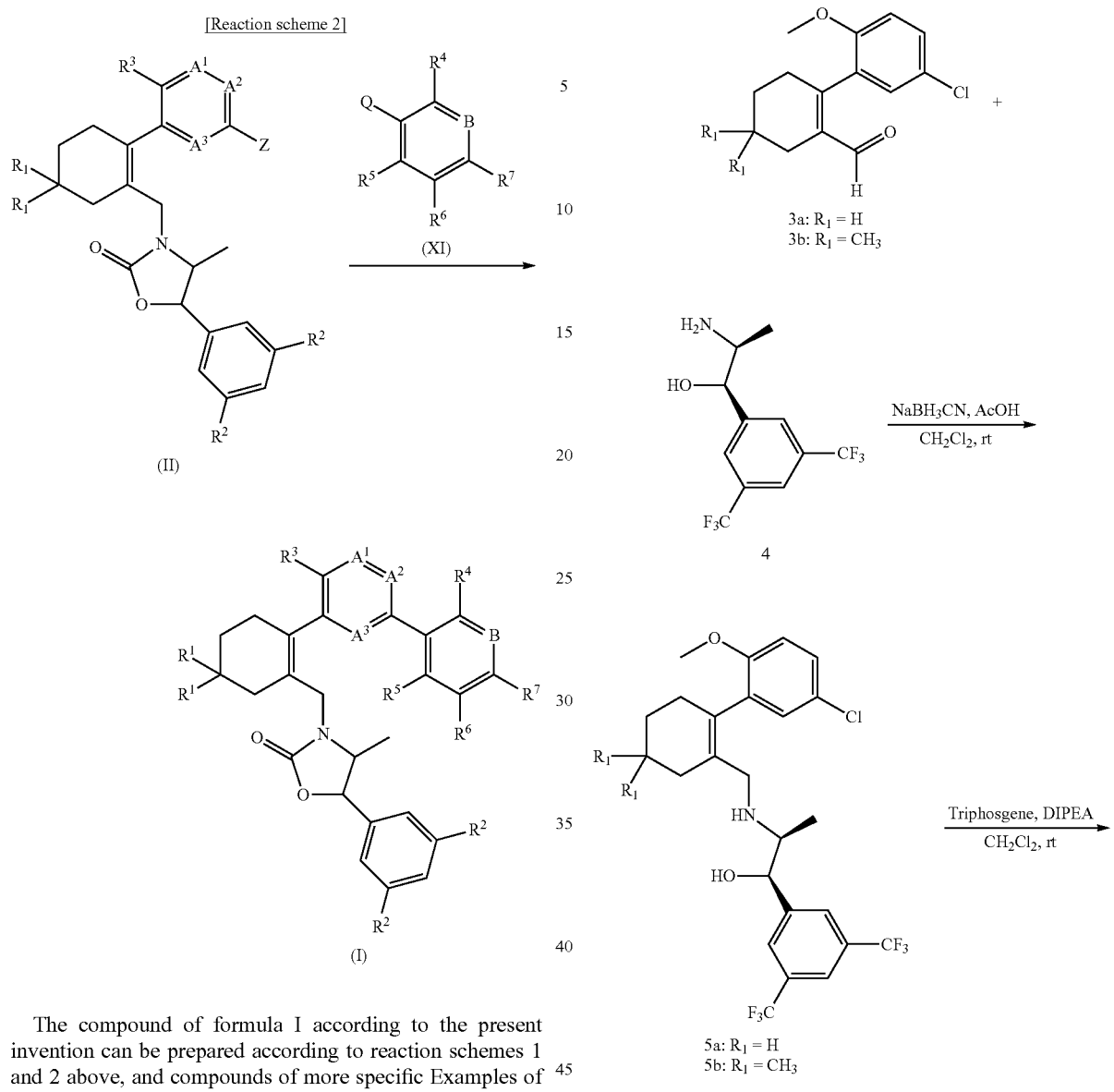
The compound of formula I according to the present invention can be prepared according to reaction schemes 1 and 2 above, and compounds of more specific Examples of the present invention can be prepared according to the following reaction schemes 3 to 18.
[Reaction scheme 3]
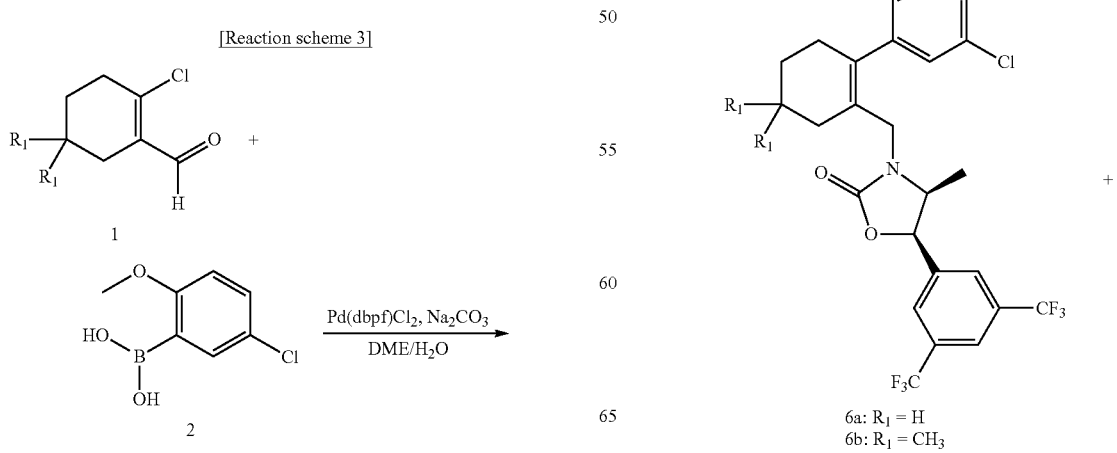

-continued

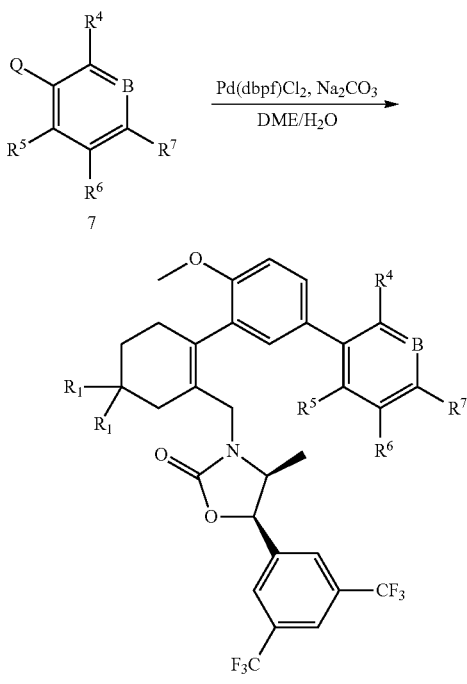

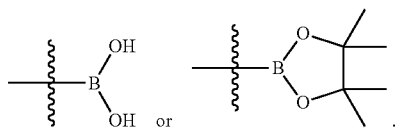

Compound 1 synthesized according to a known method is subjected to the Suzuki reaction with 5-chloro-2-methoxyphenylboronic acid in the presence of a palladium catalyst to synthesize compounds 3a and 3b, which are then reacted with compound 4 prepared according to a method described in the literature (International Patent Publication No. WO 2006/014357 A1; Jingjun Yin et al., J. Org. Chem. 2006, 840), thereby preparing compounds 5a and 5b. The prepared compounds 5a and 5b are reacted with triphosgene to synthesize compounds 6a and 6b, which are then subjected to the Suzuki reaction with various boronic acid derivatives in the presence of a palladium catalyst, thereby synthesizing ester compounds 553, 559, 560, 564, 567, 569, 579, 580, 590, 591, 599, 600 and 665. In addition, these ester compounds may be hydrolyzed with lithium hydroxide to obtain desired carboxylic acid compounds 554, 561, 565, 568, 581, 582, 592, 593, 601, 602 and 666.

[Reaction scheme 4]

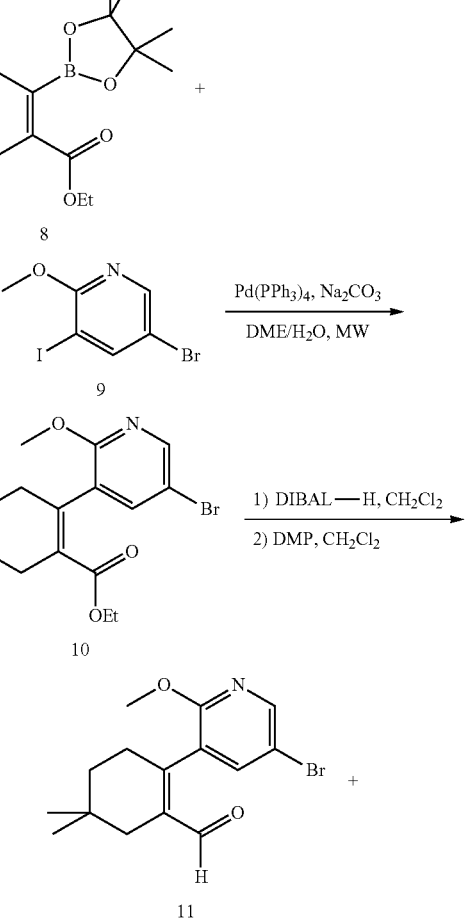

| Compounds | $R^1$ | $R^4$ | $R^5$ | $R^6$ | $R^7$ | B |
|---|---|---|---|---|---|---|
| 553 | $CH_3$ | $CH_3$ | H | H | $CO_2CH_3$ | CH |
| 554 | $CH_3$ | $CH_3$ | H | H | $CO_2H$ | CH |
| 559 | $CH_3$ | H | H | H | $CO_2CH_3$ | CH |
| 565 | $CH_3$ | H | H | H | $CO_2H$ | CH |
| 560 | $CH_3$ | F | H | H | $CO_2CH_3$ | CH |
| 561 | $CH_3$ | F | H | H | $CO_2H$ | CH |
| 564 | $CH_3$ | H | H | H | $CO_2CH_3$ | N |
| 567 | $CH_3$ | H | H | H | H | $CCO_2CH_3$ |
| 568 | $CH_3$ | H | H | H | H | $CCO_2H$ |
| 569 | $CH_3$ | $NO_2$ | H | H | $CO_2CH_3$ | CH |
| 579 | H | $CH_3$ | H | H | $CO_2CH_3$ | CH |
| 581 | H | $CH_3$ | H | H | $CO_2H$ | CH |
| 580 | H | F | H | H | $CO_2CH_3$ | CH |
| 582 | H | F | H | H | $CO_2H$ | CH |
| 590 | $CH_3$ | F | H | H | $CO_2CH_3$ | CF |
| 592 | $CH_3$ | F | H | H | $CO_2H$ | CF |
| 591 | $CH_3$ | F | F | H | $CO_2CH_3$ | CH |
| 593 | $CH_3$ | F | F | H | $CO_2H$ | CH |
| 599 | $CH_3$ | H | H | H | $CO_2CH_3$ | $COCH_3$ |
| 601 | $CH_3$ | H | H | H | $CO_2H$ | $COCH_3$ |
| 600 | $CH_3$ | H | H | $CH_3$ | $CO_2CH_3$ | N |
| 602 | $CH_3$ | H | H | $CH_3$ | $CO_2H$ | N |
| 665 | $CH_3$ | $CH_3$ | H | H | $CO_2CH_3$ | N |
| 666 | $CH_3$ | $CH_3$ | H | H | $CO_2H$ | N |

Reaction scheme 3 above shows a general process for synthesizing compounds 553, 554, 559, 560, 561, 564, 565, 567, 568, 569, 579, 580, 581, 582, 590, 591, 592, 593, 599, 600, 601, 602, 665 and 666 of the present invention, and other compounds of the present invention can also be prepared according to reaction scheme 3 above. In the above reaction scheme, $R^1$, $R^4$, $R^5$, $R^6$, $R^7$ and B are each as defined above, and Q may be 21
-continued

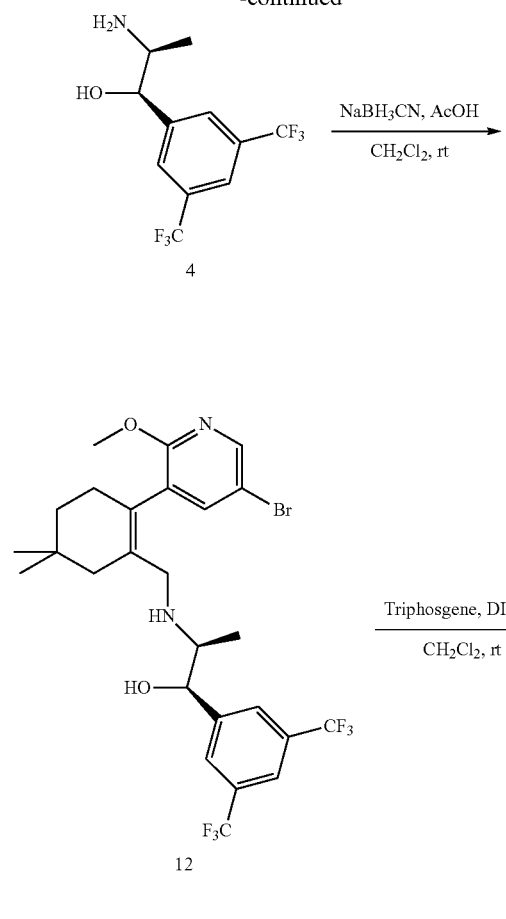

22
-continued

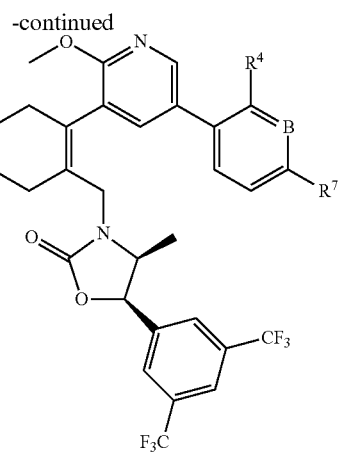

555, 556, 583, 585, 587, 595 ⟶ LiOH, dioxane, H₂O, heating ⟵ 557, 558, 584, 586, 588, 596

| Compounds | $R^4$ | $R^7$ | B |
|---|---|---|---|
| 555 | $CH_3$ | $CO_2CH_3$ | CH |
| 557 | $CH_3$ | $CO_2H$ | CH |
| 556 | H | $CO_2CH_3$ | CH |
| 558 | H | $CO_2H$ | CH |
| 583 | Cl | $CO_2CH_3$ | CH |
| 584 | Cl | $CO_2H$ | CH |
| 585 | F | $CO_2CH_3$ | CH |
| 586 | F | $CO_2H$ | CH |
| 587 | H | H | $CCO_2CH_3$ |
| 588 | H | H | $CCO_2H$ |
| 595 | F | $CO_2CH_3$ | CF |
| 596 | F | $CO_2H$ | CF |

Reaction scheme 4 above shows a general process for synthesizing compounds 555, 556, 557, 558, 583, 584, 585, 586, 587, 588, 595 and 596 of the present invention, and other compounds can also be prepared according to reaction scheme 4. In reaction scheme 4, $R^4$, $R^7$ and B are each as defined above, and Q may be

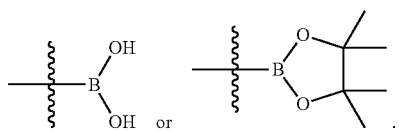

Compound 8 synthesized according to a known method is subjected to the Suzuki reaction with 5-bromo-3-iodo-2-methoxypyridine (9) in the presence of a palladium catalyst to synthesize compound 10, which is then subjected to an oxidation/reduction reaction to synthesize compound 11.

The obtained compound 11 is reacted with compound 4 prepared according to a known method, thereby preparing compound 12. The prepared compound 12 is reacted with triphosgene to synthesize compound 13, which is then subjected to the Suzuki reaction with various boronic acid derivatives in the presence of a palladium catalyst to synthesize ester compounds 555, 556, 583, 585, 587 and 595. The ester compounds may be hydrolyzed with lithium hydroxide to obtain desired carboxylic acid compounds 557, 558, 584, 586, 588 and 596.

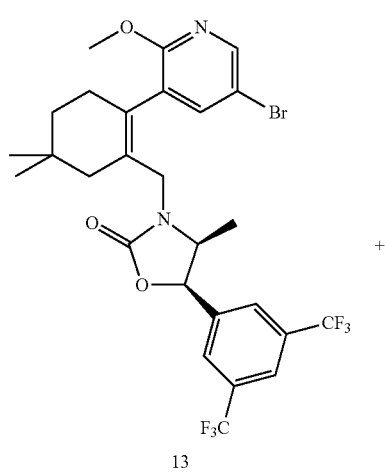

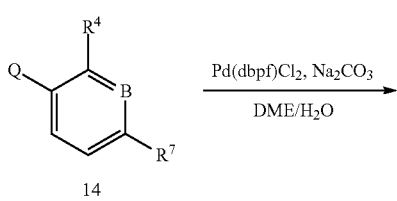

[Reaction scheme 5]

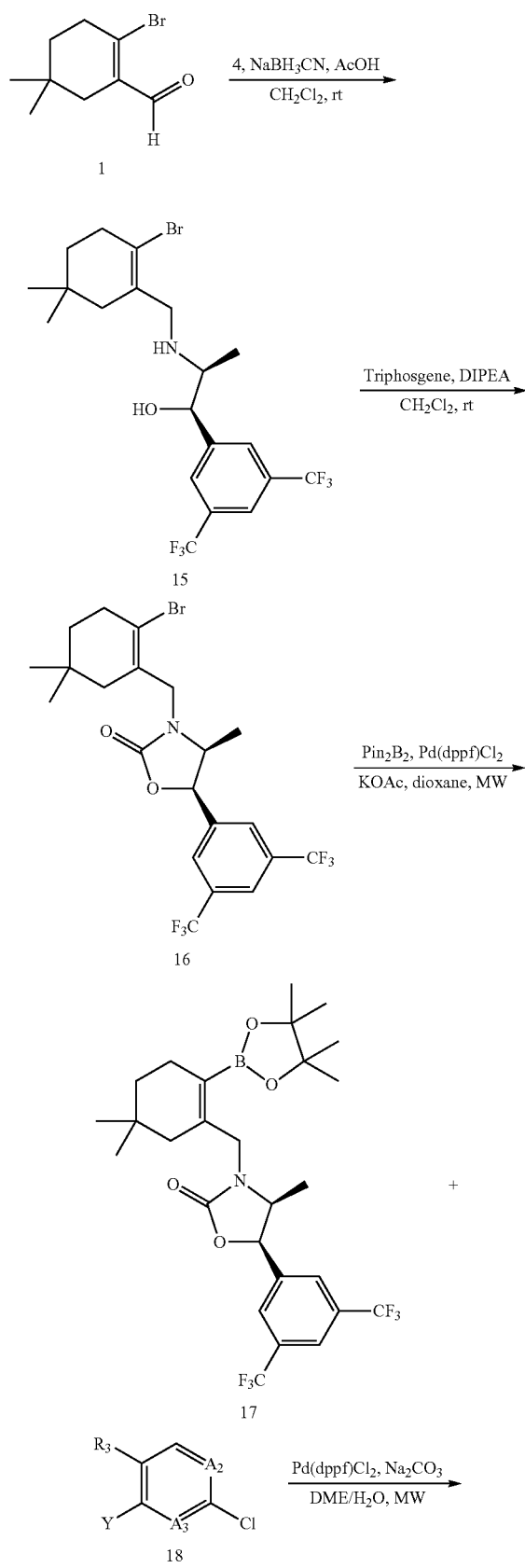
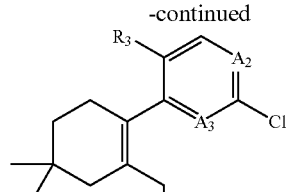
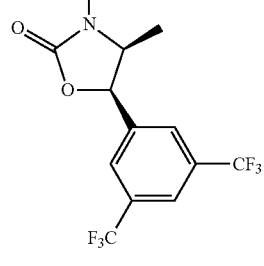
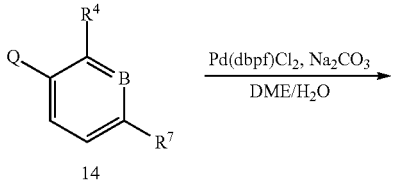
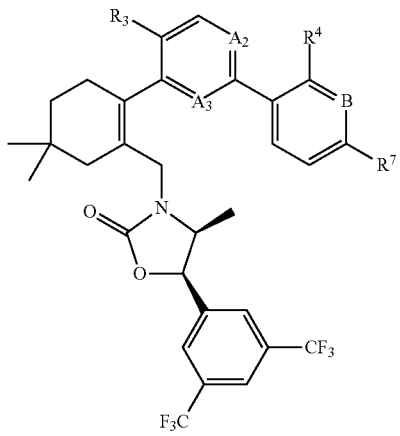

| Compounds | R³ | R⁴ | R⁷ | B | A² | A³ |
|---|---|---|---|---|---|---|
| 603 | $OCH_3$ | $CH_3$ | $CO_2CH_3$ | CH | N | N |
| 604 | $OCH_3$ | $CH_3$ | $CO_2H$ | CH | N | N |
| 610 | $OCH_3$ | F | $CO_2CH_3$ | CH | N | N |
| 617 | $OCH_3$ | F | $CO_2H$ | CH | N | N |
| 625 | $OCH_3$ | H | $CO_2CH_3$ | CH | N | N |
| 628 | $OCH_3$ | H | $CO_2H$ | CH | N | N |
| 626 | $OCH_3$ | H | $CO_2CH_2CH_3$ | CF | N | N |
| 629 | $OCH_3$ | H | $CO_2H$ | CF | N | N |
| 673 | H | H | $CO_2CH_3$ | CH | $CCH_3$ | CH |
| 676 | H | H | $CO_2H$ | CH | $CCH_3$ | CH |
| 674 | H | $CH_3$ | $CO_2CH_3$ | CH | $CCH_3$ | CH |
| 677 | H | $CH_3$ | $CO_2H$ | CH | $CCH_3$ | CH |
| 675 | H | F | $CO_2CH_3$ | CH | $CCH_3$ | CH |
| 678 | H | F | $CO_2H$ | CH | $CCH_3$ | CH |
| 763 | $OCH_3$ | $CF_3$ | $CO_2CH_3$ | CH | CH | N |
| 764 | $OCH_3$ | $CF_3$ | $CO_2H$ | CH | CH | N |

Reaction scheme 5 above shows a general process for synthesizing compounds 603, 604, 610, 617, 625, 626, 628, 629, 673, 674, 675, 676, 677, 678, 763 and 764 of the present invention, and other compounds of the present invention can also be synthesized according to reaction scheme 5. In reaction scheme 5, $R^3$, $R^4$, $R^7$, B, $A^2$ and $A^3$

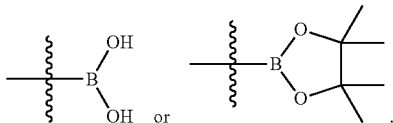

Compound 1 synthesized according to a known method is reacted with compound 4 to synthesize compound 15, which is then reacted with triphosgene to synthesize compound 16, which is then subjected to Suzuki reaction with various boronic acid derivatives in the presence of a palladium catalyst to synthesize pinacolate compound 17, which is then subjected to the Suzuki reaction with various boronic acid derivatives in the presence of a palladium catalyst to synthesize ester compounds 603, 610, 625, 626, 673, 674, 675 and 763. The ester compounds may be hydrolyzed with lithium hydroxide to obtain desired carboxylic acid compounds 604, 617, 628, 629, 676, 677, 678 and 764.

[Reaction scheme 6]

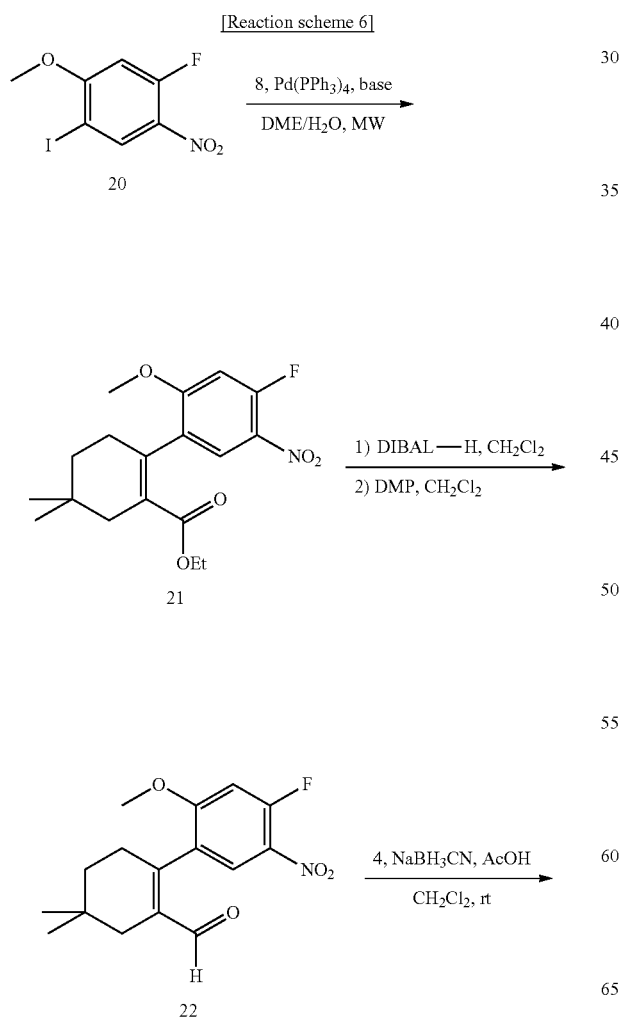

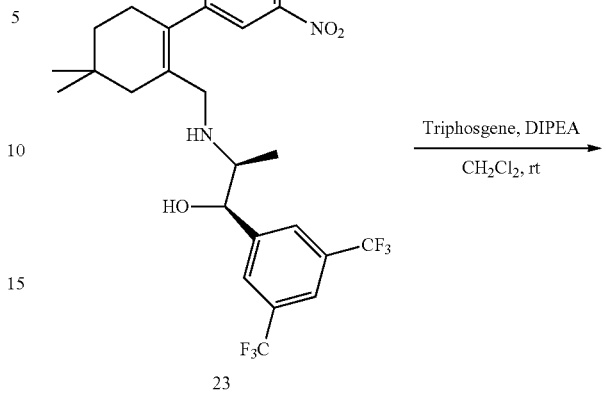

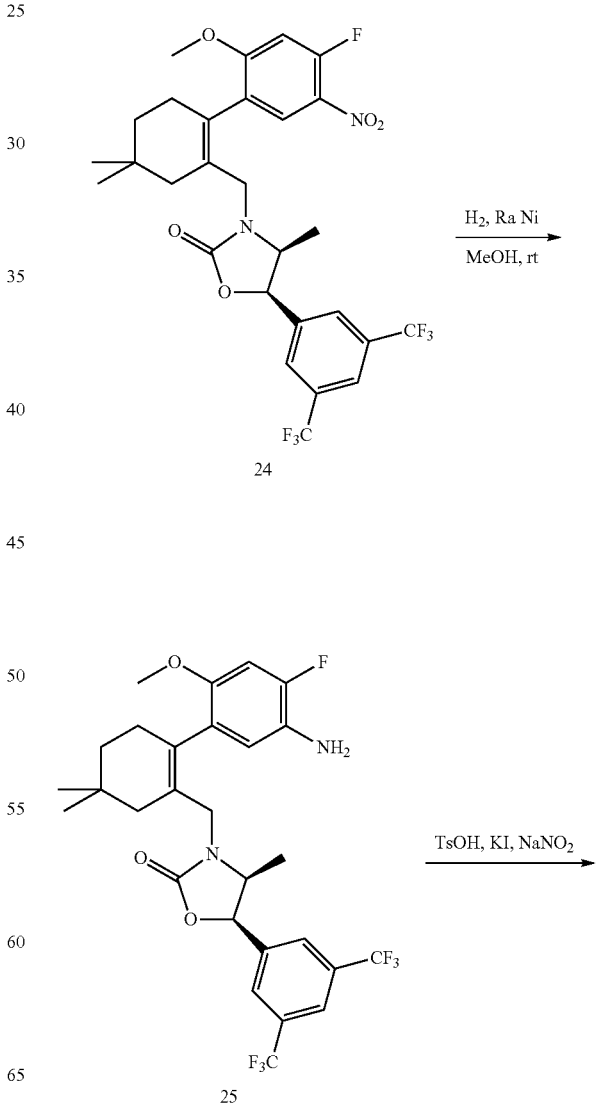

-continued

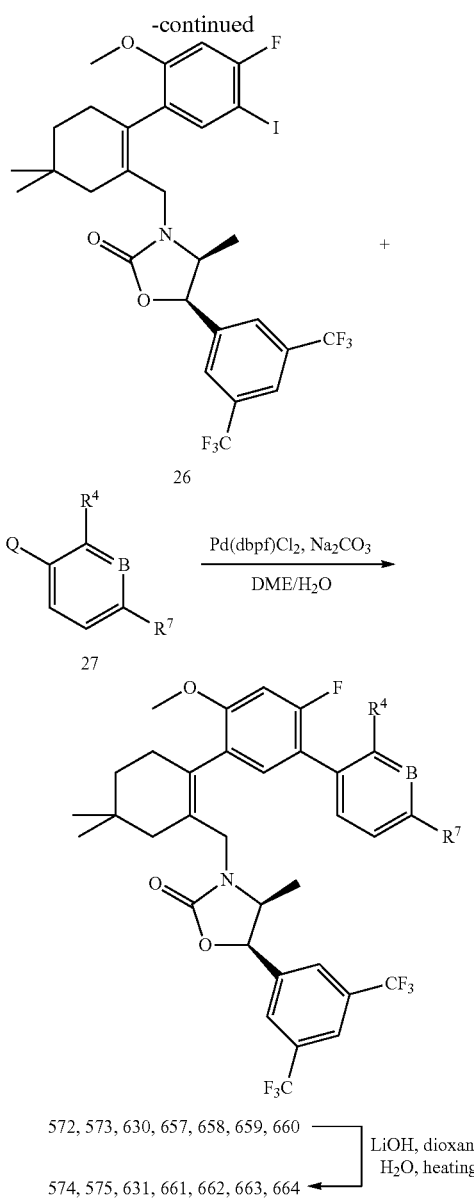

also be prepared according to reaction scheme 6. In reaction scheme 6, $R^4$, $R^7$ and B are each as defined above, and Q may be

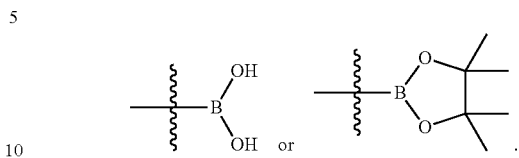

Compound 20 as a starting material is subjected to the Suzuki reaction with compound 8 to prepare compound 21, which is then subjected to an oxidation/reduction reaction to synthesize compound 22. The obtained compound 22 is reacted with compound 4 prepared according to a known method, thereby preparing compound 23. The prepared compound 23 is reacted with triphosgene to synthesize compound 24, which is then hydrogenated in the presence of a nickel catalyst to synthesize compound 25, which is then subjected to the Sandmeyer reaction to synthesize iodine-containing compound 26. The synthesized compound 26 is subjected to the Suzuki reaction with various boronic acid derivatives in the presence of a palladium catalyst to synthesize ester compounds 572, 573, 630, 657, 658, 659 and 660. The ester compounds may be hydrolyzed with lithium hydroxide to obtain desired carboxylic acid compounds 574, 575, 631, 661, 662, 663 and 664.

[Reaction scheme 7]

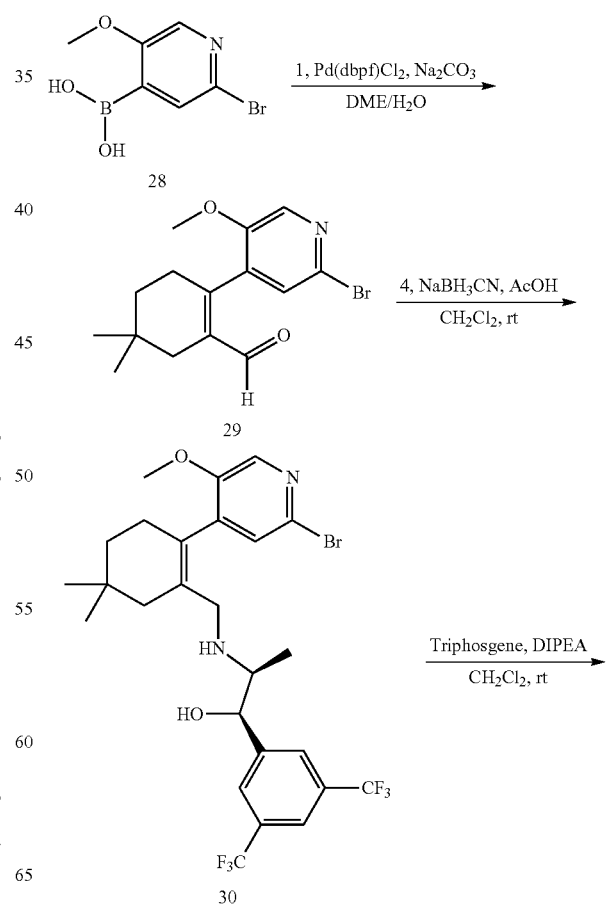

| Compounds | $R^4$ | $R^7$ | B |
|---|---|---|---|
| 572 | $CH_3$ | $CO_2CH_3$ | CH |
| 574 | $CH_3$ | $CO_2H$ | CH |
| 573 | H | $CO_2CH_3$ | CH |
| 575 | H | $CO_2H$ | CH |
| 630 | Cl | $CO_2CH_3$ | CH |
| 631 | Cl | $CO_2H$ | CH |
| 657 | F | $CO_2CH_3$ | CH |
| 661 | F | $CO_2H$ | CH |
| 658 | H | $CO_2CH_2CH_3$ | CF |
| 662 | H | $CO_2H$ | CF |
| 659 | H | $CO_2CH_3$ | $COCH_3$ |
| 663 | H | $CO_2H$ | $COCH_3$ |
| 660 | F | $CO_2CH_3$ | CF |
| 664 | F | $CO_2H$ | CF |

Reaction scheme 6 above shows a general process for synthesizing compounds 572, 573, 574, 575, 630, 631, 657, 658, 659, 660, 661, 662, 663 and 664 of the present invention, and other compounds of the present invention can Compound 1 synthesized according to a known method is subjected to the Suzuki reaction with 2-bromo-5-methoxy-pyridin-4-ylboronic acid in the presence of a palladium catalyst to synthesize compound 29, which is then reacted with compound 4 prepared according to a known method, thereby preparing compound 30. The prepared compound 30 is reacted with triphosgene to synthesize compound 31, which is then subjected to the Suzuki reaction with various boronic acid derivatives in the presence of a palladium catalyst to synthesize ester compounds 652, 653, 654, 655 and 656. The ester compounds may be hydrolyzed with lithium hydroxide to obtain desired carboxylic acid compounds 644, 645, 646 and 647.

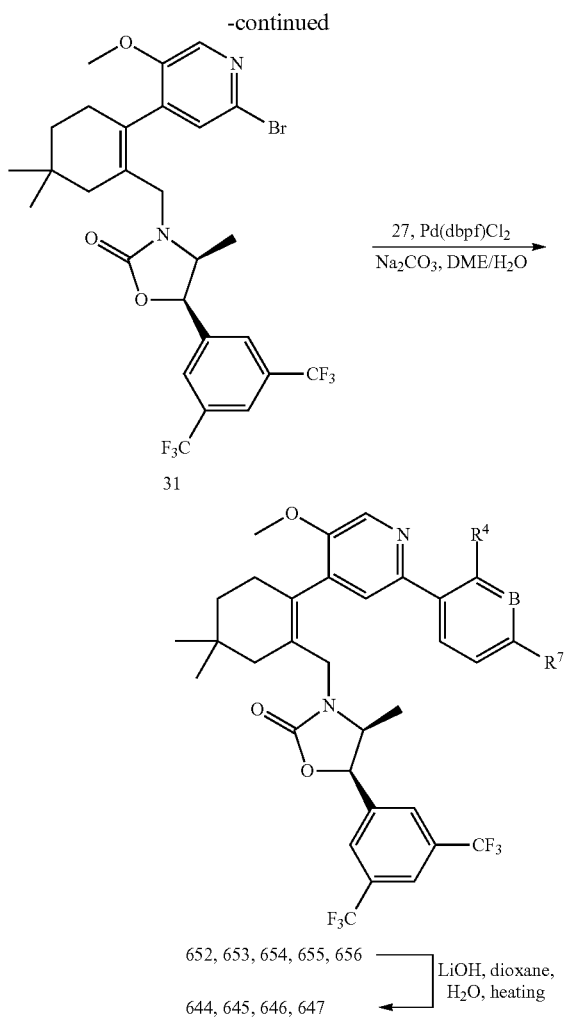

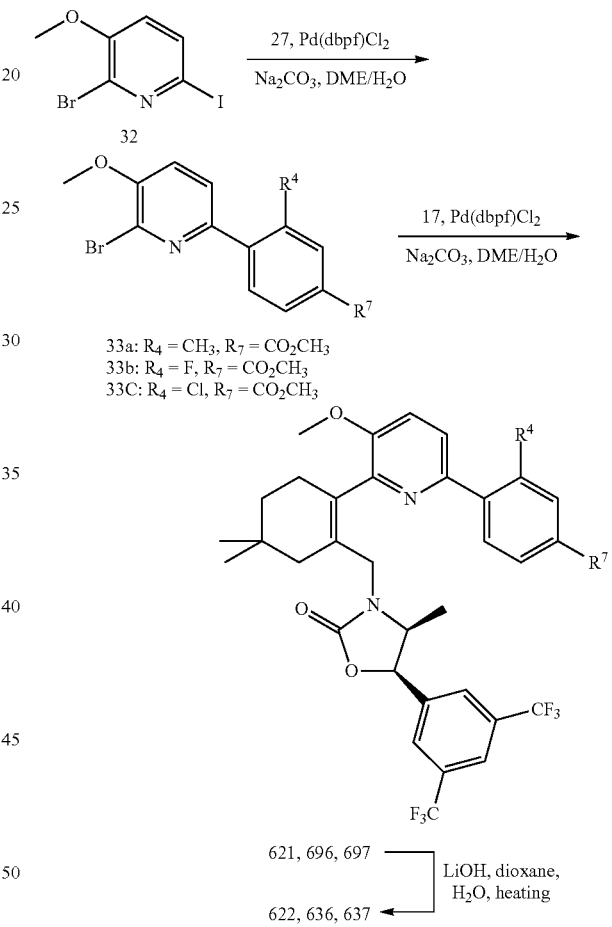

| Compounds | R⁴  | R⁷                 | B  |
|-----------|-----|--------------------|----|
| 652       | H   | CO₂CH₃             | CH |
| 644       | H   | CO₂H               | CH |
| 653       | CH₃ | CO₂CH₃             | CH |
| 645       | CH₃ | CO₂H               | CH |
| 654       | F   | CO₂CH₃             | CH |
| 646       | F   | CO₂H               | CH |
| 655       | Cl  | CO₂CH₃             | CH |
| 647       | Cl  | CO₂H               | CH |
| 656       | F   | CO₂CH₃             | CF |

Reaction scheme 7 above shows a general process for synthesizing compounds 644, 645, 646, 647, 652, 653, 654, 655 and 656 of the present invention, and other compounds of the present invention can also be synthesized according to reaction scheme 7. In reaction scheme 7, R⁴, R⁷ and B are each as defined above, and Q may be

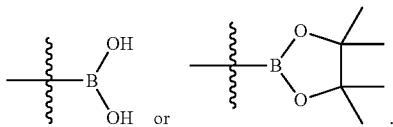

| Compounds | R⁴  | R⁷     |
|-----------|-----|--------|
| 621       | CH₃ | CO₂CH₃ |
| 622       | CH₃ | CO₂H   |
| 696       | F   | CO₂CH₃ |
| 637       | F   | CO₂H   |
| 697       | Cl  | CO₂CH₃ |
| 636       | Cl  | CO₂H   |

Reaction scheme 8 above shows a general process for synthesizing compounds 621, 622, 636, 637, 696 and 697 of the present invention, and other compounds of the present invention can also be synthesized according to reaction scheme 8. In reaction scheme 8, $R^4$ and $R^7$ are each as defined above, and Q may be

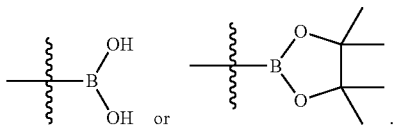

2-bromo-6-iodo-3-methoxypyridine as a starting material is subjected to the Suzuki reaction with various boronic acid derivatives to synthesize compounds 33a to 33c. The synthesized compounds are subjected to the Suzuki reaction with compound 17, synthesized as shown in reaction scheme 5, in the presence of a palladium catalyst, to synthesize ester compounds 621, 696 and 697, which may then be hydrolyzed with lithium hydroxide to obtain desired carboxylic acid compounds 622, 636 and 637.

[Reaction scheme 9]

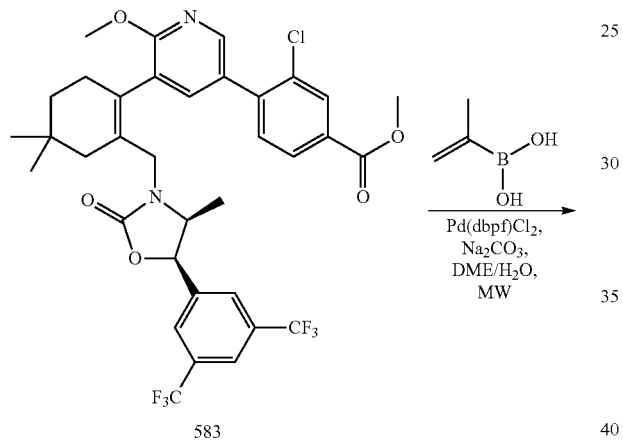

583

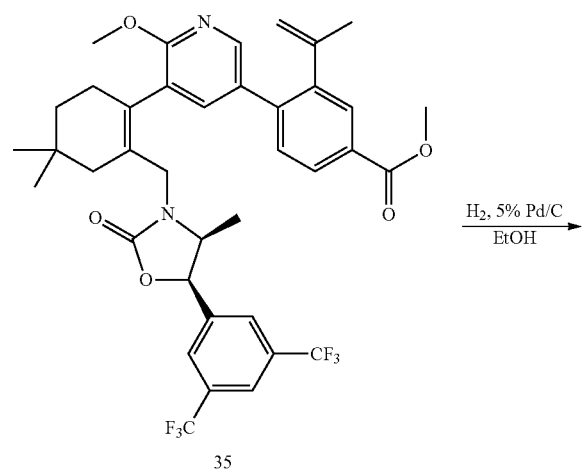

35

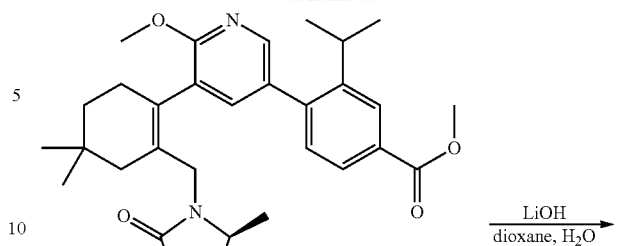

577

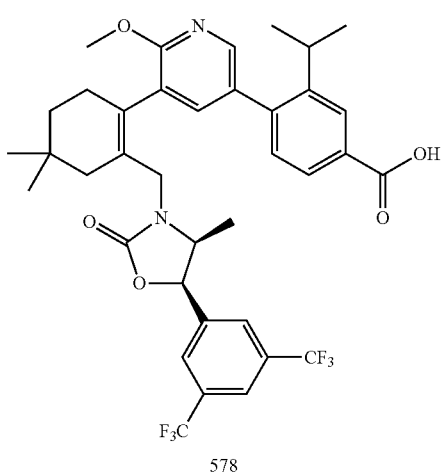 [SMILES: COc1ncc(-c2ccc(C(=O)O)cc2C(C)C)cc1C1=C(CN2C(=O)O[C@H](c3cc(C(F)(F)F)cc(C(F)(F)F)c3)[C@@H]2C)CC(C)(C)CC1]

578

Reaction scheme 9 above shows a general process for synthesizing compounds 577 and 578 of the present invention, and other compounds of the present invention can also be prepared according to reaction scheme 9.

Compound 583 as a starting material is subjected to the Suzuki reaction with propen-2-ylboronic acid in the presence of a palladium catalyst to synthesize compound 35. The synthesized compound is hydrogenated in the presence of a palladium catalyst to obtain ester compound 577, which may then be hydrolyzed with lithium hydroxide to obtain desired carboxylic acid compound 578.

[Reaction scheme 10]

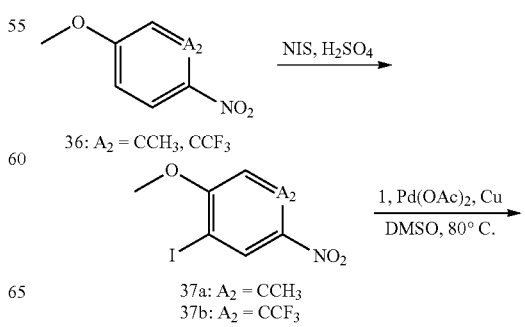

36: $A_2$ = $CCH_3$, $CCF_3$

37a: $A_2$ = $CCH_3$
37b: $A_2$ = $CCF_3$

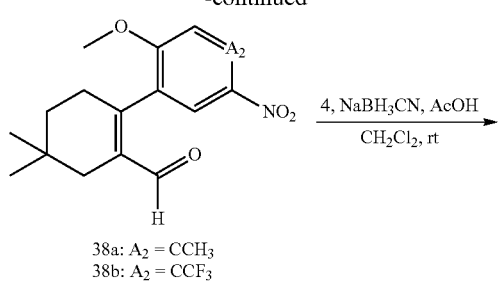
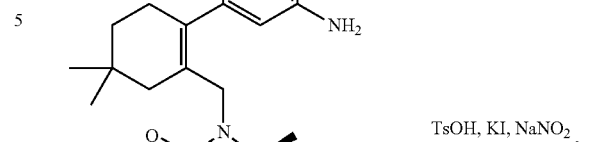
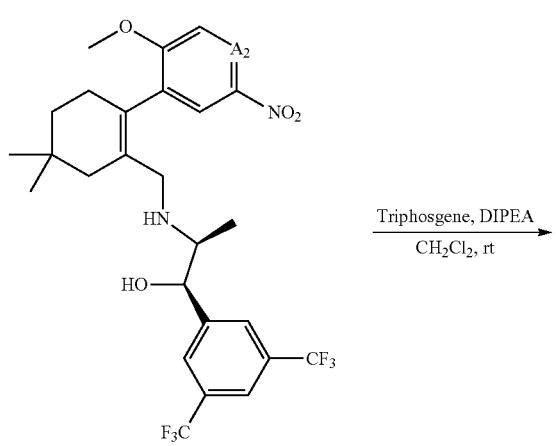
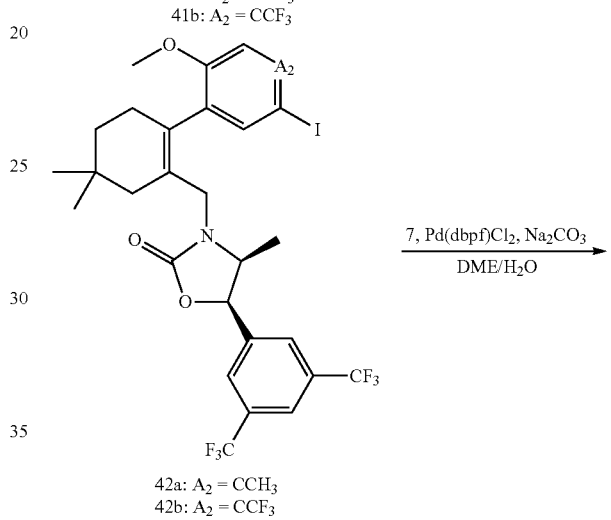
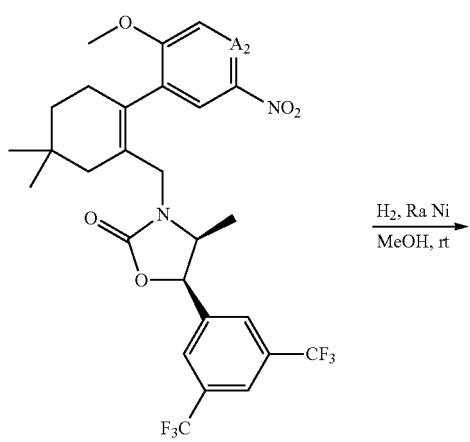
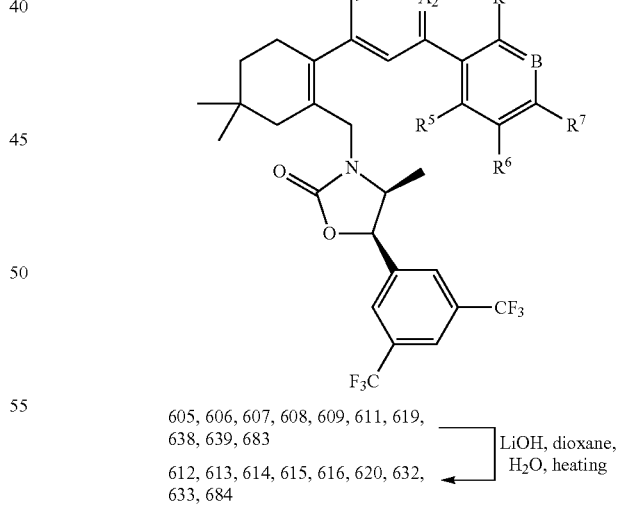
| Compounds | R⁴ | R⁵ | R⁶ | R⁷ | A² | B |
|---|---|---|---|---|---|---|
| 605 | H | H | H | $CO_2CH_3$ | $CCF_3$ | CH |
| 612 | H | H | H | $CO_2H$ | $CCF_3$ | CH |
| 606 | F | H | H | $CO_2CH_3$ | $CCF_3$ | CH |

-continued

| Compounds | R4 | R5 | R6 | R7 | A2 | B |
|---|---|---|---|---|---|---|
| 613 | F | H | H | CO$_2$H | CCF$_3$ | CH |
| 607 | H | H | H | CO$_2$Et | CCF$_3$ | CF |
| 614 | H | H | H | CO$_2$H | CCF$_3$ | CF |
| 608 | Cl | H | H | CO$_2$CH$_3$ | CCF$_3$ | CH |
| 615 | Cl | H | H | CO$_2$H | CCF$_3$ | CH |
| 609 | CH$_3$ | H | H | CO$_2$CH$_3$ | CCF$_3$ | CH |
| 616 | CH$_3$ | H | H | CO$_2$H | CCF$_3$ | CH |
| 611 | H | H | F | CO$_2$H | CCF$_3$ | N |
| 619 | H | H | H | CO$_2$CH$_3$ | CCH$_3$ | CH |
| 620 | H | H | H | CO$_2$H | CCH$_3$ | CH |
| 638 | H | H | H | CO$_2$CH$_3$ | CCF$_3$ | CCl |
| 632 | H | H | H | CO$_2$H | CCF$_3$ | CCl |
| 639 | H | H | H | CO$_2$CH$_3$ | CCF$_3$ | COCH$_3$ |
| 633 | H | H | H | CO$_2$H | CCF$_3$ | COCH$_3$ |
| 683 | CH$_3$ | H | H | CO$_2$CH$_3$ | CCH$_3$ | CH |
| 684 | CH$_3$ | H | H | CO$_2$H | CCH$_3$ | CH |

Reaction scheme 10 above shows a general process synthesizing compounds 605, 606, 607, 608, 609, 611, 612, 613, 614, 615, 616, 619, 620, 632, 633, 638, 639, 683 and 684 of the present invention, and other compounds of the present invention can also be prepared according to reaction scheme 10. In reaction scheme 10, $R^4$, $R^5$, $R^6$, $R^7$, B and $A^2$ are each as defined above, and Q may be

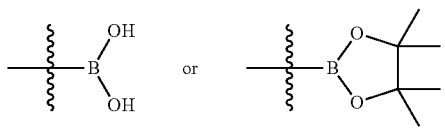

Compound 36 as a starting material is reacted with N-iodosuccinimide in a sulfuric acid solvent to synthesize compounds 37a and 37b, which are then subjected to the Ullman reaction (Martin G. Banwell et al. Org. Lett. 2004, 6, 2741) with compound 1 to synthesize compounds 38a and 38b. The synthesized compounds 38a and 38b are subjected to a reductive amination reaction with compound 4 prepared according to a known method, thereby synthesizing compounds 39a and 39b. The synthesized compounds 39a and 39b are reacted with triphosgene to synthesize compounds 40a and 40b. The synthesized compounds 40a and 40b are hydrogenated in the presence of a nickel catalyst to synthesize compounds 41a and 41b, which are then subjected to the Sandmeyer reaction to synthesize iodine-containing compounds 42a and 42b. The synthesized compounds 42a and 42b are subjected to the Suzuki reaction with various boronic acid derivatives in the presence of a palladium catalyst to synthesize ester compounds 605, 606, 607, 608, 609, 619, 638, 639 and 683. The ester compounds may be hydrolyzed with lithium hydroxide to obtain desired carboxylic acid compounds 612, 613, 614, 615, 616, 620, 632, 633 and 684. Compound 611 is converted to a desired carboxylic acid compound by the Suzuki reaction.

[Reaction scheme 11]

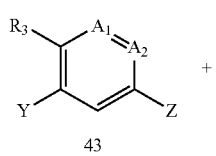

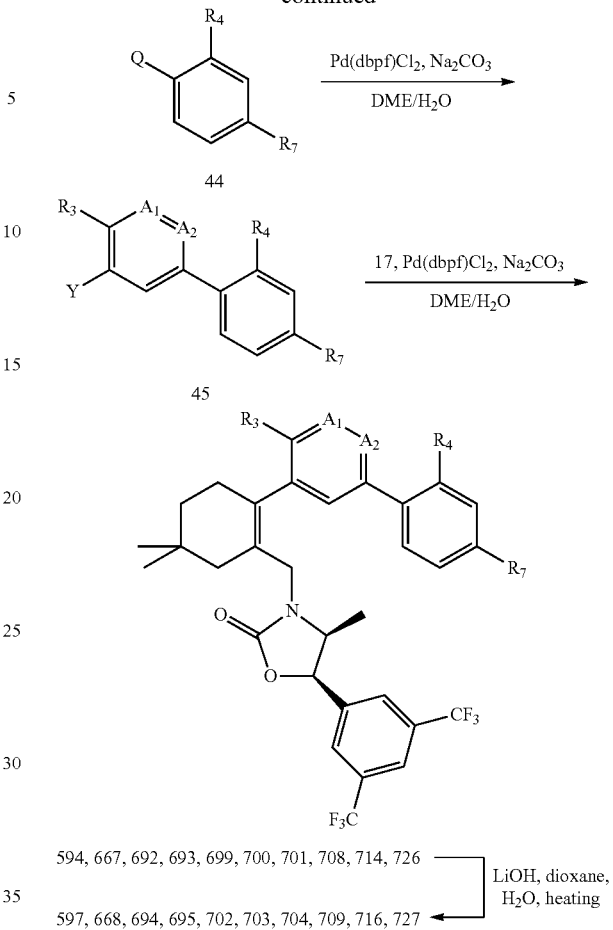

| Compounds | R3 | R4 | R7 | A1 | A2 |
|---|---|---|---|---|---|
| 594 | OCH$_3$ | OCH$_3$ | CO$_2$CH$_3$ | CH | CH |
| 597 | OCH$_3$ | OCH$_3$ | CO$_2$H | CH | CH |
| 667 | H | CF$_3$ | CO$_2$CH$_3$ | CF | CH |
| 668 | H | CF$_3$ | CO$_2$H | CF | CH |
| 692 | F | CH$_3$ | CO$_2$CH$_3$ | CH | CH |
| 694 | F | CH$_3$ | CO$_2$H | CH | CH |
| 693 | F | CF$_3$ | CO$_2$CH$_3$ | CH | CH |
| 695 | F | CF$_3$ | CO$_2$H | CH | CH |
| 699 | H | F | CO$_2$CH$_3$ | CF | CH |
| 702 | H | F | CO$_2$H | CF | CH |
| 700 | H | H | CO$_2$CH$_3$ | CF | CH |
| 703 | H | H | CO$_2$H | CF | CH |
| 701 | H | F | CO$_2$CH$_3$ | CH | CH |
| 704 | H | F | CO$_2$H | CH | CH |
| 708 | F | H | CO$_2$CH$_3$ | CH | CH |
| 709 | F | H | CO$_2$H | CH | CH |
| 714 | H | CH$_3$ | CO$_2$CH$_3$ | CH | N |
| 716 | H | CH$_3$ | CO$_2$H | CH | N |
| 726 | Cl | CH$_3$ | CO$_2$CH$_3$ | CH | CH |
| 727 | Cl | CH$_3$ | CO$_2$H | CH | CH |

Reaction scheme 11 above shows a general process for synthesizing compounds of 594, 597, 667, 668, 692, 693, 694, 695, 699, 700, 701, 702, 703, 704, 708, 709, 714, 716, 726 and 727 of the present invention, and other compounds of the present invention can also be prepared according to reaction scheme 11. In reaction scheme 11, $R^3$, $R^4$, $R^7$, $A^1$ and $A^2$ are each as defined above, and Y, Z and Q may each independently be halogen,

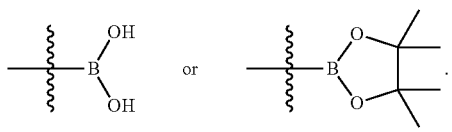

Compound 43 as a starting material is subjected to the Suzuki reaction with compound 44 in the presence of a palladium catalyst to synthesize compound 45, which is then subjected to the Suzuki reaction with compound 17 to synthesize ester compounds 594, 667, 692, 693, 699, 700, 701, 708, 714 and 726. The ester compounds may be hydrolyzed with lithium hydroxide to obtain desired carboxylic acid compounds 597, 668, 694, 695, 702, 703, 704, 709, 716 and 727.

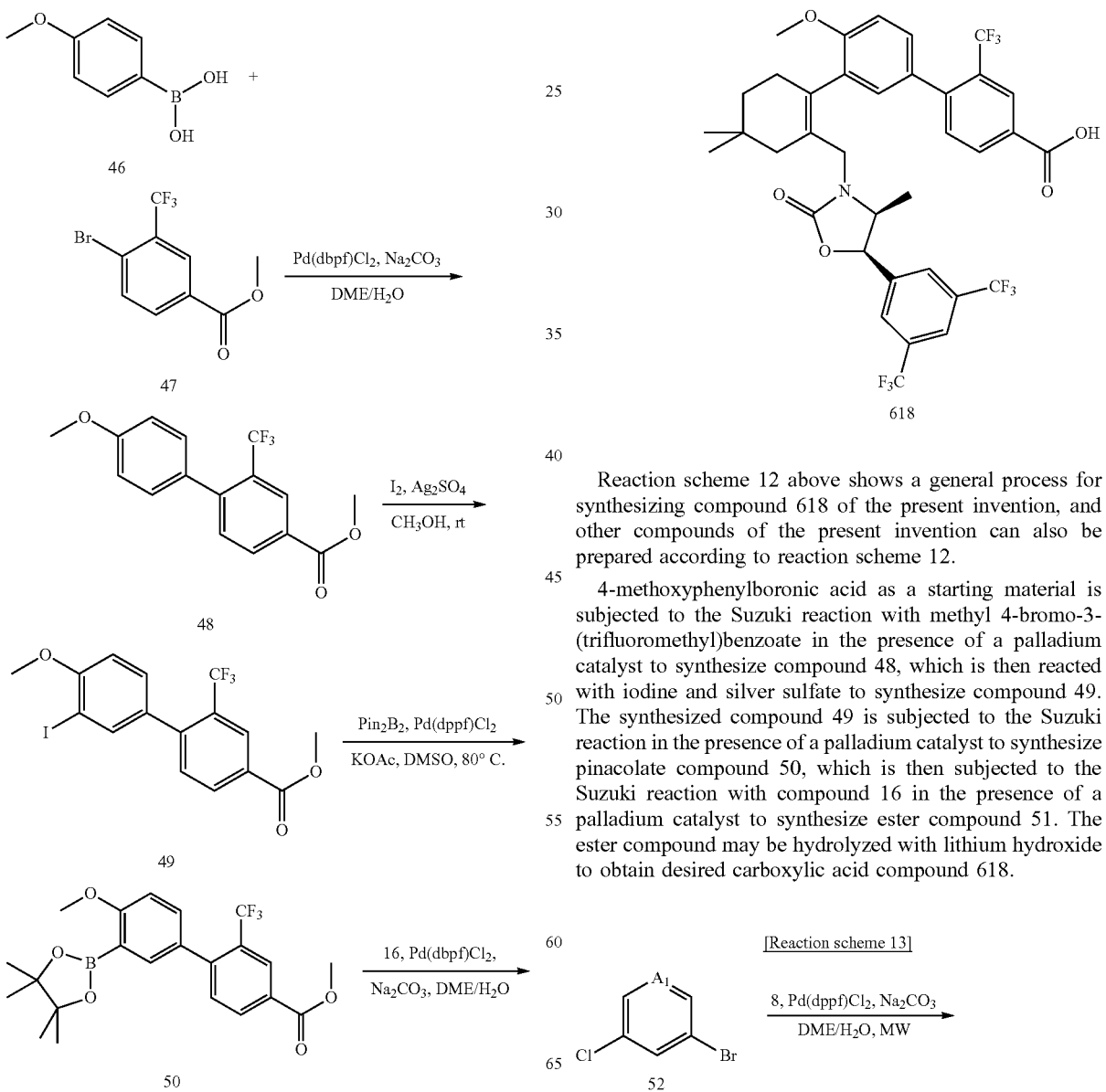

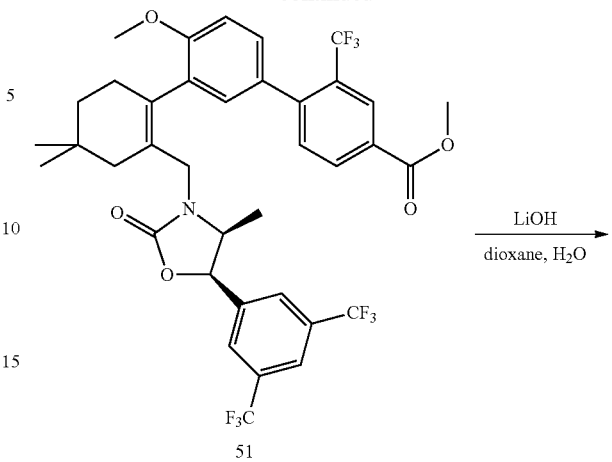

Reaction scheme 12 above shows a general process for synthesizing compound 618 of the present invention, and other compounds of the present invention can also be prepared according to reaction scheme 12.

4-methoxyphenylboronic acid as a starting material is subjected to the Suzuki reaction with methyl 4-bromo-3-(trifluoromethyl)benzoate in the presence of a palladium catalyst to synthesize compound 48, which is then reacted with iodine and silver sulfate to synthesize compound 49. The synthesized compound 49 is subjected to the Suzuki reaction in the presence of a palladium catalyst to synthesize pinacolate compound 50, which is then subjected to the Suzuki reaction with compound 16 in the presence of a palladium catalyst to synthesize ester compound 51. The ester compound may be hydrolyzed with lithium hydroxide to obtain desired carboxylic acid compound 618.

39
-continued
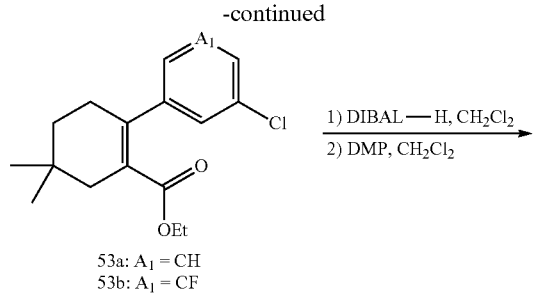
53a: A₁ = CH
53b: A₁ = CF
1) DIBAL—H, CH₂Cl₂
2) DMP, CH₂Cl₂
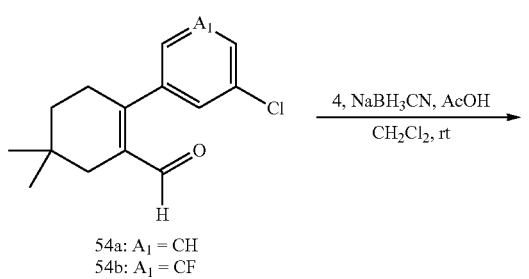
54a: A₁ = CH
54b: A₁ = CF
4, NaBH₃CN, AcOH
CH₂Cl₂, rt
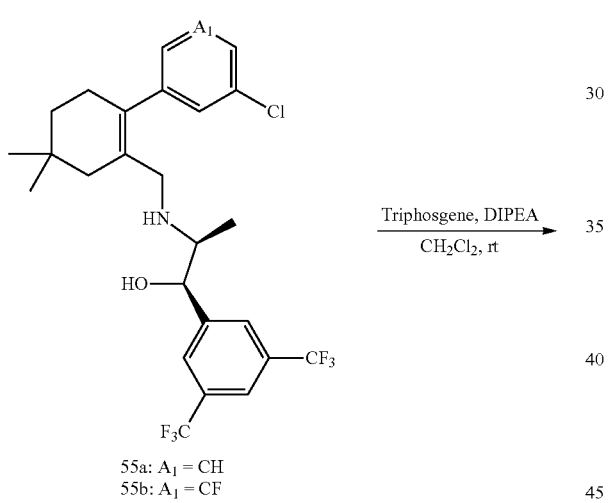
55a: A₁ = CH
55b: A₁ = CF
Triphosgene, DIPEA
CH₂Cl₂, rt
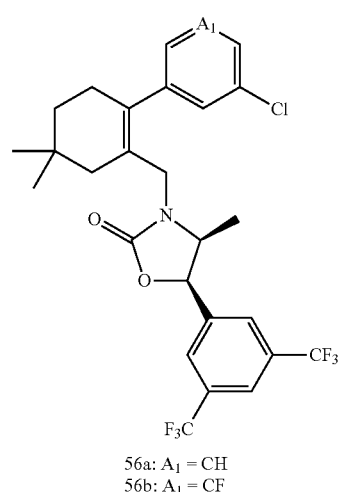
56a: A₁ = CH
56b: A₁ = CF
+
40
-continued
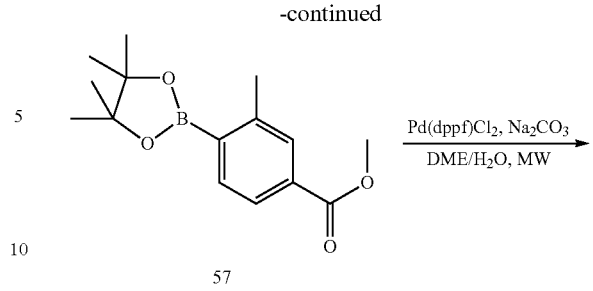
57
Pd(dppf)Cl₂, Na₂CO₃
DME/H₂O, MW
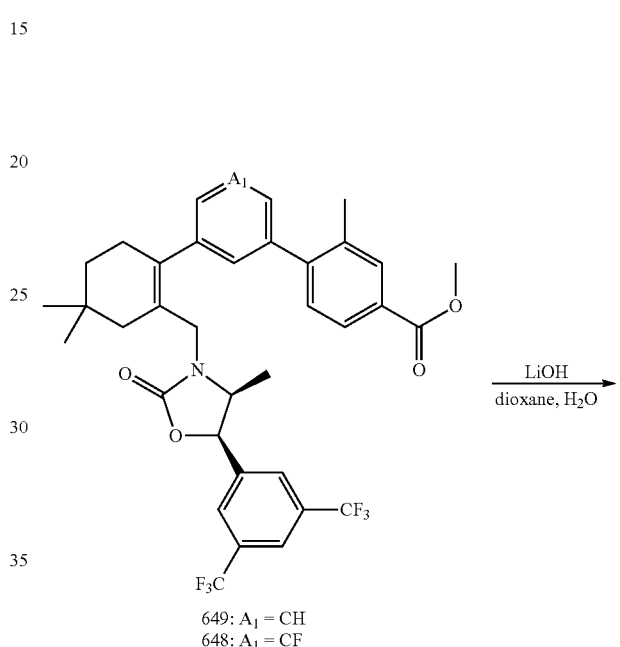
649: A₁ = CH
648: A₁ = CF
LiOH
dioxane, H₂O
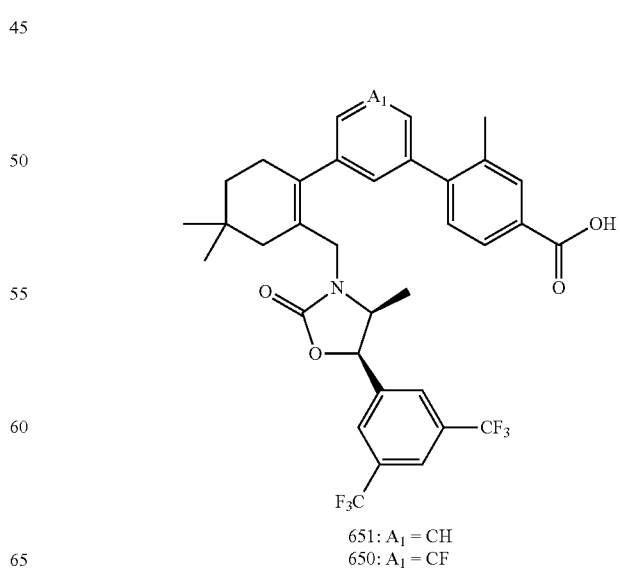
651: A₁ = CH
650: A₁ = CF Reaction scheme 13 above shows a general process for synthesizing compounds 648, 649, 650 and 651 of the present invention, and other compounds of the present invention can also be prepared according to reaction scheme 13.

Compound 52 as a starting material is subjected to the Suzuki reaction with compound 8 in the presence of a palladium catalyst to synthesize compounds 53a and 53b, which are than subjected to an oxidation/reduction reaction to synthesize aldehyde compounds 54a and 54b. The synthesized compounds 54a and 54b are reacted with compound 4 prepared according to a known method, thereby preparing compounds 55a and 55b. The synthesized compounds 55a and 55b are reacted with triphosgene to synthesize compounds 56a and 56b, which are then subjected to the Suzuki reaction with boronic acid to synthesize ester compounds 648 and 649. The ester compounds may be hydrolyzed with lithium hydroxide to obtain desired carboxylic acid compounds 650 and 651.

[Reaction scheme 14]

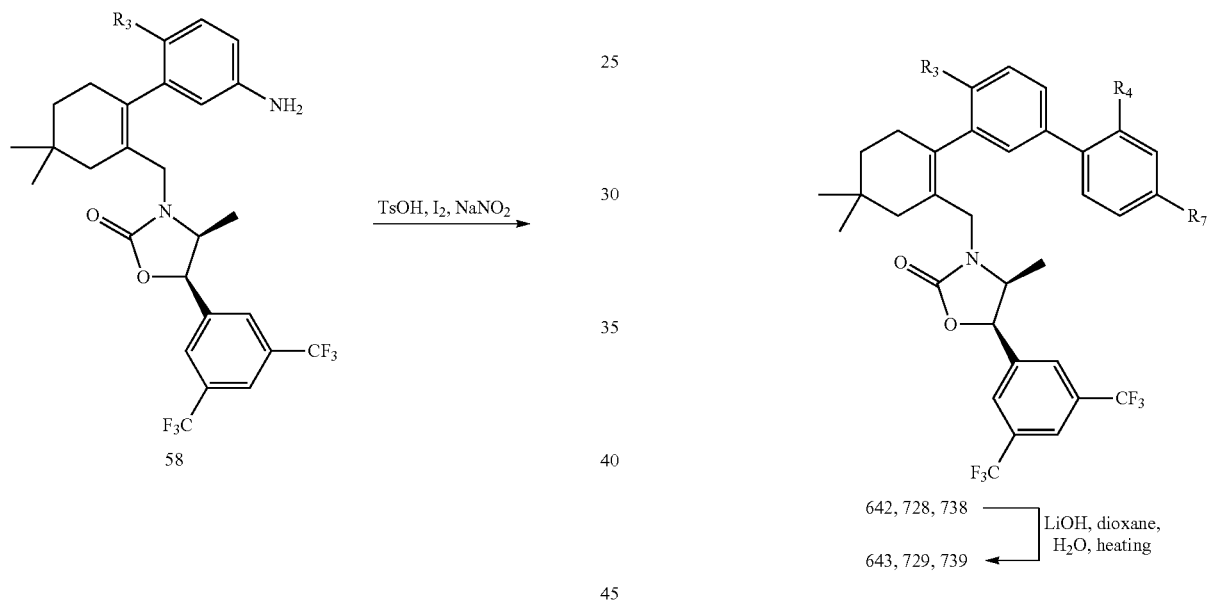

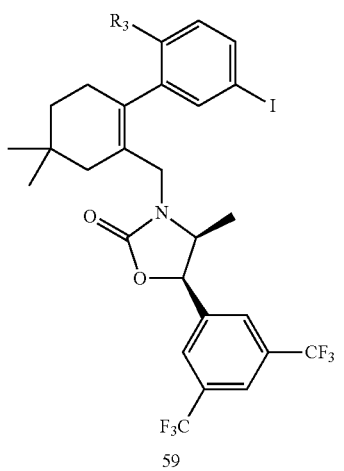

| Compounds | $R^3$ | $R^4$ | $R^7$ |
|---|---|---|---|
| 642 | $OCH_3$ | Cl | $CO_2CH_3$ |
| 643 | $OCH_3$ | Cl | $CO_2H$ |
| 728 | Cl | $CF_3$ | $CO_2CH_3$ |
| 729 | Cl | $CF_3$ | $CO_2H$ |
| 738 | F | Cl | $CO_2CH_3$ |
| 739 | F | Cl | $CO_2H$ |

Reaction scheme 14 above shows a general process for synthesizing compounds 642, 643, 728, 729, 738 and 739 of the present invention, and other compounds of the present invention can also be prepared according to reaction scheme 14. In reaction scheme 14, $R^3$, $R^4$ and $R^7$ are each as defined above, and Q may be

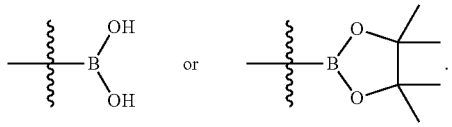

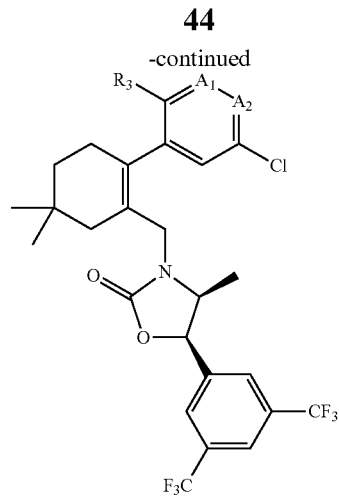

62a: $R_3$ = H $A_1$ = CH, $A_2$ = CF
62b: $R_3$ = H $A_1$ = COCH$_3$, $A_2$ = CH
62c: $R_3$ = F $A_1$ = CH, $A_2$ = CH
62d: $R_3$ = H $A_1$ = CCF$_3$, $A_2$ = CH

Compound 58 as a starting material is subjected to the Sandmeyer reaction to synthesize iodine-containing compound 59, which is then subjected to the Suzuki reaction with boronic acid compound 59 in the presence of a palladium catalyst to synthesize ester compounds 642, 728 and 738. The ester compounds may be hydrolyzed with lithium hydroxide to obtained desired carboxylic acid compounds 643, 729 and 739.

[Reaction scheme 15]

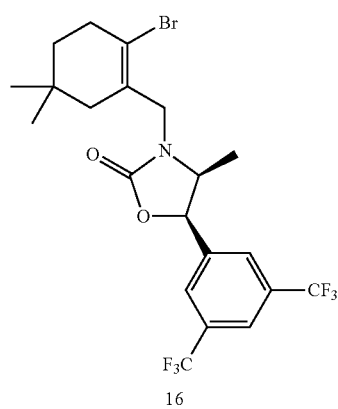

16

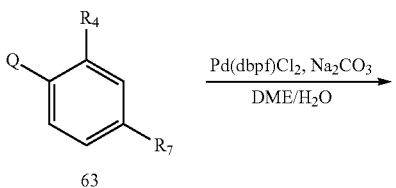

63

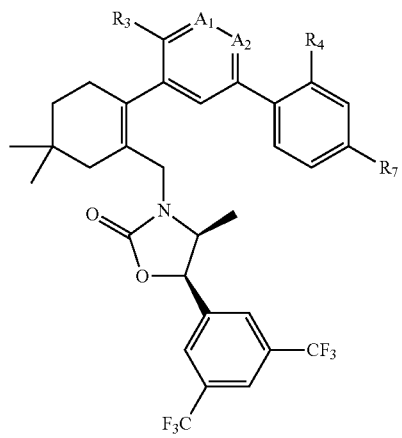

670, 671, 672, 686, 688, 690, 724, 725, 743, 745, 747 → LiOH, dioxane, H$_2$O, heating
679, 680, 681, 687, 689, 691, 722, 723, 744, 746, 748

| Compounds | $R^3$ | $R^4$ | $R^7$ | $A^1$ | $A^2$ |
|---|---|---|---|---|---|
| 670 | H | H | CO$_2$CH$_3$ | CH | CF |
| 679 | H | H | CO$_2$H | CH | CF |
| 671 | H | F | CO$_2$CH$_3$ | CH | CF |
| 680 | H | F | CO$_2$H | CH | CF |
| 672 | H | CH$_3$ | CO$_2$CH$_3$ | CH | CF |
| 681 | H | CH$_3$ | CO$_2$H | CH | CF |
| 686 | H | H | CO$_2$CH$_3$ | COCH$_3$ | CH |
| 687 | H | H | CO$_2$H | COCH$_3$ | CH |
| 688 | H | CH$_3$ | CO$_2$CH$_3$ | COCH$_3$ | CH |

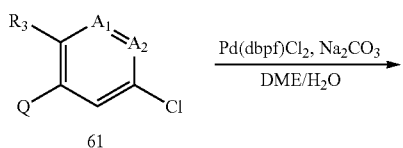

61

-continued

| Compounds | R³ | R⁴ | R⁷ | A¹ | A² |
|---|---|---|---|---|---|
| 689 | H | CH₃ | CO₂H | COCH₃ | CH |
| 690 | H | F | CO₂CH₃ | COCH₃ | CH |
| 691 | H | F | CO₂H | COCH₃ | CH |
| 724 | F | F | CO₂CH₃ | CH | CH |
| 722 | F | F | CO₂H | CH | CH |
| 725 | H | CF₃ | CO₂CH₃ | CH | CF |
| 723 | H | CF₃ | CO₂H | CH | CF |
| 743 | H | CH₃ | CO₂CH₃ | CCF₃ | CH |
| 744 | H | CH₃ | CO₂H | CCF₃ | CH |
| 745 | H | H | CO₂CH₃ | CCF₃ | CH |
| 746 | H | H | CO₂H | CCF₃ | CH |
| 747 | H | F | CO₂CH₃ | CCF₃ | CH |
| 748 | H | F | CO₂H | CCF₃ | CH |

Reaction scheme 15 above shows a general process for synthesizing compounds 670, 671, 672, 679, 680, 681, 686, 687, 688, 689, 690, 691, 722, 723, 724, 725, 743, 744, 745, 746, 747 and 748 of the present invention, and other compounds of the present invention can also be prepared according to reaction scheme 15. In reaction scheme 15,

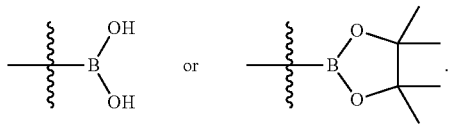

Compound 16 synthesized according to a known method is subjected to the Suzuki reaction with various boronic acid derivatives (61) in the presence of a palladium catalyst to synthesize compounds 62a to 62d, which are then subjected to the Suzuki reaction with various boronic acid derivatives (63) in the presence of a palladium catalyst to synthesize ester compounds 670, 671, 672, 686, 688, 690, 724, 725, 743, 745 and 747. The ester compounds may be hydrolyzed with lithium hydroxide to obtain desired carboxylic acid compounds 679, 680, 681, 687, 689, 691, 722, 723, 744, 746 and 748.

[Reaction scheme 16]

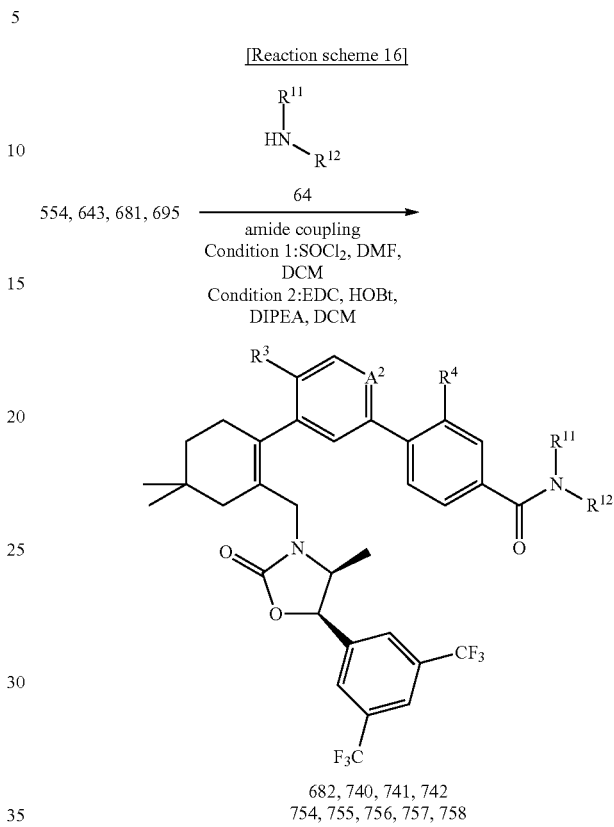

| Compounds | Stating material | Condition | R³ | R⁴ | A² | NR¹¹R¹² |
|---|---|---|---|---|---|---|
| 682 | 554 | 1 | OCH₃ | CH₃ | CH | NH₂ |
| 740 | 643 | 1 | OCH₃ | Cl | CH | NH₂ |
| 741 | 681 | 1 | H | CH₃ | CF | NH₂ |
| 742 | 695 | 1 | F | CF₃ | CH | NH₂ |
| 754 | 695 | 2 | F | CF₃ | CH | azetidine-3,3-difluoro |
| 755 | 695 | 2 | F | CF₃ | CH | 3-hydroxyazetidine |
| 756 | 695 | 2 | F | CF₃ | CH | NHEt |
| 757 | 695 | 2 | F | CF₃ | CH | NEt₂ |

-continued

| Compounds | Stating material | Condition | $R^3$ | $R^4$ | $A^2$ | $\underset{R^{12}}{\overset{R^{11}}{\underset{|}{N}}}$ |
|---|---|---|---|---|---|---|
| 758 | 695 | 2 | F | $CF_3$ | CH | 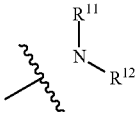 |

Reaction scheme 16 above shows a general process for synthesizing compounds 682, 740, 741, 742, 754, 755, 756, 757 and 758 of the present invention, and other compounds of the present invention can also be prepared according to reaction scheme 16. In reaction scheme 16, starting materials, conditions, $R^3$, $R^4$, $A^2$ and $\underset{R^{12}}{\overset{R^{11}}{\underset{|}{N}}}$ are as defined above.

Compounds 554, 643, 681 and 695 that are starting materials are converted to compounds 682, 740, 741 and 742 using thionyl chloride, dimethylformamide, and ammonia water. In addition, compound 695 as a starting material is reacted with compound 64 and EDC to synthesize 754, 755, 756, 757 and 758.

[Reaction scheme 17]

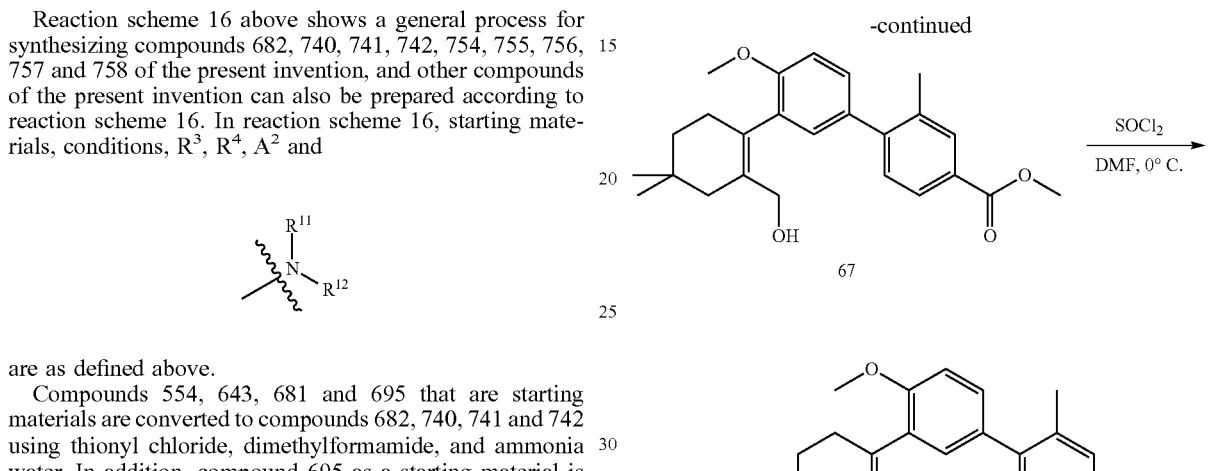

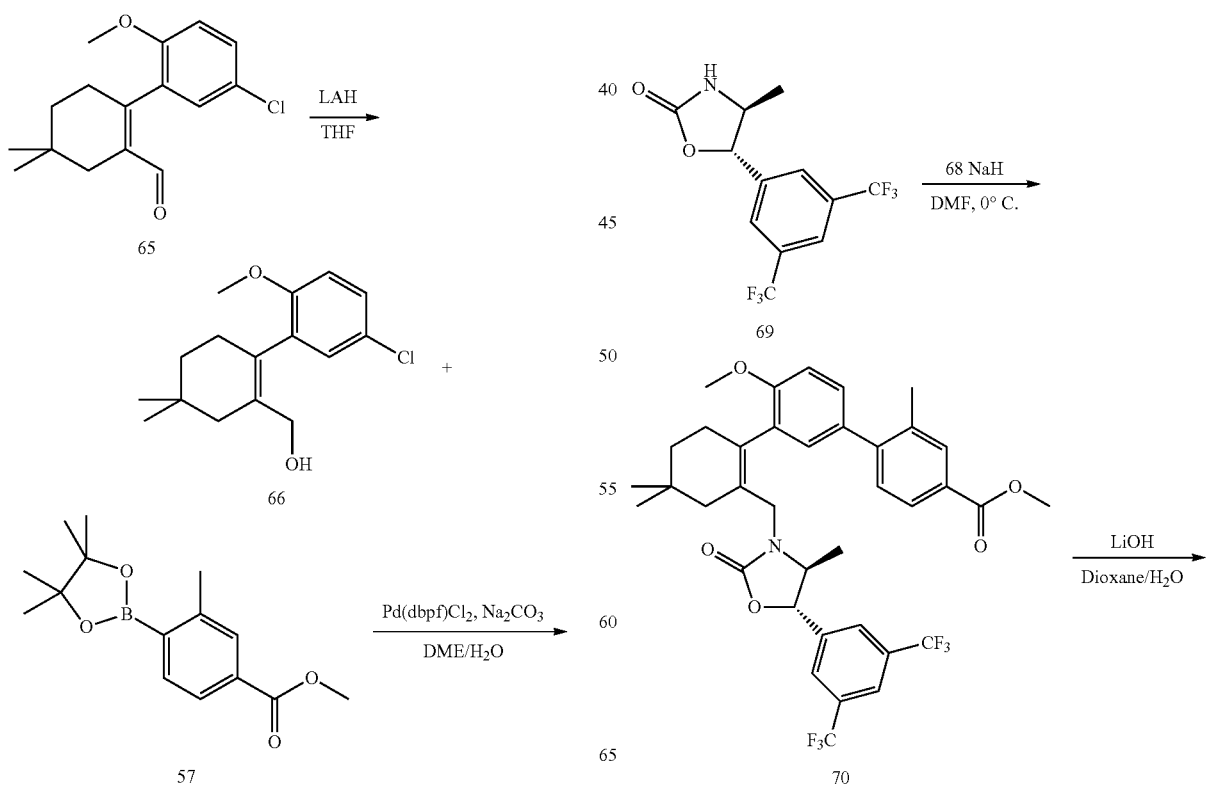

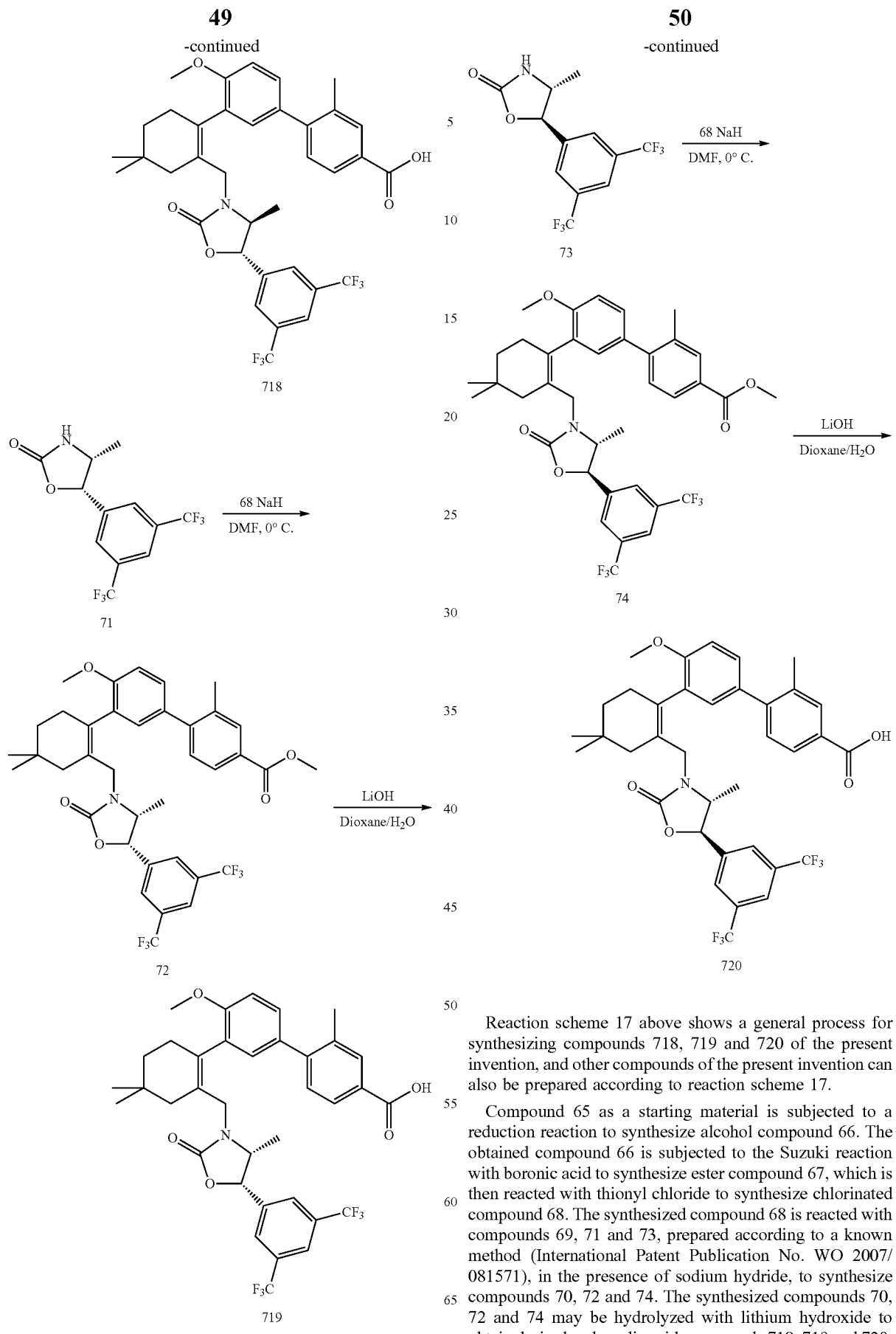

Reaction scheme 17 above shows a general process for synthesizing compounds 718, 719 and 720 of the present invention, and other compounds of the present invention can also be prepared according to reaction scheme 17.

Compound 65 as a starting material is subjected to a reduction reaction to synthesize alcohol compound 66. The obtained compound 66 is subjected to the Suzuki reaction with boronic acid to synthesize ester compound 67, which is then reacted with thionyl chloride to synthesize chlorinated compound 68. The synthesized compound 68 is reacted with compounds 69, 71 and 73, prepared according to a known method (International Patent Publication No. WO 2007/081571), in the presence of sodium hydride, to synthesize compounds 70, 72 and 74. The synthesized compounds 70, 72 and 74 may be hydrolyzed with lithium hydroxide to obtain desired carboxylic acid compounds 718, 719 and 720.

[Reaction scheme 18]

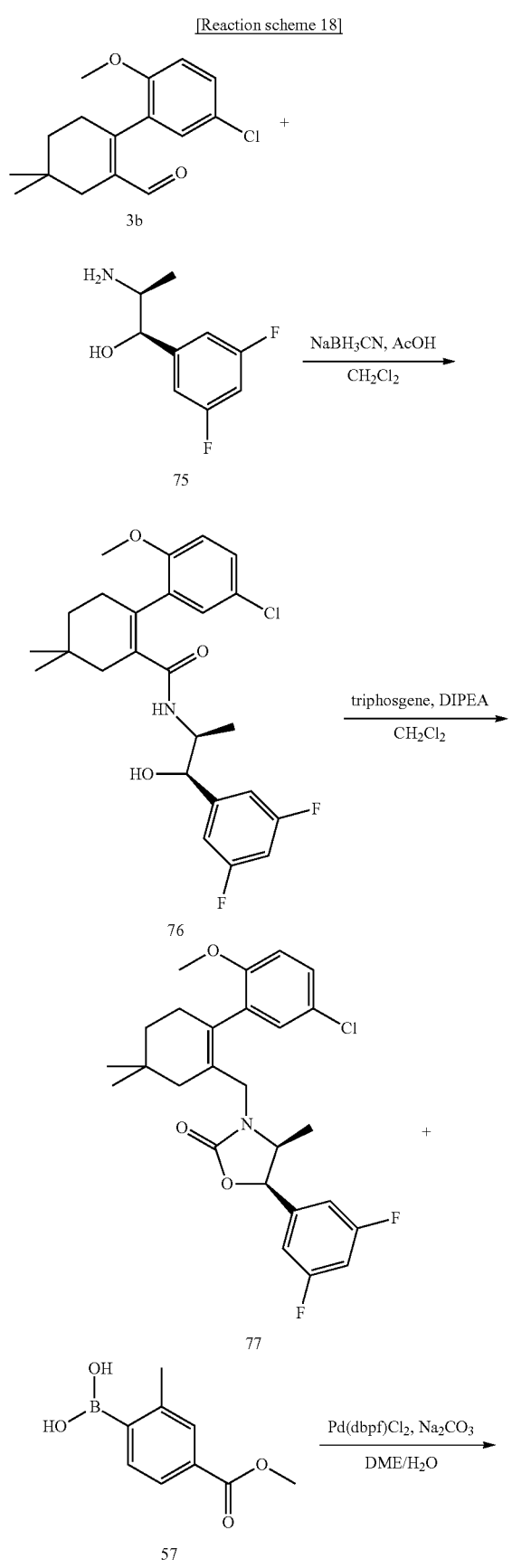

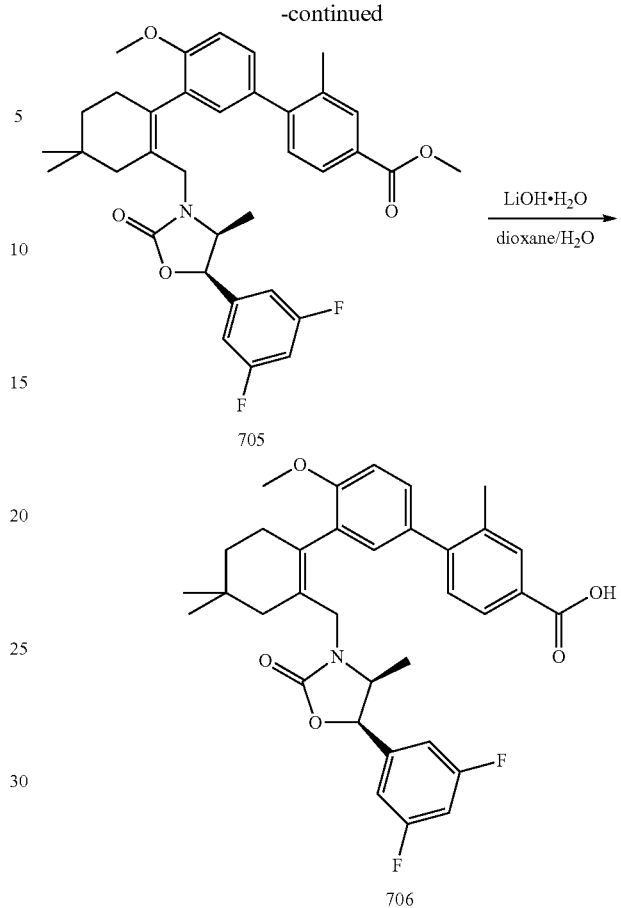

Reaction scheme 18 above shows a general process for synthesizing compounds 705 and 706 of the present invention, and other compounds of the present invention can also be prepared according to reaction scheme 18.

Compound 3b is reacted with compound 75, prepared according to a known method (International Patent Publication No. WO 2010/056849), to prepare compound 76. The prepared compound 76 is reacted with triphosgene to synthesize compound 77, which is then subjected to the Suzuki reaction with boronic acid compound 57 in the presence of a palladium catalyst to synthesize ester compound 705. The ester compound may be hydrolyzed with lithium hydroxide to obtain desired carboxylic acid compound 706.

The biaryl- or heterocyclic biaryl-substituted cyclohexene derivative compounds of formula I may contain one or more asymmetric carbon atoms, and thus can be present as racemates, racemic mixtures, single enantiomers, diastereomeric mixtures, and single diastereomers. Such isomers, for Example, biaryl- or heterocyclic biaryl-substituted cyclohexene derivative compounds of formula I, can be separated by column chromatography or HPLC. Alternatively, stereoisomers of the compounds of formula I can be stereospecifically synthesized using optically pure starting materials or reagents having a known configuration.

In the present invention, some compounds are observed as atropisomers (rotamers) in NMR spectra. Single atropisomers and mixtures thereof are included in the scope of the compounds of the present invention.

The compounds of formula I according to the present invention may be used in the form of pharmaceutically acceptable salts derived from inorganic or organic acids, and preferred cations for the salts include sodium, potassium, magnesium, calcium, zinc or tetrabutyl ammonium.

Advantageous Effects of Invention

Novel biaryl- or heterocyclic biaryl-substituted cyclohexene derivative compounds according to the present invention, isomers thereof, or pharmaceutically acceptable salts thereof, have less side effects and exhibit the effect of effectively inhibiting CETP.

Novel biaryl- or heterocyclic biaryl-substituted cyclohexene derivative compounds according to the present invention, isomers thereof, or pharmaceutically acceptable salts thereof, can be used for the prevention or treatment of dyslipidemia or dyslipidemia-related diseases.

MODE FOR THE INVENTION

Hereinafter, the present invention will be described in further detail with reference to Examples, preparation Examples and experimental Examples. It is to be understood, however, that these Examples are for illustrative purposes only and are not intended to limit the scope of the present invention.

Preparation of Novel Compounds According to Reaction Scheme 3

Intermediate Compound 3b: 2-(5-chloro-2-methoxyphenyl)-5,5-dimethylcyclohex-1-enecarbaldehyde Starting material 1 (3.5 g, 20.3 mmol), compound 2 (4.2 g, 22.3 mmol), sodium carbonate (6.4 g, 60.8 mmol) and Pd(dbpf)Cl$_2$ (0.7 g, 1.0 mmol) were dissolved in dimethoxyethane (3 mL)/water (1 mL) at room temperature, and the reaction mixture was stirred at 100° C. for 18 hours. Then, water was poured into the reaction mixture and extracted with ethyl acetate. The organic layer was dried with anhydrous magnesium sulfate, and then concentrated under reduced pressure to remove the solvent. The residue was purified by MPLC (Sift, EtOAc/hexane=0%~5%) to obtain compound 3b (3.2 g, 56.6%) as yellow oil.

Intermediate Compound 5b: (1R,2S)-1-(3,5-bis(trifluoromethyl)phenyl)-2-((2-(5-chloro-2-methoxyphenyl)-5,5-dimethylcyclohex-1-enyl)methylamino)propan-1-ol Starting material 3b (3.1 g, 11.1 mmol), compound 4 (3.5 g, 12.2 mmol) and acetic acid (0.7 mL, 12.2 mmol) were dissolved in methylene chloride (20 mL), and the reaction mixture was stirred at the same temperature for 1 hour, and then sodium cyanoborohydride (NaBH$_3$CN) (0.8 g, 12.2 mmol) was added thereto at room temperature, followed by stiffing at the same temperature for 3 hours. Then, aqueous solution of saturated sodium bicarbonate was poured into the reaction mixture, which was then extracted with ethyl acetate. The organic layer was dried with anhydrous magnesium sulfate to remove water, and then concentrated under reduced pressure to remove the solvent. The residue was purified by MPLC (SiO$_2$, EtOAc/hexane=0%~20%) to obtain compound 5b (3.5 g, 57.2%) as yellow oil.

Intermediate Compound 6a: (4S,5R)-5-(3,5-bis(trifluoromethyl)phenyl)-3-((2-(5-chloro-2-methoxyphenyl)cyclohex-1-enyl)methyl)-4-methyloxazolidin-2-one Starting material 5a (0.8 g, 1.65 mmol) and 5-chloro-2-methoxyphenylboronic acid (0.37 g, 2.0 mmol) were dissolved in dimethoxyethane/water (v/v=3:1, 1 mL), and then degassed. Then, Pd(dbpf)Cl$_2$ (54 mg, 0.08 mmol) and sodium carbonate (0.35 g, 3.3 mmol) were added to the reaction mixture, which was then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (SiO$_2$ 40 g, hexane/EtOAc=10%~20%) to obtain compound 6a (0.68 g, 75%) as brown oil.

Intermediate Compound 6b: (4S,5R)-5-(3,5-bis(trifluoromethyl)phenyl)-3-((2-(5-chloro-2-methoxyphenyl)-5,5-dim ethylcyclohex-1-enyl)methyl)-4-methyloxazolidin-2-one Starting material 5b (3.5 g, 6.4 mmol) and diisopropylethylamine (3.3 mL, 19.1 mmol) were dissolved in methylene chloride (200 mL) at room temperature, and the reaction mixture was cooled to 0° C., and triphosgene (1.9 g, 6.4 mmol) was slowly added thereto. The reaction mixture was warmed to room temperature and stirred for 3 hours. Then, water was poured into the reaction mixture and the reaction mixture was extracted with ethyl acetate. The organic layer was washed with aqueous solution of saturated sodium bicarbonate, dried with anhydrous magnesium sulfate, and then concentrated under reduced pressure to remove the solvent. The residue was purified by MPLC (Sift, EtOAc/hexane=0%~20%) to obtain compound 6b (3.0 g, 81.8%) as a white foam solid.

Example 1

Compound 553 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2-methylbiphenyl-4-carboxylate Starting material 6b (0.53 g, 0.92 mmol), boronic acid 7 (0.38 g, 1.38 mmol), Pd(dbpf)Cl$_2$ (0.03 g, 0.05 mmol) and sodium carbonate (0.29 g, 2.76 mmol) were dissolved in dimethoxyethane/water (v/v=3:1, 1.2 mL), and the reaction mixture was stirred with microwave irradiation at 120° C. for 30 minutes. After completion of the reaction, the reaction mixture was cooled to room temperature, diluted with ethyl acetate and then washed with water. The organic layer was dried with anhydrous magnesium sulfate, filtered, and then concentrated under reduced pressure to remove the solvent. The residue was purified by MPLC (SiO$_2$, EtOAc/hexane=0%~10%) to obtain compound 553 (0.3 g, 47.3%) as a white foam solid.

$^1$H NMR (400 MHz, CDCl$_3$); 1:1.3 atropisomeric mixture; δ 7.94-7.82 (m, 3H), 7.73 (d, 2H, J=11.2 Hz), 7.27-7.17 (m, 2H), 6.96-6.89 (m, 2H), 5.62-5.59 (m, 1H), 4.05-3.91

(m, 5H), 3.83-3.79 (m, 3H), 3.67-3.50 (m, 1H), 2.60-2.10 (m, 5H), 2.00-1.90 (m, 2H), 1.51-1.47 (m, 2H), 1.07-0.89 (m, 6H), 0.44-0.35 (m, 3H)

MS (ESI) m/z 690.2 (M$^+$+H).

Example 2

Compound 554

3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2-methylbiphenyl-4-carboxylic acid Starting material 553 (2.4 g, 3.48 mmol) and lithium hydroxide monohydrate (0.44 g, 10.44 mmol) were dissolved in dioxane (0.8 mL)/water (0.2 mL), and then stirred at 50° C. for 4 hours. 1M hydrochloric acid was poured into the reaction mixture and extracted with ethyl acetate, and the resulting organic layer was washed with brine, after which it was dried with anhydrous magnesium sulfate, filtered, and then concentrated under reduced pressure to remove the solvent. The residue was purified by MPLC (SiO$_2$, EtOAc/hexane=0%~20%) to obtain compound 554 (1.8 g, 76.6%) as a white foam solid.

$^1$H NMR (400 MHz, CDCl$_3$); 1:1.30 atropisomeric mixture; δ 8.02-7.75 (m, 3H), 7.75 (d, 2H, J=10.8 Hz), 7.31-7.19 (m, 2H), 6.98-6.90 (m, 2H), 5.64-5.61 (m, 1H), 4.15-3.91 (m, 2H), 3.84 (d, 3H, J=10.3 Hz), 3.68-3.52 (m, 1H), 2.60-2.01 (m, 5H), 2.00-1.93 (m, 2H), 1.54-1.46 (m, 2H), 1.07-0.88 (m, 6H), 0.45-0.37 (m, 3H)

MS (ESI) m/z 676.2 (M$^+$+H).

Example 3

Compound 559 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxybiphenyl-4-carboxylate Starting material 6b (0.15 g, 0.26 mmol) and 4-(methoxycarbonyl)phenylboronic acid (94 mg, 0.52 mmol) were added to dimethoxyethane/water (v/v=3:1, 1 mL), and then degassed. Pd(dbpf)Cl$_2$ (17 mg, 0.03 mmol) and sodium carbonate (55 mg, 0.52 mmol) were added to the reaction mixture, which was then stirred with microwave irradiation at 120° C. for 30 minutes. After completion of the reaction, the reaction mixture was cooled to room temperature, diluted with ethyl acetate and then washed with water and brine. The organic layer was dried with anhydrous magnesium sulfate, filtered, and then concentrated under reduced pressure to remove the solvent. The residue was purified by MPLC (SiO$_2$, EtOAc/hexane=0%~10%→CH$_2$Cl$_2$ 100%) to obtain compound 559 (89 mg, 51%) as a white solid.

$^1$H NMR (400 MHz, CDCl$_3$); 1:1.3 atropisomeric mixture; δ 8.08-8.02 (m, 2H), 7.84 (br s, 1H), 7.73 (br s, 2H), 7.60-7.58 (m, 1H), 7.54-7.48 (m, 2H), 7.25-7.24 (m, 1H), 6.97-6.90 (m, 1H), 5.60-5.56 (m, 1H), 4.09-3.98 (m, 2H), 3.93 (d, 3H, J=7.0 Hz), 3.81 (d, 3H, J=7.0 Hz), 3.64-3.47 (m, 1H), 2.60-2.04 (br m, 2H), 2.02-1.93 (br m, 2H), 1.54-1.47 (m, 2H), 1.27-1.24 (m, 6H), 0.42-0.34 (m, 3H)

MS (ESI) m/z 676.2 (M$^+$+H).

Example 4

Compound 560 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4'-methoxybiphenyl-4-carboxylate Starting material 6b (0.1 g, 0.17 mmol) and 2-fluoro-4-(methoxycarbonyl)phenylboronic acid (69 mg, 0.35 mmol) were dissolved in dimethoxyethane/water (v/v=3:1, 0.8 mL), and then degassed. Pd(dbpf)Cl$_2$ (11 mg, 0.02 mmol) and sodium carbonate (37 mg, 0.35 mmol) were added to the reaction mixture, which was then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentration under reduced pressure to remove the solvent. The residue was purified by MPLC (SiO$_2$, EtOAc/hexane=10%~30%) to obtain compound 560 (63 mg, 52%) as colorless oil.

$^1$H NMR (400 MHz, CDCl$_3$); 1:1.3 atropisomeric mixture; δ 7.87-7.82 (m, 2H), 7.79-7.70 (m, 3H), 7.48-7.40 (m, 2H), 7.25-7.20 (m, 1H), 6.96, 6.92 (2d, 1H, J=8.6 Hz), 5.61, 5.54 (2d, 1H, J=8.0 Hz), 4.02-3.92 (m, 5H), 3.81 (d, 3H, J=7.0 Hz), 3.66-3.45 (m, 1H), 2.60-2.02 (br m, 2H), 2.01-1.92 (br m, 2H), 1.52-1.48 (m, 2H), 1.05-1.01 (m, 6H), 0.37 (2d, 3H, J=6.5 Hz)

MS (ESI) m/z 694.2 (M$^+$+H).

Example 5

Compound 561

3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4'-methoxybiphenyl-4-carboxylic acid Starting material 560 (60 mg, 0.09 mmol) was dissolved in dioxane (4 mL), and a solution of lithium hydroxide monohydrate (18 mg, 0.43 mmol) in water (1 mL) was added dropwise thereto. Then, the reaction mixture was stirred overnight at 50° C. After completion of the reaction, the reaction mixture was cooled to room temperature, diluted with ethyl acetate, and then washed with water, saturated ammonium chloride and brine. The organic layer was dried with anhydrous magnesium sulfate, filtered, and then concentrated under reduced pressure to remove the solvent. The residue was purified by MPLC (Sift, CH$_3$OH/CH$_2$Cl$_2$=0%~10%) to obtain compound 561 (27 mg, 46%) as a yellow solid.

$^1$H NMR (400 MHz, CDCl$_3$); δ 7.95-7.90 (m, 1H), 7.87-7.80 (m, 2H), 7.74 (d, 2H, J=7.0 Hz), 7.53-7.42 (m, 2H), 7.28-7.23 (m, 1H), 6.98, 6.94 (2d, 1H, J=8.6 Hz), 5.62, 5.55 (2d, 1H, J=8.0 Hz), 4.05-3.92 (m, 2H), 3.83-3.80 (m, 3H), 3.71-3.46 (m, 1H), 2.28-2.03 (br m, 2H), 2.02-1.93 (br m, 2H), 1.53-1.47 (m, 2H), 1.06-1.02 (m, 6H), 0.39, 0.37 (2d, 3H, J=6.5 Hz)

MS (ESI) m/z 680.2 (M$^+$+H).

Example 6

Compound 564 methyl 5-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)picolinate Starting material 6b (0.1 g, 0.17 mmol) and methyl 5-(4,4,5,5-tetramethyl-1,3,2-dioxaborolan-2-yl)picolinate (78 mg, 0.3 mmol) were dissolved in dimethoxyethane/water (v/v=3:1, 1 mL), followed by degassing. $Pd(dbpf)Cl_2$ (11 mg, 0.02 mmol) and sodium carbonate (37 mg, 0.35 mmol) were added to the reaction mixture, which was then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (Sift, EtOAc/hexane=20%~50%) to obtain compound 564 (14 mg, 12%) as yellow oil.

$^1$H NMR (400 MHz, $CDCl_3$); 1:1.3 atropisomeric mixture; δ 8.89, 8.82 (2d, 1H, J=2.2 Hz), 8.17, 8.13 (2d, 1H, J=8.1 Hz), 7.97-7.91 (m, 1H), 7.85 (s, 1H), 7.71 (d, 2H, J=7.0 Hz), 7.53-7.50 (m, 1H), 7.23 (d, 1H, J=7.0 Hz), 7.01-6.95 (m, 1H), 5.61-5.58 (m, 1H), 4.04-3.96 (m, 5H), 3.82 (d, 3H, J=7.0 Hz), 3.61-3.43 (m, 1H), 2.60-1.96 (br m, 2H), 1.94-1.92 (br m, 2H), 1.53-1.48 (br m, 2H), 1.07-1.01 (m, 6H), 0.45-0.36 (m, 3H)

MS (ESI) m/z 677.2 ($M^++H$).

Example 7

Compound 565

3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxybiphenyl-4-carboxylic acid Starting material 559 (68 mg, 0.1 mmol) was dissolved in dioxane (4 mL), and a solution of lithium hydroxide monohydrate (21 mg, 0.5 mmol) in water (1 mL) was added dropwise thereto, followed by stirring overnight at 50° C. After completion of the reaction, the reaction mixture was cooled to room temperature, diluted with ethyl acetate, and then washed with saturated ammonium chloride and brine. The organic layer was dried with anhydrous magnesium sulfate, filtered, and then concentrated under reduced pressure to remove the solvent. The residue was purified by MPLC ($SiO_2$, EtOAc/hexane=30%-50%) to obtain compound 565 (34 mg, 51%) as a white solid.

$^1$H NMR (400 MHz, $CDCl_3$); 1:1.4 atropisomeric mixture; δ 8.15, 8.11 (2d, 2H, J=8.2 Hz), 7.85 (br s, 1H), 7.72 (br s, 2H), 7.64 (d, 1H, J=8.2 Hz), 7.57 (d, 1H, J=8.2 Hz), 7.54-7.50 (m, 1H), 7.27-7.26 (m, 1H), 6.97, 6.93 (2d, 1H, J=8.6 Hz), 5.61-5.57 (m, 1H), 4.06-3.91 (m, 2H), 3.82 (d, 3H, J=7.0 Hz), 3.65-3.48 (m, 1H), 2.55-1.99 (br m, 2H), 1.96-1.90 (br m, 2H), 1.55-1.46 (m, 2H), 1.07-1.02 (m, 6H), 0.43-0.36 (m, 3H)

MS (ESI) m/z 662.2 ($M^++H$).

Example 8

Compound 567 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxybiphenyl-3-carboxylate Starting material 6b (80 mg, 0.14 mmol) and 3-(methoxycarbonyl)phenylboronic acid (38 mg, 0.21 mmol) were dissolved in dimethoxyethane/water (v/v=4:1, 0.5 mL), followed by degassing. $Pd(dbpf)Cl_2$ (9 mg, 0.01 mmol) and sodium carbonate (29 mg, 0.28 mmol) were added to the reaction mixture, which was then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (Sift, EtOAc/hexane=10%-15%) to obtain compound 567 (75 mg, 80%) as colorless oil.

$^1$H NMR (400 MHz, $CDCl_3$); 1:1.4 atropisomeric mixture; δ 8.20-8.13 (m, 1H), 7.98-7.92 (m, 1H), 7.84 (d, 1H, J=6.8 Hz), 7.72-7.65 (m, 3H), 7.50-7.42 (m, 2H), 7.24 (dd, 1H, J=5.4, 2.4 Hz), 6.96, 6.91 (2d, 1H, J=8.6 Hz), 5.63-5.56 (m, 1H), 4.03-3.89 (m, 5H), 3.81, 3.79 (2s, 3H), 3.65-3.46 (m, 1H), 2.16-1.93 (br m, 2H), 1.98-1.63 (br m, 2H), 1.50-1.45 (m, 2H), 1.06-1.02 (m, 6H), 0.42-0.35 (m, 3H)

MS (ESI) m/z 676.2 ($M^++H$).

Example 9

Compound 568

3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxybiphenyl-3-carboxylic acid Stating material 567 (50 mg, 0.07 mmol) was dissolved in dioxane (4 mL), and a solution of lithium hydroxide monohydrate (16 mg, 0.37 mmol) in water (1 mL) was added dropwise thereto, followed by stirring overnight at 50° C. After completion of the reaction, the reaction mixture was cooled to room temperature, diluted with ethyl acetate, and then washed with water, saturated ammonium chloride and brine. The organic layer was dried with anhydrous magnesium sulfate, filtered, and then concentrated under reduced pressure to remove the solvent. The residue was purified by MPLC (Sift, EtOAc/hexane=10%-70%) to obtain compound 568 (40 mg, 82%) as a white solid.

$^1$H NMR (400 MHz, $CDCl_3$); 1:1.4 atropisomeric mixture; δ 8.27-8.21 (m, 1H), 8.06-8.01 (m, 1H), 7.84-7.72 (m, 4H), 7.54-7.47 (m, 2H), 7.26-7.22 (m, 1H), 6.97, 6.92 (2d, 1H, J=8.5 Hz), 5.63-5.56 (m, 1H), 4.06-3.93 (m, 2H), 3.82, 3.80 (2S,3H), 3.66-3.47 (m, 1H), 2.56-2.04 (br m, 2H), 2.00-1.90 (br m, 2H), 1.57-1.47 (m, 2H), 1.07-0.98 (m, 6H), 0.42-0.36 (m, 3H)

MS (ESI) m/z 662.2 ($M^++H$).

Example 10

Compound 569 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2-nitrobiphenyl-4-carboxylate Starting material 6b (0.13 g, 0.23 mmol) and 4-(methoxycarbonyl)-2-nitrophenylboronic acid (76 mg, 0.34 mmol) were dissolved in dimethoxyethane/water (v/v=3:1, 0.5 mL), followed by degassing. Pd(dbpf)Cl$_2$ (7 mg, 0.01 mmol) and sodium carbonate (48 mg, 0.45 mmol) were added to the reaction mixture, which was then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (SiO$_2$, EtOAc/hexane=5%~50%) to obtain compound 569 (15 mg, 9%) as yellow oil.

$^1$H NMR (400 MHz, CDCl$_3$); δ 8.45, 8.40 (2d, 1H, J=1.6 Hz), 8.24-8.17 (m, 1H), 7.85-7.79 (m, 1H), 7.75-7.71 (m, 2H), 7.53, 7.47 (2d, 1H, J=8.0 Hz), 7.23-7.20 (m, 1H), 6.97-6.92 (m, 2H), 5.59 (d, 1H, J=8.0 Hz), 4.02-3.97 (m, 4H), 3.85-3.71 (m, 4H), 3.69-3.49 (m, 1H), 2.55-2.20 (m, 2H), 1.96-1.85 (m, 2H), 1.50-1.43 (m, 2H), 1.04-0.98 (m, 6H), 0.43-0.39 (m, 3H)

MS (ESI) m/z 721.1 (M$^+$+H).

Example 11

Compound 579 methyl 3'-(2-(((4S,5R)-5-(3,5-bis(trifluoromethyl)phenyl)-4-methyl-2-oxooxazolidin-3-yl)methyl)cyclohex-1-enyl)-4'-methoxy-2-methylbiphenyl-4-carboxylate Starting material 6a (0.1 g, 0.18 mmol) and methyl 3-methyl-4-(4,4,5,5-tetramethyl-1,3,2-dioxaborolan-2-yl)benzoate (55 mg, 0.2 mmol) were dissolved in dimethoxyethane/water (v/v=4:1, 0.3 mL), followed by degassing. Pd(dbpf)Cl$_2$ (6 mg, 0.009 mmol) and sodium carbonate (39 mg, 0.37 mmol) were added to the reaction mixture, which was then stirred with microwave irradiation at 120° C. for 15 minutes. After completion of the reaction, the reaction mixture was cooled to room temperature, diluted with ethyl acetate, and then washed with water and brine. The organic layer was dried with anhydrous magnesium sulfate, filtered, and then under reduce pressure to remove the solvent. The residue was purified by MPLC (SiO$_2$, EtOAc/hexane=10%~20%) to obtain compound 579 (50 mg, 41%) as colorless oil.

$^1$H NMR (400 MHz, CDCl$_3$); 1:1.3 atropisomeric mixture; δ 7.90-7.81 (m, 3H), 7.72 (d, 2H, J=13.4 Hz), 7.24-7.16 (m, 2H), 6.97-6.87 (m, 2H), 5.62-5.57 (m, 1H), 4.09-3.90 (m, 5H), 3.82, 3.79 (2s, 3H), 3.65-3.49 (m, 1H), 2.57-2.09 (m, 7H), 1.79-1.74 (br m, 4H), 0.43-0.36 (m, 3H)

MS (ESI) m/z 662.2 (M$^+$+H).

Example 12

Compound 580 methyl 3'-(2-(((4S,5R)-5-(3,5-bis(trifluoromethyl)phenyl)-4-methyl-2-oxooxazolidin-3-yl)methyl)cyclohex-1-enyl)-2-fluoro-4'-methoxybiphenyl-4-carboxylate Starting material 6a (0.1 g, 0.18 mmol) and 2-fluoro-4-(methoxycarbonyl)phenylboronic acid (54 mg, 0.27 mmol) were dissolved in dimethoxyethane/water (v/v=4:1, 0.3 mL), followed by degassing. Pd(dbpf)Cl$_2$ (6 mg, 0.009 mmol) and sodium carbonate (39 mg, 0.37 mmol) were added to the reaction mixture, which was then stirred with microwave irradiation at 120° C. for 15 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (SiO$_2$, EtOAc/hexane=10%~20%) to obtain compound 580 (50 mg, 41%) as brown oil.

$^1$H NMR (400 MHz, CDCl$_3$); 1:1.1 atropisomeric mixture; δ 7.87-7.73 (m, 5H), 7.51-7.40 (m, 2H), 7.27-7.23 (m, 1H), 6.98-6.91 (m, 1H), 5.61, 5.54 (2d, 1H, J=8.0 Hz), 4.03-3.90 (m, 5H), 3.83, 3.80 (2s, 3H), 3.66-3.45 (m, 1H), 2.42-2.11 (br m, 4H), 1.82-1.74 (br m, 4H), 0.41-0.34 (m, 3H)

MS (ESI) m/z 666.2 (M$^+$+H).

Example 13

Compound 581

3'-(2-(((4S,5R)-5-(3,5-bis(trifluoromethyl)phenyl)-4-methyl-2-oxooxazolidin-3-yl)methyl)cyclohex-1-enyl)-4'-methoxy-2-methylbiphenyl-4-carboxylic acid Starting material 579 (46 mg, 0.07 mmol) was dissolved in dioxane (4 mL), and a solution of lithium hydroxide monohydrate (15 mg, 0.35 mmol) in water (1 mL) was added dropwise thereto, followed by stirring at 50° C. for 3 hours. After completion of the reaction, the reaction mixture was cooled to room temperature, diluted with ethyl acetate, and then washed with water, saturated ammonium chloride and brine. The organic layer was dried with anhydrous magnesium sulfate, filtered, and then concentrated under reduced pressure to remove the solvent. The residue was purified by MPLC (SiO$_2$, EtOAc/hexane=20%~50%) to obtain compound 581 (21 mg, 47%) as a white solid.

$^1$H NMR (400 MHz, CDCl$_3$); 1:1.4 atropisomeric mixture; δ 7.97-7.90 (m, 2H), 7.85 (s, 1H), 7.73 (d, 2H, J=13.0 Hz), 7.30-7.18 (m, 2H), 6.99-6.89 (m, 2H), 5.63-5.58 (m, 1H), 4.06-3.85 (m, 2H), 3.83-3.79 (m, 3H), 3.66-3.50 (m, 1H), 2.46-2.04 (m, 7H), 1.81-1.74 (br m, 4H), 0.44, 0.38 (2d, 3H, J=6.5 Hz)

MS (ESI) m/z 648.2 (M$^+$+H).

Example 14

Compound 582

3'-(2-(((4S,5R)-5-(3,5-bis(trifluoromethyl)phenyl)-4-methyl-2-oxooxazolidin-3-yl)methyl)cyclohex-1-enyl)-2-fluoro-4'-methoxybiphenyl-4-carboxylic acid Starting material 580 (45 mg, 0.07 mmol) was dissolved in dioxane (2 mL), and a solution of lithium hydroxide monohydrate (14 mg, 0.34 mmol) in water (0.5 mL) was added dropwise thereto, followed by stirring at 50° C. for 3 hours. After completion of the reaction, the reaction mixture was cooled to room temperature, diluted with ethyl acetate, and then washed with water, saturated ammonium chloride and brine. The organic layer was dried with anhydrous magnesium sulfate, filtered, and then concentrated under reduced pressure to remove the solvent. The residue was purified by MPLC (SiO$_2$, EtOAc/hexane=20%~50%) to obtain compound 582 (10 mg, 23%) as a yellow solid.

$^1$H NMR (400 MHz, CDCl$_3$); 1:1.1 atropisomeric mixture; δ 7.92-7.78 (m, 3H), 7.73 (s, 2H), 7.51-7.32 (m, 2H), 7.28-7.09 (m, 1H), 6.98-6.92 (m, 1H), 5.62-5.53 (m, 1H), 4.03-3.89 (m, 2H), 3.92-3.79 (m, 3H), 3.66-3.46 (m, 1H), 2.43-2.17 (br m, 4H), 1.80-1.74 (br m, 4H), 0.42-0.35 (m, 3H)

MS (ESI) m/z 650.2 (M$^+$−H).

Example 15

Compound 590 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2,3-difluoro-4'-methoxybiphenyl-4-carboxylate Starting material 6b (0.105 g, 0.18 mmol) and 2,3-difluoro-4-(methoxycarbonyl)phenylboronic acid (51 mg, 0.24 mmol) were dissolved in dimethoxyethane/water (v/v=3:1, 0.4 mL), and then degassed. Pd(dbpf)Cl$_2$ (6 mg, 0.009 mmol) and sodium carbonate (39 mg, 0.37 mmol) were added to the reaction mixture, which was then stirred with microwave irradiation at 120° C. for 20 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (SiO$_2$, EtOAc/hexane=10%~15%) to obtain compound 590 (28 mg, 22%) as colorless oil.

$^1$H NMR (400 MHz, CDCl$_3$); δ 7.85 (s, 1H), 7.75-7.69 (m, 3H), 7.47-7.40 (m, 1H), 7.25-7.16 (m, 2H), 6.97, 6.93 (2d, 1H, J=8.6 Hz), 5.62-5.55 (m, 1H), 4.02-3.92 (m, 5H), 3.82 (d, 3H, J=10.0 Hz), 3.64-3.44 (m, 1H), 2.58-1.98 (br m, 2H), 1.96-1.90 (br m, 2H), 1.54-1.42 (m, 2H), 1.05-1.01 (m, 6H), 0.42-0.37 (m, 3H)

MS (ESI) m/z 712.2 (M$^+$+H).

Example 16

Compound 591 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2,6-difluoro-4'-methoxybiphenyl-4-carboxylate Starting material 6b (0.31 g, 0.53 mmol) and methyl 3,5-difluoro-4-(4,4,5,5-tetramethyl-1,3,2-dioxaborolan-2-yl)benzoate (0.19 g, 0.64 mmol) were dissolved in dimethoxyethane/water (v/v=3:1, 0.6 mL), followed by degassing. Pd(dbpf)Cl$_2$ (17 mg, 0.03 mmol) and sodium carbonate (0.11 g, 1.06 mmol) were added to the reaction mixture, which was then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (SiO$_2$, EtOAc/hexane=10%~15%) to obtain compound 591 (31 mg, 8%) as yellow oil.

$^1$H NMR (400 MHz, CDCl$_3$); 1:1.1 atropisomeric mixture; δ 7.84 (s, 1H), 7.73 (d, 2H, J=6.7 Hz), 7.63, 7.60 (2d, 2H, J=7.5 Hz), 7.39-7.34 (m, 1H), 7.13-7.12 (m, 1H), 6.98-6.92 (m, 1H), 5.62-5.52 (m, 1H), 4.00-3.87 (m, 5H), 3.82 (d, 3H, J=7.6 Hz), 3.68-3.45 (m, 1H), 2.60-2.20 (br m, 2H), 2.04-1.94 (br m, 2H), 1.53-1.43 (m, 2H), 1.06-1.00 (m, 6H), 0.38-0.32 (m, 3H)

MS (ESI) m/z 712.3 (M$^+$+H).

Example 17

Compound 592

3'-(2-(((4S,5R)-5-(3,5-bis(trifluoromethyl)phenyl)-4-methyl-2-oxooxazolidin-3-yl)methyl)-4,4-dimethylcyclohex-1-enyl)-2,3-difluoro-4'-methoxybiphenyl-4-carboxylic acid Starting material 590 (25 mg, 0.04 mmol) was dissolved in dioxane (2 mL), and a solution of lithium hydroxide monohydrate (7 mg, 0.18 mmol) in water (0.5 mL) was added dropwise thereto, followed by stirring at 50° C. for 4 hours. After completion of the reaction, the reaction mixture was cooled to room temperature, diluted with ethyl acetate, and then washed with water, saturated ammonium chloride and brine. The organic layer was dried with anhydrous magnesium sulfate, filtered, and then concentrated under reduced pressure to remove the solvent. The residue was purified by MPLC (SiO$_2$, EtOAc/hexane=10%~60%) to obtain compound 592 (15 mg, 61%) as a yellow solid.

$^1$H NMR (400 MHz, CDCl$_3$); δ 7.92-7.76 (m, 2H), 7.73 (br s, 2H), 7.54-7.42 (m, 1H), 7.22-7.17 (m, 2H), 6.99, 6.95 (2d, 1H, J=8.6 Hz), 5.66-5.58 (m, 1H), 4.03-3.92 (m, 2H), 3.84-3.80 (m, 3H), 3.65-3.45 (m, 1H), 2.60-2.04 (br m, 2H), 1.96-1.93 (br m, 2H), 1.54-1.46 (m, 2H), 1.06-1.02 (m, 6H), 0.41-0.38 (m, 3H)

MS (ESI) m/z 698.2 (M$^+$+H).

Example 18

Compound 593

3'-(2-(((4S,5R)-5-(3,5-bis(trifluoromethyl)phenyl)-4-methyl-2-oxooxazolidin-3-yl)methyl)-4,4-dimethyl-cyclohex-1-enyl)-2,6-difluoro-4'-methoxybiphenyl-4-carboxylic acid Starting material 591 (31 mg, 0.04 mmol) was dissolved in dioxane (2 mL), and a solution of lithium hydroxide monohydrate (9 mg, 0.22 mmol) in water (0.5 mL) was added dropwise thereto, followed by stirring at 50° C. for 6 hours. After completion of the reaction, the reaction mixture was cooled to room temperature, diluted with ethyl acetate, and then washed with water, saturated ammonium chloride and brine. The organic layer was dried with anhydrous magnesium sulfate, filtered, and then concentrated under reduced pressure to remove the solvent. The residue was purified by MPLC ($SiO_2$, EtOAc/hexane=10%~70%) to obtain compound 593 (10 mg, 33%) as a white solid.

$^1$H NMR (400 MHz, $CDCl_3$); 1:1.2 atropisomeric mixture; δ 7.85 (s, 1H), 7.74 (d, 2H, J=6.8 Hz), 7.70-7.65 (m, 2H), 7.40-7.36 (m, 1H), 7.15 (d, 1H, J=5.0 Hz), 6.99-6.93 (m, 1H), 5.63-5.53 (m, 1H), 4.01-3.90 (m, 2H), 3.83-3.79 (m, 3H), 3.67, 3.47 (2d, 1H, J=14.8 Hz), 2.60-2.13 (br m, 2H), 2.04-1.94 (br m, 2H), 1.52-1.46 (m, 2H), 1.05-1.00 (m, 6H), 0.39-0.33 (m, 3H)

MS (ESI) m/z 698.2 ($M^++H$).

Example 19

Compound 599 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-3,4'-dimethoxybiphenyl-4-carboxylate Starting material 6b (0.08 g, 0.13 mmol), methyl 2-methoxy-4-(4,4,5,5-tetramethyl-1,3,2-dioxaborolan-2-yl)benzoate (0.06 g, 0.2 mmol), Pd(dbpf)$Cl_2$ (8.0 mg, 0.01 mmol) and sodium carbonate (0.04 g, 0.39 mmol) were dissolved in dimethoxyethane (3 mL)/water (1 mL) and heated by microwave irradiation at 120° C. for 30 minutes. After completion of the reaction, the reaction mixture was cooled to room temperature, diluted with ethyl acetate, and then washed with brine. The organic layer was dried with anhydrous magnesium sulfate, filtered, and then concentrated under reduced pressure to remove the solvent. The residue was purified by MPLC ($SiO_2$, hexane/EtOAc=10%~50%) to obtain compound 599 (64 mg, 69.7%) as colorless oil.

$^1$H NMR (400 MHz, $CDCl_3$); atropisomeric mixture; δ 7.88-7.80 (m, 2H), 7.71 (2s, 2H), 7.47 (2t, 1H, J=2.6 Hz), 7.21 (t, 1H, J=2.0 Hz), 7.15-7.04 (m, 2H), 6.93 (2d, 1H, J=8.6 Hz), 5.58 (2d, 1H, J=4.4 Hz), 4.02-3.79 (m, 11H), 3.56 (2d, 1H, J=14.6 Hz), 2.56-1.94 (m, 4H), 1.51 (m, 2H), 1.04 (2d, 6H, J=12.3 Hz), 0.40 (2d, 3H, J=6.6 Hz)

MS (ESI) m/z 706.2 ($M^++H$).

Example 20

Compound 600 methyl 5-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3-methylpicolinate Starting material 6b (0.08 g, 0.14 mmol), methyl 3-methyl-5-(4,4,5,5-tetramethyl-1,3,2-dioxaborolan-2-yl)picolinate (0.06 g, 0.21 mmol), Pd(dbpf)$Cl_2$ (9.0 mg, 0.01 mmol) and sodium carbonate (0.05 g, 0.43 mmol) were dissolved in dimethoxyethane (3 mL)/water (1 mL) and heated by microwave irradiation at 120° C. for 30 minutes. After completion of the reaction, the reaction mixture was cooled to room temperature, diluted with ethyl acetate, and then washed with brine. The organic layer was dried with anhydrous magnesium sulfate, filtered, and then concentrated under reduced pressure to remove the solvent. The residue was purified by MPLC ($SiO_2$, hexane/EtOAc=10%~50%) to obtain compound 600 (15 mg, 15.3%) as colorless oil.

$^1$H NMR (400 MHz, $CDCl_3$); atropisomeric mixture; δ 8.67 (2d, 1H, J=2.1 Hz), 7.85 (s, 1H), 7.72-7.66 (m, 3H), 7.52-7.47 (m, 1H), 7.21 (d, 1H, J=2.4 Hz), 6.97 (2d, 1H, J=8.6 Hz), 5.59 (d, 1H, J=8.1 Hz), 4.06-3.91 (m, 5H), 3.87 (2s, 3H), 3.54 (2d, 1H, J=13.5 Hz), 2.65 (2s, 3H), 2.54-1.93 (m, 4H), 1.51 (m, 2H), 1.05 (2d, 6H, J=15.9 Hz), 0.41 (2d, 3H, J=6.6 Hz)

MS (ESI) m/z 691.2 ($M^++H$).

Example 21

Compound 601

3'-(2-(((4S,5R)-5-(3,5-bis(trifluoromethyl)phenyl)-4-methyl-2-oxooxazolidin-3-yl)methyl)-4,4-dimethyl-cyclohex-1-enyl)-3,4'-dimethoxybiphenyl-4-carboxylic acid Starting material 599 (0.06 g, 0.08 mmol) and lithium hydroxide monohydrate (0.01 g, 0.41 mmol) were dissolved in dioxane (3 mL)/water (1 mL) at room temperature and stirred overnight at 50° C. After completion of the reaction, a solution of 1 M hydrochloric acid was added dropwise to the reaction mixture until a pH of 6.5 was reached, after which water was poured into the reaction mixture and the reaction mixture was extracted with ethyl acetate. The organic layer was washed with brine, dried with anhydrous magnesium sulfate, filtered, and then concentrated under reduced pressure to remove the solvent. The residue was purified by preparative TLC ($SiO_2$, hexane/EtOAc=0%~30%) to obtain compound 601 (30 mg, 52.9%) as colorless oil.

$^1$H NMR (400 MHz, $CDCl_3$); atropisomeric mixture; δ 8.17 (2d, 1H, J=8.20 Hz), 7.85 (s, 1H), 7.71 (2s, 2H), 7.49 (2t, 1H, J=2.6 Hz), 7.30-7.21 (m, 2H), 7.15 (2s, 1H), 6.95 (2d, 1H, J=8.6 Hz), 5.57 (2d, 1H, J=8.1 Hz), 4.12 (2s, 3H), 4.05-3.93 (m, 2H), 3.81 (2s, 3H), 3.54 (2d, 1H, J=14.6 Hz), 2.55-1.93 (m, 4H), 1.51 (m, 2H), 1.04 (2d, 6H, J=12.2 Hz), 0.42 (2d, 3H, J=6.5 Hz)

MS (ESI) m/z 692.3 ($M^++H$).

Example 22

Compound 602

5-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-3-methylpicolinic acid Staring material 600 (13 mg, 0.02 mmol) and lithium hydroxide monohydrate (2 mg, 0.09 mmol) were dissolved in dioxane (3 mL)/water (1 mL) at room temperature and stirred overnight at 50° C. After completion of the reaction, a solution of 1 M hydrochloric acid was added dropwise to the reaction mixture until a pH of 6.5 was reached, after which water was poured into the reaction mixture and the reaction mixture was extracted with ethyl acetate. The organic layer was washed with brine, dried with anhydrous magnesium sulfate, filtered, and then concentrated under reduced pressure to remove the solvent. The residue was purified by preparative TLC ($SiO_2$, hexane/EtOAc=0%~30%) to obtain compound 602 (2.5 mg, 23.6%) as colorless oil.

MS (ESI) m/z 677.3 ($M^++H$)

Example 23

Compound 665 methyl 5-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-6-methylpicolinate Starting material 6b (0.190 g, 0.686 mmol), boronic acid 7 (0.474 g, 0.823 mmol), Pd(dbpf)Cl$_2$ (0.022 g, 0.034 mmol) and sodium carbonate (0.218 g, 2.057 mmol) were dissolved in dimethoxyethane (0.9 mL)/water (0.3 mL) and heated by microwave irradiation at 120° C. for 30 minutes. Then, the reaction mixture was cooled to room temperature, after which water was poured into the reaction mixture and the reaction mixture was extracted with ethyl acetate. The organic layer was dried with anhydrous magnesium sulfate to remove water, and then concentrated under reduced pressure. The residue was purified by MPLC ($SiO_2$, EtOAc/hexane=0%~100%) to obtain desired compound 665 (0.160 g, 33.8%) as clear oil.

$^1$H NMR (400 MHz, CDCl$_3$); δ 8.00 (2d, 1H, J=7.9 Hz), 7.86 (s, 1H), 7.73 (2s, 2H), 7.61 (2d, 1H, J=7.9 Hz), 7.23 (m, 1H), 6.97 (m, 2H), 5.61 (2d, 1H, J=8.2 Hz), 4.06-3.95 (m, 5H), 3.94 (2s, 3H), 3.56 (2d, 1H, J=14.7 Hz), 2.59 (2s, 3H), 2.20-2.00 (m, 2H), 1.95-1.92 (m, 2H), 1.52 (m, 2H), 1.07-0.97 (m, 6H), 0.29 (m, 3H)

MS (ESI) m/z 691.2 ($M^++H$).

Example 24

Compound 666

5-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-6-methylpicolinic acid Starting material 665 (0.160 g, 0.232 mmol) and lithium hydroxide monohydrate (0.029 g, 0.695 mmol) were dissolved in dioxane (8 ml)/water (2 ml) at room temperature, and the reaction mixture was stirred for 16 hours at the same temperature. 1M hydrochloric acid was added to the reaction mixture and the reaction mixture was extracted with ethyl acetate. The organic layer was washed with brine, dried with anhydrous magnesium sulfate to remove water, and then concentrated under reduced pressure. The residue was purified by MPLC ($SiO_2$, EtOAc/hexane=0%~100%) to obtain desired compound 666 (0.020 g, 12.8%) as a white foam solid.

$^1$H NMR (400 MHz, CDCl$_3$); δ 8.00 (m, 5H), 7.22 (m, 1H), 7.08 (m, 2H), 5.80 (m, 1H), 4.20 (m, 1H), 3.82 (m, 4H), 3.60 (m, 1H), 2.6 (m, 3H), 2.40-1.80 (m, 4H), 1.45 (m, 2H), 1.0 (m, 6H), 0.4 (m, 3H)

MS (ESI) m/z 677.2 ($M^++H$).

Preparation of Novel Compounds According to Reaction Scheme 4

Intermediate Compound 10: ethyl 2-(5-bromo-2-methoxypyridin-3-yl)-5,5-dimethylcyclohex-1-enecarboxylate Starting material 8 (1.14 g, 3.70 mmol), 5-bromo-3-iodo-2-methoxypyridine (1.40 g, 4.44 mmol), Pd(PPh$_3$)$_4$ (0.85 g, 0.74 mmol) and cesium carbonate (2.41 g, 7.40 mmol) were dissolved in dioxane/water (v/v 9:1, 10 mL), and then reacted by microwave irradiation at 120° C. for 30 minutes. After completion of the reaction, the reaction mixture was cooled to room temperature, diluted with ethyl acetate, and then washed with a saturated ammonium chloride solution. The organic layer was dried with anhydrous magnesium sulfate, filtered, and then concentrated under reduced pressure to remove the solvent. The residue was purified by MPLC ($SiO_2$, EtOAc/hexane=1:9) to obtain compound 10 (0.37 g, 27%) as colorless oil.

MS (ESI) m/z 368.0 ($M^++H$).

Intermediate Compound 11: 2-(5-bromo-2-methoxypyridin-2-yl)-5,5-dimethylcyclohex-1-enecarbaldehyde Starting material 10 (0.32 g, 0.87 mmol) was dissolved in tetrahydrofuran (THF) (10 mL), and lithium aluminum hydride (1.73 mL, 1.73 mmol) was added dropwise thereto at 0° C., followed by stirring at 0° C. for 1 hour. Water was added dropwise to stop the reaction, and the reaction mixture was extracted with ethyl acetate. The organic layer was dried with anhydrous magnesium sulfate, filtered, and then concentrated under reduced pressure to remove the solvent. The residue was purified by MPLC (Sift, EtOAc/hexane=10%) to obtain an alcohol compound (0.17 g, 61%) as colorless oil. The obtained alcohol compound (0.17 g, 0.53 mmol) was dissolved in methylene chloride (5 mL), and then DMP (0.25 g, 0.58 mmol) was slowly added dropwise thereto at 0° C., followed by stirring at room temperature for 30 minutes. After completion of the reaction, the reaction mixture was diluted with methylene chloride, and then washed with water. The organic solvent was dried with anhydrous magnesium sulfate, filtered, and then concentrated under reduced pressure to remove the solvent. The residue was purified by MPLC ($SiO_2$, EtOAc/hexane=10%) to aldehyde obtain 11 (0.12 g, 71%) as colorless oil.

MS (ESI) m/z 324.0 ($M^++H$).

Intermediate Compound 12: (1R,2S)-1-(3,5-bis(trifluoromethyl)phenyl)-2-((2-(5-bromo-2-methoxypyridin-3-yl)-5,5-dimethylcyclohex-1-enyl)methylamino)propan-1-ol Starting material 11 (0.12 g, 0.36 mmol), amino alcohol compound 4 (0.12 g, 0.43 mmol) and sodium cyanoborohydride (26.7 mg, 0.43 mmol) were dissolved in methylene chloride (5 mL), and acetic acid (0.02 mL, 0.43 mmol) was slowly added dropwise thereto at room temperature. The reaction mixture was stirred at room temperature for 2 hours, diluted with methylene chloride, and then washed with water. The organic layer was dried with anhydrous magnesium sulfate, filtered, and then concentrated under reduced pressure to remove the solvent. The obtained product (197 mg, 93.3%) was used in the next reaction.

MS (ESI) m/z 595.2 (M$^+$+H).

Intermediate Compound 13: (4S,5R)-5-(3,5-bis(trifluoromethyl)phenyl)-3-((2-(5-bromo-2-methoxypyridin-3-yl)-5,5-dimethylcyclohex-1-enyl)methyl)-4-methyloxazolidin-2-one Starting material 12 (0.2 g, 0.33 mmol) and triphosgene (0.12 g, 0.4 mmol) were dissolved in methylene chloride (5 mL), and diisopropylethylamine (0.35 mL, 2.0 mmol) was slowly added dropwise thereto. The reaction mixture was stirred at room temperature for 1 hour, diluted with methylene chloride, and then washed with water. The organic solvent was dried with anhydrous magnesium sulfate, filtered, and then concentrated under reduced pressure to remove the solvent. The residue was purified by MPLC (SiO$_2$, EtOAc/hexane=10%) to obtain compound 13 (0.15 g, 73%) as colorless oil.

MS (ESI) m/z 621.1 (M$^+$+H).

Example 25

Compound 555 methyl 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-3-methylbenzoate Starting material 13 (0.07 g, 0.11 mmol), 2-methyl-4-methoxycarbonylphenylboronic acid, pinacol ester (0.04 g, 0.13 mmol), Pd(dbpf)Cl$_2$ (4 mg, 0.005 mmol) and sodium carbonate (0.03 g, 0.32 mmol) were dissolved in dimethoxyethane/water (v/v=3:1, 1.6 mL), and the reaction mixture was stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (SiO$_2$, EtOAc/hexane=1:4) to obtain compound 555 (42 mg, 56%) as a white solid.

$^1$H NMR (400 MHz, CDCl$_3$); 1:1.5 atropisomeric mixture; δ 8.06-8.04 (m, 1H), 7.96-7.86 (m, 3H), 7.74-7.71 (m, 2H), 7.31-7.19 (m, 2H), 5.64 (d, 0.6H, J=7.7 Hz), 5.57 (d, 0.4H, J=7.7 Hz), 4.07-4.00 (m, 2H), 3.98-3.92 (m, 6H), 3.59-3.51 (m, 1H), 2.58-2.03 (m, 5H), 1.98-1.87 (m, 2H), 1.57-1.43 (m, 2H), 1.06-1.00 (m, 6H), 0.51 (d, 1.2H, J=6.3 Hz), 0.36 (d, 1.8H, J=6.3 Hz)

MS (ESI) m/z 691.2 (M$^+$+H).

Example 26

Compound 556 methyl 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)benzoate Starting material 13 (0.06 g, 0.1 mmol), 4-methoxycarbonylphenylboronic acid (0.02 g, 0.12 mmol), Pd(dbpf)Cl$_2$ (3 mg, 0.005 mmol) and sodium carbonate (0.03 g, 0.3 mmol) were dissolved in dimethoxyethane/water (v/v=3:1, 1.6 mL), and then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (SiO$_2$, EtOAc/hexane=1:4) to obtain compound 556 (12 mg, 18%) as a white solid.

$^1$H NMR (400 MHz, CDCl$_3$); 1:1.6 atropisomeric mixture; δ 8.37-8.35 (m, 1H), 8.16-8.11 (m, 2H), 7.88-7.87 (m, 1H), 7.74-7.72 (m, 2H), 7.61-7.54 (m, 3H), 5.64 (d, 0.6H, J=8.2 Hz), 5.57 (d, 0.4H, J=8.2 Hz), 4.10-4.03 (m, 2H), 3.99-3.94 (m, 6H), 3.58-3.52 (m, 1H), 2.58-2.18 (m, 2H), 2.02-1.98 (m, 2H), 1.60-1.48 (m, 2H), 1.08-1.02 (m, 6H), 0.53 (d, 1.2H, J=6.4 Hz), 0.39 (d, 1.8H, J=6.4 Hz)

MS (ESI) m/z 677.2 (M$^+$+H).

Example 27

Compound 557

4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-3-methylbenzoic acid Starting material 555 (36 mg, 0.05 mmol) was dissolved in dioxane (0.4 mL), and a solution of lithium hydroxide monohydrate (0.01 g, 0.26 mmol) in water (0.1 mL) was added dropwise thereto. The reaction mixture was stirred overnight at 50° C. After completion of the reaction, the reaction mixture was cooled to room temperature, and a solution of 1M hydrochloric acid solution was added dropwise thereto until a pH of 2 was reached. Then, the reaction mixture was extracted with ethyl acetate, and the organic layer was dried with anhydrous magnesium sulfate, filtered, and then concentrated under reduced pressure to remove the solvent, thereby obtaining compound 557 (28 mg, 79%) as a white solid.

$^1$H NMR (400 MHz, CDCl$_3$); 1:1.6 atropisomeric mixture; δ 8.08-8.07 (m, 1H), 8.02-7.92 (m, 2H), 7.87-7.86 (m, 1H), 7.74-7.71 (m, 2H), 7.31-7.25 (m, 2H), 5.64 (d, 0.6H, J=8.2 Hz), 5.57 (d, 0.4H, J=8.2 Hz), 4.07-3.92 (m, 5H), 3.59-3.51 (m, 1H), 2.59-2.04 (m, 5H), 1.99-1.88 (m, 2H), 1.58-1.45 (m, 2H), 1.07-1.01 (m, 6H), 0.52 (d, 1.2H, J=6.5 Hz), 0.38 (d, 1.8H, J=6.5 Hz)

MS (ESI) m/z 677.2 (M$^+$+H).

Example 28

Compound 558

4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)benzoic acid Starting material 556 (10 mg, 0.02 mmol) was dissolved in dioxane (0.4 mL), and a solution of lithium hydroxide monohydrate (3 mg, 0.07 mmol) in water (0.1 mL) was added dropwise thereto. The reaction mixture was stirred overnight at 50° C. After completion of the reaction, the reaction mixture was cooled to room temperature, and a solution of 1M hydrochloric acid was added dropwise thereto until a pH of 2 was reached. Then, the reaction mixture was extracted with ethyl acetate, and the organic layer was dried with anhydrous magnesium sulfate, filtered, and then concentrated under reduced pressure to remove the solvent, thereby obtaining compound 558 (8 mg, 77%) as a white solid.

$^1$H NMR (400 MHz, CDCl$_3$); 1:1.6 atropisomeric mixture; δ 8.31-8.29 (m, 1H), 8.11-8.06 (m, 2H), 7.80-7.79 (m, 1H), 7.74-7.72 (m, 2H), 7.66-7.50 (m, 3H), 5.58-5.48 (m, 1H), 3.99-3.95 (m, 2H), 3.92-3.87 (m, 3H), 3.51-3.44 (m, 1H), 2.51-2.04 (m, 2H), 1.90-1.88 (m, 2H), 1.49-1.44 (m, 2H), 1.01-0.95 (m, 6H), 0.46 (d, 1.1H, J=6.5 Hz), 0.39 (d, 1.9H, J=6.5 Hz)

MS (ESI) m/z 663.2 (M$^+$+H).

Example 29

Compound 583 methyl 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-3-chlorobenzoate Starting material 13 (0.15 g, 0.24 mmol), boronic acid 14 (0.06 g, 0.27 mmol), Pd(dbpf)Cl$_2$ (8.0 mg, 0.01 mmol) and sodium carbonate (0.05 g, 0.48 mmol) were dissolved in dimethoxyethane/water (v/v=3:1, 4 mL), and then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (SiO$_2$, EtOAc/hexane=0%-20%) to obtain compound 583 (0.12 g, 68.7%) as colorless oil.

$^1$H NMR (400 MHz, CDCl$_3$); atropisomeric mixture; δ 8.13-8.16 (m, 2H), 7.95-8.00 (m, 1H), 7.87 (s, 1H), 7.74 (d, 2H, J=6.6 Hz), 7.37-7.47 (m, 2H), 5.59-5.64 (m, 1H), 3.84-4.06 (m, 8H), 3.53-3.66 (m, 1H), 2.00-2.56 (m, 2H), 2.00-1.97 (m, 2H), 1.50-1.55 (m, 2H), 1.02-1.07 (m, 6H), 0.52 (d, 1.3H, J=6.6 Hz), 0.36 (d, 1.7H, J=6.6 Hz)

MS (ESI) m/z 710.2 (M$^+$+H).

Example 30

Compound 584

4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-3-chlorobenzoic acid Starting material 583 (0.07 g, 0.10 mmol) and anhydrous lithium hydroxide (12 mg, 0.49 mmol) were dissolved in dioxane/water (v/v=4:1, 1.25 mL), and then stirred overnight at 40° C. After completion of the reaction, the reaction mixture was cooled to room temperature, diluted with ethyl acetate, and then washed with 1M hydrochloric acid solution and brine. The organic layer was dried with anhydrous magnesium sulfate, filtered, and then concentrated under reduced pressure to remove the solvent. The residue was purified by MPLC (SiO$_2$, EtOAc/hexane=0%-50%) to obtain compound 584 (2 mg, 2.5%) as colorless oil.

$^1$H NMR (400 MHz, CDCl$_3$); atropisomeric mixture; δ 8.16-8.23 (m, 2H), 8.02-8.07 (m, 1H), 7.87 (s, 1H), 7.74 (d, 2H, J=9.0 Hz), 7.41-7.49 (m, 2H), 5.65 (d, 0.6H, J=8.2 Hz), 5.59 (d, 0.4H, J=8.3 Hz), 3.93-4.06 (m, 5H), 3.65 (d, 0.6H, J=14.6 Hz), 3.57 (d, 0.4H, J=15.0 Hz), 2.05-2.60 (m, 2H), 1.96-1.98 (m, 2H), 1.51-1.57 (m, 2H), 1.02-1.08 (m, 6H), 0.53 (d, 1.2H, J=6.6 Hz), 0.38 (d, 1.8H, J=6.6 Hz)

MS (ESI) m/z 697.1 (M$^+$+H).

Example 31

Compound 585 methyl 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-3-fluorobenzoate Starting material 13 (0.15 g, 0.24 mmol), boronic acid 14 (0.05 g, 0.27 mmol), Pd(dbpf)Cl$_2$ (8.0 mg, 0.01 mmol) and sodium carbonate (0.05 g, 0.48 mmol) were dissolved in dimethoxyethane/water (v/v=3:1, 4 mL), and the reaction mixture was stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (SiO$_2$, EtOAc/hexane=0%~20%) to obtain compound 585 (0.14 g, 82.9%) as colorless oil.

$^1$H NMR (400 MHz, CDCl$_3$); atropisomeric mixture; δ 8.27-8.30 (m, 1H), 7.81-7.92 (m, 3H), 7.80 (s, 2H), 7.56-7.45 (m, 2H), 5.59-5.63 (m, 1H), 3.94-4.14 (m, 8H), 3.48-3.62 (m, 1H), 2.05-2.53 (m, 2H), 1.97 (m, 2H), 1.48-1.52 (m, 2H), 1.03-1.07 (m, 6H), 0.48 (d, 1.3H, J=6.6 Hz), 0.37 (d, 1.7H, J=6.5 Hz)

MS (ESI) m/z 694.2 (M$^+$+H)

Example 32

Compound 586

4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-3-fluorobenzoic acid Starting material 585 (0.06 g, 0.09 mmol) and anhydrous lithium hydroxide (11 mg, 0.46 mmol) were dissolved in dioxane/water (v/v=4:1, 1.25 mL), and then stirred overnight at 40° C. After completion of the reaction, the reaction mixture was cooled to room temperature, diluted with ethyl acetate, and then washed with 1M hydrochloric acid solution and brine. The organic layer was dried with anhydrous magnesium sulfate, filtered, and then concentrated under reduced pressure to remove the solvent. The residue was purified by MPLC (SiO$_2$, EtOAc/hexane=0%~50%) to obtain compound 586 (15 mg, 23.9%) as colorless oil.

$^1$H NMR (400 MHz, CDCl$_3$); atropisomeric mixture; δ 8.30-8.32 (s, 1H), 7.90-7.99 (m, 1H), 7.83-7.87 (m, 2H), 7.75 (s, 2H), 7.51-7.58 (m, 2H), 5.60-5.64 (m, 1H), 3.95-4.05 (m, 5H), 3.50-3.62 (m, 1H), 2.00-2.60 (m, 2H), 1.97 (s, 2H), 1.50-1.54 (m, 2H), 1.03-1.08 (m, 6H), 0.49 (d, 1.3H, J=6.5 Hz), 0.41 (d, 1.7H, J=6.5 Hz)

MS (ESI) m/z 681.2 (M$^+$+H).

Example 33

Compound 587 methyl 3-(3-(2-(((4S,5R)-5-(3,5-bis(trifluoromethyl) phenyl)-4-methyl-2-oxooxazolidin-3-yl)methyl)-4,4-dimethylcyclohex-1-enyl)-2-methoxypyridin-5-yl) benzoate Starting material 13 (0.14 g, 0.22 mmol), boronic acid 14 (0.04 g, 0.24 mmol), Pd(dbpf)Cl$_2$ (7.0 mg, 0.01 mmol) and sodium carbonate (0.05 g, 0.43 mmol) were dissolved in dimethoxyethane/water (v/v=3:1, 4 mL), and the reaction mixture was stirred with microwave irradiation at 120° C. for 20 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (SiO$_2$, EtOAc/hexane=0%~20%) to obtain compound 587 (0.12 g, 79.7%) as colorless oil.

$^1$H NMR (400 MHz, CDCl$_3$); atropisomeric mixture; δ 8.33-8.34 (m, 1H), 8.14-8.20 (m, 1H), 8.01-8.05 (m, 1H), 7.99 (s, 1H), 7.68-7.87 (m, 3H), 7.48-7.56 (m, 2H), 5.58-5.65 (m, 1H), 3.99-4.14 (m, 2H), 3.96-3.97 (m, 3H), 3.92-3.93 (m, 3H), 3.50-3.60 (m, 1H), 2.00-2.60 (m, 2H), 1.96-1.98 (m, 2H), 1.51-1.58 (m, 2H), 1.03-1.08 (m, 6H), 0.37-0.52 (m, 3H)

MS (ESI) m/z 677.2 (M$^+$+H).

Example 34

Compound 588

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl) benzoic acid Starting material 587 (0.08 g, 0.11 mmol) and anhydrous lithium hydroxide (14 mg, 0.57 mmol) were dissolved in dioxane/water (v/v=4:1, 1.25 mL), and then stirred overnight at 40° C. After completion of the reaction, the reaction mixture was cooled to room temperature, diluted with ethyl acetate, and then washed with 1M hydrochloric acid solution and brine. The organic layer was dried with anhydrous magnesium sulfate, filtered, and then concentrated under reduced pressure to remove the solvent. The residue was purified by MPLC (SiO$_2$, EtOAc/hexane=0%~50%) to obtain compound 588 (10 mg, 13.3%) as colorless oil.

$^1$H NMR (400 MHz, CDCl$_3$); atropisomeric mixture; δ 8.35-8.37 (m, 1H), 8.21-8.26 (m, 1H), 8.07-8.12 (m, 1H), 7.85-7.87 (m, 1H), 7.73-7.79 (m, 3H), 7.52-7.59 (m, 2H), 5.65 (d, 0.6H, J=8.1 Hz), 5.60 (d, 0.4H, J=8.2 Hz), 3.96-4.09 (m, 5H), 3.51-3.60 (m, 1H), 2.21-2.58 (m, 2H), 2.05 (s, 2H), 1.50-1.58 (m, 2H), 1.00-1.08 (m, 6H), 0.53 (d, 1.1H, J=6.6 Hz), 0.39 (d, 1.9H, J=6.5 Hz)

MS (ESI) m/z 663.2 (M$^+$+H).

Example 35

Compound 595 methyl 4-(3-(2-(((4S,5R)-5-(3,5-bis(trifluoromethyl) phenyl)-4-methyl-2-oxooxazolidin-3-yl)methyl)-4,4-dimethylcyclohex-1-enyl)-2-methoxypyridin-5-yl)-2, 3-difluorobenzoate Starting material 13 (6 mg, 0.009 mmol), difluorophenyl pinacol ester (3 mg, 0.01 mmol), Pd(dbpf)Cl$_2$ (0.3 mg) and sodium carbonate (3.0 mg, 0.03 mmol) were dissolved in dimethoxyethane/water (v/v=3:1, 2 mL), and the reaction mixture was stirred with microwave irradiation at 120° C. for 30 minutes. After completion of the reaction, the reaction mixture was cooled to room temperature, diluted with ethyl acetate, and then washed with water and saturated ammonium chloride solution. The organic layer was dried with anhydrous magnesium sulfate, filtered, and then concentrated under reduced pressure to remove the solvent. The residue was purified by MPLC (SiO$_2$, EtOAc/ hexane=10%~20%) to obtain compound 595 (6 mg, 91.8%) as a solid.

$^1$H NMR (400 MHz, CDCl$_3$); 1:1.3 atropisomeric mixture; δ 8.29-8.27 (m, 1H), 7.86 (s, 1H), 7.79-7.74 (m, 1H), 7.73 (brs, 2H), 7.54-7.49 (m, 1H), 7.25-7.18 (m, 1H), 5.62-5.57 (m, 1H), 4.04-3.90 (m, 8H), 3.58-3.46 (m, 1H), 2.55-1.99 (m, 2H), 1.69-1.68 (m, 2H), 1.56-1.48 (m, 2H), 1.06-1.01 (m, 6H), 0.49 (d, 1.3H, J=6.5 Hz), 0.39 (d, 1.7H, J=6.5 Hz)

MS (ESI) m/z 713.2 (M$^+$+H).

Example 36

Compound 596

4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-2, 3-difluorobenzoic acid Starting material 595 (5.0 mg, 0.007 mmol) and lithium hydroxide monohydrate (1 mg, 0.04 mmol) were dissolved in dioxane/water (v/v=3:1, 0.8 mL), and then stirred overnight at 50° C. After completion of the reaction, the reaction mixture was cooled to room temperature, and 1M hydrochloric acid solution was added dropwise thereto until a pH of 2 was reached, followed by extraction with ethyl acetate. The organic layer was washed with water, dried with anhydrous magnesium sulfate, filtered, and then concentrated under reduced pressure to remove the solvent, thereby obtaining compound 596 (1.4 mg, 28.6%) as a solid.

$^1$H NMR (400 MHz, CDCl$_3$); 1:1.4 atropisomeric mixture; δ 8.30-8.29 (m, 1H), 7.86-7.79 (m, 2H), 7.73-7.72 (m, 2H), 7.55-7.52 (m, 1H), 7.33-7.21 (m, 1H), 5.63-5.57 (m, 1H), 4.07-3.94 (m, 5H), 3.57 (d, 0.5H, J=14.7 Hz), 3.49 (d, 0.5H, J=14.7 Hz), 2.55-2.04 (m, 2H), 1.96-1.95 (m, 2H), 1.54-1.46 (m, 2H), 1.06-1.01 (m, 6H), 0.50 (d, 1.2H, J=6.6 Hz), 0.40 (d, 1.8H, J=6.6 Hz)

MS (ESI) m/z 699.1 (M$^+$+H).

Preparation of Novel Compounds According to Reaction Scheme 5

Intermediate Compound 19: (4S,5R)-5-(3,5-bis(trifluoromethyl)phenyl)-3-((2-(2-chloro-5-methoxypyrimidin-4-yl)-5,5-dimethylcyclohex-1-enyl)methyl)-4-methyloxazolidin-2-one Starting material 17 (0.21 g, 0.37 mmol), 2,4-dichloro-5-methoxypyrimidine 18 (0.07 g, 0.37 mmol), sodium carbonate (0.09 g, 0.86 mmol) and Pd(dppf)Cl$_2$ (3.0 mg, 0.004 mmol) were dissolved in dimethoxyethane/water (v/v=3:1, 4 mL), and the reaction mixture was stirred with microwave irradiation at 120° C. for 40 minutes. After completion of the reaction, the reaction mixture was cooled to room temperature, poured into water and extracted with ethyl acetate. The organic layer was washed with brine, dried with anhydrous magnesium sulfate, and then concentrated under reduced pressure to remove the solvent. The residue was purified by preparative TLC (SiO$_2$, hexane/EtOAc=3:1) to obtain compound 19 (43 mg, 20%) as colorless oil.

$^1$H NMR (400 MHz, CDCl$_3$); δ 8.20 (s, 1H), 7.87 (s, 1H), 7.75 (s, 1H), 5.53 (d, 1H, J=8.0 Hz), 4.11 (m, 2H), 3.92 (s, 3H), 3.32 (d, 1H, J=15.1 Hz), 2.31 (m, 2H), 1.96 (s, 2H), 1.51 (t, 2H, J=6.4 Hz), 1.02 (d, 6H, J=9.4 Hz), 0.57 (d, 3H, J=6.6 Hz)

MS (ESI) m/z 578.1 (M$^+$+H).

Example 37

Compound 603 methyl 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyrimidin-2-yl)-3-methylbenzoate Starting material 19 (0.04 g, 0.074 mmol), boronic acid pinacol ester 14 (0.03 g, 0.09 mmol), sodium carbonate (0.02 g, 0.17 mmol) and Pd(dppf)Cl$_2$ (3.0 mg, 0.004 mmol) were dissolved in dimethoxyethane/water (v/v=3:1, 4 mL), and the reaction mixture was stirred with microwave irradiation at 120° C. for 30 minutes. After completion of the reaction, the reaction mixture was cooled to room temperature, poured into water and extracted with ethyl acetate. The organic layer was washed with brine, dried with anhydrous magnesium sulfate, and then concentrated under reduced pressure to remove the solvent. The residue was purified by MPLC (SiO$_2$, hexane/EtOAc=10%~50%) to obtain compound 603 (27 mg, 52.5%) as colorless oil.

$^1$H NMR (400 MHz, CDCl$_3$); δ 8.45 (s, 1H), 7.93-7.76 (m, 4H), 7.61 (s, 2H), 5.40 (d, 1H, J=8.0 Hz), 4.09 (m, 1H), 4.00 (m, 1H), 3.97 (s, 3H), 3.92 (s, 3H), 3.39 (d, 1H, J=15.1 Hz), 2.52 (s, 3H), 2.39 (m, 2H), 2.01 (s, 2H), 1.54 (t, 2H, J=6.4 Hz), 1.03 (d, 6H, J=9.3 Hz), 0.35 (d, 3H, J=6.5 Hz)

MS (ESI) m/z 692.2 (M$^+$+H).

Example 38

Compound 604

4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyrimidin-2-yl)-3-methylbenzoic acid Starting material 603 (0.03 g, 0.04 mmol) and lithium hydroxide monohydrate (5.0 mg, 0.2 mmol) were dissolved in dioxane/water (v/v=3:1, 4 mL), and then stirred overnight at 50° C. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by preparative TLC (SiO$_2$, CH$_2$Cl$_2$/CH$_3$OH=20:1) to obtain compound 604 (17 mg, 64.3%) as colorless oil.

$^1$H NMR (400 MHz, CDCl$_3$); δ 8.48 (s, 1H), 8.0 (s, 1H), 7.95 (d, 1H, J=8.6 Hz), 7.82 (s, 1H), 7.79 (d, 1H, J=8.1 Hz), 7.62 (s, 2H), 5.41 (d, 1H, J=7.8 Hz), 4.13-3.98 (m, 5H), 3.41 (d, 1H, J=15.1 Hz), 2.54-2.34 (m, 5H), 1.98 (s, 2H), 1.55 (t, 2H, J=6.2 Hz), 1.04 (d, 6H, J=9.8 Hz), 0.37 (d, 3H, J=6.4 Hz)

MS (ESI) m/z 678.2 (M$^+$+H).

Example 39

Compound 610 methyl 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyrimidin-2-yl)-3-fluorobenzoate Starting material 19 (0.05 g, 0.09 mmol), boronic acid pinacol ester 14 (0.02 g, 0.1 mmol), sodium carbonate (0.02 g, 0.2 mmol) and Pd(dppf)Cl$_2$ (4.0 mg, 0.004 mmol) were dissolved in dimethoxyethane/water (v/v=3:1, 4 mL), and the reaction mixture was stirred with microwave irradiation at 120° C. for 30 minutes. After completion of the reaction, the reaction mixture was cooled to room temperature, poured into water, and extracted with ethyl acetate. The organic layer was washed with brine, dried with anhydrous magnesium sulfate, and then concentrated under reduced pressure to remove the solvent. The residue was purified by preparative TLC (SiO$_2$, hexane/EtOAc=1:1) to obtain compound 610 (3.3 mg, 5.5%) as colorless oil.

MS (ESI) m/z 696.2 (M$^+$+H).

Example 40

Compound 617

4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyrimidin-2-yl)-3-fluorobenzoic acid Starting material 610 (0.04 g, 0.06 mmol) and lithium hydroxide monohydrate (8.0 mg, 0.32 mmol) were dissolved in dioxane/water (v/v=3:1, 4 mL), and then stirred overnight at 50° C. After completion of the reaction, the reaction mixture was cooled to room temperature, and 1M hydrochloric acid solution was added dropwise thereto until a pH of 6 was reached. Then, the reaction mixture was diluted with ethyl acetate, and then washed with water and brine. The organic layer was dried with anhydrous magnesium sulfate, filtered, and then concentrated under reduced pressure to remove the solvent. The residue was purified by preparative TLC (Sift, hexane/EtOAc=1:2) to obtain compound 617 (26 mg, 60.3%) as colorless oil.

MS (ESI) m/z 682.3 (M$^+$+H).

Example 41

Compound 625 methyl 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyrimidin-2-yl)benzoate Starting material 19 (0.06 g, 0.1 mmol), phenylboronic acid (0.02 g, 0.12 mmol), Pd(dbpf)Cl$_2$ (3.0 mg, 0.005 mmol) and sodium carbonate (0.03 g, 0.3 mmol) were dissolved in dimethoxyethane/water (v/v=3:1, 0.5 mL), and the reaction mixture was stirred with microwave irradiation at 120° C. for 30 minutes. After completion of the reaction, the reaction mixture was cooled to room temperature, diluted with ethyl acetate, and then washed with water and saturated ammonium chloride. The organic layer was dried with anhydrous magnesium sulfate, filtered, and then concentrated under reduced pressure to remove the solvent. The residue was purified by MPLC (SiO$_2$, EtOAc/hexane=30%) to obtain compound 625 (36 mg, 53.9%) as a solid.

$^1$H NMR (400 MHz, CDCl$_3$); δ 8.42 (s, 1H), 8.42-8.38 (m, 2H), 8.09-8.07 (m, 2H), 7.82-7.81 (m, 1H), 7.62-7.61 (m, 2H), 5.42-5.40 (m, 1H), 4.09-4.05 (m, 2H), 3.96 (s, 3H), 3.93 (s, 3H), 3.40 (d, 1H, J=15.1 Hz), 2.48-2.30 (m, 2H), 2.01-1.99 (m, 2H), 1.56-1.49 (m, 2H), 1.07 (s, 3H), 1.04 (s, 3H), 0.41 (d, 3H, J=6.4 Hz)

MS (ESI) m/z 678.2 (M$^+$+H).

Example 42

Compound 626 ethyl 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyrimidin-2-yl)-2-fluorobenzoate Starting material 19 (0.06 g, 0.1 mmol), 3-fluorophenyl boronic acid (0.03 g, 0.12 mmol), Pd(dbpf)Cl$_2$ (3.0 mg, 0.005 mmol) and sodium carbonate (0.03 g, 0.3 mmol) were dissolved in dimethoxyethane/water (v/v=3:1, 0.5 mL), and the reaction mixture was stirred with microwave irradiation at 120° C. for 30 minutes. After completion of the reaction, the reaction mixture was cooled to room temperature, diluted with ethyl acetate, and then washed with water and saturated ammonium chloride. The organic layer was dried with anhydrous magnesium sulfate, filtered, and then concentrated under reduced pressure to remove the solvent. The residue was purified by MPLC (SiO$_2$, EtOAc/hexane=30%) to obtain compound 626 (59 mg, 84.3%) as a solid.

$^1$H NMR (400 MHz, CDCl$_3$); 1:1.2 atropisomeric mixture; δ 8.41 (s, 0.6H), 8.20 (s, 0.4H), 8.16 (dd, 1H, J=8.2 Hz, 1.6 Hz), 8.10 (dd, 1H, J=12.2 Hz, 1.5 Hz), 7.99-7.95 (m, 1H), 7.86-7.64 (m, 3H), 5.53 (d, 0.4H, J=8.0 Hz), 5.44-5.42 (m, 0.6H), 5.53 (q, 1.3H, J=7.1 Hz), 4.13 (q, 0.7H, J=7.1 Hz), 4.11-4.04 (m, 2H), 3.96 (s, 1.8H), 3.92 (s, 1.2H), 3.38 (d, 0.6H, J=15.1 Hz), 3.32 (d, 0.4H, J=15.1 Hz), 2.38-2.30 (m, 2H), 1.99-1.96 (m, 2H), 1.56-1.54 (m, 2H), 1.52-1.49 (m, 1H), 1.41 (t, 2H, J=7.1 Hz), 1.07-1.01 (m, 6H), 0.57 (d, 1.3H, J=6.5 Hz), 0.37 (d, 1.7H, J=6.5 Hz)

MS (ESI) m/z 710.2 (M$^+$+H).

Example 43

Compound 628

4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyrimidin-2-yl)benzoic acid Starting material 625 (0.03 g, 0.05 mmol) and lithium hydroxide monohydrate (10 mg, 0.2 mmol) were dissolved in dioxane/water (v/v=4:1, 0.5 mL), and then stirred overnight at 45° C. After completion of the reaction, the reaction mixture was cooled to room temperature, and 1M hydrochloric acid solution was added dropwise thereto until a pH of 2 was reached, followed by extraction with ethyl acetate. The organic layer was washed with water, dried with anhydrous magnesium sulfate, filtered, and then concentrated under reduced pressure to remove the solvent. The residue was purified by MPLC (Sift, CH$_3$OH/CH$_2$Cl$_2$=10%) to obtain compound 628 (15 mg, 49.7%) as a solid.

$^1$H NMR (400 MHz, CDCl$_3$); δ 8.44 (s, 1H), 8.43 (d, 2H, J=8.4 Hz), 8.17 (d, 2H, J=8.4 Hz), 7.82 (brs, 1H), 7.63 (brs, 2H), 5.41 (d, 1H, J=7.6 Hz), 4.13-4.03 (m, 2H), 3.97 (s, 3H), 3.41 (d, 1H, J=14.8 Hz), 2.45-2.32 (m, 2H), 2.00-1.99 (m, 2H), 1.58-1.55 (m, 2H), 1.08 (s, 3H), 1.04 (s, 3H), 0.43 (d, 3H, J=6.5 Hz)

MS (ESI) m/z 664.2 (M$^+$+H).

Example 44

Compound 629

4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyrimidin-2-yl)-2-fluorobenzoic acid Starting material 626 (0.06 g, 0.08 mmol) and lithium hydroxide monohydrate (16 mg, 0.39 mmol) were dissolved in dioxane/water (v/v=4:1, 0.5 mL), and then stirred overnight at 45° C. After completion of the reaction, the reaction mixture was cooled to room temperature, and 1M hydrochloric acid solution was added dropwise thereto until a pH of 2 was reached, followed by extraction with ethyl acetate. The organic layer was washed with water, dried with anhydrous magnesium sulfate, filtered, and then concentrated under reduced pressure to remove the solvent. The residue was purified by MPLC (Sift, CH$_3$OH/CH$_2$Cl$_2$=10%) to obtain compound 629 (22 mg, 41.6%) as a solid.

$^1$H NMR (400 MHz, CDCl$_3$); δ 8.44 (s, 1H), 8.20-8.18 (m, 1H), 8.15-8.12 (m, 1H), 8.09-8.05 (m, 1H), 7.82 (brs, 1H), 7.65 (brs, 2H), 5.45 (d, 1H, J=7.2 Hz), 4.10-4.02 (m, 2H), 3.98 (s, 3H), 3.42-3.38 (m, 1H), 2.44-2.31 (m, 2H), 2.00-1.99 (m, 2H), 1.57-1.54 (m, 2H), 1.08 (s, 3H), 1.04 (s, 3H), 0.45 (d, 3H, J=6.3 Hz)

MS (ESI) m/z 682.2 (M$^+$+H).

Example 45

Compound 673 methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-methylbiphenyl-4-carboxylate Starting material 19 (0.090 g, 0.161 mmol), 4-(methoxycarbonyl)phenylboronic acid (0.038 g, 0.209 mmol), Pd(dbpf)Cl$_2$ (0.005 g, 0.008 mmol) and sodium carbonate (0.051 g, 0.482 mmol) were dissolved in dimethoxyethane/water (v/v=3:1, 1 ml) and heated by microwave irradiation at 120° C. for 30 minutes. Then, the reaction mixture was cooled to room temperature, and water was poured into the reaction mixture, which was then extracted with ethyl acetate. The organic layer was washed with aqueous solution of saturated ammonium chloride, dried with anhydrous magnesium sulfate, and then concentrated under reduced pressure. The residue was purified by MPLC (Sift, EtOAc/hexane=5%~10%) to obtain compound 673 (0.052 g, 49.0%) as a white solid.

$^1$H NMR (400 MHz, CDCl$_3$); atropisomeric mixture; δ 8.07-8.04 (m, 2H), 7.85 (s, 1H), 7.71 (s, 2H), 7.33-7.31 (m, 2H), 7.22 (d, 1H, J=7.8 Hz), 7.01 (dd, 1H, J=7.7, 1.9 Hz), 6.94 (d, 1H, J=1.8 Hz), 5.58 (d, 1H, J=8.2 Hz), 4.06-4.02 (m, 1H), 3.94 (s, 3H), 3.91-3.87 (m, 1H), 3.75 (d, 1H, J=14.7 Hz), 2.44-2.36 (m, 2H), 2.21 (s, 3H), 1.95-1.91 (m, 2H), 1.49 (t, 2H, J=6.5 Hz), 1.02 (s, 3H), 0.99 (s, 3H), 0.39 (d, 3H, J=6.6 Hz)

MS (ESI) m/z 660.2 (M$^+$+H).

Example 46

Compound 674 methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2,2'-dimethylbiphenyl-4-carboxylate Starting material 19 (0.090 g, 0.161 mmol), 4-(methoxycarbonyl)2-methylphenylboronic acid (0.058 g, 0.209 mmol), Pd(dbpf)Cl$_2$ (0.005 g, 0.008 mmol) and sodium carbonate (0.051 g, 0.482 mmol) were dissolved in dimethoxyethane/water (v/v=3:1, 1 ml) and heated by microwave irradiation at 120° C. for 30 minutes. Then, the reaction mixture was cooled to room temperature, and water was poured into the reaction mixture, which was then extracted with ethyl acetate. The organic layer was washed with aqueous solution of saturated ammonium chloride, dried with anhydrous magnesium sulfate to remove water, and then concentrated under reduced pressure. The residue was purified by MPLC (SiO$_2$, EtOAc/hexane=10%) to obtain compound 674 (0.053 g, 49.2%) as a white solid.

$^1$H NMR (400 MHz, CDCl$_3$); atropisomeric mixture; δ 7.94-7.91 (m, 1H), 7.89-7.83 (m, 2H), 7.72 (m, 2H), 7.22 (dd, 1H, J=7.8, 2.7 Hz), 7.15 (d, 0.5H, J=7.8 Hz), 7.07 (d, 0.5H, J=7.9 Hz), 7.02-6.98 (m, 1H), 6.82 (dd, 1H, J=6.8, 1.8 Hz), 5.60 (d, 1H, J=8.2 Hz), 4.06-4.00 (m, 1H), 3.92 (s, 3H), 3.91-3.85 (m, 1H), 3.82-3.74 (m, 1H), 2.43-2.25 (m, 2H), 2.07-2.04 (m, 3H), 1.99-1.98 (m, 3H), 1.94-1.90 (m, 2H), 1.49-1.46 (m, 2H), 1.02-0.98 (m, 6H), 0.39-0.35 (m, 3H)

MS (ESI) m/z 674.2 (M$^+$+H).

Example 47

Compound 675 methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-2'-methylbiphenyl-4-carboxylate Starting material 19 (0.090 g, 0.161 mmol), 2-fluoro-4-(methoxycarbonyl)phenylboronic acid (0.059 g, 0.209 mmol), Pd(dbpf)Cl$_2$ (0.005 g, 0.008 mmol) and sodium carbonate (0.051 g, 0.482 mmol) were dissolved in dimethoxyethane/water (v/v=3:1, 1 ml) and heated by microwave irradiation at 120° C. for 30 minutes. Then, the reaction mixture was cooled to room temperature, and water was poured into the reaction mixture, which was then extracted with ethyl acetate. The organic layer was washed with aqueous solution of saturated ammonium chloride, dried with anhydrous magnesium sulfate, and then concentrated under reduced pressure. The residue was purified by MPLC (SiO$_2$, EtOAc/hexane=10%) to obtain compound 675 (0.034 g, 31.1%) as a white solid.

$^1$H NMR (400 MHz, CDCl$_3$); atropisomeric mixture; δ 7.88-7.85 (m, 2H), 7.77 (dd, 1H, J=10.0, 1.5 Hz), 7.72 (s, 2H), 7.30-7.23 (m, 2H), 7.06 (dd, 1H, J=7.7, 1.8 Hz), 7.95 (d, 1H, J=1.5 Hz), 5.56 (d, 1H, J=8.1 Hz), 4.04-4.00 (m, 1H), 3.95 (s, 3H), 3.90-3.83 (m, 1H), 3.76 (d, 1H, J=14.8 Hz), 2.45-2.36 (m, 2H), 2.14 (s, 3H), 1.96-1.92 (m, 2H), 1.50-1.47 (m, 2H), 1.02 (s, 3H), 0.99 (s, 3H), 0.35 (d, 3H, J=6.5 Hz)

MS (ESI) m/z 678.2 (M$^+$+H).

Example 48

Compound 676

5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-methylbiphenyl-4-carboxylic acid Starting material 673 (0.048 g, 0.074 mmol) and lithium hydroxide monohydrate (0.016 g, 0.372 mmol) were dissolved in dioxane/water (v/v=4:1, 1 ml) at 50° C., and the reaction mixture was stirred at the same temperature for 4 hours. The reaction mixture was concentrated, and water was poured into the reaction mixture, which was then extracted with ethyl acetate. The organic layer was washed with aqueous solution of 1M hydrochloric acid, dried with anhydrous magnesium sulfate, and then concentrated under reduced pressure. The residue was purified by MPLC (SiO$_2$, CH$_3$OH/CH$_2$Cl$_2$=2%) to obtain compound 676 (0.033 g, 69.2%) as a white solid.

$^1$H NMR (400 MHz, CDCl$_3$); atropisomeric mixture; δ 8.14 (d, 2H, J=8.3 Hz), 7.85 (s, 1H), 7.72 (s, 2H), 7.37 (d, 2H, J=8.4 Hz), 7.24 (d, 1H, J=8.0 Hz), 7.02 (dd, 1H, J=7.7, 1.8 Hz), 6.96 (d, 1H, J=1.7 Hz), 5.59 (d, 1H, J=8.2 Hz), 4.04-4.00 (m, 1H), 3.95-3.88 (m, 1H), 3.77-3.74 (m, 1H), 2.43-2.27 (m, 2H), 2.23 (s, 3H), 1.95-1.91 (m, 2H), 1.51-1.48 (m, 2H), 1.03 (s, 3H), 0.99 (s, 3H), 0.40 (d, 3H, J=6.6 Hz)

MS (ESI) m/z 646.2 (M$^+$+H).

Example 49

Compound 677

5'-(2-(((4S,5R)-5-(3,5-bis(trifluoromethyl)phenyl)-4-methyl-2-oxooxazolidin-3-yl)methyl)-4,4-dimethylcyclohex-1-enyl)-2,2'-dimethylbiphenyl-4-carboxylic acid Starting material 674 (0.053 g, 0.079 mmol) and lithium hydroxide monohydrate (0.017 g, 0.396 mmol) were dissolved in dioxane/water (v/v=4:1, 1 ml) at 50° C., and the reaction mixture was stirred at the same temperature for 4 hours. The reaction mixture was concentrated, and water was poured into the reaction mixture, which was then extracted with ethyl acetate. The organic layer was washed with aqueous solution of 1M hydrochloric acid, dried with anhydrous magnesium sulfate, and then concentrated under reduced pressure. The residue was purified by MPLC (SiO$_2$, CH$_3$OH/CH$_2$Cl$_2$=5%) to obtain compound 677 (0.037 g, 71.3%) as a white solid.

$^1$H NMR (400 MHz, CDCl$_3$); atropisomeric mixture; δ 8.01-7.98 (m, 1H), 7.97-7.91 (m, 1H), 7.86 (s, 1H), 7.72 (s, 2H), 7.24-7.21 (m, 1H), 7.20 (d, 0.5H, J=7.8 Hz), 7.11 (d, 0.5H, J=7.7 Hz), 7.04-6.99 (m, 1H), 6.83 (dd, 1H, J=6.5, 1.8 Hz), 5.60 (d, 1H, J=8.3 Hz), 4.03-4.01 (m, 1H), 3.91-3.82 (m, 1H), 3.78-3.74 (m, 1H), 2.45-2.28 (m, 2H), 2.10 (s, 1.5H), 2.04 (s, 1.5H), 2.01-2.00 (m, 3H), 1.95-1.91 (m, 2H), 1.50-1.47 (m, 2H), 1.02 (s, 3H), 0.99 (s, 3H), 0.40-0.36 (m, 3H)

MS (ESI) m/z 660.2 (M$^+$+H).

Example 50

Compound 678

5'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-2'-methylbiphenyl-4-carboxylic acid Starting material 675 (0.030 g, 0.044 mmol) and lithium hydroxide monohydrate (0.009 g, 0.221 mmol) were dissolved in dioxane/water (v/v=4:1, 1 ml) at 50° C., and the reaction mixture was stirred at the same temperature for 4 hours. The reaction mixture was concentrated, and water was poured into the reaction mixture, which was then extracted with ethyl acetate. The organic layer was washed with aqueous solution of 1M hydrochloric acid, dried with anhydrous magnesium sulfate, and then concentrated under reduced pressure. The residue was purified by MPLC (SiO$_2$, CH$_3$OH/CH$_2$Cl$_2$=5%) to obtain compound 678 (0.022 g, 74.9%) as a white solid.

$^1$H NMR (400 MHz, CDCl$_3$); atropisomeric mixture; δ 7.95-7.93 (m, 1H), 7.85-7.80 (m, 2H), 7.72 (s, 2H), 7.35-7.31 (m, 1H), 7.26-7.25 (m, 1H), 7.07 (dd, 1H, J=7.7, 1.8 Hz), 6.96 (d, 1H, J=1.4 Hz), 5.57 (d, 1H, J=8.1 Hz), 4.05-4.01 (m, 1H), 3.91-3.84 (m, 1H), 3.79-3.75 (m, 1H), 2.43-2.25 (m, 2H), 2.16 (s, 3H), 1.95-1.94 (m, 2H), 1.50-1.47 (m, 2H), 1.02 (s, 3H), 0.99 (s, 3H), 0.36 (d, 3H, J=6.5 Hz)

MS (ESI) m/z 664.2 (M$^+$+H).

Example 51

Compound 763 methyl 4-(2-(2-(((4S,5R)-5-(3,5-bis(trifluoromethyl)phenyl)-4-methyl-2-oxooxazolidin-3-yl)methyl)-4,4-dimethylcyclohex-1-enyl)-3-methoxypyridin-6-yl)-3-(trifluoromethyl)benzoate Starting material 19 (0.100 g, 0.173 mmol), methyl-4-(4,4,5,5-tetramethyl-1,3,2-dioxaborolan-2-yl)-3-(trifluoromethyl)benzoate compound (0.086 g, 0.260 mmol), potassium acetate (0.049 g, 0.520 mmol) and Pd(dbpf)Cl$_2$ (0.006 g, 0.009 mmol) were added to N,N-dimethylformamide (0.8 mL)/water (0.4 mL) and heated by microwave irradiation at 120° C. for 20 minutes, and then the temperature was lowered to room temperature to stop the reaction. Water was poured into the reaction mixture, which was then extracted with ethyl acetate. The organic layer was dried with anhydrous magnesium sulfate to remove water, filtered, and then concentrated under pressure. The residue was purified by MPLC (SiO$_2$, EtOAc/hexane=0%~20%) to obtain desired compound 763 (0.020 g, 15.5%) as a brown solid.

$^1$H NMR (400 MHz, CDCl$_3$); δ 8.42 (s, 1H), 8.22 (d, 1H, J=6.9 Hz), 7.84 (s, 1H), 7.68 (m, 2H), 7.54 (m, 1H), 7.34-7.29 (m, 2H), 5.58 (m, 1H), 4.12-4.05 (m, 2H), 3.98 (s, 3H), 3.91 (s, 3H), 3.40 (m, 1H), 2.47-2.33 (m, 2H), 1.95 (m, 2H), 1.55 (t, 2H, J=6.3 Hz), 1.06 (d, 6H, J=6.6 Hz), 0.32 (m, 3H)

MS (ESI) m/z 745.1 (M$^+$+H).

Example 52

Compounds 764

4-(2-(2-(((4S,5R)-5-(3,5-bis(trifluoromethyl)phenyl)-4-methyl-2-oxooxazolidin-3-yl)methyl)-4,4-dimethylcyclohex-1-enyl)-3-methoxypyridin-6-yl)-3-(trifluoromethyl)benzoic acid Starting material 763 (0.010 g, 0.014 mmol) and lithium hydroxide monohydrate (0.006 g, 0.144 mmol) were dissolved in 1,4-dioxane (4 mL)/water (1 mL) at room temperature, and the reaction mixture was stirred at the same temperature for 16 hours. An aqueous solution of 1M hydrochloric acid was poured into the reaction mixture, which was then extracted with ethyl acetate. The organic layer was washed, dried with anhydrous magnesium sulfate, filtered, and then concentrated under reduced pressure. The residue was purified by MPLC (SiO$_2$, EtOAc/hexane=20%~50%) to obtain compound 764 (0.005 g, 47.6%) as a white solid.

$^1$H NMR (400 MHz, CDCl$_3$); δ 8.41 (s, 1H), 8.19 (d, 1H, J=8.0 Hz), 7.84 (s, 1H), 7.72 (s, 2H), 7.54 (d, 1H, J=7.8 Hz), 7.37-7.29 (m, 2H), 5.55 (m, 1H), 4.12-4.05 (m, 2H), 3.90 (s, 3H), 3.47-3.43 (m, 1H), 2.60-2.23 (m, 2H), 1.98 (m, 2H), 1.55 (m, 2H), 1.06 (m, 6H), 0.32 (m, 3H)

MS (ESI) m/z 731.1 (M$^+$+H).

Preparation of Novel Compounds According to Reaction Scheme 6

Intermediate Compound 23: (1R,2S)-1-(3,5-bis(trifluoromethyl)phenyl)-2-((2-(4-fluoro-2-methoxy-5-nitrophenyl)-5,5-dimethylcyclohex-1-enyl)methylamino)propan-1-ol Starting material 22 (0.2 g, 0.65 mmol), aminoalcohol compound 4 (0.2 g, 0.78 mmol) and sodium cyanoborohydride (49 mg, 0.78 mmol) were dissolved in methylene chloride (10 mL), and acetic acid (0.05 mL, 0.78 mmol) was slowly added dropwise thereto at room temperature. The reaction mixture was stirred at room temperature for 1 hour, diluted with methylene chloride, and then washed with water. The organic layer was dried with anhydrous magnesium sulfate, filtered, and then concentrated under reduced pressure to remove the solvent. The obtained compound 23 (369 mg, 98%) as a white solid was used in the next reaction.

MS (ESI) m/z 579.2 (M$^+$+H).

Intermediate Compound 24: (4S,5R)-5-(3,5-bis(trifluoromethyl)phenyl)-3-((2-(4-fluoro-2-methoxy-5-nitrophenyl-5,5-dimethylcyclohex-1-enyl)methyl)-4-methyloxazolidin-2-one Starting material 23 (0.37 g, 0.64 mmol) and triphosgene (0.23 g, 0.77 mmol) were dissolved in methylene chloride (10 mL), and diisopropylethylamine (0.67 mL, 3.83 mmol) was slowly added dropwise thereto. The reaction mixture was stirred at room temperature for 1 hour, diluted with methylene chloride, and then washed with water. The organic layer was dried with anhydrous magnesium sulfate, filtered, and then concentrated under reduced pressure to remove the solvent. The residue was purified by MPLC (SiO$_2$ 12 g, EtOAc/hexane=10%) to obtain compound 24 (0.29 g, 75%) as a yellow solid.

MS (ESI) m/z 605.1 (M$^+$+H).

Intermediate Compound 25: (4S,5R)-3-((2-(5-amino-4-fluoro-2-methoxyphenyl)-5,5-dimethylcyclohex-1-enyl)methyl)-5-(3,5-bis(trifluoromethyl)phenyl)-4-methyloxazolidin-2-one Starting material 24 (0.29 g, 0.47 mmol) was dissolved in methanol (3 mL), and Raney Ni (1 spoon) was added dropwise thereto, and the reaction mixture was hydrogenated overnight. After completion of the reaction, the reaction mixture was filtered through celite under reduced pressure, and then concentrated under reduced pressure to remove the solvent. The obtained yellow solid compound 25 (0.27 g, 103.3%) was used in the next reaction.

MS (ESI) m/z 575.3 (M$^+$+H).

Intermediate Compound 26: (4S,5R)-5-(3,5-bis(trifluoromethyl)phenyl)-3-((2-(4-fluoro-5-iodo-2-methoxyphenyl)-5,5-dimethylcyclohex-1-enyl)methyl-4-methyloxazolidin-2-one Starting material 25 (0.28 g, 0.48 mmol) was dissolved in acetonitrile (5 mL), and para-toluenesulfonic acid monohydrate (0.27 g, 1.4 mmol) and a solution of sodium nitrite (0.03 g, 0.5 mmol) in water (2 mL) were sequentially added dropwise thereto, followed by stirring at room temperature for 2 hours. Potassium iodide (0.09 g, 0.53 mmol) was added dropwise to the reaction mixture, which was then stirred at room temperature for 1 hour. After completion of the reaction, the reaction mixture was diluted with ethyl acetate, and then washed with water and sodium thiosulfate solution. The organic layer was dried with anhydrous magnesium sulfate, filtered, and then concentrated under reduced pressure to remove the solvent. The residue was purified by MPLC (Sift, EtOAc/hexane=1:9) to obtain compound 26 (0.17 g, 51%).

MS (ESI) m/z 686.1 (M$^+$+H).

Example 53

Compound 572 methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-4'-methoxy-2-methylbiphenyl-4-carboxylate Starting material 26 (0.05 g, 0.07 mmol), 2-methyl-4-methoxycarbonylphenylboronic acid pinacol ester (0.02 g, 0.09 mmol), Pd(dbpf)Cl$_2$ (2.4 mg, 0.004 mmol) and sodium carbonate (23.2 mg, 0.22 mmol) were dissolved in dimethoxyethane/water (v/v=3:1, 1 mL), and then stirred with microwave irradiation at 120° C. for 30 minutes. After completion of the reaction, the reaction mixture was cooled to room temperature, diluted with ethyl acetate, and then washed with water and saturated ammonium chloride solution. The organic layer was dried with anhydrous magnesium sulfate, filtered, and then concentrated under reduced pressure to remove the solvent. The residue was purified by MPLC (Sift, EtOAc/hexane=1:4) to obtain compound 572 (28 mg, 55%) as a solid.

$^1$H NMR (400 MHz, CDCl$_3$); 1:1.2 atropisomeric mixture; δ 7.94-7.83 (m, 3H), 7.74-7.71 (m, 2H), 7.23-7.12 (m, 1H), 6.86-6.82 (m, 1H), 6.70-6.64 (m, 1H), 5.62-5.59 (m, 1H), 4.04-3.86 (m, 5H), 3.78 (s, 1.4H), 3.75 (s, 1.6H), 3.63-3.45 (m, 1H), 2.52-2.04 (m, 5H), 1.97-1.85 (m, 2H), 1.55-1.42 (m, 2H), 1.05-0.98 (m, 6H), 0.45 (d, 1.4H, J=6.5 Hz), 0.39 (d, 1.6H, J=6.5 Hz)

MS (ESI) m/z 708.2 (M$^+$+H).

Example 54

Compound 573 methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-4'-methoxybiphenyl-4-carboxylate Starting material 26 (0.05 g, 0.07 mmol), 4-methoxycarbonylphenylboronic acid (0.02 g, 0.09 mmol), Pd(dbpf)Cl$_2$ (2.4 mg, 0.004 mmol) and sodium carbonate (23.2 mg, 0.22 mmol) were dissolved in dimethoxyethane/water (v/v=3:1, 1 mL), and then stirred with microwave irradiation at 120° C. for 30 minutes. After completion of the reaction, the reaction mixture was cooled to room temperature, diluted with ethyl acetate, and then washed with water and saturated ammonium chloride solution. The organic layer was dried with anhydrous magnesium sulfate, filtered, and then concentrated under reduced pressure to remove the solvent. The residue was purified by MPLC (Sift, EtOAc/hexane=1:4) to obtain compound 573 (17 mg, 33%) as a solid.

$^1$H NMR (400 MHz, CDCl$_3$); 1:1.3 atropisomeric mixture; δ 8.09-8.01 (m, 2H), 7.86 (brs, 1H), 7.72-7.71 (m, 2H), 7.58-7.50 (m, 2H), 7.08-7.05 (m, 1H), 6.72-6.66 (m, 1H), 5.61-5.58 (m, 1H), 4.04-3.97 (m, 2H), 3.93-3.92 (m, 3H), 3.81-3.78 (m, 3H), 3.62-3.46 (m, 1H), 2.17-2.04 (m, 2H), 1.97-1.87 (m, 2H), 1.55-1.43 (m, 2H), 1.05-1.00 (m, 6H), 0.45 (d, 1.3H, J=6.5 Hz), 0.40 (d, 1.7H, J=6.5 Hz)

MS (ESI) m/z 694.2 (M$^+$+H).

Example 55

Compound 574

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-2'-fluoro-4'-methoxy-2-methylbiphenyl-4-carboxylic acid Starting material 572 (23 mg, 0.03 mmol) was dissolved in dioxane (1 mL), and a solution of lithium hydroxide monohydrate (6.8 mg, 0.16 mmol) in water (1 mL) was added dropwise thereto, followed by stirring overnight at 50° C. After completion of the reaction, the reaction mixture was cooled to room temperature, and 1M hydrochloric acid solution was added dropwise thereto until a pH of 2 was reached, followed by extraction with ethyl acetate. The organic layer was washed with water, dried with anhydrous magnesium sulfate, filtered, and then concentrated under reduced pressure, thereby obtaining compound 574 (19 mg, 83%) as a solid.

$^1$H NMR (400 MHz, CDCl$_3$); 1:1.2 atropisomeric mixture; δ 8.01-7.98 (m, 1H), 7.97-7.90 (m, 1H), 7.87-7.86 (m, 1H), 7.74-7.71 (m, 2H), 7.28 (d, 0.6H, J=7.9 Hz), 7.19 (d, 0.4H, J=7.9 Hz), 6.85 (t, 1H, J=8.2 Hz), 6.71-6.65 (m, 1H), 5.63-5.59 (m, 1H), 4.03-3.89 (m, 2H), 3.82 (s, 1.4H), 3.78 (s, 1.6H), 3.64-3.46 (m, 1H), 2.53-2.09 (m, 5H), 1.97-1.85 (m, 2H), 1.53-1.42 (m, 2H), 1.05-0.99 (m, 6H), 0.46 (d, 1.4H, J=6.5 Hz), 0.40 (d, 1.6H, J=6.5 Hz)

MS (ESI) m/z 694.2 (M$^+$+H).

Example 56

Compound 575

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-2'-fluoro-4'-methoxybiphenyl-4-carboxylic acid Starting material 573 (23 mg, 0.03 mmol) was dissolved in dioxane (1 mL), a solution of lithium hydroxide monohydrate (6.8 mg, 0.16 mmol) in water (1 mL) was added dropwise thereto, followed by stirring overnight at 50° C. After completion of the reaction, the reaction mixture was cooled to room temperature, and 1M hydrochloric acid solution was added dropwise thereto until a pH of 2 was reached, followed by extraction with ethyl acetate. The organic layer was washed with water, dried with anhydrous magnesium sulfate, filtered, and then concentrated under reduced pressure, thereby obtaining compound 575 (7 mg, 62%) as a solid.

$^1$H NMR (400 MHz, CDCl$_3$); 1:1.3 atropisomeric mixture; δ 8.16-8.10 (m, 2H), 7.86-7.85 (m, 1H), 7.73-7.71 (m, 2H), 7.62-7.53 (m, 2H), 7.08 (dd, 1H, J=8.9 Hz, 1.5 Hz), 6.74-6.67 (m, 1H), 5.61 (dd, 1H, J=8.2, 2.8 Hz), 4.03-3.92 (m, 2H), 3.81-3.78 (m, 3H), 3.63-3.46 (m, 1H), 2.51-2.04 (m, 2H), 1.98-1.92 (m, 2H), 1.54-1.42 (m, 2H), 1.05-1.01 (m, 6H), 0.46 (d, 1.3H, J=6.5 Hz), 0.41 (d, 1.7H, J=6.5 Hz)

MS (ESI) m/z 680.2 (M$^+$+H).

Example 57

Compound 630 methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2-chloro-2'-fluoro-4'-methoxybiphenyl-4-carboxylate Starting material 26 (0.10 g, 0.14 mmol), methyl 3-chloro-4-(4,4,5,5-tetramethyl-1,3,2-dioxaborolan-2-yl)benzoate (0.04 g, 0.17 mmol), Pd(dppf)Cl$_2$ (6.0 mg, 0.007 mmol) and sodium carbonate (34 mg, 0.32 mmol) were dissolved in dimethoxyethane/water (v/v=3:1, 4 mL), and then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by preparative TLC (SiO$_2$, hexane/EtOAc=4:1) to obtain compound 630 (39 mg, 39%) as colorless oil.

$^1$H NMR (400 MHz, CDCl$_3$); atropisomeric mixture; δ 8.12 (2d, 1H, J=1.6 Hz), 7.94 (2dd, 1H, J=8.0, 1.7 Hz), 7.86 (s, 1H), 7.72 (2s, 2H), 7.36 (2d, 1H, J=8.0 Hz), 6.93 (2d, 1H, J=2.0 Hz), 6.69 (2d, 1H, J=11.6 Hz), 5.60 (2d, 1H, J=3.6 Hz), 4.04-3.88 (m, 5H), 3.80 (2s, 3H), 3.49 (2d, 1H, J=14.6 Hz), 2.56-1.89 (m, 4H), 1.49 (m, 2H), 1.01 (2d, 6H, J=11.2 Hz), 0.42 (2d, 3H, J=6.6 Hz)

MS (ESI) m/z 728.2 (M$^+$+H).

Example 58

Compound 631

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-2-chloro-2'-fluoro-4'-methoxybiphenyl-4-carboxylic acid Starting material 630 (25 mg, 0.03 mmol) and lithium hydroxide monohydrate (4 mg, 0.17 mmol) were dissolved in dioxane/water (v/v=3:1, 4 mL), and then stirred overnight at 45° C. After completion of the reaction, the reaction mixture was cooled to room temperature, diluted with ethyl acetate, and then washed with water. The organic layer was dried with anhydrous magnesium sulfate, filtered, and then concentrated under reduced pressure to remove the solvent. The residue was purified by preparative TLC (SiO$_2$, hexane/EtOAc=1:2) to obtain compound 631 (13 mg, 53%) as colorless oil.

$^1$H NMR (400 MHz, CDCl$_3$); atropisomeric mixture; δ 8.19 (2d, 1H, J=1.5 Hz), 8.01 (2dd, 1H, J=8.0, 1.5 Hz), 7.87 (s, 1H), 7.72 (2s, 2H), 7.40 (2d, 1H, J=8.0 Hz), 6.95 (2d, 1H, J=2.8 Hz), 6.70 (2d, 1H, J=11.7 Hz), 5.60 (2d, 1H, J=4.1 Hz), 4.05-3.85 (m, 2H), 3.81 (2s, 3H), 3.57 (2d, 1H, J=14.8 Hz), 2.54-1.87 (m, 4H), 1.48 (m, 2H), 1.01 (2d, 6H, J=11.1 Hz), 0.43 (2d, 3H, J=6.5 Hz)

MS (ESI) m/z 714.2 (M$^+$+H).

Example 59

Compound 657 methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2,2'-difluoro-4'-methoxybiphenyl-4-carboxylate Starting material 26 (0.100 g, 0.146 mmol), methyl-3-fluoro-4-(4,4,5,5-tetramethyl-1,3,2-dioxaborolan-2-yl)benzoate (27, 0.049 g, 0.175 mmol), Pd(dbpf)Cl$_2$ (0.005 g, 0.007 mmol) and sodium carbonate (0.046 g, 0.438 mmol) were added to dimethoxyethane/water (v/v=3:1, 1 ml) and heated by microwave irradiation at 120° C. for 20 minutes. Then, the temperature was lowered to room temperature, and water was poured into the reaction mixture, which was then extracted with ethyl acetate. The organic layer was washed with aqueous solution of saturated ammonium chloride, dried with anhydrous magnesium sulfate, and then concentrated under reduced pressure. The residue was purified by MPLC (SiO$_2$, EtOAc/hexane=20%) to obtain compound 657 (0.049 g, 47.2%) as a white solid.

$^1$H NMR (400 MHz, CDCl$_3$); atropisomeric mixture; δ 7.88-7.83 (m, 2H), 7.81-7.74 (m, 3H), 7.44-7.40 (m, 1H), 7.05-7.00 (m, 1H), 6.74-6.67 (m, 1H), 5.62-5.56 (m, 1H), 4.01-3.92 (m, 5H), 3.81 (s, 1.5H), 3.78 (s, 1.5H), 3.63 (d, 0.5H, J=14.7 Hz), 3.46 (d, 0.5H, J=14.8 Hz), 2.52-2.03 (m, 2H), 1.96-1.90 (m, 2H), 1.49-1.47 (m, 2H), 1.04-0.99 (m, 6H), 0.42-0.40 (m, 3H)

MS (ESI) m/z 712.3 (M$^+$+H).

Example 60

Compound 658 ethyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2,3'-difluoro-4'-methoxybiphenyl-4-carboxylate Starting material 26 (0.050 g, 0.073 mmol), 4-(ethoxycarbonyl)-3-fluorophenyl boronic acid (0.019 g, 0.088 mmol), Pd(dbpf)Cl$_2$ (0.002 g, 0.004 mmol) and sodium carbonate (0.023 g, 0.219 mmol) were added to dimethoxyethane/water (v/v=3:1, 0.5 ml) and heated by microwave irradiation at 120° C. for 20 minutes. Then, the temperature was lowered to room temperature, and water was poured into the reaction mixture, which was then extracted with ethyl acetate. The organic layer was washed with aqueous solution of saturated ammonium chloride, dried with anhydrous magnesium sulfate, and then concentrated under reduced pressure. The residue was purified by MPLC (SiO$_2$, EtOAc/hexane=20%) to obtain compound 658 (0.021 g, 39.7%) as a white solid.

$^1$H NMR (400 MHz, CDCl$_3$); 1:1.31 atropisomeric mixture; δ 7.99-7.91 (m, 1H), 7.86-7.85 (m, 1H), 7.72-7.71 (m, 2H), 7.35-7.21 (m, 2H), 7.06 (d, 1H, J=8.9 Hz), 6.72-6.66 (m, 1H), 5.61 (dd, 1H, J=8.1, 3.3 Hz), 4.43-4.36 (m, 2H), 4.02-3.91 (m, 2H), 3.81-3.78 (m, 3H), 3.58 (d, 0.5H, J=14.6 Hz), 3.46 (d, 0.5H, J=15.0 Hz), 2.48-2.04 (m, 2H), 1.97-1.87 (m, 2H), 1.50-1.45 (m, 2H), 1.41-1.37 (m, 3H), 1.05-1.00 (m, 6H), 0.45 (d, 1.3H, J=6.6 Hz), 0.41 (d, 1.7H, J=6.4 Hz)

MS (ESI) m/z 726.3 (M$^+$+H).

Example 61

Compound 659 methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-3,4'-dimethoxybiphenyl-4-carboxylate Starting material 26 (0.100 g, 0.146 mmol), methyl-2-methoxy-4-(4,4,5,5,-tetramethyl-1,3,2-dioxaborolan-2-yl)benzoate (0.051 g, 0.175 mmol), Pd(dbpf)Cl$_2$ (0.005 g, 0.007 mmol) and sodium carbonate (0.046 g, 0.438 mmol) were added to dimethoxyethane/water (v/v=3:1, 1 ml) and heated by microwave irradiation at 120° C. for 20 minutes. Then, the temperature was lowered to room temperature, and water was poured into the reaction mixture, which was then extracted with ethyl acetate. The organic layer was washed with aqueous solution of saturated ammonium chloride, dried with anhydrous magnesium sulfate, and then concentrated under reduced pressure. The residue was purified by MPLC (SiO$_2$, EtOAc/hexane=20%) to obtain compound 659 (0.047 g, 44.5%) as a white solid.

$^1$H NMR (400 MHz, CDCl$_3$); 1:1.36 atropisomeric mixture; δ 7.86-7.80 (m, 2H), 7.72-7.71 (m, 2H), 7.11-6.98 (m, 3H), 6.72-6.65 (m, 1H), 5.61-5.58 (m, 1H), 4.03-3.89 (m, 8H), 3.81-3.77 (m, 3H), 3.60 (d, 0.5H, J=14.6 Hz), 3.48 (d, 0.5H, J=15.0 Hz), 2.50-2.03 (m, 2H), 1.99-1.87 (m, 2H), 1.52-1.47 (m, 2H), 1.05-1.00 (m, 6H), 0.47 (d, 1.3H, J=6.6 Hz), 0.41 (d, 1.7H, J=6.5 Hz).

MS (ESI) m/z 724.3 (M$^+$+H).

Example 62

Compound 660 methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2,2',3-trifluoro-4'-methoxybiphenyl-4-carboxylate Starting material 26 (0.100 g, 0.146 mmol), 2,3-difluoro-4-(methoxycarbonyl)phenylboronic acid (0.038 g, 0.175 mmol), Pd(dbpf)Cl$_2$ (0.005 g, 0.007 mmol) and sodium carbonate (0.046 g, 0.438 mmol) were added to dimethoxyethane/water (v/v=3:1, 1 ml) and heated by microwave irradiation at 120° C. for 20 minutes. Then, the temperature was lowered to room temperature, and water was poured into the reaction mixture, which was then extracted with ethyl acetate. The organic layer was washed with aqueous solution of saturated ammonium chloride, dried with anhydrous magnesium sulfate, and then concentrated under reduced pressure. The residue was purified by MPLC (SiO$_2$, EtOAc/hexane=20%) to obtain compound 660 (0.031 g, 29.1%) as a white solid.

$^1$H NMR (400 MHz, CDCl$_3$); atropisomeric mixture; δ 7.86-7.85 (m, 1H), 7.74-7.70 (m, 3H), 7.22-7.12 (m, 1H), 7.04-7.00 (m, 1H), 6.75-6.68 (m, 1H), 5.62-5.57 (m, 1H), 3.99-3.95 (m, 5H), 3.82-3.79 (m, 3H), 3.61 (d, 0.5H, J=14.8 Hz), 3.45 (d, 0.5H, J=14.9 Hz), 2.51-2.06 (m, 2H), 1.99-1.87 (m, 2H), 1.49-1.47 (m, 2H), 1.04-0.99 (m, 6H), 0.44-0.41 (m, 3H)

MS (ESI) m/z 730.3 (M$^+$+H).

Example 63

Compound 661

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-2,2'-difluoro-4'-methoxybiphenyl-4-carboxylic acid Starting material 657 (0.046 g, 0.064 mmol) and lithium hydroxide monohydrate (0.013 g, 0.320 mmol) were dissolved in dioxane/water (v/v=4:1, 1 ml) at 50° C., and the reaction mixture was stirred overnight at the same temperature. Then, the reaction mixture was concentrated, and water was added thereto, followed by extraction with ethyl acetate. The organic layer was washed with aqueous solution of 1M hydrochloric acid, dried with anhydrous magnesium sulfate, and then concentrated under reduced pressure, thereby obtaining compound 661 (0.035 g, 78.7%) as a white solid.

$^1$H NMR (400 MHz, CDCl$_3$); atropisomeric mixture; δ 7.95-7.80 (m, 3H), 7.74-7.73 (m, 2H), 7.48-7.44 (m, 1H), 7.07-7.02 (m, 1H), 6.75-6.69 (m, 1H), 5.62-5.57 (m, 1H), 4.00-3.94 (m, 2H), 3.82 (s, 1.5H), 3.79 (s, 1.5H), 3.63 (d, 0.6H, J=15.1 Hz), 3.47 (d, 0.4H, J=14.9 Hz), 2.50-2.05 (m, 2H), 1.95-1.91 (m, 2H), 1.50-1.48 (m, 2H), 1.05-1.00 (m, 6H), 0.43-0.41 (m, 3H)

MS (ESI) m/z 698.2 (M$^+$+H).

Example 64

Compound 662

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-2',3-difluoro-4'-methoxybiphenyl-4-carboxylic acid Starting material 658 (0.021 g, 0.029 mmol) and lithium hydroxide monohydrate (0.006 g, 0.145 mmol) were dissolved in dioxane/water (v/v=4:1, 1 ml) at 50° C., and the reaction mixture was stirred overnight at the same temperature. Then, the reaction mixture was concentrated, and water was added thereto, followed by extraction with ethyl acetate. The organic layer was washed with aqueous solution of 1M hydrochloric acid, dried with anhydrous magnesium sulfate, and then concentrated under reduced pressure, thereby obtaining compound 662 (0.016 g, 80.2%) as a white solid.

$^1$H NMR (400 MHz, CDCl$_3$); 1:1.38 atropisomeric mixture; δ 8.08-8.02 (m, 1H), 7.86-7.85 (m, 1H), 7.73-7.71 (m, 2H), 7.39-7.29 (m, 2H), 7.09-7.07 (m, 1H), 6.74-6.67 (m, 1H), 5.62-5.60 (m, 1H), 4.02-3.97 (m, 2H), 3.82-3.78 (m, 3H), 3.59 (d, 0.6H, J=14.4 Hz), 3.46 (d, 0.4H, J=15.4 Hz), 2.50-2.05 (m, 2H), 1.94-1.92 (m, 2H), 1.50-1.47 (m, 2H), 1.05-1.00 (m, 6H), 0.46 (d, 1.3H, J=6.5 Hz), 0.42 (d, 1.7H, J=6.5 Hz)

MS (ESI) m/z 698.2 (M$^+$+H).

Example 65

Compound 663

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-2'-fluoro-3,4'-dimethoxybiphenyl-4-carboxylic acid Starting material 659 (0.043 g, 0.059 mmol) and lithium hydroxide monohydrate (0.012 g, 0.297 mmol) were dissolved in dioxane/water (v/v=4:1, 1 ml) at 50° C., and the reaction mixture was stirred overnight at the same temperature. Then, the reaction mixture was concentrated, and water was added thereto, followed by extraction with ethyl acetate. The organic layer was washed with aqueous solution of 1M hydrochloric acid, dried with anhydrous magnesium sulfate, and then concentrated under reduced pressure, thereby obtaining compound 663 (0.017 g, 40.8%) as a white solid.

$^1$H NMR (400 MHz, CDCl$_3$); 1:1.44 atropisomeric mixture; δ 8.23-8.16 (m, 1H), 7.87-7.86 (m, 1H), 7.73-7.70 (m, 2H), 7.24-7.07 (m, 3H), 6.74-6.67 (m, 1H), 5.63-5.60 (m, 1H), 4.12-4.08 (m, 3H), 4.02-3.95 (m, 2H), 3.82-3.79 (m, 3H), 3.58-3.46 (m, 1H), 2.50-2.04 (m, 2H), 1.94-1.92 (m, 2H), 1.51-1.49 (m, 2H), 1.06-1.00 (m, 6H), 0.49 (d, 1.2H, J=6.6 Hz), 0.43 (d, 1.8H, J=6.6 Hz)

MS (ESI) m/z 710.2 (M$^+$+H).

Example 66

Compound 664

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-22',3-trifluoro-4'-methoxybiphenyl-4-carboxylic acid Starting material 660 (0.026 g, 0.036 mmol) and lithium hydroxide monohydrate (0.007 g, 0.178 mmol) were dissolved in dioxane/water (v/v=4:1, 1 ml) at 50° C., and the reaction mixture was stirred overnight at the same temperature. Then, the reaction mixture was concentrated, and water was added thereto, followed by extraction with ethyl acetate. The organic layer was washed with aqueous solution of 1M hydrochloric acid, dried with anhydrous magnesium sulfate, and then concentrated under reduced pressure, thereby obtaining compound 664 (0.023 g, 89.9%) as a white solid.

$^1$H NMR (400 MHz, CDCl$_3$); atropisomeric mixture; δ 7.86-7.73 (m, 4H), 7.22-7.18 (m, 1H), 7.06-7.01 (m, 1H), 6.76-6.69 (m, 1H), 5.63-5.58 (m, 1H), 4.03-3.91 (m, 2H), 3.83-3.80 (m, 3H), 3.61 (d, 0.5H, J=14.8 Hz), 3.46 (d, 0.5H, J=15.0 Hz), 2.50-2.05 (m, 2H), 1.95-1.91 (m, 2H), 1.51-1.46 (m, 2H), 1.05-1.00 (m, 6H), 0.45-0.42 (m, 3H)

MS (ESI) m/z 716.2 (M$^+$+H).

Preparation of Novel Compounds According to Reaction Scheme 7

Intermediate Compound 29: 2-(2-bromo-5-methoxypyridin-4-yl)-5,5-dimethylcyclohex-1-enecarboaldehyde Starting material 1 (0.05 g, 0.22 mmol), boronic acid 28 (0.07 g, 0.22 mmol), Pd(PPh$_3$)$_4$ (0.03 g, 0.03 mmol) and cesium carbonate (0.14 g, 0.43 mmol) were dissolved in dimethylformamide/water (v/v=2:1, 3 mL), and then stirred at 80° C. for 3 hours. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (SiO$_2$, EtOAc/hexane=0%~15%) to obtain compound 29 (0.06 g, 75.8%) as colorless oil.

Intermediate Compound 30: (1R,2S)-1-(3,5-bis(trifluoromethyl)phenyl)-2-((2-(2-bromo-5-methoxypyridin-4-yl)-5,5-dimethylcyclohex-1-enyl)methylamino)propan-1-ol Starting material 29 (0.68 g, 2.09 mmol), aminoalcohol compound 4 (0.51 g, 2.09 mmol) and acetic acid (0.14 mL, 2.30 mmol) were dissolved in methylene chloride (5 mL), and then stirred at room temperature for 30 minutes, and sodium cyanoborohydride (0.14 g, 2.30 mmol) was added dropwise thereto, followed by stirring for 2 hours. After completion of the reaction, the reaction mixture was diluted with methylene chloride, and then washed with water and brine. The organic layer was dried with anhydrous magnesium sulfate, filtered, and then concentrated under reduced pressure to remove the solvent. The residue was purified by MPLC (Sift, $CH_3OH/CH_2Cl_2$=0%~10%) to obtain compound 30 (1.06 g, 85.3%) as colorless oil.

Intermediate Compound 31: (4S,5R)-5-(3,5-bis(trifluoromethyl)phenyl)-2-((2-(2-bromo-5-methoxypyridin-4-yl)-5,5-dimethylcyclohex-1-enyl)methyl)-4-methyloxazolidin-2-one Starting material 30 (1.06 g, 1.78 mmol) was dissolved in methylene chloride (10 mL), and diisopropylethylamine (1.38 mL, 10.68 mmol) was added dropwise thereto at 0° C., followed by stirring for 30 minutes. Then, triphosgene (0.79 g, 2.67 mmol) was added dropwise to the reaction mixture, followed by stirring for 2 hours. After completion of the reaction, the reaction mixture was diluted with methylene chloride, and then washed with water and brine. The organic layer was dried with anhydrous magnesium sulfate, filtered, and then concentrated under reduced pressure to remove the solvent. The residue was purified by MPLC ($SiO_2$, EtOAc/hexane=0%~30%) to obtain compound 31 (0.6 g, 54.2%) as colorless oil.

Example 67

Compound 652 methyl 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyridin-2-yl)benzoate Starting material 31 (0.07 g, 0.11 mmol), boronic acid 26 (0.02 g, 0.12 mmol), Pd(dbpf)Cl$_2$ (3.7 mg, 0.006 mmol) and sodium carbonate (24 mg, 0.23 mmol) were dissolved in dimethoxyethane/water (v/v 4:1, 1.25 mL), and then stirred with microwave irradiation at 120° C. for 15 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC ($SiO_2$, EtOAc/hexane=0%~20%) to obtain compound 652 (35 mg, 45.9%) as colorless oil.

$^1$H NMR (400 MHz, CDCl$_3$); atropisomeric mixture; δ 8.35 (d, 1H, J=13.7 Hz), 8.01-8.09 (m, 2H), 7.94-8.01 (m, 2H), 7.85 (s, 1H), 7.71 (s, 2H), 7.44 (s, 1H), 5.59-5.63 (m, 1H), 3.95-4.04 (m, 2H), 3.86-3.94 (m, 6H), 3.46-3.57 (m, 1H), 2.00-2.60 (m, 4H), 1.96 (s, 2H), 1.50-1.56 (m, 2H), 1.01-1.12 (m, 6H), 0.42-0.49 (m, 3H)

MS (ESI) m/z 677.2 (M$^+$+H).

Example 68

Compound 644

4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyridin-2-yl)benzoic acid Starting material 652 (0.04 g, 0.05 mmol) and lithium hydroxide monohydrate (6 mg, 0.27 mmol) were dissolved in dioxane/water (v/v=4:1, 1.25 mL), and then stirred at 50° C. for 8 hours. After completion of the reaction, the reaction mixture was cooled to room temperature, diluted with ethyl acetate, and then washed with 1M hydrochloric acid solution and brine. The organic layer was dried with anhydrous magnesium sulfate, filtered, and then concentrated under reduced pressure to remove the solvent. The residue was purified by MPLC ($SiO_2$, EtOAc/hexane=0%~50%) to obtain compound 644 (20 mg, 56.7%) as a white foam solid.

$^1$H NMR (400 MHz, CDCl$_3$); atropisomeric mixture; δ 8.39-8.44 (m, 1H), 8.23-8.30 (m, 2H), 8.04-8.17 (m, 2H), 7.87 (s, 1H), 7.60-7.80 (m, 2H), 7.47-7.52 (m, 2H), 5.60-5.67 (m, 1H), 3.50-3.59 (m, 5H), 2.00-2.60 (m, 2H), 1.80-2.00 (m, 2H), 1.20-1.40 (m, 2H), 1.00-1.20 (m, 6H), 0.45-0.60 (m, 3H)

MS (ESI) m/z 663.2 (M$^+$+H).

Example 69

Compound 653 methyl 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyridin-2-yl)-3-methylbenzoate Starting material 31 (0.07 g, 0.11 mmol), boronic acid 26 (0.03 g, 0.12 mmol), Pd(dbpf)Cl$_2$ (4.0 mg, 0.006 mmol) and sodium carbonate (24 mg, 0.23 mmol) were added to dimethoxyethane/water (v/v 4:1, 1.25 mL), and then stirred with microwave irradiation at 120° C. for 15 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC ($SiO_2$, EtOAc/hexane=0%~20%) to obtain compound 653 (51 mg, 65.6%) as colorless oil.

$^1$H NMR (400 MHz, CDCl$_3$); atropisomeric mixture; δ 8.35 (d, 1H, J=11.9 Hz), 7.86-7.95 (m, 3H), 7.69-7.74 (m, 2H), 7.44 (d, 0.5H, J=7.9 Hz), 7.35 (d, 0.5H, J=8.0 Hz), 7.07 (s, 1H), 5.60-5.63 (m, 1H), 3.87-4.02 (m, 8H), 3.58 (d, 0.5H, J=14.8 Hz), 3.49 (d, 0.5H, J=15.1 Hz), 2.00-2.60 (m, 5H), 1.94-1.95 (m, 2H), 1.52-1.56 (m, 2H), 1.01-1.06 (m, 6H), 0.42-0.48 (m, 3H)

MS (ESI) m/z 691.2 (M$^+$+H).

Example 70

Compound 645

4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyridin-2-yl)-3-methylbenzoic acid Starting material 653 (0.05 g, 0.07 mmol) and lithium hydroxide monohydrate (8 mg, 0.34 mmol) were dissolved in dioxane/water (v/v=4:1, 1.25 mL), and then stirred at 50° C. for 8 hours. After completion of the reaction, the reaction mixture was cooled to room temperature, diluted with ethyl acetate, and then washed with 1M hydrochloric acid solution and brine. The organic layer was dried with anhydrous magnesium sulfate, filtered, and then concentrated under reduced pressure to remove the solvent. The residue was purified by MPLC (SiO$_2$, EtOAc/hexane=0%~50%) to obtain compound 645 (20 mg, 43.4%) as a white foam solid.

$^1$H NMR (400 MHz, CDCl$_3$); atropisomeric mixture; δ 8.42 (d, 1H, J=7.9 Hz), 7.92-7.98 (m, 2H), 7.88 (s, 1H), 7.74 (d, 2H, J=6.4 Hz), 7.44 (dd, 1H, J=27.4, 5.8 Hz), 7.10 (s, 1H), 5.61-5.64 (m, 1H), 3.94-4.07 (m, 5H), 3.48-3.67 (m, 1H), 2.19-2.60 (m, 5H), 1.80-2.01 (m, 2H), 1.50-1.60 (m, 2H), 0.82-1.05 (m, 6H), 0.33-0.50 (m, 3H)

MS (ESI) m/z 677.2 (M$^+$+H).

Example 71

Compound 654 methyl 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyridin-2-yl)-3-fluorobenzoate Starting material 31 (0.07 g, 0.11 mmol), boronic acid 26 (0.04 g, 0.12 mmol), Pd(dbpf)Cl$_2$ (4.0 mg, 0.006 mmol) and sodium carbonate (24 mg, 0.23 mmol) were added to dimethoxyethane/water (v/v 4:1, 1.25 mL), and then stirred with microwave irradiation at 120° C. for 15 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (SiO$_2$, EtOAc/hexane=0%-20%) to obtain compound 654 (61 mg, 78%) as colorless oil.

$^1$H NMR (400 MHz, CDCl$_3$); atropisomeric mixture; δ 8.39 (d, 1H, J=10.5 Hz), 8.01-8.06 (m, 1H), 7.88-7.92 (m, 1H), 7.85 (s, 1H), 7.71-7.82 (m, 3H), 7.50-7.52 (m, 1H), 5.65 (d, 0.5H, J=8.0 Hz), 5.55 (d, 0.5H, J=8.0 Hz), 3.93-4.05 (m, 8H), 3.62 (d, 0.5H, J=15.0 Hz), 3.41 (d, 0.5H, J=15.0 Hz), 2.00-2.60 (m, 2H), 1.92-1.96 (m, 2H), 1.46-1.55 (m, 2H), 1.02-1.05 (m, 6H), 0.47 (d, 1.5H, J=6.5 Hz), 0.40 (d, 1.5H, J=6.5 Hz)

MS (ESI) m/z 695.2 (M$^+$+H).

Example 72

Compound 646

4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyridin-2-yl)-3-fluorobenzoic acid Starting material 654 (0.05 g, 0.07 mmol) and lithium hydroxide monohydrate (8 mg, 0.35 mmol) were dissolved in dioxane/water (v/v=4:1, 1.25 mL), and then stirred at 50° C. for 8 hours. After completion of the reaction, the reaction mixture was cooled to room temperature, diluted with ethyl acetate, and then washed with 1M hydrochloric acid solution and brine. The organic layer was dried with anhydrous magnesium sulfate, filtered, and then concentrated under reduced pressure to remove the solvent. The residue was purified by MPLC (SiO$_2$, EtOAc/hexane=0%-50%) to obtain compound 646 (20 mg, 41.7%) as a white foam solid.

$^1$H NMR (400 MHz, CDCl$_3$); atropisomeric mixture; δ 8.48 (d, 1H, J=6.4 Hz), 7.95-8.05 (m, 2H), 7.81-7.89 (m, 2H), 7.75 (d, 2H, J=5.9 Hz), 7.52-7.54 (m, 1H), 5.66 (d, 0.5H, J=6.0 Hz), 5.57 (d, 0.5H, J=6.1 Hz), 3.96-4.07 (m, 5H), 3.64 (d, 0.5H, J=11.2 Hz), 3.43 (d, 0.5H, J=11.3 Hz), 2.00-2.60 (m, 2H), 1.93-1.98 (m, 2H), 1.50-1.60 (m, 2H), 1.03-1.07 (m, 6H), 0.42-0.50 (m, 3H)

MS (ESI) m/z 681.2 (M$^+$+H).

Example 73

Compound 655 methyl 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyridin-2-yl)-3-chlorobenzoate Starting material 31 (0.07 g, 0.11 mmol), boronic acid 26 (0.03 g, 0.12 mmol), Pd(dbpf)Cl$_2$ (4.0 mg, 0.006 mmol) and sodium carbonate (24 mg, 0.23 mmol) were added to dimethoxyethane/water (v/v 4:1, 1.25 mL), and then stirred with microwave irradiation at 120° C. for 15 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (SiO$_2$, EtOAc/hexane=0%~30%) to obtain compound 655 (40 mg, 49.9%) as colorless oil.

$^1$H NMR (400 MHz, CDCl$_3$); atropisomeric mixture; δ 8.34 (m, 1H), 8.10-8.14 (m, 1H), 7.96-8.02 (m, 1H), 7.87 (s, 1H), 7.63-7.73 (m, 3H), 7.37-7.39 (m, 1H), 5.59-5.63 (m, 1H), 3.91-4.02 (m, 8H), 3.47-3.67 (m, 1H), 2.00-2.60 (m, 2H), 1.97 (s, 2H), 1.50-1.53 (m, 2H), 1.00-1.07 (m, 6H), 0.42-0.48 (m, 3H)

MS (ESI) m/z 711.2 (M$^+$+H).

Example 74

Compound 647

4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyridin-2-yl)-3-chlorobenzoic acid Starting material 655 (0.03 g, 0.04 mmol) and lithium hydroxide monohydrate (5 mg, 0.20 mmol) were dissolved in dioxane/water (v/v=4:1, 1.25 mL), and then stirred at 50° C. for 8 hours. After completion of the reaction, the reaction mixture was cooled to room temperature, diluted with ethyl acetate, and then washed with 1M hydrochloric acid solution and brine. The organic layer was dried with anhydrous magnesium sulfate, filtered, and then concentrated under reduced pressure to remove the solvent. The residue was purified by MPLC (Sift, EtOAc/hexane=0%~50%) to obtain compound 647 (10 mg, 35.2%) as white foam solid.

$^1$H NMR (400 MHz, CDCl$_3$); atropisomeric mixture; δ 8.40-8.48 (m, 1H), 8.14-8.17 (m, 1H), 8.01-8.06 (m, 1H), 7.86-7.87 (m, 1H), 7.62-7.74 (m, 3H), 7.34-7.40 (m, 1H), 5.58-5.62 (m, 1H), 3.90-4.05 (m, 5H), 3.49-3.69 (m, 1H), 2.00-2.60 (m, 2H), 1.97 (s, 2H), 1.20-1.30 (m, 2H), 1.01-1.06 (m, 6H), 0.43-0.48 (m, 3H)

MS (ESI) m/z 697.1 (M$^+$+H).

Example 75

Compound 656 methyl 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)-5-methoxypyridin-2-yl)-2,3-difluorobenzoate Starting material 30 (0.070 g, 0.113 mmol), 2,3-difluoro-4-(methoxycarbonyl)phenyl boronic acid compound (0.027 g, 0.124 mmol), Pd(di-t-Bupf)Cl$_2$ (0.004 g, 0.006 mmol) and sodium carbonate (0.024 g, 0.225 mmol) were added to dimethoxyethane (1 mL)/water (0.25 mL) and heated by microwave irradiation at 120° C. for 20 minutes. Then, the temperature was lowered to room temperature, and water was poured into the reaction mixture, which was then extracted with ethyl acetate. The organic layer was washed with brine, dried with anhydrous magnesium sulfate, and then concentrated under reduced pressure. The concentrate was purified by column chromatography (SiO$_2$, EtOAc/hexane=0%~20%) to obtain desired compound 656 (0.0410 g, 49.8%) as brown oil.

$^1$H NMR (400 MHz, CDCl$_3$); 1:1 atropisomeric mixture; δ 8.39 (d, 1H, J=9.9 Hz), 7.73-7.86 (m, 5H), 7.52 (dd, 1H, J=6.8, 2.2 Hz), 5.66 (d, 0.54H, J=8.1 Hz), 5.57 (d, 0.46H, J=8.1 Hz), 3.94-4.07 (m, 8H), 3.61 (d, 0.46H, J=14.1 Hz), 3.40 (d, 0.56H, J=15.0 Hz), 2.13-2.43 (m, 2H), 1.96 (s, 2H), 1.47-1.55 (m, 2H), 1.20-1.06 (m, 6H), 0.42-0.48 (m, 3H)

MS (ESI) m/z 713.2 (M$^+$+H).

Preparation of Novel Compounds According to Reaction Scheme 8

Intermediate Compound 33a: methyl 4-(6-bromo-5-methoxypyridin-2-yl)-3-methylbenzoate Starting material 32 (0.2 g, 0.64 mmol) and boronic acid pinacol ester (0.18 g, 0.64 mmol) were added to dimethoxyethane/water (v/v=3:1, 0.4 mL), and then degassed. Pd(dbpf)Cl$_2$ (26 mg, 0.03 mmol) and sodium carbonate (0.14 g, 1.27 mmol) were added thereto, and the mixture was stirred with microwave irradiation at 120° C. for 20 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (SiO$_2$, EtOAc/hexane=10%~15%) to obtain compound 33a (80 mg, 37%) as a white solid.

$^1$H NMR (400 MHz, CDCl$_3$); δ 7.94 (s, 1H), 7.91-7.89 (m, 1H), 7.46 (d, 1H, J=7.9 Hz), 7.36 (d, 1H, J=8.2 Hz), 7.23 (d, 1H, J=8.3 Hz), 3.97 (s, 3H), 3.93 (s, 3H), 2.42 (s, 3H)

MS (ESI) m/z 336.0, 338.0 (M, M$^+$+2H).

Intermediate Compound 33b: methyl 4-(6-bromo-5-methoxypyridin-2-yl)-3-fluorobenzoate Starting material 32 (0.1 g, 0.32 mmol) and 2-fluoro-4-(methoxycarbonyl)phenylboronic acid (70 mg, 0.35 mmol) were added to dimethoxyethane/water (v/v=3:1, 0.4 mL), and then degassed. Pd(dbpf)Cl$_2$ (10 mg, 0.02 mmol) and sodium carbonate (68 mg, 0.64 mmol) were added thereto, and the mixture was stirred with microwave irradiation at 120° C. for 20 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (Sift, EtOAc/hexane=5%-20%) to obtain compound 33b (70 mg, 65%) as a white solid.

$^1$H NMR (400 MHz, CDCl$_3$); δ 8.15 (t, 1H, J=8.0 Hz), 7.91-7.78 (m, 3H), 7.22 (d, 1H, J=8.5 Hz), 3.98-3.94 (m, 6H)

MS (ESI) m/z 340.0, 342.0 (M, M$^+$+2H).

Intermediate Compound 33c: methyl 4-(6-bromo-5-methoxypyridin-2-yl)-3-chlorobenzoate Starting material 32 (0.1 mg, 0.32 mmol) and 2-chloro-4-(methoxycarbonyl)phenylboronic acid (68 mg, 0.32 mmol) were added to dimethoxyethane/water (v/v=3:1, 0.4 mL), and then degassed. Pd(dbpf)Cl$_2$ (10 mg, 0.02 mmol) and sodium carbonate (68 mg, 0.64 mmol) were added thereto, and the mixture was stirred with microwave irradiation at 120° C. for 20 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (Sift, EtOAc/hexane=5%-15%) to obtain compound 33c (33 mg, 29%) as a white solid.

$^1$H NMR (400 MHz, CDCl$_3$); δ 8.13 (d, 1H, J=1.6 Hz), 7.99 (dd, 1H, J=8.0, 1.6 Hz), 7.74-7.68 (m, 2H), 7.24 (d, 1H, J=8.4 Hz), 3.98 (s, 3H), 3.94 (s, 3H)

MS (ESI) m/z 356.0, 358.0 (M, M$^+$+2H).

Example 76

Compound 621 methyl 4-(2-(2-(((4S,5R)-5-(3,5-bis(trifluoromethyl)phenyl)-4-methyl-2-oxooxazolidin-3-yl)methyl)-4,4-dimethylcyclohex-1-enyl)-3-methoxypyridin-6-yl)-3-methylbenzoate Starting material 17 (0.1 mg, 0.18 mmol) and methyl 4-(6-bromo-5-methoxypyridin-2-yl)-3-methylbenzoate (78 mg, 0.23 mmol) were added to dimethoxyethane/water (v/v=3:1, 0.4 mL), and then degassed. Pd(dbpf)Cl$_2$ (7 mg, 0.009 mmol) and sodium carbonate (38 mg, 0.36 mmol) were added thereto, and the mixture was stirred with microwave irradiation at 120° C. for 20 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (SiO$_2$, EtOAc/hexane=20%) to obtain compound 621 (26 mg, 21%) as a white solid.

$^1$H NMR (400 MHz, CDCl$_3$); δ 7.92 (s, 1H), 7.86-7.81 (m, 2H), 7.60 (s, 2H), 7.35 (d, 1H, J=7.9 Hz), 7.28 (d, 1H, J=8.5 Hz), 7.24 (d, 1H, J=7.0 Hz), 5.38 (br s, 1H), 4.08-3.95 (m, 2H), 3.91 (s, 3H), 3.86 (s, 3H), 3.41-3.36 (m, 1H), 2.48-2.32 (m, 5H), 1.99-1.90 (br m, 2H), 1.53 (t, 2H, J=6.4 Hz), 1.04 (d, 6H, J=7.0 Hz), 0.29 (br m, 3H)

MS (ESI) m/z 691.2 (M$^+$+H).

Example 77

Compound 622

4-(2-(2-(((4S,5R)-5-(3,5-bis(trifluoromethyl)phenyl)-4-methyl-2-oxooxazolidin-3-yl)methyl)-4,4-dimethylcyclohex-1-enyl)-3-methoxypyridin-6-yl)-3-methylbenzoic acid Starting material 621 (24 mg, 0.04 mmol) was dissolved in dioxane (1 mL), and a solution of lithium hydroxide monohydrate (7 mg, 0.17 mmol) in water (0.25 mL) was added dropwise thereto, followed by stirring overnight at 50° C. After completion of the reaction, the reaction mixture was cooled to room temperature, diluted with ethyl acetate, and then washed with water, saturated ammonium chloride and brine. The organic layer was dried with anhydrous magnesium sulfate, filtered, and then concentrated under reduced pressure to remove the solvent. The residue was purified by preparative TLC (EtOAc/hexane=33%) to obtain compound 622 (12 mg, 51%) as a white solid.

$^1$H NMR (400 MHz, CDCl$_3$); δ 7.95 (s, 1H), 7.89 (d, 1H, J=7.0 Hz), 7.81 (s, 1H), 7.65 (s, 2H), 7.60-7.27 (m, 3H), 5.60-5.33 (br m, 1H), 4.17-4.01 (m, 2H), 3.92 (s, 3H), 3.44-3.38 (m, 1H), 2.51-2.23 (m, 5H), 1.95-1.91 (br m, 2H), 1.60-1.47 (br m, 2H), 4.01 (d, 6H, J=7.0 Hz), 0.31 (br s, 3H)

MS (ESI) m/z 677.2 (M$^+$+H).

Example 78

Compound 696 methyl 4-(2-(2-(((4S,5R)-5-(3,5-bis(trifluoromethyl)phenyl-4-methyl-2-oxooxazolidin-3-yl)methyl)-4,4-dimethylcyclohex-1-enyl)-3-methoxypyridin-6-yl)-3-fluorobenzoate Starting material 17 (56 mg, 0.09 mmol) and methyl 4-(6-bromo-5-methoxypyridin-2-yl)-3-fluorobenzoate (33 mg, 0.1 mmol) were added to dimethoxyethane/water (v/v=3:1, 0.4 mL), and then degassed. Pd(dbpf)Cl$_2$ (4 mg, 0.004 mmol) and sodium carbonate (19 mg, 0.18 mmol) were added thereto, and the mixture was stirred with microwave irradiation at 120° C. for 20 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (SiO$_2$, EtOAc/hexane=10%~20%) to obtain compound 696 (9 mg, 15%) as yellow oil.

$^1$H NMR (400 MHz, CDCl$_3$); δ 8.03-7.99 (m, 1H), 7.87-7.73 (m, 4H), 7.62 (br s, 2H), 7.24-7.22 (m, 1H), 5.39 (br s, 1H), 4.08-3.96 (br m, 2H), 3.94-3.82 (m, 6H), 3.42-3.38 (br m, 1H), 2.45-2.32 (br m, 2H), 2.01-1.93 (br m, 2H), 1.56-1.53 (m, 2H), 1.04 (d, 6H, J=7.0 Hz), 0.30 (br s, 3H)

MS (ESI) m/z 695.2 (M$^+$+H).

Example 79

Compound 637

4-(2-(2-(((4S,5R)-5-(3,5-bis(trifluoromethyl)phenyl)-4-methyl-2-oxooxazolidin-3-yl)methyl)-4,4-dimethylcyclohex-1-enyl)-3-methoxypyridin-6-yl)-3-fluorobenzoic acid Starting material 696 (9 mg, 0.01 mmol) was dissolved in dioxane (1 mL), and a solution of lithium hydroxide monohydrate (3 mg, 0.07 mmol) in water (0.25 mL) was added dropwise thereto, followed by stirring at 50° C. for 2 hours. After completion of the reaction, the reaction mixture was cooled to room temperature, diluted with ethyl acetate, and then washed with water, saturated ammonium chloride and brine. The organic layer was dried with anhydrous magnesium sulfate, filtered, and then concentrated under reduced pressure to remove the solvent. The residue was purified by preparative TLC (EtOAc/hexane=35%→CH$_3$OH/CH$_2$Cl$_2$=5%) to obtain compound 637 (6 mg, 68%) as colorless oil.

$^1$H NMR (400 MHz, CDCl$_3$); δ 8.05 (t, 1H, J=7.8 Hz), 7.93 (dd, 1H, J=8.1, 1.4 Hz), 7.84-7.80 (m, 2H), 7.77-7.74 (m, 1H), 7.51 (s, 2H), 7.26-7.24 (m, 1H), 5.52-5.21 (br m, 1H), 4.13-4.02 (m, 2H), 3.87 (s, 3H), 3.42-3.37 (m, 1H), 2.46-2.26 (br m, 2H), 2.01-1.88 (br m, 2H), 1.55 (t, 2H, J=6.5 Hz), 1.06 (d, 6H, J=7.0 Hz), 0.40-0.20 (br m, 3H)

MS (ESI) m/z 681.2 (M$^+$+H).

Example 80

Compound 697 methyl 4-(2-(2-(((4S,5R)-5-(3,5-bis(trifluoromethyl)phenyl-4-methyl-2-oxooxazolidin-3-yl)methyl)-4,4-dimethylcyclohex-1-enyl)-3-methoxypyridin-6-yl)-3-chlorobenzoate Starting material 17 (56 mg, 0.09 mmol) and methyl 4-(6-bromo-5-methoxypyridin-2-yl)-3-chlorobenzoate (35 mg, 0.1 mmol) were added to dimethoxyethane/water (v/v=3:1, 0.4 mL), and then degassed. Pd(dbpf)Cl$_2$ (4 mg, 0.004 mmol) and sodium carbonate (19 mg, 0.18 mmol) were added thereto, and the mixture was stirred with microwave irradiation at 120° C. for 20 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (Sift, EtOAc/hexane=10%~20%) to obtain compound 697 (9 mg, 14%) as oil.

$^1$H NMR (400 MHz, CDCl$_3$); δ 8.09 (m, 1H), 7.96-7.94 (m, 1H), 7.81 (s, 1H), 7.67-7.54 (m, 4H), 7.23 (s, 1H), 5.40 (br s, 1H), 4.11-3.84 (m, 8H), 3.43-3.39 (br m, 1H), 2.44-2.35 (m, 2H), 2.00-1.93 (m, 2H), 1.55-1.52 (m, 2H), 1.09-1.03 (m, 6H), 0.31-0.30 (br m, 3H)

MS (ESI) m/z 711.1 (M$^+$+H).

Example 81

Compound 636

4-(2-(2-(((4S,5R)-5-(3,5-bis(trifluoromethyl)phenyl)-4-methyl-2-oxooxazolidin-3-yl)methyl)-4,4-dimethylcyclohex-1-enyl)-3-methoxypyridin-6-yl)-3-chlorobenzoic acid Starting material 697 (9 mg, 0.01 mmol) was dissolved in dioxane (1 mL), and a solution of lithium hydroxide monohydrate (3 mg, 0.06 mmol) in water (0.25 mL) was added dropwise thereto, followed by stirring at 50° C. for 2 hours. After completion of the reaction, the reaction mixture was cooled to room temperature, diluted with ethyl acetate, and then washed with water, saturated ammonium chloride and brine. The organic layer was dried with anhydrous magnesium sulfate, filtered, and then concentrated under reduced pressure to remove the solvent. The residue was purified by preparative TLC (EtOAc/hexane=35%→CH$_3$OH/CH$_2$Cl$_2$=5%) to obtain compound 636 (4 mg, 45%) as colorless oil.

$^1$H NMR (400 MHz, CDCl$_3$); δ 8.13 (d, 1H, J=7.0 Hz), 7.97 (dd, 1H, J=8.0, 1.6 Hz), 7.81 (s, 1H), 7.65 (s, 2H), 7.61-7.55 (m, 2H), 7.27 (d, 1H, J=7.0 Hz), 5.44-5.26 (br m, 1H), 4.14-3.98 (m, 2H), 3.88 (s, 3H), 3.43-3.40 (m, 1H), 2.52-2.35 (br m, 2H), 1.96-1.90 (br m, 2H), 1.56-1.52 (m, 2H), 1.04 (d, 6H, J=7.0 Hz), 0.35-0.30 (m, 3H)

MS (ESI) m/z 697.2 (M$^+$+H).

Preparation of Novel Compounds According to Reaction Scheme 9

Intermediate Compound 35: methyl 4-(5-(2-(((4S, 5R)-5-(3,5-bis(trifluoromethyl)phenyl)-4-methyl-2-oxooxazolidin-3-yl)methyl)-4,4-dimethylcyclohex-1-enyl)-6-methoxypyridin-3-yl)-3-(prope-1-en-2-yl)benzoate Starting material compound 583 (0.1 g, 0.14 mmol) and propan-2-ylboronic acid (47 mg, 0.28 mmol) were added to dimethoxyethane/water (v/v=4:1, 0.5 mL), followed by degassing. Pd(dbpf)Cl$_2$ (9 mg, 0.01 mmol) and sodium carbonate (30 mg, 0.28 mmol) were added thereto, and the mixture was stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (Sift, EtOAc/hexane=5%~15%) to obtain compound 35 (48 mg, 48%) as brown oil.

$^1$H NMR (400 MHz, CDCl$_3$); 1:1.9 atropisomeric mixture; δ 8.15-8.11 (m, 1H), 7.99-7.94 (m, 2H), 7.86 (br s, 1H), 7.74-7.71 (br m, 2H), 7.38-7.28 (m, 2H), 5.64-5.56 (m, 1H), 5.16-5.13 (m, 1H), 4.99-4.96 (m, 1H), 4.04-3.96 (m, 2H), 3.95-3.91 (m, 6H), 3.58-3.55 (m, 1H), 2.60-2.17 (br m, 2H), 1.98-1.95 (br m, 2H), 1.71 (d, 3H, J=8.7 Hz), 1.53-1.45 (m, 2H), 1.06-0.99 (m, 6H), 0.51-0.31 (m, 3H)

MS (ESI) m/z 717.2 (M$^+$+H).

Example 82

Compound 577 methyl 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-3-isopropylbenzoate Starting material 35 (41 mg, 0.06 mmol) was dissolved in ethanol (3 mL), and 5% palladium/carbon (4 mg) was added dropwise thereto, followed by hydrogenation overnight. After completion of the reaction, the reaction mixture was filtered through celite under reduced pressure to remove palladium, and then concentrated under reduced pressure to remove the solvent. The residue was purified by MPLC (Sift, EtOAc/hexane=10%-20%) to obtain compound 577 (41 mg, 100%) as colorless oil.

$^1$H NMR (400 MHz, CDCl$_3$); 1:1.5 atropisomeric mixture; δ 8.06, 8.04 (2d, 1H, J=1.6 Hz), 8.01-8.00 (m, 1H), 7.88-7.82 (m, 2H), 7.74-7.71 (br m, 2H), 7.24-7.13 (m, 2H), 5.65-5.57 (m, 1H), 4.07-3.88 (m, 8H), 3.59-3.49 (m, 1H), 3.03-2.94 (m, 1H), 2.58-2.07 (br m, 2H), 1.94-1.66 (br m, 2H), 1.55-1.38 (m, 2H), 1.20-1.11 (m, 6H), 1.06-0.94 (m, 6H), 0.50, 0.36 (2d, 3H, J=6.5 Hz)

MS (ESI) m/z 719.2 (M$^+$+H).

Example 83

Compound 578

4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-3-isopropylbenzoic acid Starting material 577 (36 mg, 0.05 mmol) was dissolved in dioxane (2 mL), and a solution of lithium hydroxide monohydrate (11 mg, 0.25 mmol) in water (0.5 mL) was added dropwise thereto, followed by stirring overnight at 50° C. After completion of the reaction, the reaction mixture was cooled to room temperature, diluted with ethyl acetate, and then washed with water, saturated ammonium chloride and brine. The organic layer was dried with anhydrous magnesium sulfate, filtered, and then concentrated under reduced pressure to remove the solvent. The residue was purified by MPLC (Sift, EtOAc/hexane=10%-70%) to obtain compound 578 (26 mg, 74%) as a white solid.

$^1$H NMR (400 MHz, CDCl$_3$); 1:1.5 atropisomeric mixture; δ 8.14-8.12 (m, 1H), 8.04-8.03 (m, 1H), 7.96-7.90 (m, 2H), 7.87 (s, 1H), 7.74 (d, 2H, J=11.4 Hz), 7.24-7.17 (m, 1H), 5.66-5.58 (m, 1H), 4.06-3.90 (m, 5H), 3.60-3.42 (m, 1H), 3.05-2.97 (m, 1H), 2.60-2.07 (br m, 2H), 1.95-1.92 (br m, 2H), 1.55-1.47 (m, 2H), 1.23-1.13 (m, 6H), 1.06-1.00 (m, 6H), 0.52-0.37 (m, 3H)

MS (ESI) m/z 705.2 (M$^+$+H).

Preparation of Novel Compounds According to Reaction Scheme 10

Intermediate Compound 38a: 2-(2-methoxy-4-methyl-5-nitrophenyl)-5,5-dimethylcyclohex-1-enecarbaldehyde Starting material 37a (2.7 g, 9.2 mmol), compound 1 (2.0 g, 9.2 mmol), Pd2dba3 (0.42 g, 0.46 mmol) and copper (2.93 g, 46.1 mmol) were dissolved in dimethylsulfoxide (20 mL), and then stirred at 80° C. for 16 hours. After completion of the reaction, the reaction mixture was cooled to room temperature, diluted with ethyl acetate, and then washed with water and brine. The residue was purified by MPLC (SiO$_2$, EtOAc/hexane=0%-25%) to obtain compound 38a (0.7 g, 25%) as yellow oil.

Intermediate Compound 38b: 2-(2-methoxy-5-nitro-4-(trifluoromethyl)phenyl)-5,5-dimethylcyclohex-1-enecarbaldehyde Starting material 37b (2.65 g, 7.64 mmol), compound 1 (1.66 g, 7.64 mmol), Pd2dba3 (0.35 g, 0.38 mmol) and copper (2.43 g, 38.2 mmol) were dissolved in dimethylsulfoxide (10 mL), and then stirred overnight at 80° C. After completion of the reaction, the reaction mixture was cooled to room temperature, diluted with ethyl acetate, and then washed with water and brine. The residue was purified by MPLC (SiO$_2$, hexane/EtOAc=10%-60%) to obtain compound 38b (1.6 g, 59.4%) as a gray solid.

Intermediate Compound 39a: (1R,2S)-1-(3,5-bis(trifluoromethyl)phenyl)-2-((2-(2-methoxy-4-methyl-5-nitrophenyl)-5,5-dimethylcyclohex-1-enyl)methylamino)propan-1-ol Starting material 38a (0.7 g, 2.31 mmol), aminoalcohol compound 4 (0.66 g, 2.31 mmol) and acetic acid (0.16 mL, 2.54 mmol) were dissolved in methylene chloride (10 mL), and then stirred at room temperature for 30 minutes. Then, sodium cyanoborohydride (0.16 g, 2.54 mmol) was added to the reaction mixture, and water was added thereto, followed by extraction with methylene chloride. The organic layer was washed with brine, dried with anhydrous magnesium sulfate, and then concentrated under reduced pressure to remove the solvent. The residue was purified by MPLC (Sift, $CH_3OH/CH_2Cl_2$=0%-10%) to obtain compound 39a (0.98 g, 74.0%) as yellow oil.

Intermediate Compound 39b: (1R,2S)-1-(3,5-bis(trifluoromethyl)phenyl)-2-((2-(2-methoxy-5-nitro-4-(trifluoromethyl)phenyl)-5,5-dimethylcyclohex-1-enyl)methylamino)propan-1-ol Starting material 38b (1.6 g, 5.3 mmol) and aminoalcohol compound 4 (1.8 g) were dissolved in methylene chloride (10 mL), and acetic acid (0.3 mL) and sodium cyanoborohydride (0.4 g) were added thereto at the same temperature. The mixture was stirred at the same temperature for 5 hours, and water was added thereto, followed by extraction with ethyl acetate. The organic layer was washed with brine, dried with anhydrous magnesium sulfate to remove water, and then concentrated under reduced pressure to remove the solvent. The residue was purified by MPLC ($SiO_2$, EtOAc/hexane=20%~70%) to obtain compound 39b (1.9 g, 57.9%) as colorless oil.

Intermediate Compound 40a: (4S,5R)-5-(3,5-bis(trifluoromethyl)phenyl)-3-((2-(2-methoxy-4-methyl-5-nitrophenyl)-5,5-dimethylcyclohex-1-enyl)methyl)-4-methyloxazolidin-2-one Starting material 39a (0.98 g, 1.71 mmol) was dissolved in methylene chloride (10 mL), and diisopropylethylamine (1.32 g, 10.2 mmol) was added dropwise thereto at 0° C., followed by stiffing for 30 minutes. Then, triphosgene (0.76 g, 2.56 mmol) was slowly added dropwise to the mixture, followed by stirring at the same temperature for 2 hours. After completion of the reaction, water was added to the reaction mixture, followed by extraction with methylene chloride. The organic layer was washed with brine, dried with anhydrous magnesium sulfate, and then concentrated under reduced pressure to remove the solvent. The residue was purified by MPLC (Sift, EtOAc/hexane=0%~30%) to obtain compound 40a (0.6 g, 58.5%) as colorless oil.

Intermediate Compound 40b: (4S,5R)-5-(3,5-bis(trifluoromethyl)phenyl)-3-((2-(2-methoxy-5-nitro-4-(trifluoromethyl)phenyl)-5,5-dimethylcyclohex-1-enyl)methyl)-4-methyloxazolidin-2-one Starting material 39b (1.9 g, 3.3 mmol) was dissolved in methylene chloride (5 mL), and diisopropylethylamine (3.5 mL) and triphosgene (0.6 g) were slowly added dropwise thereto at 0° C., followed by stirring at room temperature for 3 hours. After completion of the reaction, the reaction mixture was diluted with ethyl acetate, and then washed with water and brine. The residue was dried with anhydrous magnesium sulfate, filtered, and then concentrated under reduced pressure to remove the solvent. The residue was purified by MPLC ($SiO_2$, EtOAc/hexane=15%~50%) to obtain compound 40b (0.9 g, 41.9%) as colorless oil.

Intermediate Compound 41a: (4S,5R)-3-((2-(5-amino-2-methox-4-methylphenyl)-5,5-dimethylcyclohex-1-enyl)methyl)-5-(3,5-bis(trifluoromethyl)phenyl)-4-methyloxazolidin-2-one Starting material 40a (0.6 g, 1.0 mmol) was dissolved in methanol (10 mL), and Raney nickel (small amount) was added dropwise thereto, followed by hydrogenation at room temperature for 2 hours. After completion of the reaction, the reaction mixture was filtered through celite to remove a solid compound, and then concentrated under reduced pressure to remove the solvent. The residue was purified by MPLC ($SiO_2$, EtOAc/hexane=0%~30%) to obtain compound 41a (0.41 g, 71.9%) as a yellow solid.

Intermediate Compound 41b: (4S,5R)-3-((2-(5-amino-2-methoxy-4-(trifluoromethyl)phenyl)-5,5-dimethylcyclohex-1-enyl)methyl)-5-(3,5-bis(trifluoromethyl)phenyl)-4-methyloxazolidin-2-one Starting material 40b (0.9 g, 1.38 mmol) was dissolved in methanol (5 mL), and Raney nickel (3 mL) was added dropwise thereto, followed by hydrogenation overnight at room temperature. After completion of the reaction, the reaction mixture was filtered through celite to remove a solid compound, and then concentrated under reduced pressure to remove the solvent. The residue was diluted with ethyl acetate, washed with water and brine, dried with anhydrous magnesium sulfate, filtered, and then concentrated under reduced pressure to remove the solvent. The residue was purified by MPLC (Sift, hexane/EtOAc=20%-60%) to obtain compound 41b (0.7 g, 91.5%) as a white foam solid.

Intermediate Compound 42a: (4S,5R)-5-(3,5-bis(trifluoromethyl)phenyl)-3-((2-(5-iodo-2-methoxy-4-methylphenyl)-5,5-dimethylcyclohex-1-enyl)methyl)-4-methyloxazolidin-2-one Starting material 41a (0.4 g, 0.70 mmol) was dissolved in acetonitrile (20 mL), and then para-toluenesulfonic acid monohydrate (0.4 g, 2.1 mmol) and a solution of sodium nitrite (0.05 g, 0.74 mmol) in water (2 mL) were sequentially slowly added dropwise thereto, followed by stirring at room temperature for 2 hours. Then, potassium iodide (0.13 g, 0.77 mmol) was added dropwise thereto, followed by stirring at room temperature for 1 hour. After completion of the reaction, the reaction mixture was diluted with ethyl acetate, and then washed with water and sodium thiosulfate solution. The organic layer was dried with anhydrous magnesium sulfate, filtered, and then concentrated under reduced pressure to remove the solvent. The residue was purified by MPLC ($SiO_2$, EtOAc/hexane=0%~20%) to obtain compound 42a (0.18 g, 37.7%) as colorless oil.

Intermediate Compound 42b: (4S,5R)-5-(3,5-bis(trifluoromethyl)phenyl)-3-((2-(5-iodo-2-methoxy-4-(trifluoromethyl)phenyl)-5,5-dicyclohex-1-enyl)methyl)-4-methyloxazolidin-2-one Starting material 41b (0.7 g, 1.12 mmol) was dissolved in acetonitrile (15 mL), and then para-toluenesulfonic acid monohydrate (0.64 g) and a solution of sodium nitrite (0.08 g) in water (2 mL) were sequentially slowly added dropwise thereto, followed by stirring at room temperature for 1 hour. Then, potassium iodide (0.2 g) was added dropwise thereto, followed by stirring overnight at room temperature. After completion of the reaction, the reaction mixture was diluted with ethyl acetate, and then washed with water and sodium thiosulfate solution. The organic layer was dried with anhydrous magnesium sulfate, filtered, and then concentrated under reduced pressure to remove the solvent. The residue was purified by MPLC ($SiO_2$, hexane/EtOAc=10~50%) to obtain compound 42b (0.48 g, 58.2%) as colorless oil.

Example 84

Compound 605 methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2'-(trifluoromethyl)biphenyl-4-carboxylate Starting material 42b (0.06 g, 0.08 mmol), boronic acid 7 (0.02 g, 0.1 mmol), Pd(dppf)$Cl_2$ (3.0 mg, 0.004 mmol) and sodium carbonate (0.02 g, 0.18 mmol) were dissolved in dimethoxyethane/water (v/v=3:1, 4 mL), and then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by preparative TLC (Sift, hexane/EtOAc=4:1) to obtain compound 605 (24 mg, 40.9%) as colorless oil.
MS (ESI) m/z 744.2 ($M^++H$).

Example 85

Compound 606 methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4'-methoxy-2'-(trifluoromethyl)biphenyl-4-carboxylate Starting material 42b (0.06 g, 0.08 mmol), boronic acid 7 (0.02 g, 0.1 mmol), Pd(dppf)$Cl_2$ (3.0 mg, 0.004 mmol) and sodium carbonate (0.02 g, 0.18 mmol) were dissolved in dimethoxyethane/water (v/v=3:1, 4 mL), and then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by preparative TLC (Sift, hexane/EtOAc=4:1) to obtain compound 606 (14 mg, 23.3%) as colorless oil.
MS (ESI) m/z 762.2 ($M^++H$).

Example 86

Compound 607 ethyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-3-fluoro-4'-methoxy-2'-(trifluoromethyl)biphenyl-4-carboxylate Starting material 42b (0.06 g, 0.08 mmol), boronic acid 7 (0.02 g, 0.1 mmol), Pd(dppf)$Cl_2$ (3.0 mg, 0.004 mmol) and sodium carbonate (0.02 g, 0.18 mmol) were dissolved in dimethoxyethane/water (v/v=3:1, 4 mL), and then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by preparative TLC ($SiO_2$, hexane/EtOAc=4:1) to obtain compound 607 (21 mg, 34.3%) as colorless oil.
MS (ESI) m/z 776.2 ($M^++H$).

Example 87

Compound 608 methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2-chloro-4'-methoxy-2'-(trifluoromethyl)biphenyl-4-carboxylate Starting material 42b (0.06 g, 0.08 mmol), boronic acid 7 (0.02 g, 0.1 mmol), Pd(dppf)$Cl_2$ (3.0 mg, 0.004 mmol) and sodium carbonate (0.02 g, 0.18 mmol) were dissolved in dimethoxyethane/water (v/v=3:1, 4 mL), and then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by preparative TLC ($SiO_2$, hexane/EtOAc=4:1) to obtain compound 608 (14 mg, 22.9%) as colorless oil.
MS (ESI) m/z 778.1 ($M^++H$).

Example 88

Compound 609 methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2-methyl-2'-(trifluoromethyl)biphenyl-4-carboxylate Starting material 42b (0.06 g, 0.08 mmol), boronic acid 7 (0.03 g, 0.1 mmol), Pd(dppf)$Cl_2$ (3.0 mg, 0.004 mmol) and sodium carbonate (0.02 g, 0.18 mmol) were dissolved in dimethoxyethane/water (v/v=3:1, 4 mL), and then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by preparative TLC ($SiO_2$, hexane/EtOAc=4:1) to obtain compound 609 (27 mg, 45.2%) as colorless oil.
MS (ESI) m/z 758.2 ($M^++H$).

Example 89

Compound 611

5-(5-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxy-2-(trifluoromethyl)phenyl)-3-fluoro picolinic acid Starting material 42b (0.06 g, 0.08 mmol), boronic acid 7 (0.03 g, 0.1 mmol), Pd(dppf)$Cl_2$ (3.0 mg, 0.004 mmol) and sodium carbonate (0.02 g, 0.18 mmol) were dissolved in dimethoxyethane/water (v/v=3:1, 4 mL), and then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by preparative TLC (SiO$_2$, CH$_2$Cl$_2$/CH$_3$OH=15:1) to obtain compound 611 (2.1 mg, 3.4%) as colorless oil.

MS (ESI) m/z 749.1 (M$^+$+H).

Example 90

Compound 612

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-4'-methoxy-2'-(trifluoromethyl)biphenyl-4-carboxylic acid Starting material 605 (0.02 g, 0.03 mmol) and lithium hydroxide monohydrate (3.0 mg, 0.13 mmol) were dissolved in dioxane/water (v/v=3:1, 4 mL), and then stirred overnight at 50° C. After completion of the reaction, the reaction mixture was cooled to room temperature, and 1M hydrochloric acid solution was added dropwise thereto until a pH of 6.0 was reached. The reaction mixture was diluted with ethyl acetate, and then washed with brine. The organic layer was dried with anhydrous magnesium sulfate, filtered, and then concentrated under reduced pressure to remove the solvent. The residue was purified by preparative TLC (Sift, hexane/EtOAc=1:1) to obtain compound 612 (10 mg, 53.6%) as colorless oil.

$^1$H NMR (400 MHz, CDCl$_3$); atropisomeric mixture; δ 7.90 (2d, 2H, J=8.4 Hz), 7.67 (s, 1H), 7.53 (2s, 2H), 7.16 (2d, 2H, J=8.1 Hz), 7.0 (2s, 1H), 6.75 (s, 1H), 5.41 (t, 1H, J=8.3 Hz), 3.85-3.65 (m, 5H), 3.30 (2d, 1H, J=14.4 Hz), 2.49-1.66 (m, 4H), 1.46 (m, 2H), 0.82 (3s, 6H), 0.25 (2d, 3H, J=6.5 Hz)

MS (ESI) m/z 730.3 (M$^+$+H).

Example 91

Compound 613

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-2-fluoro-4'-methoxy-2'-(trifluoromethyl)biphenyl-4-carboxylic acid Starting material 606 (0.01 g, 0.02 mmol) and lithium hydroxide monohydrate (2.0 mg, 0.09 mmol) were dissolved in dioxane/water (v/v=3:1, 4 mL), and then stirred overnight at 50° C. After completion of the reaction, the reaction mixture was cooled to room temperature, and 1M hydrochloric acid solution was added dropwise thereto until a pH of 6.0 was reached. The reaction mixture was diluted with ethyl acetate, and then washed with brine. The organic layer was dried with anhydrous magnesium sulfate, filtered, and then concentrated under reduced pressure to remove the solvent. The residue was purified by preparative TLC (Sift, hexane/EtOAc=1:1) to obtain compound 613 (9 mg, 62.7%) as colorless oil.

$^1$H NMR (400 MHz, CDCl$_3$); atropisomeric mixture; δ 7.98-7.73 (m, 5H), 7.39-7.22 (m, 3H), 6.98 (2s, 1H), 5.59 (m, 1H), 4.04-3.87 (m, 5H), 3.42 (2s, 1H), 2.45-1.89 (m, 4H), 1.48 (m, 2H), 1.01 (t, 6H, J=14.1 Hz), 0.43 (d, 3H, J=6.4 Hz)

MS (ESI) m/z 749.2 (M$^+$+H).

Example 92

Compound 614

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-3-fluoro-4'-methoxy-2'-(trifluoromethyl)biphenyl-4-carboxylic acid Starting material 607 (0.02 g, 0.03 mmol) and lithium hydroxide monohydrate (3.0 mg, 0.13 mmol) were dissolved in dioxane/water (v/v=3:1, 4 mL), and then stirred overnight at 50° C. After completion of the reaction, the reaction mixture was cooled to room temperature, and 1M hydrochloric acid solution was added dropwise thereto until a pH of 6.0 was reached. The reaction mixture was diluted with ethyl acetate, and then washed with brine. The organic layer was dried with anhydrous magnesium sulfate, filtered, and then concentrated under reduced pressure to remove the solvent. The residue was purified by preparative TLC (Sift, hexane/EtOAc=1:1) to obtain compound 614 (8 mg, 41.5%) as colorless oil.

$^1$H NMR (400 MHz, CDCl$_3$); atropisomeric mixture; δ 7.96 (m, 1H), 7.89 (s, 1H), 7.72 (2s, 2H), 7.23-6.94 (m, 4H), 5.61 (t, 1H, J=8.4 Hz), 4.04-3.85 (m, 5H), 3.47 (2d, 1H, J=15.1 Hz), 2.45-1.89 (m, 4H), 1.49 (m, 2H), 1.01 (2d, 6H, J=14.8 Hz), 0.49 (2d, 3H, J=6.6 Hz)

MS (ESI) m/z 748.2 (M$^+$+H).

Example 93

Compound 615

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-2-chloro-4'-methoxy-2'-(trifluoromethyl)biphenyl-4-carboxylic acid Starting material 608 (0.01 g, 0.02 mmol) and lithium hydroxide monohydrate (2.0 mg, 0.08 mmol) were dissolved in dioxane/water (v/v=3:1, 4 mL), and then stirred overnight at 50° C. After completion of the reaction, the reaction mixture was cooled to room temperature, and 1M hydrochloric acid solution was added dropwise thereto until a pH of 6.0 was reached. The reaction mixture was diluted with ethyl acetate, and then washed with brine. The organic layer was dried with anhydrous magnesium sulfate, filtered, and then concentrated under reduced pressure to remove the solvent. The residue was purified by preparative TLC (Sift, hexane/EtOAc=1:1) to obtain compound 615 (9 mg, 71.3%) as colorless oil.

$^1$H NMR (400 MHz, CDCl$_3$); atropisomeric mixture; δ 8.16-7.66 (m, 5H), 7.38 (t, 1H, J=11.8 Hz), 7.26 (2s, 1H), 6.95 (2s, 1H), 5.63 (m, 1H), 4.05-3.85 (m, 5H), 3.71-3.39 (m, 1H), 2.54-1.89 (m, 4H), 1.49 (m, 2H), 0.96 (m, 6H), 0.43 (m, 3H)

MS (ESI) m/z 762.2 (M$^+$−H).

Example 94

Compound 616

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-4'-methoxy-2-methyl-2'-(trifluoromethyl)biphenyl-4-carboxylic acid Starting material 609 (0.03 g, 0.03 mmol) and lithium hydroxide monohydrate (4.0 mg, 0.17 mmol) were dissolved in dioxane/water (v/v=3:1, 4 mL), and then stirred overnight at 50° C. After completion of the reaction, the reaction mixture was cooled to room temperature, and 1M hydrochloric acid solution was added dropwise thereto until a pH of 6.0 was reached. The reaction mixture was diluted with ethyl acetate, and then washed with brine. The organic layer was dried with anhydrous magnesium sulfate, filtered, and then concentrated under reduced pressure to remove the solvent. The residue was purified by preparative TLC (Sift, hexane/EtOAc=1:1) to obtain compound 616 (16 mg, 65.2%) as colorless oil.

$^1$H NMR (400 MHz, CDCl$_3$); atropisomeric mixture; δ 7.99-7.84 (m, 3H), 7.74-7.71 (m, 2H), 7.22 (m, 2H), 7.06-6.84 (m, 1H), 5.62 (m, 1H), 4.13-3.92 (m, 2H), 3.87 (4s, 3H), 3.59-3.39 (m, 1H), 2.53-1.85 (m, 7H), 1.46 (m, 2H), 1.01 (m, 6H), 0.44 (m, 3H)

MS (ESI) m/z 744.3 (M$^+$+H).

Example 95

Compound 619 methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2'-methylbiphenyl-4-carboxylate Starting material 42a (0.05 g, 0.07 mmol), boronic acid 7 (14 mg, 0.08 mmol), Pd(dppf)Cl$_2$ (2.0 mg, 0.003 mmol) and sodium carbonate (15 mg, 0.14 mmol) were dissolved in dimethoxyethane/water (v/v=3:1, 1.3 mL), and then stirred with microwave irradiation at 120° C. for 15 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (Sift, EtOAc/hexane=0%~30%) to obtain compound 619 (18 mg, 38.6%) as colorless oil.

$^1$H NMR (400 MHz, CDCl$_3$); atropisomeric mixture; δ 8.01-8.08 (m, 2H), 7.86 (s, 1H), 7.73 (d, 2H, J=10.1 Hz), 7.27-7.37 (m, 2H), 6.85 (d, 1H, J=4.2 Hz), 6.76 (d, 1H, J=19.4 Hz), 5.58-5.62 (m, 1H), 3.93-4.01 (m, 5H), 3.80 (d, 3H, J=13.7 Hz), 3.66 (d, 0.6H, J=13.7 Hz), 3.51 (d, 0.4H, J=14.6 Hz), 2.00-2.60 (m, 5H), 1.90-1.98 (m, 2H), 1.43-1.54 (m, 2H), 1.00-1.06 (m, 6H), 0.38-0.44 (m, 3H)

MS (ESI) m/z 690.2 (M$^+$+H).

Example 96

Compound 620

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-4'-methoxy-2'-methylbiphenyl-4-carboxylic acid Starting material 619 (0.02 g, 0.02 mmol) and lithium hydroxide monohydrate (3.0 mg, 0.11 mmol) were dissolved in dioxane/water (v/v=5:1, 0.6 mL), and then stirred overnight at 50° C. After completion of the reaction, the reaction mixture was cooled to room temperature, diluted with ethyl acetate, and then washed with 1M hydrochloric acid solution and brine. The organic layer was dried with anhydrous magnesium sulfate, filtered, and then concentrated under reduced pressure to remove the solvent. The residue was purified by MPLC (SiO$_2$, EtOAc/hexane=0%~50%) to obtain compound 620 (9 mg, 61.2%) as colorless oil.

$^1$H NMR (400 MHz, CDCl$_3$); atropisomeric mixture; δ 8.09 (m, 2H), 7.87 (s, 1H), 7.74 (d, 2H, J=9.7 Hz), 7.41 (d, 1H, J=8.3 Hz), 7.32 (d, 1H, J=8.3 Hz), 6.86 (d, 1H, J=5.0 Hz), 6.77 (d, 1H, J=19.3 Hz), 5.59-5.62 (m, 1H), 3.89-4.07 (m, 2H), 3.78-3.82 (m, 3H), 3.49-3.68 (m, 1H), 2.00-2.60 (m, 5H), 1.86-1.98 (m, 2H), 1.43-1.54 (m, 2H), 0.96-1.06 (m, 6H), 0.39-0.45 (m, 3H)

MS (ESI) m/z 676.2 (M$^+$+H).

Example 97

Compound 638 methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-3-chloro-4'-methoxy-2'-(trifluoromethyl)biphenyl-4-carboxylate Starting material 42b (0.06 g, 0.08 mmol), boronic acid 7 (0.04 g, 0.12 mmol), Pd(dppf)Cl$_2$ (3.0 mg, 0.004 mmol) and sodium carbonate (0.03 g, 0.24 mmol) were dissolved in dimethoxyethane/water (v/v=3:1, 4 mL), and then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by preparative TLC (Sift, hexane/EtOAc=4:1) to obtain compound 638 (15 mg, 25.7%) as colorless oil.

$^1$H NMR (400 MHz, CDCl$_3$); atropisomeric mixture; δ 7.86-7.80 (m, 2H), 7.72 (2s, 2H), 7.36 (2d, 1H, J=1.6 Hz), 7.24-7.16 (m, 2H), 6.92 (d, 1H, J=1.1 Hz), 5.61 (t, 1H, J=7.9 Hz), 4.04-3.84 (m, 8H), 3.47 (2d, 1H, J=14.5 Hz), 2.51-1.89 (m, 4H), 1.49 (m, 2H), 1.01 (2d, 6H, J=14.0 Hz), 0.46 (2d, 3H, J=6.6 Hz)

MS (ESI) m/z 778.1 (M$^+$+H).

Example 98

Compound 639 methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-3,4'-dimethoxy-2'-(trifluoromethyl)biphenyl-4-carboxylate Starting material 42b (0.06 g, 0.08 mmol), boronic acid 7 (0.03 g, 0.1 mmol), Pd(dppf)Cl$_2$ (3.0 mg, 0.004 mmol) and sodium carbonate (0.02 g, 0.19 mmol) were dissolved in dimethoxyethane/water (v/v=3:1, 4 mL), and then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by preparative TLC (Sift, hexane/EtOAc=4:1) to obtain compound 639 (11 mg, 20.3%) as colorless oil.

$^1$H NMR (400 MHz, CDCl$_3$); atropisomeric mixture; δ 7.87 (s, 1H), 7.79 (2d, 1H, J=7.8 Hz), 7.72 (2s, 2H), 7.18 (2s, 1H), 6.96-6.79 (m, 3H), 5.60 (2d, 1H, J=8.2 Hz), 4.05-3.83 (m, 11H), 3.48 (2d, 1H, J=14.7 Hz), 2.49-1.89 (m, 4H), 1.49 (m, 2H), 1.01 (2d, 6H, J=15.0 Hz), 0.46 (2d, 3H, J=6.6 Hz)

MS (ESI) m/z 774.2 (M$^+$+H).

Example 99

Compound 632

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-3-chloro-4'-methoxy-2'-(trifluoromethyl)biphenyl-4-carboxylic acid Starting material 638 (0.02 g, 0.02 mmol) and lithium hydroxide monohydrate (2.0 mg, 0.1 mmol) were dissolved in dioxane/water (v/v=3:1, 4 mL), and then stirred overnight at 45° C. After completion of the reaction, the reaction mixture was cooled to room temperature, and 1M hydrochloric acid solution was added dropwise thereto until a pH of 6.0 was reached. The reaction mixture was diluted with ethyl acetate, and then washed with brine. The organic layer was dried with anhydrous magnesium sulfate, filtered, and then concentrated under reduced pressure to remove the solvent. The residue was purified by preparative TLC (Sift, hexane/EtOAc=1:2) to obtain compound 632 (4 mg, 27.2%) as colorless oil.

$^1$H NMR (400 MHz, CDCl$_3$); atropisomeric mixture; δ 7.99 (2d, 1H, J=8.0 Hz), 7.87 (s, 1H), 7.73 (2s, 2H), 7.39 (2d, 1H, J=1.5 Hz), 7.31-7.19 (m, 2H), 6.94 (2s, 1H), 5.62 (t, 1H, J=8.1 Hz), 4.04-3.89 (m, 2H), 3.83 (2s, 3H), 3.48 (2d, 1H, J=14.6 Hz), 2.49-1.86 (m, 4H), 1.48 (m, 2H), 1.01 (2d, 6H, J=14.0 Hz), 0.46 (2d, 3H, J=6.6 Hz)

MS (ESI) m/z 764.1 (M$^+$+H).

Example 100

Compound 633

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-3,4'-dimethoxy-2'-(trifluoromethyl)biphenyl-4-carboxylic acid Starting material 639 (9.0 mg, 0.01 mmol) and lithium hydroxide monohydrate (1.0 mg, 0.06 mmol) were dissolved in dioxane/water (v/v=3:1, 4 mL), and then stirred overnight at 45° C. After completion of the reaction, the reaction mixture was cooled to room temperature, and 1M hydrochloric acid solution was added dropwise thereto until a pH of 6.0 was reached. The reaction mixture was diluted with ethyl acetate, and then washed with brine. The organic layer was dried with anhydrous magnesium sulfate, filtered, and then concentrated under reduced pressure to remove the solvent. The residue was purified by preparative TLC (Sift, hexane/EtOAc=1:2) to obtain compound 633 (7 mg, 73.6%) as colorless oil.

$^1$H NMR (400 MHz, CDCl$_3$); atropisomeric mixture; δ 8.18 (2d, 1H, J=8.2 Hz), 7.85 (s, 1H), 7.71 (2s, 2H), 7.23 (2s, 1H), 7.09-6.97 (m, 3H), 5.60 (2d, 1H, J=8.1 Hz), 4.13 (2s, 3H), 4.01 (m, 2H), 3.81 (2s, 3H), 3.47 (2d, 1H, J=14.6 Hz), 2.55-1.93 (m, 4H), 1.52 (m, 2H), 1.04 (2d, 6H, J=12.2 Hz), 0.42 (2d, 3H, J=6.5 Hz)

MS (ESI) m/z 760.2 (M$^+$+H).

Example 101

Compound 683 methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2,2'-dimethyl-biphenyl-4-carboxylate Starting material 42a (0.080 g, 0.117 mmol), methyl 3-methyl-4-(4,4,5,5-tetramethyl-1,3,2-dioxaborolan-2-yl)benzoate (0.036 g, 0.129 mmol), Pd(di-t-Bupf)Cl$_2$ (0.004 g, 0.006 mmol) and sodium carbonate (0.025 g, 0.235 mmol) were added to dimethoxyethane (1 mL)/water (0.3 mL) and heated by microwave irradiation at 120° C. for 15 minutes. Then, the reaction mixture was cooled to room temperature, and water was added thereto, followed by extraction with ethyl acetate. The organic layer was washed with brine, dried with anhydrous magnesium sulfate, and then concentrated under reduced pressure. The concentrate was purified by column chromatography (Sift, EtOAc/hexane=0%~15%) to obtain compound 683 (0.025 g, 30.3%) as colorless oil.

$^1$H NMR (400 MHz, CDCl$_3$); 1:1 atropisomeric mixture; δ 7.94 (s, 1H), 7.87-7.88 (m, 2H), 7.72-7.75 (m, 2H), 6.95-7.18 (m, 1H), 6.68-6.78 (m, 2H), 5.60-5.64 (m, 1H), 3.87-4.06 (m, 2H), 3.91-3.93 (m, 3H), 3.77-3.81 (m, 3H), 3.48-3.64 (m, 1H), 2.20-2.60 (m, 2H), 2.01-2.18 (m, 6H), 1.87-1.98 (m, 2H), 1.42-1.52 (m, 2H), 0.96-1.05 (m, 6H), 0.32-0.46 (m, 3H)

MS (ESI) m/z 704.2 (M$^+$+H).

Example 102

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-4'-methoxy-2,2'-dimethylbiphenyl-4-carboxylic acid Starting material 683 (0.025 g, 0.036 mmol) and anhydrous lithium hydroxide (0.004 g, 0.178 mmol) were dissolved in dioxane (1 mL)/water (0.25 mL) at 50° C., and the reaction mixture was stirred at the same temperature for 8 hours. Then, an aqueous solution of 1M hydrochloric acid was added to the reaction mixture, followed by extraction with ethyl acetate. The organic layer was washed with brine, dried with anhydrous magnesium sulfate, and then concentrated under reduced pressure. The concentrate was purified by column chromatography (Sift, EtOAc/hexane=0%~50%) to obtain desired compound 684 (0.011 g, 44.9%) as a white foam solid.

$^1$H NMR (400 MHz, CDCl$_3$); 1:1 atropisomeric mixture; δ 7.94-8.02 (m, 2H), 7.87 (s, 1H), 7.74 (d, 1H, J=9.6 Hz), 7.00-7.23 (m, 1H), 6.69-6.79 (m, 2H), 5.61-5.63 (m, 1H), 3.88-4.02 (m, 2H), 3.78-3.82 (m, 3H), 3.50-3.36 (m, 1H), 2.20-2.60 (m, 2H), 2.03-2.18 (m, 6H), 1.87-1.94 (m, 2H), 1.40-1.60 (m, 2H), 0.96-1.06 (m, 6H), 0.33-0.47 (m, 3H)

MS (ESI) m/z 690.3 (M$^+$+H).

Preparation of Novel Compounds According to Reaction Scheme 11

Example 103

Compound 594 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2,4'-dimethoxybiphenyl-4-carboxylate Starting material 17 (50 mg, 0.09 mmol) and methyl 5'-chloro-2,4'-dimethoxybiphenyl-4-carboxylate 45 (36 mg, 0.12 mmol) were dissolved in dimethoxyethane/water (v/v=3:1, 0.4 mL), followed by degassing. Then, Pd(dbpf)Cl$_2$ (13 mg, 0.02 mmol) and sodium carbonate (87 mg, 0.83 mmol) were added dropwise to the reaction mixture, and the mixture was stirred with microwave irradiation at 120° C. for 20 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (SiO$_2$, EtOAc/hexane=10%~30%) to obtain compound 594 (15 mg, 24%) as colorless oil.
MS (ESI) m/z 706.2 (M$^+$+H).

Example 104

Compound 597

3'-(2-(((4S,5R)-5-(3,5-bis(trifluoromethyl)phenyl)-4-methyl-2-oxooxazolidin-3-yl)methyl)-4,4-dimethylcyclohex-1-enyl)-2,4'-dimethoxybiphenyl-4-carboxylic acid Starting material 594 (13 mg, 0.02 mmol) was dissolved in dioxane (1 mL), and a solution of lithium hydroxide monohydrate (4 mg, 0.09 mmol) in water (0.25 mL) was added dropwise thereto, followed by stirring at 50° C. for 3 hours. After completion of the reaction, the reaction mixture was cooled to room temperature, diluted with ethyl acetate, and then washed with water, saturated ammonium chloride and brine. The organic layer was dried with anhydrous magnesium sulfate, filtered, and then concentrated under reduced pressure to remove the solvent. The residue was purified by preparative TLC (hexane/EtOAc=50%) to obtain compound 597 (5 mg, 39%) as a yellow solid.
$^1$H NMR (400 MHz, CDCl$_3$); 1:1.6 atropisomeric mixture; δ 7.85-7.83 (br m, 1H), 7.79-7.72 (m, 3H), 7.66-7.62 (m, 1H), 7.45-7.42 (m, 1H), 7.38-7.28 (m, 1H), 7.20-7.17 (m, 1H), 6.92-6.87 (m, 1H), 5.60-5.55 (m, 1H), 4.01-3.79 (m, 8H), 3.72-3.53 (m, 1H), 2.57-2.02 (br m, 2H), 1.99-1.94 (br m, 2H), 1.50-1.41 (m, 2H), 1.06-1.01 (m, 6H), 0.44-0.34 (m, 3H)
MS (ESI) m/z 692.2 (M$^+$+H).

Example 105

Compound 667 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-fluoro-2-(trifluoromethyl)biphenyl-4-carboxylate Starting material 17 (0.26 g, 0.47 mmol), methyl 3'-chloro-5'-fluoro-2-(trifluoromethyl)biphenyl-4-carboxylate (0.13 g, 0.39 mmol), sodium carbonate (0.11 g, 1.02 mmol) and Pd(dppf)Cl$_2$ (12.7 mg, 0.02 mmol) were dissolved in dimethoxyethane/water (v/v=3:1, 12 mL), and then stirred with microwave irradiation at 120° C. for 30 minutes. After completion of the reaction, the reaction mixture was cooled to room temperature, and water was added thereto, followed by extraction with ethyl acetate. The organic layer was washed with brine, dried with anhydrous magnesium sulfate, filtered, and then concentrated under reduced pressure to remove the solvent. The residue was purified by MPLC (Sift, hexane/EtOAc=5%~20%) to obtain compound 667 (0.31 g, 100%) as colorless oil.
$^1$H NMR (400 MHz, CDCl$_3$); atropisomeric mixture; δ 8.41 (2d, 1H, J=1.5 Hz), 8.21 (dd, 1H, J=8.0, 1.3 Hz), 7.88-7.71 (m, 4H), 7.39 (d, 1H, J=8.0 Hz), 6.95-6.86 (m, 2H), 5.67-5.59 (m, 1H), 4.12-3.98 (m, 4H), 3.87 (m, 1H), 3.63 (2d, 1H, J=14.7 Hz), 2.38-2.08 (m, 2H), 1.95, 1.76 (2s, 2H), 1.50, 1.35 (2t, 2H, J=6.4 Hz), 1.05-0.88 (m, 6H), 0.74, 0.41 (2d, 3H, J=6.6 Hz)
MS (ESI) m/z 732.2 (M$^+$+H).

Example 106

Compound 668

3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-fluoro-2-(trifluoromethyl)biphenyl-4-carboxylic acid Starting material 667 (0.05 g, 0.07 mmol) and anhydrous lithium hydroxide (8.2 mg, 0.34 mmol) were dissolved in dioxane/water (v/v=4:1, 4.0 mL), and then stirred at 50° C. for 12 hours. After completion of the reaction, the reaction mixture was cooled to room temperature, and 1M hydrochloric acid solution was added dropwise thereto until a pH of 2 was reached. Then, the reaction mixture was extracted with ethyl acetate, and then washed with brine. The organic layer was washed with brine, dried with anhydrous magnesium sulfate, filtered, and then concentrated under reduced pressure to remove the solvent. The residue was purified by preparative TLC (Sift, hexane/EtOAc=1:2) to obtain compound 668 (17 mg, 34%) as colorless oil.
$^1$H NMR (400 MHz, CDCl$_3$); δ 8.47 (s, 1H), 8.27 (d, 1H, J=7.7 Hz), 7.86 (s, 1H), 7.74 (s, 2H), 7.42 (d, 1H, J=7.9 Hz), 6.94-6.87 (m, 3H), 5.61 (d, 1H, J=8.1 Hz), 4.04 (d, 1H, J=14.8 Hz), 3.88 (m, 1H), 3.77 (d, 1H, J=14.8 Hz), 2.34 (m, 2H), 1.95 (s, 2H), 1.50 (t, 2H, J=6.2 Hz), 1.01 (d, 6H, J=16.3 Hz), 0.41 (d, 3H, J=6.6 Hz)
MS (ESI) m/z 718.2 (M$^+$+H).

Example 107

Compound 692 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-fluoro-2-methylbiphenyl-4-carboxylate Starting material 17 (0.050 g, 0.089 mmol), methyl 3'-chloro-4'-fluoro-2-methyl-[1,1'-biphenyl]-4-carboxylate (0.023 g, 0.081 mmol), Pd(dbpf)Cl$_2$ (0.003 g, 0.004 mmol) and sodium carbonate (0.019 g, 0.178 mmol) were added to dimethoxyethane/water (v/v=3/1, 0.5 mL) and stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by preparative TLC (Sift, EtOAc/hexane=14%) to obtain compound 692 (0.053 g, 97%) as a white foam solid.

$^1$H NMR (400 MHz, CDCl$_3$); δ 7.92-7.86 (m, 3H), 7.76-7.72 (m, 2H), 7.26-7.17 (m, 2H), 7.11-7.01 (m, 2H), 5.66-5.59 (m, 1H), 4.08-3.91 (m, 5H), 3.64-3.61 (m, 1H), 2.50-2.24 (m, 5H), 1.97 (s, 2H), 1.55-1.49 (m, 2H), 1.06-1.01 (m, 6H), 0.46-0.42 (m, 3H)

MS (ESI) m/z 678.1 (M$^+$+H).

Example 108

Compound 694

3'-(2-(((4S,5R)-5-(3,5-bis(trifluoromethyl)phenyl)-4-methyl-2-oxooxazolidin-3-yl)methyl)-4,4-dimethyl-cyclohex-1-enyl)-4'-fluoro-2-methylbiphenyl-4-carboxylic acid Starting material 692 (0.053 g, 0.078 mmol) and lithium hydroxide monohydrate (0.016 g, 0.392 mmol) were dissolved in dioxane/water (v/v=4:1, 1.0 mL), and then stirred at 50° C. for 4 hours. After completion of the reaction, the reaction mixture was cooled to room temperature, concentrated under reduced pressure to remove the solvent, and then diluted with ethyl acetate, and 1M hydrochloric acid solution was added dropwise thereto until a pH of 2 was reached, followed by washing with water. The organic layer was dried with anhydrous magnesium sulfate, filtered, and then concentrated under reduced pressure to remove the solvent. The residue was purified by preparative TLC (SiO$_2$, CH$_3$OH/CH$_2$Cl$_2$=10%) to obtain compound 694 (0.031 g, 59%) as colorless oil.

$^1$H NMR (400 MHz, CDCl$_3$); δ 8.02-7.96 (m, 2H), 7.86-7.77 (m, 3H), 7.31-7.20 (m, 2H), 7.19-7.03 (m, 2H), 5.67-5.60 (m, 1H), 4.13-4.01 (m, 2H), 3.65-3.62 (m, 1H), 2.53-2.22 (m, 5H), 1.98 (s, 2H), 1.56-1.49 (m, 2H), 1.07-1.00 (m, 6H), 0.48-0.44 (m, 3H)

MS (ESI) m/z 664.2 (M$^+$+H).

Example 109

Compound 693 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-fluoro-2-(trifluoromethyl)biphenyl-4-carboxylate Starting material 17 (0.050 g, 0.089 mmol), methyl 3'-chloro-4'-fluoro-2-(trifluoromethyl)-[1,1'-biphenyl]-4-carboxylate (0.027 g, 0.081 mmol), Pd(dbpf)Cl$_2$ (0.003 g, 0.004 mmol) and sodium carbonate (0.019 g, 0.178 mmol) were added to dimethoxyethane/water (v/v=3/1, 0.5 mL) and stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by preparative TLC (SiO$_2$, EtOAc/hexane=14%) to obtain compound 693 (0.036 g, 61%) as a pale yellow foam solid.

$^1$H NMR (400 MHz, CDCl$_3$); δ 8.43 (d, 1H, J=5.3 Hz), 8.23 (t, 1H, J=8.9 Hz), 7.88 (s, 1H), 7.78-7.74 (m, 2H), 7.42 (dd, 1H, J=19.7, 8.0 Hz), 7.23-7.21 (m, 1H), 7.17-7.06 (m, 2H), 5.67-5.61 (m, 1H), 4.15-3.91 (m, 5H), 3.68-3.60 (m, 1H), 2.50-2.19 (m, 2H), 2.06-1.94 (m, 2H), 1.59-1.49 (m, 2H), 1.08-1.02 (m, 6H), 0.48-0.41 (m, 3H)

MS (ESI) m/z 732.1 (M$^+$+H).

Example 110

Compound 695

3'-(2-(((4S,5R)-5-(3,5-bis(trifluoromethyl)phenyl)-4-methyl-2-oxooxazolidin-3-yl)methyl)-4,4-dimethyl-cyclohex-1-enyl)-4'-fluoro-2-(trifluoromethyl)biphenyl-4-carboxylic acid Starting material 693 (0.036 g, 0.050 mmol) and lithium hydroxide monohydrate (0.010 g, 0.248 mmol) were dissolved in dioxane/water (v/v=4:1, 1.0 mL), and then stirred at 50° C. for 4 hours. After completion of the reaction, the reaction mixture was cooled to room temperature, concentrated under reduced pressure to remove the solvent, and then diluted with ethyl acetate, and 1M hydrochloric acid solution was added dropwise thereto until a pH of 2 was reached, followed by washing with water.

The organic layer was dried with anhydrous magnesium sulfate, filtered, and then concentrated under reduced pressure to remove the solvent. The residue was purified by preparative TLC (SiO$_2$, CH$_3$OH/CH$_2$Cl$_2$=10%) to obtain compound 695 (0.018 g, 51%) as a white foam solid.

$^1$H NMR (400 MHz, CDCl$_3$); δ 8.51 (d, 1H, J=4.6 Hz), 8.31 (t, 1H, J=8.5 Hz), 7.89 (s, 1H), 7.78 (d, 2H, J=15.4 Hz), 7.47 (dd, 1H, J=18.9, 8.0 Hz), 7.24 (s, 1H), 7.19-7.08 (m, 2H), 5.70-5.63 (m, 1H), 4.16-3.92 (m, 2H), 3.69-3.62 (m, 1H), 2.56-2.18 (m, 2H), 2.06-1.95 (m, 2H), 1.61-1.50 (m, 2H), 1.08-1.03 (m, 6H), 0.45-0.39 (m, 3H)

MS (ESI) m/z 718.1 (M$^+$+H).

Example 111

Compound 699 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2,5'-difluorobiphenyl-4-carboxylate Starting material 17 (0.16 g, 0.28 mmol), methyl 3'-chloro-2,5'-difluorobiphenyl-4-carboxylate (0.06 g, 0.23 mmol), sodium carbonate (0.06 g, 0.6 mmol) and Pd(dppf)Cl$_2$ (7.5 mg, 0.01 mmol) were dissolved in dimethoxyethane/water (v/v=3:1, 4 mL), and then stirred with microwave irradiation at 120° C. for 30 minutes. After completion, the reaction mixture was cooled to room temperature, and water was added thereto, followed by extraction with ethyl acetate. The organic layer was washed with brine, dried with anhydrous magnesium sulfate, filtered, and then concentrated under reduced pressure to remove the solvent. The residue was purified by MPLC (SiO$_2$, hexane/EtOAc=5%~30%) to obtain compound 699 (67 mg, 56.7%) as colorless oil.

$^1$H NMR (400 MHz, CDCl$_3$); atropisomeric mixture; δ 7.89-7.73 (m, 4H), 7.49-7.42 (m, 2H), 7.17-7.10 (m, 2H), 6.89-6.86 (m, 1H), 5.68-5.55 (m, 1H), 4.12-3.90 (m, 5H), 3.62 (2d, 1H, J=14.9 Hz), 2.37-2.07 (m, 2H), 1.97, 1.76 (2s, 2H), 1.51, 1.34 (2t, 2H, J=6.4 Hz), 1.06-0.94 (m, 6H), 0.37 (2d, 3H, J=6.5 Hz)

MS (ESI) m/z 682.2 (M$^+$+H).

Example 112

Compound 702

3'-(2-(((4S,5R)-5-(3,5-bis(trifluoromethyl)phenyl)-4-methyl-2-oxooxazolidin-3-yl)methyl)-4,4-dimethyl-cyclohex-1-enyl)-2,5'-difluorobiphenyl-4-carboxylic acid Starting material 699 (0.02 g, 0.03 mmol) and anhydrous lithium hydroxide (3.3 mg, 0.14 mmol) were dissolved in dioxane/water (v/v=4:1, 1.25 mL), and then stirred at 45° C. for 12 hours. After completion of the reaction, the reaction mixture was cooled to room temperature, and 1M hydrochloric acid solution was added dropwise thereto until a pH of 2 was reached. Next, the reaction mixture was extracted with ethyl acetate, and then washed with brine. The organic layer was dried with anhydrous magnesium sulfate, filtered, and then concentrated under reduced pressure to remove the solvent. The residue was purified by preparative TLC (SiO$_2$, hexane/EtOAc=1:2) to obtain compound 702 (11 mg, 59.1%) as colorless oil.

$^1$H NMR (400 MHz, CDCl$_3$); δ 8.01-7.88 (m, 3H), 7.74 (s, 2H), 7.52 (m, 1H), 7.21-7.12 (m, 2H), 6.90 (m, 1H), 5.59 (d, 1H, J=6.8 Hz), 4.07 (d, 1H, J=15.0 Hz), 3.96 (m, 1H), 3.81 (d, 1H, J=14.9 Hz), 2.26 (m, 2H), 1.93 (s, 2H), 1.47 (m, 2H), 1.04 (d, 6H, J=12.9 Hz), 0.46 (d, 3H, J=6.7 Hz)

MS (ESI) m/z 669.1 (M$^+$+H).

Example 113

Compound 700 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-fluorobiphenyl-4-carboxylate Starting material 17 (0.14 g, 0.25 mmol), methyl 3'-chloro-5'-fluorobiphenyl-4-carboxylate (0.05 g, 0.2 mmol), sodium carbonate (56.2 mg, 0.5 mmol) and Pd(dppf)Cl$_2$ (6.6 mg, 0.01 mmol) were dissolved in dimethoxyethane/water (v/v=3:1, 4 mL), and then stirred with microwave irradiation at 120° C. for 30 minutes. After completion, the reaction mixture was cooled to room temperature, poured into water, and extracted with ethyl acetate. The organic layer was washed with brine, dried with anhydrous magnesium sulfate, filtered, and then concentrated under reduced pressure to remove the solvent. The residue was purified by MPLC (SiO$_2$, hexane/EtOAc=5%~30%) to obtain compound 700 (88 mg, 65%) as colorless oil.

$^1$H NMR (400 MHz, CDCl$_3$); δ 8.09 (m, 2H), 7.85 (s, 1H), 7.71 (s, 2H), 7.59 (m, 2H), 7.21 (m, 1H), 7.13 (t, 1H, J=1.5 Hz), 6.84 (m, 1H), 5.60 (d, 1H, J=8.1 Hz), 4.07 (d, 1H, J=12.9 Hz), 3.94 (m, 4H), 3.73 (d, 1H, J=14.9 Hz), 2.33 (m, 2H), 2.04 (m, 2H), 1.52 (t, 2H, J=6.4 Hz), 1.03 (d, 6H, J=15.4 Hz), 0.43 (d, 3H, J=6.6 Hz)

MS (ESI) m/z 664.2 (M$^+$+H).

Example 114

Compound 703

3'-(2-(((4S,5R)-5-(3,5-bis(trifluoromethyl)phenyl)-4-methyl-2-oxooxazolidin-3-yl)methyl)-4,4-dimethyl-cyclohex-1-enyl)-5'-fluorobiphenyl-4-carboxylic acid Starting material 700 (0.02 g, 0.04 mmol) and anhydrous lithium hydroxide (4.3 mg, 0.18 mmol) were dissolved in dioxane/water (v/v=4:1, 1.25 mL), and then stirred at 45° C. for 12 hours. After completion of the reaction, the reaction mixture was cooled to room temperature, and 1M hydrochloric acid solution was added dropwise thereto until a pH of 2 was reached. Next, the reaction mixture was extracted with ethyl acetate, and then washed with brine. The organic layer was dried with anhydrous magnesium sulfate, filtered, and then concentrated under reduced pressure to remove the solvent. The residue was purified by preparative TLC (SiO$_2$, hexane/EtOAc=1:2) to obtain compound 703 (15 mg, 63.8%) as colorless oil.

$^1$H NMR (400 MHz, CDCl$_3$); δ 8.16 (d, 2H, J=4.1 Hz), 7.85 (s, 1H), 7.72 (s, 2H), 7.59 (d, 2H, J=11.5 Hz), 7.21-7.13 (m, 2H), 6.85 (m, 1H), 5.61 (d, 1H, J=8.2 Hz), 4.09 (d, 1H, J=14.9 Hz), 3.94 (m, 1H), 3.73 (d, 1H, J=14.9 Hz), 2.36 (m, 2H), 2.01 (m, 2H), 1.52 (t, 2H, J=6.2 Hz), 1.04 (d, 6H, J=15.6 Hz), 0.43 (d, 3H, J=6.5 Hz)

MS (ESI) m/z 650.1 (M$^+$+H).

Example 115

Compound 701 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluorobiphenyl-4-carboxylate Starting material 17 (0.16 g, 0.28 mmol), methyl 3'-chloro-2-fluorobiphenyl-4-carboxylate (0.06 g, 0.2 mmol), sodium carbonate (63.5 mg, 0.6 mmol) and Pd(dppf)Cl$_2$ (7.5 mg, 0.01 mmol) were dissolved in dimethoxyethane/water (v/v=3:1, 4 mL), and then stirred with microwave irradiation at 120° C. for 30 minutes. After completion, the reaction mixture was cooled to room temperature, poured into water, and extracted with ethyl acetate. The organic layer was washed with brine, dried with anhydrous magnesium sulfate, filtered, and then concentrated under reduced pressure to remove the solvent. The residue was purified by MPLC (SiO$_2$, hexane/EtOAc=5%~30%) to obtain compound 701 (64 mg, 41.8%) as colorless oil.

$^1$H NMR (400 MHz, CDCl$_3$); δ 7.88 (2d, 1H, J=1.6 Hz), 7.84 (s, 1H), 7.79 (2d, 1H, J=1.5 Hz), 7.73 (s, 2H), 7.50-7.42 (m, 3H), 7.32 (s, 1H), 7.15 (m, 1H), 5.56 (d, 1H, J=8.1 Hz), 4.04 (d, 1H, J=14.8 Hz), 3.94-3.89 (m, 4H), 3.75 (d, 1H, J=14.8 Hz), 2.38 (m, 2H), 1.97 (s, 2H), 1.51 (t, 2H, J=6.4 Hz), 1.03 (d, 6H, J=12.9 Hz), 0.33 (d, 3H, J=6.5 Hz)

MS (ESI) m/z 664.1 (M$^+$+H).

Example 116

Compound 704

3'-(2-(((4S,5R)-5-(3,5-bis(trifluoromethyl)phenyl)-4-methyl-2-oxooxazolidin-3-yl)methyl)-4,4-dimethyl-cyclohex-1-enyl)-2-fluorobiphenyl-4-carboxylic acid Starting material 701 (0.02 g, 0.04 mmol) and anhydrous lithium hydroxide (4.3 mg, 0.18 mmol) were dissolved in dioxane/water (v/v=4:1, 1.25 mL), and then stirred at 45° C. for 12 hours. After completion of the reaction, the reaction mixture was cooled to room temperature, and 1M hydrochloric acid solution was added dropwise thereto until a pH of 2 was reached. Next, the reaction mixture was extracted with ethyl acetate, and then washed with brine. The organic layer was dried with anhydrous magnesium sulfate, filtered, and then concentrated under reduced pressure to remove the solvent. The residue was purified by preparative TLC (SiO$_2$, hexane/EtOAc=1:2) to obtain compound 704 (7 mg, 29.8%) as colorless oil.

$^1$H NMR (400 MHz, CDCl$_3$); δ 7.95 (dd, 1H, J=8.0, 1.6 Hz), 7.88-7.86 (m, 3H), 7.73 (s, 2H), 7.53 (t, 1H, J=7.8 Hz), 7.44 (m, 2H), 7.34 (s, 1H), 7.18 (m, 1H), 5.57 (d, 1H, J=8.1 Hz), 4.06 (d, 1H, J=15.0 Hz), 3.93 (m, 1H), 3.76 (d, 1H, J=14.9 Hz), 2.42 (m, 2H), 2.00 (m, 2H), 1.52 (t, 2H, J=6.3 Hz), 1.04 (d, 6H, J=12.9 Hz), 0.29 (d, 3H, J=6.6 Hz)

MS (ESI) m/z 650.2 (M$^+$+H).

Example 117

Compound 708 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-fluorobiphenyl-4-carboxylate Starting material 17 (0.050 g, 0.089 mmol), methyl 3'-chloro-4'-fluoro-[1,1'-biphenyl]-4-carboxylate (0.021 g, 0.081 mmol), Pd(dbpf)Cl$_2$ (0.003 g, 0.004 mmol) and sodium carbonate (0.019 g, 0.178 mmol) were dissolved in dimethoxyethane/water (v/v=3/1, 1.0 mL) and stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (SiO$_2$, EtOAc/hexane=0%~20%) to obtain compound 708 (0.028 g, 51%) as colorless oil.

$^1$H NMR (400 MHz, CDCl$_3$); δ 8.10-8.02 (m, 2H), 7.85 (s, 1H), 7.73 (d, 2H, J=12.2 Hz), 7.57 (dd, 2H, J=20.1, 8.2 Hz), 7.51-7.47 (m, 1H), 7.32-7.30 (m, 1H), 7.18-7.09 (m, 1H), 5.64-5.58 (m, 1H), 4.07-3.97 (m, 2H), 3.94-3.92 (m, 3H), 3.63-3.57 (m, 1H), 2.50-2.20 (m, 2H), 1.99-1.98 (m, 2H), 1.58-1.51 (m, 2H), 1.09-1.01 (m, 6H), 0.44 (t, 3H, J=7.2 Hz)

MS (ESI) m/z 664.3 (M$^+$+H).

Example 118

Compound 709

3'-(2-(((4S,5R)-5-(3,5-bis(trifluoromethyl)phenyl)-4-methyl-2-oxooxazolidin-3-yl)methyl)-4,4-dimethyl-cyclohex-1-enyl)-4'-fluorobiphenyl-4-carboxylic acid Starting material 708 (0.012 g, 0.019 mmol) and lithium hydroxide monohydrate (0.004 g, 0.093 mmol) were dissolved in dioxane/water (v/v=4:1, 1.0 mL), and then stirred at 50° C. for 4 hours. After completion of the reaction, the reaction mixture was cooled to room temperature, concentrated under reduced pressure to remove the solvent, and then diluted with ethyl acetate, and 1M hydrochloric acid solution was added dropwise thereto until a pH of 2 was reached, followed by washing with water. The organic layer was dried with anhydrous magnesium sulfate, filtered, and then concentrated under reduced pressure to remove the solvent. The residue was purified by preparative TLC (SiO$_2$, EtOAc/hexane=50%) to obtain compound 709 (0.008 g, 64%) as colorless liquid.

$^1$H NMR (400 MHz, CDCl$_3$); δ 8.21-8.15 (m, 2H), 7.86 (s, 1H), 7.73 (d, 2H, J=12.6 Hz), 7.61 (dd, 2H, J=20.0, 8.4 Hz), 7.53-7.49 (m, 1H), 7.35-7.31 (m, 1H), 7.20-7.11 (m, 1H), 5.65-5.58 (m, 1H), 4.10-3.93 (m, 2H), 3.63-3.59 (m, 1H), 2.52-2.21 (m, 2H), 1.94 (s, 2H), 1.59-1.53 (m, 2H), 1.08-1.03 (m, 6H), 0.48-0.43 (m, 3H)

MS (ESI) m/z 650.2 (M$^+$+H).

Example 119

Compound 714 methyl 4-(4-(2-(((4S,5R)-5-(3,5-bis(trifluoromethyl)phenyl)-4-methyl-2-oxooxazolidin-3-yl)methyl)-4,4-dimethylcyclohex-1-enyl)pyridin-2-yl)-3-methylbenzoate Starting material 17 (0.056 g, 0.099 mmol), methyl 4-(4-chloropyridin-2-yl)-3-methylbenzoate (0.026 g, 0.099 mmol), sodium carbonate (0.032 g, 0.298 mmol) and Pd(dbpf)Cl$_2$ (0.003 g, 0.005 mmol) were added to dimethoxyethane (0.9 mL)/water (0.3 mL) and heated by microwave irradiation at 120° C. for 30 minutes. Then, the reaction mixture was cooled to room temperature, and water was added thereto, followed by extraction with ethyl acetate. The organic layer was dried with anhydrous magnesium sulfate, and then concentrated under reduced pressure. The residue was purified by MPLC (SiO$_2$, EtOAc/hexane=0%~50%) to obtain desired compound 714 (0.020 g, 30.5%) as clear oil.

$^1$H NMR (400 MHz, CDCl$_3$); δ 8.66 (d, 1H, J=4.8 Hz), 7.94-7.85 (m, 3H), 7.70 (s, 2H), 7.41 (d, 1H, J=8.0 Hz), 7.18 (s, 1H), 7.07 (m, 1H), 5.60 (d, 1H, J=7.6 Hz), 4.08-4.04 (m, 1H), 3.91 (s, 4H), 3.70 (m, 1H), 2.45-2.20 (m, 5H), 1.95 (m, 2H), 1.51 (m, 2H), 1.25 (m, 2H), 1.01 (d, 6H, J=14.8 Hz), 0.43 (d, 3H, J=6.0 Hz)

MS (ESI) m/z 661.1 (M$^+$+H).

Example 120

Compound 716

4-(4-(2-(((4S,5R)-5-(3,5-bis(trifluoromethyl)phenyl)-4-methyl-2-oxooxazolidin-3-yl)methyl)-4,4-dimethylcyclohex-1-enyl)pyridin-2-yl)-3-methylbenzoic acid Starting material 714 (0.020 g, 0.030 mmol) and lithium hydroxide monohydrate (0.025 g, 0.605 mmol) were dissolved in dioxane (8 mL)/water (2 mL) at room temperature, and the reaction mixture was stirred at the same temperature for 16 hours. Then, 1M hydrochloric acid was added to the reaction mixture, followed by extraction with ethyl acetate. The organic layer was dried with anhydrous magnesium sulfate, and then concentrated under reduced pressure. The residue was purified by MPLC (SiO$_2$, EtOAc/hexane=0%~100%) to obtain desired compound 716 (0.012 g, 61.3%) as a white foam solid.

$^1$H NMR (400 MHz, CDCl$_3$); δ 8.72 (m, 1H), 7.97-7.81 (m, 3H), 7.66 (s, 2H), 7.45-7.14 (m, 3H), 5.58 (m, 1H), 3.97-3.91 (m, 2H), 3.61-3.54 (m, 1H), 2.36 (s, 3H), 2.28-2.09 (m, 2H), 1.91 (m, 2H), 1.50 (m, 2H), 1.01 (m, 6H), 0.46 (m, 3H)

MS (ESI) m/z 647.2 (M$^+$+H).

Example 121

Compound 726 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-chloro-2-methylbiphenyl-4-carboxylate Starting material 17 (0.150 g, 0.267 mmol), methyl 3'-bromo-4'-chloro-2-methylbiphenyl-4-carboxylate (WO 2007/79186 A2) (0.136 g, 0.401 mmol), Pd(PPh$_3$)$_2$Cl$_2$ (0.009 g, 0.013 mmol) and sodium carbonate (0.085 g, 0.802 mmol) were added to dimethylformamide (0.8 mL)/water (0.4 mL) and heated by microwave irradiation at 90° C. for 20 minutes. Then, the reaction mixture was cooled to room temperature, and water was added thereto, followed by extraction with ethyl acetate. The organic layer was dried with anhydrous magnesium sulfate, and then concentrated under reduced pressure. The residue was purified by MPLC (SiO$_2$, EtOAc/hexane=0%~20%) to obtain desired compound 726 (0.030 g, 16.2%) in an impure form.

$^1$H NMR (400 MHz, CDCl$_3$); δ 7.97-7.73 (m, 5H), 7.46 (m, 1H), 7.18 (m, 2H), 7.05 (m, 1H), 5.67 (m, 1H), 4.15 (m, 2H), 3.95 (m, 3H), 3.55 (m, 1H), 2.60-2.35 (m, 2H), 2.30-2.26 (m, 3H), 2.00-1.90 (m, 2H), 1.57-1.45 (m, 2H), 1.00-0.91 (m, 6H), 0.50-0.46 (m, 3H)

MS (ESI) m/z 694.1 (M$^+$+H).

Example 122

Compound 727

3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-chloro-2-methylbiphenyl-4-carboxylic acid Starting material 726 (0.020 g, 0.029 mmol) and lithium hydroxide monohydrate (0.012 g, 0.288 mmol) were dissolved in dioxane (4 mL)/water (1 mL) at room temperature, and the reaction mixture was stirred at the same temperature for 16 hours. Then, 1M hydrochloric acid was added to the reaction mixture, followed by extraction with ethyl acetate. The organic layer was dried with anhydrous magnesium sulfate, and then concentrated under reduced pressure. The concentrate was purified by PTLC to obtain desired compound 727 (0.010 g, 51.0%) as a white foam solid.

$^1$H NMR (400 MHz, CDCl$_3$); δ 8.04-7.94 (m, 2H), 7.89 (m, 1H), 7.78-7.74 (m, 2H), 7.50-7.44 (m, 1H), 7.33-7.18 (m, 2H), 7.08 (m, 1H), 5.67 (2d, 1H, J=8.1 Hz), 4.17-3.95 (m, 2H), 3.53 (2d, 1H, J=14.8 Hz), 2.60-2.35 (m, 2H), 2.33-2.29 (m, 3H), 1.98 (m, 2H), 1.60-1.50 (m, 2H), 1.11-1.04 (m, 6H), 0.50 (2d, 3H, J=5.0 Hz)

MS (ESI) m/z 680.1 (M$^+$+H).

Preparation of Novel Compounds According to Reaction Scheme 12

Intermediate Compound 48: methyl 4'-methoxy-2-(trifluoromethyl)biphenyl-4-carboxylate Starting material 4-methoxyboronic acid 46 (0.32 g, 2.12 mmol), methyl 4-bromo-3-(trifluoromethyl)benzoate 47 (0.6 g, 2.12 mmol), Pd(dppf)Cl$_2$ (0.07 g, 0.11 mmol) and sodium carbonate (0.45 g, 4.24 mmol) were dissolved in dimethoxyethane/water (v/v=4:1, 5 mL), and then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (Sift 12 g, EtOAc/hexane=0%~15%) to obtain compound 48 (0.46 g, 70%) as colorless oil.

Intermediate Compound 49: Methyl 3'-iodo-4'-methoxy-2-(trifluoromethyl)biphenyl-4-carboxylate Starting material 48 (0.46 g, 1.48 mmol), iodine (0.41 g, 1.63 mmol) and silver sulfate (0.51 g, 1.63 mmol) were dissolved in methanol (10 mL), and then stirred at room temperature for 2 hours. After completion of the reaction, the reaction mixture was diluted with ethyl acetate, and then washed with saturated sodium thiosulfate solution and brine. The organic layer was dried with anhydrous magnesium sulfate, filtered, and then concentrated under reduced pressure to remove the solvent. The residue was purified by MPLC (SiO$_2$EtOAc/hexane=0%~15%) to obtain compound 49 (0.25 g, 39.1%) as a white solid.

Intermediate Compound 50: methyl 4'-methoxy-3'-(4,4,5,5-tetramethyl-1,3,2-dioxaborolan-2-yl)-2-(trifluoromethyl)biphenyl-4-carboxylate Starting material 49 (0.253 g, 0.580 mmol), bis(pinacolate)diboron (0.22 g, 0.87 mmol), Pd(dppf)Cl$_2$ (0.02 g, 0.03 mmol) and sodium carbonate (0.18 g, 1.74 mmol) were dissolved in dimethylsulfoxide (10 mL), and then stirred at 80° C. for 8 hours. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (SiO$_2$, EtOAc/hexane=0%~25%) to obtain compound 50 (75 mg, 29.6%) as colorless oil.

Intermediate Compound 51: methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2-(trifluoromethyl)biphenyl-4-carboxylate Starting material 50 (75 mg, 0.17 mmol), compound 16 (0.09 g, 0.17 mmol), Pd(dbpf)Cl$_2$ (6.0 mg, 0.009 mmol) and sodium carbonate (36 mg, 0.34 mmol) were dissolved in dimethoxyethane/water (v/v=4:1, 1.25 mL), and then stirred at 80° C. for 3 hours. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (Sift, EtOAc/hexane=0%~30%) to obtain compound 51 (0.4 g, 31.3%) as colorless oil.

Example 123

Compound 618

3'-(2-(((4S,5R)-5-(3,5-bis(trifluoromethyl)phenyl)-4-methyl-2-oxooxazolidin-3-yl)methyl)-4,4-dimethyl-cyclohex-1-enyl)-4'-methoxy-2-(trifluoromethyl) biphenyl-4-carboxylic acid Starting material 51 (0.04 g, 0.06 mmol) and anhydrous lithium hydroxide (7.0 mg, 0.29 mmol) were dissolved in dioxane/water (v/v=4:1, 1.25 mL), and then stirred at 50° C. for 8 hours. After completion of the reaction, the reaction mixture was cooled to room temperature, diluted with ethyl acetate, and then washed with 1M hydrochloric acid solution and brine. The organic layer was dried with anhydrous magnesium sulfate, filtered, and then concentrated under reduced pressure to remove the solvent. The residue was purified by MPLC ($SiO_2$, EtOAc/hexane=0%~50%) to obtain compound 618 (20 mg, 47.4%) as colorless oil.

$^1$H NMR (400 MHz, $CDCl_3$); 2:3 atropisomeric mixture; δ 8.50 (d, 0.6H, J=1.1 Hz), 8.48 (d, 0.4H, J=1.1 Hz), 8.29 (dd, 0.6H, J=6.0, 1.2 Hz), 8.26 (dd, 0.4H, J=6.0, 1.2 Hz), 7.88 (s, 1H), 7.77-7.74 (m, 2H), 7.49 (d, 0.6H, J=6.0 Hz), 7.42 (d, 0.4H, J=6.0 Hz), 7.24 (d, 0.4H, J=1.6 Hz), 7.22 (d, 0.6H, J=1.6 Hz), 7.03-6.99 (m, 1H), 6.96 (d, 0.4H, J=8.6 Hz), 6.92 (d, 0.6H, J=8.6 Hz), 5.66-5.62 (m, 1H), 4.07-3.90 (m, 2H), 3.86-3.84 (m, 3H), 3.69 (d, 0.6H, J=10.9 Hz), 3.54 (d, 0.4H, J=11.2 Hz), 2.60-2.02 (br m, 2H), 1.98-1.90 (br m, 2H), 1.58-1.45 (br m, 2H), 1.08-1.01 (m, 6H), 0.45 (d, 1.2H, J=4.9 Hz), 0.35 (d, 1.8H, J=4.9 Hz)

MS (ESI) m/z 730.1 ($M^+$+H).

Preparation of Novel Compounds According to Reaction Scheme 13

Intermediate Compound 53a: ethyl 2-(3-chlorophenyl)-5,5-dimethylcyclohex-1-enecarboxylate Starting material 52 (0.31 g, 1.01 mmol), compound 8 (0.12 mL, 1.0 mmol), Pd(dppf)$Cl_2$ (0.04 g, 0.05 mmol) and sodium carbonate (0.27 g, 2.5 mmol) were dissolved in dimethoxyethane/water (v/v=3:1, 12 mL), and then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC ($SiO_2$, EtOAc/hexane=5%) to obtain compound 53a (0.25 g, 84.9%) as colorless oil.

$^1$H NMR (400 MHz, $CDCl_3$); δ 7.22 (m, 2H), 7.12 (dd, 1H, J=2.6, 1.6 Hz), 7.00 (m, 1H), 3.89 (q, 2H, J=7.2 Hz), 2.37 (m, 2H), 2.21 (t, 2H, J=2.4 Hz), 1.49 (t, 2H, J=6.4 Hz), 1.01 (s, 6H), 0.89 (t, 3H, J=7.2 Hz).

Intermediate Compound 53b: ethyl 2-(3-chloro-5-fluorophenyl)-5,5-dimethylcyclohex-1-enecarboxylate Starting material 52 (0.51 g, 1.66 mmol), compound 8 (0.20 mL, 1.62 mmol), Pd(dppf)$Cl_2$ (0.07 g, 0.08 mmol) and sodium carbonate (0.44 g, 4.14 mmol) were dissolved in dimethoxyethane/water (v/v=3:1, 12 mL), and then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC ($SiO_2$, EtOAc/hexane=5%~35%) to obtain compound 53b (0.37 g, 71.9%) as colorless oil.

$^1$H NMR (400 MHz, $CDCl_3$); δ 6.97 (m, 1H), 6.91 (d, 1H, J=1.4 Hz), 6.75 (m, 1H), 3.93 (q, 2H, J=7.2 Hz), 2.34 (m, 2H), 2.20 (t, 2H, J=2.4 Hz), 1.48 (t, 2H, J=6.4 Hz), 0.99 (s, 6H), 0.93 (t, 3H, J=7.2 Hz).

Intermediate Compound 54a: 2-(3-chlorophenyl)-5,5-dimethylcyclohex-1-enecarbaldehyde Starting material 53a (0.25 g, 1.0 mmol) was dissolved in tetrahydrofuran (10 mL), and lithium aluminum hydride (2.6 mL) was added dropwise thereto at 0° C., followed by stirring overnight at room temperature. After completion of the reaction, the reaction mixture was diluted with ethyl acetate, and then washed with brine. The organic layer was dried with anhydrous magnesium sulfate, filtered, and then concentrated under reduced pressure to remove the solvent, thereby obtaining an alcohol compound (0.17 g, 79.4%) as colorless oil, which was then used in the next reaction without any additional purification.

The alcohol compound (0.17 g, 0.68 mmol) prepared as described above was dissolved in methylene chloride (10 mL), and DMP (0.43 g, 1.02 mmol) was added dropwise thereto. The reaction mixture was stirred at room temperature for 3 hours, diluted with ethyl acetate, and then washed with brine. The organic layer was dried with anhydrous magnesium sulfate, filtered, and then concentrated under reduced pressure to remove the solvent. The residue was purified by MPLC ($SiO_2$, EtOAc/hexane=5%~20%) to obtain compound 54a (0.13 g, 74.7%) as colorless oil.

Intermediate Compound 54b: 2-(3-chloro-5-fluorophenyl)-5,5-dimethylcyclohex-1-enecarbaldehyde Starting material 53b (0.31 g, 1.0 mmol) was dissolved in tetrahydrofuran (10 mL), and lithium aluminum hydride (1.5 mL) was added dropwise thereto at 0° C., followed by stirring at room temperature for 5 hours. After completion of the reaction, the reaction mixture was diluted with ethyl acetate, and then washed with brine. The organic layer was dried with anhydrous magnesium sulfate, filtered, and then concentrated under reduced pressure to remove the solvent, thereby obtaining an alcohol compound (0.29 g, 100%) as colorless oil, which was then used in the next reaction without any additional purification.

The alcohol compound (0.29 g, 1.06 mmol) was dissolved in methylene chloride (10 mL), and Dess-Martin periodinane (DMP) (0.68 g, 1.60 mmol) was added dropwise thereto. The reaction mixture was stirred overnight at room temperature, diluted with ethyl acetate, and then washed with brine. The organic layer was dried with anhydrous magnesium sulfate, filtered, and then concentrated under reduced pressure to remove the solvent. The residue was purified by MPLC (SiO$_2$, EtOAc/hexane=5%~25%) to obtain compound 54b (0.15 g, 53%) as yellow oil.

$^1$H NMR (400 MHz, CDCl$_3$); δ 9.52 (s, 1H), 7.11 (m, 1H), 7.03 (m, 1H), 6.88 (m, 1H), 2.51 (m, 2H), 2.15 (t, 2H, J=2.1 Hz), 1.54 (t, 2H, J=6.4 Hz), 0.99 (s, 6H).

Intermediate Compound 55a: (1R,2S)-1-(3,5-bis(trifluoromethyl)phenyl)-2-((2-(3-chlorophenyl)-5,5-dimethylcyclohex-1-enyl)methylamino)propan-1-ol Starting material 54a (0.13 g, 0.51 mmol), aminoalcohol compound 4 (0.17 g) and acetic acid (0.03 mL) were dissolved in methylene chloride (10 mL), and sodium cyanoborohydride (33.5 mg) was added dropwise thereto at room temperature, followed by stirring overnight. After completion of the reaction, the reaction mixture was diluted with ethyl acetate, and then washed with water and brine. The organic layer was dried with anhydrous magnesium sulfate, filtered, and then concentrated under reduced pressure to remove the solvent, thereby obtaining compound 55a (0.28 g, 100%) as colorless oil without additional purification.

Intermediate Compound 55b: (1R,2S)-1-(3,5-bis(trifluoromethyl)phenyl)-2-((2-(3-chloro-5-fluorophenyl)-5,5-dimethylcyclohex-1-enyl)methylamino)propan-1-ol Starting material 54b (0.15 g, 0.55 mmol), aminoalcohol compound 4 (0.19 g) and acetic acid (0.03 mL) were dissolved in methylene chloride (10 mL), and sodium cyanoborohydride (36.2 mg) was added dropwise thereto at room temperature, followed by stirring for 3 hours. After completion of the reaction, the reaction mixture was diluted with ethyl acetate, and then washed with water and brine. The organic layer was dried with anhydrous magnesium sulfate, filtered, and then concentrated under reduced pressure to remove the solvent, thereby obtaining compound 55b (0.33 g, 100%) as yellow oil without additional purification.

Intermediate Compound 56a: (4S,5R)-5-(3,5-bis(trifluoromethyl)phenyl)-3-((2-(3-chlorophenyl)-5,5-dimethylcyclohex-1-enyl)methyl)-4-methyloxazolidin-2-one Starting material 55a (0.28 g, 0.54 mmol) was dissolved in methylene chloride (5 mL), and diisopropylethylamine (0.56 mL) and triphosgene (0.1 g) were added thereto, followed by stirring overnight. After completion of the reaction, the reaction mixture was diluted with ethyl acetate, and then washed with water and brine. The organic layer was dried with anhydrous magnesium sulfate, filtered, and then concentrated under reduced pressure to remove the solvent. The residue was purified by MPLC (SiO$_2$, EtOAc/hexane=5%~20%) to obtain compound 56a (0.19 g, 63.3%) as colorless oil.

$^1$H NMR (400 MHz, CDCl$_3$); δ 7.85 (s, 1H), 7.73 (s, 2H), 7.25-7.20 (m, 2H), 7.09 (t, 1H, J=1.8 Hz), 6.98 (dt, 1H, J=7.0, 1.6 Hz), 5.59 (d, 1H, J=8.2 Hz), 4.01 (d, 1H, J=14.8 Hz), 3.89 (m, 1H), 3.64 (d, 1H, J=14.8 Hz), 2.37-2.25 (m, 2H), 1.93 (s, 2H), 1.49 (t, 2H, J=6.4 Hz), 1.00 (m, 6H), 0.39 (d, 3H, J=6.6 Hz)

MS (ESI) m/z 546.1 (M$^+$+H).

Intermediate Compound 56b: (4S,5R)-5-(3,5-bis(trifluoromethyl)phenyl)-3-((2-(3-chloro-5-fluorophenyl)-5,5-dimethylcyclohex-1-enyl)methyl)-4-methyloxazolidin-2-one Starting material 55b (0.33 g, 0.61 mmol) was dissolved in methylene chloride (5 mL), and diisopropylethylamine (0.64 mL) and triphosgene (0.1 g) were added thereto, followed by stirring overnight. After completion of the reaction, the reaction mixture was diluted with ethyl acetate, and then washed with water and brine. The organic layer was dried with anhydrous magnesium sulfate, filtered, and then concentrated under reduced pressure to remove the solvent. The residue was purified by MPLC (SiO$_2$, EtOAc/hexane=5%~20%) to obtain compound 56b (0.17 g, 48.9%) as colorless oil.

$^1$H NMR (400 MHz, CDCl$_3$); δ 7.86 (s, 1H), 7.74 (s, 2H), 6.99 (dt, 1H, J=8.4, 2.1 Hz), 6.89 (t, 1H, J=1.4 Hz), 6.73 (m, 1H), 5.61 (d, 1H, J=8.1 Hz), 4.03 (d, 1H, J=14.9 Hz), 3.91 (m, 1H), 3.63 (d, 1H, J=14.9 Hz), 2.32-2.24 (m, 2H), 1.93 (s, 2H), 1.49 (t, 2H, J=6.5 Hz), 1.01 (2s, 6H), 0.45 (d, 3H, J=6.6 Hz).

Example 124

Compound 649 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-methylbiphenyl-4-carboxylate Starting material 56a (0.13 g, 0.24 mmol), boronic acid pinacol ester 57 (0.08 g, 0.29 mmol), Pd(dbpf)Cl$_2$ (8.0 mg, 0.01 mmol) and sodium carbonate (0.06 g, 0.57 mmol) were dissolved in dimethoxyethane/water (v/v=3:1, 4 mL), and then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (Sift, EtOAc/hexane=5%~30%) to obtain compound 649 (15 mg, 9.5%) as colorless oil.

MS (ESI) m/z 660.3 (M$^+$+H).

Example 125

Compound 648 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-fluoro-2-methylbiphenyl-4-carboxylate Starting material 56b (0.07 g, 0.13 mmol), boronic acid pinacol ester 57 (0.04 g, 0.15 mmol), Pd(dbpf)Cl$_2$ (4.0 mg, 0.006 mmol) and sodium carbonate (0.03 g, 0.3 mmol) were dissolved in dimethoxyethane/water (v/v=3:1, 4 mL), and then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by preparative TLC (Sift, hexane/EtOAc=1:4) to obtain compound 648 (21 mg, 24.6%) as colorless oil.

$^1$H NMR (400 MHz, CDCl$_3$); δ 7.94 (s, 1H), 7.88-7.87 (m, 2H), 7.73 (s, 2H), 7.21 (d, 1H, J=8.0 Hz), 6.92 (dt, 1H, J=6.9, 2.2 Hz), 6.84-6.82 (m, 2H), 5.61 (d, 1H, J=8.1 Hz), 4.06 (d, 1H, J=14.6 Hz), 3.93-3.90 (m, 4H), 3.74 (d, 1H, J=14.8 Hz), 2.38-2.27 (m, 5H), 1.95 (s, 2H), 1.51 (t, 2H, J=6.5 Hz), 1.03, 1.00 (2s, 6H), 0.42 (d, 3H, J=6.6 Hz)

MS (ESI) m/z 678.2 (M$^+$+H).

Example 126

Compound 651

3'-(2-(((4S,5R)-5-(3,5-bis(trifluoromethyl)phenyl)-4-methyl-2-oxooxazolidin-3-yl)methyl)-4,4-dimethyl-cyclohex-1-enyl)-2-methylbiphenyl-4-carboxylic acid Starting material 649 (0.02 g, 0.02 mmol) and lithium hydroxide monohydrate (3.0 mg, 0.11 mmol) were dissolved in dioxane/water (v/v=3:1, 4 mL), and then stirred overnight at 45° C. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by preparative TLC (SiO$_2$, hexane/EtOAc=1:2) to obtain compound 651 (6.4 mg, 40.9%) as colorless oil.

$^1$H NMR (400 MHz, CDCl$_3$); δ 8.00 (s, 1H), 7.94 (d, 1H, J=8.0 Hz), 7.85 (s, 1H), 7.72 (s, 2H), 7.39 (t, 1H, J=7.6 Hz), 7.22 (m, 2H), 7.11 (d, 1H, J=7.6 Hz), 7.00 (s, 1H), 5.59 (d, 1H, J=8.0 Hz), 4.06 (d, 1H, J=14.6 Hz), 3.78 (m, 1H), 3.77 (d, 1H, J=14.7 Hz), 2.46-2.27 (m, 5H), 1.95 (s, 2H), 1.51 (t, 2H, J=6.2 Hz), 1.04, 1.01 (2s, 6H), 0.37 (d, 3H, J=6.5 Hz)

MS (ESI) m/z 646.2 (M$^+$+H).

Example 127

Compound 650

3'-(2-(((4S,5R)-5-(3,5-bis(trifluoromethyl)phenyl)-4-methyl-2-oxooxazolidin-3-yl)methyl)-4,4-dimethyl-cyclohex-1-enyl)-5'-fluoro-2-methylbiphenyl-4-carboxylic acid Starting material 648 (0.02 g, 0.03 mmol) and lithium hydroxide monohydrate (4.0 mg, 0.15 mmol) were dissolved in dioxane/water (v/v=3:1, 4 mL), and then stirred overnight at 45° C. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by preparative TLC (SiO$_2$, hexane/EtOAc=1:2) to obtain compound 650 (5.5 mg, 30.6%) as colorless oil.

$^1$H NMR (400 MHz, CDCl$_3$); δ 8.00 (s, 1H), 7.94 (d, 1H, J=8.0 Hz), 7.86 (s, 1H), 7.73 (s, 2H), 7.23 (s, 1H), 6.92-6.83 (m, 3H), 5.61 (d, 1H, J=8.0 Hz), 4.07 (d, 1H, J=14.8 Hz), 3.92 (m, 1H), 3.75 (d, 1H, J=14.7 Hz), 2.43-2.28 (m, 5H), 1.90 (s, 2H), 1.51 (t, 2H, J=6.4 Hz), 1.04, 1.00 (2s, 6H), 0.43 (d, 3H, J=6.6 Hz)

MS (ESI) m/z 664.2 (M$^+$+H).

Preparation of Novel Compounds According to Reaction Formula 14

Example 128

Compound 642 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-chloro-4'-methoxybi-phenyl-4-carboxylate Starting material 59 (0.26 g, 0.39 mmol), boronic acid 60 (0.09 g, 0.43 mmol), Pd(dbpf)Cl$_2$ (13 mg, 0.02 mmol) and sodium carbonate (0.12 g, 1.17 mmol) were dissolved in dimethoxyethane/water (v/v=3:1, 4 mL), and then stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (SiO$_2$, EtOAc/hexane=20%) to obtain compound 642 (0.12 g, 41.6%) as a white solid.

$^1$H NMR (400 MHz, CDCl$_3$); 1:1.40 atropisomeric mixture; δ 8.14 (d, 0.6H, J=1.6 Hz), 8.10 (d, 0.4H, J=1.6 Hz), 7.96 (dd, 0.6H, J=8.0, 1.7 Hz), 7.92 (dd, 0.4H, J=8.0, 1.7 Hz), 7.86-7.85 (m, 1H), 7.74-7.71 (m, 2H), 7.41-7.30 (m, 2H), 7.13-7.11 (m, 1H), 6.96 (d, 0.4H, J=8.5 Hz), 6.92 (d, 0.6H, J=8.5 Hz), 5.59 (d, 1H, J=8.1 Hz), 4.00-3.89 (m, 5H), 3.84-3.81 (m, 3H), 3.70 (d, 0.6H, J=14.7 Hz), 3.53 (d, 0.4H, J=14.7 Hz), 2.58-2.05 (m, 2H), 1.95-1.93 (m, 2H), 1.55-1.45 (m, 2H), 1.07-1.02 (m, 6H), 1.42 (d, 1.2H, J=6.5 Hz), 0.36 (d, 1.8H, J=6.5 Hz)

MS (ESI) m/z 710.1 (M$^+$+H).

Example 129

Compound 643

3'-(2-(((4S,5R)-5-(3,5-bis(trifluoromethyl)phenyl)-4-methyl-2-oxooxazolidin-3-yl)methyl)-4,4-dimethyl-cyclohex-1-enyl)-2-chloro-4'-methoxybiphenyl-4-carboxylic acid Starting material 642 (0.02 g, 0.03 mmol) and lithium hydroxide monohydrate (6.0 mg, 0.14 mmol) were dissolved in dioxane/water (v/v=4:1, 0.5 mL), and then stirred overnight at 45° C. After completion of the reaction, the reaction mixture was cooled to room temperature, concentrated under reduced pressure to remove the solvent, and then diluted with ethyl acetate, and 1M hydrochloric acid solution was added dropwise thereto until a pH of 2 was reached, followed by washing with water. The organic layer was dried with anhydrous magnesium sulfate, filtered, and then concentrated under reduced pressure to remove the solvent. The residue was purified by MPLC (Sift, CH$_2$Cl$_2$/CH$_3$OH=5%) to obtain compound 643 (19 mg, 95.9%) as a white solid.

$^1$H NMR (400 MHz, CDCl$_3$); 1:1.4 atropisomeric mixture; δ 8.19 (d, 0.6H, J=1.6 Hz), 8.16 (d, 0.4H, J=1.6 Hz), 8.01 (dd, 0.6H, J=8.0, 1.7 Hz), 7.98 (dd, 0.4H, J=8.0, 1.7 Hz), 7.85-7.84 (m, 1H), 7.73-7.71 (m, 2H), 7.43 (d, 0.6H, J=8.0 Hz), 7.37 (d, 0.4H, J=8.0 Hz), 7.34-7.31 (m, 1H), 7.13-7.11 (m, 1H), 6.96 (d, 0.4H, J=8.6 Hz), 6.92 (d, 0.6H, J=8.6 Hz), 5.59 (d, 1H, J=8.1 Hz), 4.04-3.89 (m, 2H), 3.83-3.81 (m, 3H), 3.67-3.50 (m, 1H), 2.52-2.03 (m, 2H), 1.99-1.92 (m, 2H), 1.54-1.45 (m, 2H), 1.06-1.01 (m, 6H), 0.42 (d, 1.2H, J=6.5 Hz), 0.36 (d, 1.8H, J=6.5 Hz)

MS (ESI) m/z 696.1 (M$^+$+H).

Example 130

Compound 728 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-chloro-2-(trifluoromethyl)biphenyl-4-carboxylate (4S,5R)-5-(3,5-bis(trifluoromethyl)phenyl)-3-((2-(2-chloro-5-iodophenyl)-5,5-dimethylcyclohex-1-enyl)methyl)-4-oxooxazolidin-2-one (0.030 g, 0.045 mmol), methyl-4-(4,4,5,5-tetramethyl-1,3,2-dioxaborolan-2-yl)-3-(trifluoromethyl)benzoate (0.015 g, 0.045 mmol), Pd(PPh$_3$)$_2$Cl$_2$ (0.002 g, 0.002 mmol) and sodium carbonate (0.014 g, 0.134 mmol) were added to dimethylformamide (0.8 mL)/water (0.4 mL) and heated by microwave irradiation at 90° C. for 20 minutes. Then, the reaction mixture was cooled to room temperature, and water was added thereto, followed by extraction with ethyl acetate. The organic layer was dried with anhydrous magnesium sulfate to remove, and then concentrated under reduced pressure. The residue was purified by MPLC (SiO$_2$, EtOAc/hexane=0%-20%) to obtain observed compound 728 (0.025 g, 76.5%) in an impure form.

$^1$H NMR (400 MHz, CDCl$_3$); δ 8.51 (m, 1H), 8.33 (m, 1H), 7.88 (s, 1H), 7.78-7.75 (m, 2H), 7.50-7.41 (m, 2H), 7.22-7.19 (m, 1H), 7.12-7.09 (m, 1H), 5.68 (m, 1H), 4.17-3.93 (m, 5H), 3.60-3.46 (m, 1H), 2.60-2.35 (m, 2H), 1.98 (m, 2H), 1.60-1.45 (m, 2H), 1.12-1.02 (m, 6H), 0.50 (m, 3H)

MS (ESI) m/z 748.1 (M$^+$+H).

Example 131

Compound 729

3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-chloro-2-(trifluoromethyl)biphenyl-4-carboxylic acid Starting material 728 (0.018 g, 0.024 mmol) and lithium hydroxide monohydrate (0.010 g, 0.241 mmol) were dissolved in dioxane (4 mL)/water (1 mL) at room temperature, and the reaction mixture was stirred at the same temperature for 16 hours. Then, 1M hydrochloric acid was added to the reaction mixture, followed by extraction with ethyl acetate. The organic layer was dried with anhydrous magnesium sulfate, filtered, and then concentrated under reduced pressure to remove the solvent. The concentrate was purified and concentrated by PTLC to obtain desired compound 729 (0.010 g, 56.6%) as a white foam solid.

$^1$H NMR (400 MHz, CDCl$_3$); δ 8.44 (m, 1H), 8.23 (m, 1H), 7.88 (m, 1H), 7.78-7.74 (m, 2H), 7.40 (m, 2H), 7.20-7.18 (m, 1H), 7.10-7.07 (m, 1H), 5.67 (2d, 1H, J=7.8 Hz), 4.15-3.93 (m, 2H), 3.54 (2d, 1H, J=14.9 Hz), 2.60-2.35 (m, 2H), 1.58 (m, 2H), 1.58-1.49 (m, 2H), 1.10-1.03 (m, 6H), 0.50 (m, 3H)

MS (ESI) m/z 734.1 (M$^+$+H).

Example 132

Compound 738 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-chloro-4'-fluorobiphenyl-4-carboxylate (4S,5R)-5-(3,5-bis(trifluoromethyl)phenyl)-3-((2'-fluoro-5'-iodo-4,4-dimethyl-3,4,5,6-tetrahydro-[1,1'-biphenyl]-2-yl)methyl)-4-methyloxazolidin-2-one (0.067 g, 0.102 mmol), (2-chloro-4-(methoxycarbonyl)phenyl)boronic acid (0.024 g, 0.112 mmol), Pd(dbpf)Cl$_2$ (0.007 g, 0.010 mmol) and potassium acetate (0.001 g, 0.307 mmol) were added to dimethylformamide/water (v/v=2/1, 0.6 mL) and stirred with microwave irradiation at 120° C. for 20 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by preparative TLC (SiO$_2$, EtOAc/hexane=20%) to obtain compound 738 (0.024 g, 34%) as colorless oil.

$^1$H NMR (400 MHz, CDCl$_3$); δ 8.15 (dd, 1H, J=11.9, 1.2 Hz), 8.00-7.95 (m, 1H), 7.88 (s, 1H), 7.76 (d, 2H, J=15.5 Hz), 7.43-7.31 (m, 2H), 7.23-7.11 (m, 2H), 5.67-5.60 (m, 1H), 4.07-3.92 (m, 5H), 3.71-3.61 (m, 1H), 2.55-2.19 (m, 2H), 2.04-1.96 (m, 2H), 1.59-1.50 (m, 2H), 1.09-1.04 (m, 6H), 0.47-0.43 (m, 3H)

MS (ESI) m/z 698.1 (M$^+$+H).

Example 133

Compound 739

3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-chloro-4'-fluorobiphenyl-4-carboxylic acid Starting material 738 (0.024 g, 0.035 mmol) and lithium hydroxide monohydrate (0.007 g, 0.174 mmol) were dissolved in dioxane/water (v/v=4:1, 1.0 mL), and then stirred at room temperature for 4 hours. After completion of the reaction, the reaction mixture was cooled to room temperature and concentrated under reduced pressure to remove the solvent, after which it was diluted with ethyl acetate, and 1M hydrochloric acid solution was added dropwise thereto until a pH of 2 was reached, followed by washing with water. The organic layer was dried with anhydrous magnesium sulfate, filtered, and then concentrated under reduced pressure to remove the solvent. The residue was purified by preparative TLC (SiO$_2$, CH$_3$OH/CH$_2$Cl$_2$=5%) to obtain compound 739 (0.016 g, 67%) as a white foam solid.

$^1$H NMR (400 MHz, CDCl$_3$); δ 8.24-8.21 (m, 1H), 8.07-8.03 (m, 1H), 7.89 (s, 1H), 7.76 (d, 2H, J=15.5 Hz), 7.44 (dd, 1H, J=18.5, 8.0 Hz), 7.37-7.33 (m, 1H), 7.24-7.13 (m, 2H), 5.68-5.61 (m, 1H), 4.12-3.93 (m, 2H), 3.72-3.62 (m, 1H), 2.51-2.21 (m, 2H), 2.04-1.96 (m, 2H), 1.58-1.52 (m, 2H), 1.09-1.04 (m, 6H), 0.49-0.44 (m, 3H)

MS (ESI) m/z 684.1 (M$^+$+H).

Preparation of Novel Compounds According to Reaction Scheme 15

Intermediate Compound 62a: (4S,5R)-5-(3,5-bis(trifluoromethyl)phenyl)-3-((3'-chloro-4'-fluoro-4,4-dimethyl-3,4,5,6-tetrahydro-[1,1'-biphenyl]-2-yl)methyl)-4-methyloxazolidin-2-one Starting material 16 (0.500 g, 0.972 mmol), (3-chloro-4-fluorophenyl)boronic acid (0.186 g, 1.069 mmol), Pd(dbpf)$Cl_2$ (0.032 g, 0.049 mmol) and sodium carbonate (0.227 g, 2.139 mmol) were added to dimethoxyethane/water (v/v=3/1, 1.0 mL) and stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC ($SiO_2$, EtOAc/hexane=0%~20%) to obtain compound 62a (0.455 g, 83%) as a pale yellow foam solid.

Intermediate Compound 62b: (4S,5R)-5-(3,5-bis(trifluoromethyl)phenyl)-3-((2-(3-chloro-5-methoxyphenyl)-5,5-dimethylcyclohex-1-enyl)methyl)-4-methoxyoxazolidin-2-one Starting material 16 (0.500 g, 2.682 mmol), 3-chloro-5-methoxyphenyl boronic acid (1.380 g, 2.682 mmol), Pd(di-t-Bupf)$Cl_2$ (0.087 g, 0.134 mmol) and sodium carbonate (0.569 g, 5.365 mmol) were added to dimethoxyethane (6 mL)/water (2 mL) and heated by microwave irradiation at 120° C. for 15 minutes. Then, the reaction mixture was cooled to room temperature, and water was added thereto, followed by extraction with ethyl acetate. The organic layer was washed with brine and dried with anhydrous magnesium sulfate, followed by concentration under reduced pressure. The residue was purified and concentrated by MPLC (Sift, EtOAc/hexane=0%-15%) to obtain desired compound 62b (0.900 g, 58.3%) as a brown foam solid.

Intermediate Compound 62c: (4S,5R)-5-(3,5-bis(trifluoromethyl)phenyl)-3-((2-(5-chloro-2-fluorophenyl)-5,5-dimeth ylcyclohex-1-enyl)methyl)-4-methyloxazolidin-2-one Starting material 16 (0.300 g, 0.583 mmol), 5-chloro-2-fluorophenylboronic acid (0.153 g, 0.875 mmol), Pd(dbpf)$Cl_2$ (0.019 g, 0.029 mmol) and $Na_2CO_3$ (0.185 g, 1.750 mmol) were added to dimethoxyethane (0.9 mL)/water (0.3 mL) and stirred with microwave irradiation at 120° C. for 20 minutes. Then, the reaction mixture was cooled to room temperature, and water was added thereto, followed by extraction with ethyl acetate. The organic layer was dried with anhydrous magnesium sulfate, followed by concentration under reduced pressure. The residue was purified and concentrated by MPLC ($SiO_2$, cartridge; EtOAc/hexane=0%-10%) to obtain compound 62c (0.250 g, 76.0%) as brown oil.

Intermediate Compound 62d: methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-methyl-5'-(trifluoromethyl)biphenyl-4-carboxylate Starting material 16 (0.500 g, 0.972 mmol), 3-chloro-5-(trifluoromethyl)phenylboronic acid (0.327 g, 1.458 mmol), Pd(PPh$_3$)$_2$Cl$_2$ (0.034 g, 0.049 mmol) and sodium carbonate (0.309 g, 2.917 mmol) were added to dimethylformamide (2 mL)/water (1 mL) and heated by microwave irradiation at 100° C. for 20 minutes. Then, the reaction mixture was cooled to room temperature, and water was added thereto, followed by extraction with ethyl acetate. The organic layer was dried with anhydrous magnesium sulfate, followed by concentration under reduced pressure. The residue was purified by MPLC ($SiO_2$, EtOAc/hexane=0%~20%) to obtain desired compound 62d (0.380 g, 63.7%) as colorless oil.

Example 134

Compound 670 methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluorobiphenyl-4-carboxylate Compound 62a (0.100 g, 0.177 mmol), (4-(methoxycarbonyl)phenyl)boronic acid (0.048 g, 0.266 mmol), Pd(dbpf)$Cl_2$ (0.006 g, 0.009 mmol) and sodium carbonate (0.056 g, 0.532 mmol) were added to dimethoxyethane/water (v/v=3/1, 1.0 mL) and stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC($SiO_2$, EtOAc/hexane=0%~10%) to obtain compound 670 (0.087 g, 74%) as pale yellow oil.

$^1$H NMR (400 MHz, $CDCl_3$); δ 8.09 (d, 2H, J=6.7 Hz), 7.86 (s, 1H), 7.72 (s, 2H), 7.57 (dd, 2H, J=8.4, 1.4 Hz), 7.18-7.06 (m, 3H), 5.60 (d, 1H, J=8.0 Hz), 4.07 (d, 1H, J=15.5 Hz), 3.95-3.90 (m, 4H), 3.72 (d, 1H, J=15.0 Hz), 2.43-2.25 (m, 2H), 1.94 (s, 2H), 1.51 (t, 2H, J=6.4 Hz), 1.03 (d, 6H, J=15.7 Hz), 0.41 (d, 3H, J=6.6 Hz)

MS (ESI) m/z 664.1 ($M^+$+H).

Example 135

Compound 679

5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluorobiphenyl-4-carboxylic acid Starting material 670 (0.078 g, 0.117 mmol) and lithium hydroxide monohydrate (0.025 g, 0.587 mmol) were dissolved in dioxane/water (v/v=4:1, 1.0 mL), and then stirred at 50° C. for 4 hours. After completion of the reaction, the reaction mixture was cooled to room temperature, concentrated under reduced pressure to remove the solvent, and then diluted with ethyl acetate, and 1M hydrochloric acid solution was added dropwise thereto until a pH of 2 was reached, followed by washing with water. The organic layer was dried with anhydrous magnesium sulfate, filtered, and then concentrated under reduced pressure to remove the solvent. The residue was purified by preparative TLC (Sift, $CH_3OH/CH_2Cl_2$=5%) to obtain compound 679 (0.024 g, 31%) as white oil.

$^1$H NMR (400 MHz, $CDCl_3$); δ 8.02-8.00 (m, 3H), 7.93 (s, 2H), 7.52 (d, 2H, J=7.5 Hz), 7.29 (d, 1H, J=6.9 Hz), 7.18

(d, 2H, J=8.2 Hz), 5.82 (d, 1H, J=8.3 Hz), 4.18-4.14 (m, 1H), 3.99 (d, 1H, J=14.6 Hz), 3.77 (d, 1H, J=14.7 Hz), 2.47-2.31 (m, 2H), 2.04-1.92 (m, 2H), 1.58-1.52 (m, 2H), 1.05 (d, 6H, J=22.6 Hz), 0.44 (d, 3H, J=6.5 Hz)

MS (ESI) m/z 650.1 (M$^+$+H).

Example 136

Compound 671 methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2,2'-difluorobiphenyl-4-carboxylate Compound 62a (0.100 g, 0.177 mmol), methyl 3-fluoro-4-(4,4,5,5-tetramethyl-1,3,2-dioxaborolan-2-yl)benzoate (0.075 g, 0.266 mmol), Pd(dbpf)Cl$_2$ (0.006 g, 0.009 mmol) and sodium carbonate (0.056 g, 0.532 mmol) were added to dimethoxyethane/water (v/v=3/1, 1.0 mL) and stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (Sift, EtOAc/hexane=0%-10%) to obtain compound 671 (0.039 g, 33%) as colorless oil.

$^1$H NMR (400 MHz, CDCl$_3$); δ 7.90-7.77 (m, 3H), 7.73 (s, 2H), 7.47-7.45 (m, 1H), 7.16-7.13 (m, 3H), 5.59 (d, 1H, J=8.1 Hz), 4.08 (d, 1H, J=11.1 Hz), 3.95 (s, 3H), 3.90-3.88 (m, 1H), 3.73 (d, 1H, J=14.8 Hz), 2.42-2.24 (m, 2H), 1.96 (s, 2H), 1.50 (t, 2H, J=6.5 Hz), 1.02 (d, 6H, J=13.9 Hz), 0.38 (d, 3H, J=5.4 Hz)

MS (ESI) m/z 682.1 (M$^+$+H).

Example 137

Compound 680

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-2,2'-difluorobiphenyl-4-carboxylic acid Compound 671 (0.029 g, 0.042 mmol) and lithium hydroxide monohydrate (0.009 g, 0.211 mmol) were dissolved in dioxane/water (v/v=4:1, 1.0 mL), and then stirred at 50° C. for 4 hours. After completion of the reaction, the reaction mixture was cooled to room temperature, concentrated under reduced pressure to remove the solvent, and then diluted with ethyl acetate, and 1M hydrochloric acid solution was added dropwise thereto until a pH of 2 was reached, followed by washing with water. The organic layer was dried with anhydrous magnesium sulfate, filtered, and then concentrated under reduced pressure to remove the solvent. The residue was purified by preparative TLC (Sift, CH$_3$OH/CH$_2$Cl$_2$=5%) to obtain compound 680 (0.011 g, 38%) as colorless oil.

$^1$H NMR (400 MHz, CDCl$_3$); δ 7.97-7.87 (m, 3H), 7.74 (s, 2H), 7.50 (t, 1H, J=7.3 Hz), 7.16 (d, 3H, J=7.5 Hz), 5.59 (d, 1H, J=8.1 Hz), 4.06 (d, 1H, J=14.9 Hz), 3.93-3.89 (m, 1H), 3.74 (d, 1H, J=14.7 Hz), 2.43-2.26 (m, 2H), 1.96 (s, 2H), 1.51 (t, 2H, J=6.4 Hz), 1.02 (d, 6H, J=13.7 Hz), 0.40 (d, 3H, J=6.6 Hz)

MS (ESI) m/z 668.1 (M$^+$+H).

Example 138

Compound 672 methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-2-methylbiphenyl-4-carboxylate Compound 62a (0.100 g, 0.177 mmol), methyl 3-methyl-4-(4,4,5,5-tetramethyl-1,3,2-dioxaborolan-2-yl)benzoate (0.073 g, 0.266 mmol), Pd(dbpf)Cl$_2$ (0.006 g, 0.009 mmol) and sodium carbonate (0.056 g, 0.532 mmol) were added to dimethoxyethane/water (v/v=3/1, 1.0 mL) and stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (Sift, EtOAc/hexane=0%~10%) to obtain compound as 672 (0.073 g, 61%) as colorless oil.

$^1$H NMR (400 MHz, CDCl$_3$); δ 7.95-7.87 (m, 3H), 7.73 (s, 2H), 7.23 (d, 1H, J=7.9 Hz), 7.11 (d, 2H, J=8.2 Hz), 6.98 (d, 1H, J=7.2 Hz), 5.62 (d, 1H, J=8.2 Hz), 4.06 (d, 1H, J=14.8 Hz), 3.93 (s, 3H), 3.92-3.88 (m, 1H), 3.74 (d, 1H, J=14.7 Hz), 2.43-2.28 (m, 2H), 2.20 (s, 3H), 1.94 (s, 2H), 1.50 (t, 2H, J=6.5 Hz), 1.02 (d, 6H, J=14.6 Hz), 0.41 (d, 3H, J=6.6 Hz)

MS (ESI) m/z 678.1 (M$^+$+H).

Example 139

Compound 681

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-2'-fluoro-2-methylbiphenyl-4-carboxylic acid Compound 672 (0.100 g, 0.148 mmol) and lithium hydroxide monohydrate (0.031 g, 0.738 mmol) were dissolved in dioxane/water (v/v=4:1, 1.0 mL), and then stirred at 50° C. for 4 hours. After completion of the reaction, the reaction mixture was cooled to room temperature, concentrated under reduced pressure to remove the solvent, and then diluted with ethyl acetate, and 1M hydrochloric acid solution was added dropwise thereto until a pH of 2 was reached, followed by washing with water. The organic layer was dried with anhydrous magnesium sulfate, filtered, and then concentrated under reduced pressure to remove the solvent. The residue was purified by preparative TLC (Sift, CH$_3$OH/CH$_2$Cl$_2$=5%) to obtain compound 681 (0.024 g, 25%) as colorless oil.

$^1$H NMR (400 MHz, CDCl$_3$); δ 8.03-7.96 (m, 2H), 7.87 (s, 1H), 7.73 (s, 2H), 7.27 (d, 1H, J=1.3 Hz), 7.12 (dd, 2H, J=7.3, 1.0 Hz), 6.99 (d, 1H, J=7.2 Hz), 5.62 (d, 1H, J=8.1 Hz), 4.07 (d, 1H, J=15.2 Hz), 3.95-3.90 (m, 1H), 3.75 (d, 1H, J=14.7 Hz), 2.42-2.28 (m, 2H), 2.23 (s, 3H), 1.95 (s, 2H), 1.51 (t, 2H, J=6.5 Hz), 1.02 (d, 6H, J=14.7 Hz), 0.42 (d, 3H, J=6.5 Hz)

MS (ESI) m/z 664.2 (M$^+$+H).

Example 140

Compound 686 methyl 3'-(2-(((4S,5R)-5-(3,5-bis(trifluoromethyl)
phenyl)-4-methyl-2-oxooxazolidin-3-yl)methyl)-4,4-
dimethylcyclohex-1-enyl)-5'-methoxybiphenyl-4-
carboxylate Starting material 62b (0.100 g, 0.174 mmol), 4-(methoxy-carbonyl)phenylboronic acid (0.034 g, 0.191 mmol), Pd(di-t-Bupf)Cl$_2$ (0.006 g, 0.009 mmol) and sodium carbonate (0.037 g, 0.347 mmol) were added to dimethoxyethane (1 mL)/water (0.3 mL) and heated by microwave irradiation at 120° C. for 15 minutes. Then, the reaction mixture was cooled to room temperature, and water was added thereto, followed by extraction with ethyl acetate. The organic layer was washed with brine, dried with anhydrous magnesium sulfate, and then concentrated under reduced pressure. The residue was purified and concentrated by MPLC (Sift, EtOAc/hexane=0%-20%) to obtain compound 686 (0.100 g, 85.2%) as colorless oil.

$^1$H NMR (400 MHz, CDCl$_3$); δ 8.10 (d, 2H, J=1.5 Hz), 7.85 (s, 1H), 7.72 (s, 2H), 7.61 (d, 2H, J=7.7 Hz), 7.02 (s, 1H), 6.92 (s, 1H), 6.67 (s, 1H), 5.60 (d, 1H, J=6.1 Hz), 3.90-4.06 (m, 2H), 3.94 (s, 3H), 3.85 (s, 3H), 3.77 (d, 1H, J=11.1 Hz), 2.05-2.45 (m, 2H), 1.95-2.00 (m, 2H), 1.52 (t, 2H, J=4.8 Hz), 1.01-1.06 (m, 6H), 0.43 (d, 3H, J=4.9 Hz)

MS (ESI) m/z 676.2 (M$^+$+H).

Example 141

Compound 687

3'-(2-(((4S,5R)-5-(3,5-bis(trifluoromethyl)phenyl)-4-
methyl-2-oxooxazolidin-3-yl)methyl)-4,4-dimethyl-
cyclohex-1-enyl)-5'-methoxybiphenyl-4-carboxylic
acid Starting material 686 (0.100 g, 0.148 mmol) and anhydrous lithium hydroxide (0.018 g, 0.740 mmol) were dissolved in dioxane (1 mL)/water (0.25 mL) at 50° C., and the reaction mixture was stirred at the same temperature for 8 hours. Then, an aqueous solution of 1M hydrochloric acid was added to the reaction mixture, followed by extraction with ethyl acetate. The organic layer was washed with brine, dried with anhydrous magnesium sulfate, and then concentrated under reduced pressure. The residue was purified and concentrated by MPLC (Sift, EtOAc/hexane=0%-35%) to obtain desired compound 687 (0.045 g, 46.0%) as colorless oil.

$^1$H NMR (400 MHz, CDCl$_3$); δ 7.98-8.00 (m, 3H), 7.92 (s, 2H), 7.58 (d, 2H, J=6.2 Hz), 7.09 (s, 1H), 7.00 (s, 1H), 6.71 (s, 1H), 5.80 (d, 1H, J=6.2 Hz), 4.15-4.20 (m, 1H), 3.99 (d, 1H, J=11.1 Hz), 3.79-3.84 (m, 4H), 2.33-2.49 (m, 2H), 1.98 (dd, 2H, J=28.5, 12.5 Hz), 1.50-1.60 (m, 2H), 1.00 (d, 6H, J=11.2 Hz), 0.44 (d, 3H, J=4.9 Hz)

MS (ESI) m/z 662.2 (M$^+$+H).

Example 142

Compound 688 methyl 3'-(2-(((4S,5R)-5-(3,5-bis(trifluoromethyl)
phenyl)-4-methyl-2-oxooxazolidin-3-yl)methyl)-4,4-
dimethylcyclohex-1-enyl)-5'-methoxy-2-methylbi-
phenyl-4-carboxylate Starting material 62b (0.100 g, 0.174 mmol), methyl 3-methyl-4-(4,4,5,5-tetramethyl-1,3,2-dioxaborolan-2-yl) benzoate (0.072 g, 0.260 mmol), Pd(di-t-Bupf)Cl$_2$ (0.006 g, 0.009 mmol) and sodium carbonate (0.037 g, 0.347 mmol) were added to dimethoxyethane (1 mL)/water (0.3 mL) and heated by microwave irradiation at 120° C. for 15 minutes. Then, the reaction mixture was cooled to room temperature, and water was added thereto, followed by extraction with ethyl acetate. The organic layer was washed with brine, dried with anhydrous magnesium sulfate, and then concentrated under reduced pressure. The residue was purified by MPLC (Sift, ethyl acetate/hexane=0%~20%) to obtain desired compound 688 (0.070 g, 58.5%) as colorless oil.

$^1$H NMR (400 MHz, CDCl$_3$); δ 7.93 (s, 1H), 7.86-7.88 (m, 2H), 7.74 (s, 2H), 7.23 (d, 1H, J=6.0 Hz), 6.72 (s, 1H), 6.62-6.64 (m, 2H), 5.61 (d, 1H, J=6.1 Hz), 4.05-4.10 (m, 1H), 3.78-3.93 (m, 8H), 2.20-2.50 (m, 5H), 1.94 (s, 2H), 1.51 (t, 2H, J=4.9 Hz), 1.02 (d, 6H, J=10.6 Hz), 0.43 (d, 3H, J=4.9 Hz)

MS (ESI) m/z 690.2 (M$^+$+H).

Example 143

Compound 689

3'-(2-(((4S,5R)-5-(3,5-bis(trifluoromethyl)phenyl)-4-
methyl-2-oxooxazolidin-3-yl)methyl)-4,4-dimethyl-
cyclohex-1-enyl)-5'-methoxy-2-methylbiphenyl-4-
carboxylic acid Compound 688 (0.072 g, 0.104 mmol) and anhydrous lithium hydroxide (0.013 g, 0.522 mmol) were dissolved in dioxane (1 mL)/water (0.25 mL) at 50° C., and the reaction mixture was stirred at the same temperature for 8 hours. Then, an aqueous solution of 1M hydrochloric acid was added to the reaction mixture, followed by extraction with ethyl acetate. The organic layer was washed with brine, dried with anhydrous magnesium sulfate, and then concentrated under reduced pressure. The residue was purified and concentrated by MPLC (Sift, EtOAc/hexane=0%~35%) to obtain compound 689 (0.035 g, 49.6%) as colorless oil.

$^1$H NMR (400 MHz, CDCl$_3$); δ 8.01 (s, 1H), 7.95 (d, 1H, J=6.0 Hz), 7.87 (s, 1H), 7.73 (s, 2H), 7.26-7.28 (m, 1H), 6.73 (s, 1H), 6.65 (d, 2H, J=5.1 Hz), 5.61 (d, 1H, J=8.1 Hz), 4.08 (d, 1H, J=10.7 Hz), 3.90-3.96 (m, 1H), 3.82 (s, 3H), 3.50-3.77 (m, 1H), 2.20-2.50 (m, 5H), 1.95 (s, 2H), 1.52 (t, 2H, J=4.7 Hz), 1.03 (d, 6H, J=13.8 Hz), 0.38 (d, 3H, J=6.4 Hz)

MS (ESI) m/z 676.2 (M$^+$+H).

Example 144

Compound 690 methyl 3'-(2-(((4S,5R)-5-(3,5-bis(trifluoromethyl)
phenyl)-4-methyl-2-oxooxazolidin-3-yl)methyl)-4,4-
dimethylcyclohex-1-enyl)-2-fluoro-5'-methoxybi-
phenyl-4-carboxylate Starting material 62b (0.100 g, 0.174 mmol), methyl 3-fluoro-4-(4,4,5,5-tetramethyl-1,3,2-dioxaborolan-2-yl) benzoate (0.073 g, 0.260 mmol), Pd(di-t-Bupf)Cl$_2$ (0.006 g, 0.009 mmol) and sodium carbonate (0.037 g, 0.347 mmol) were added to dimethoxyethane (1 mL)/water (0.3 mL) and heated by microwave irradiation at 120° C. for 15 minutes. Then, the reaction mixture was cooled to room temperature, and water was added thereto, followed by extraction with ethyl acetate. The organic layer was washed with brine, dried with anhydrous magnesium sulfate, and then concentrated under reduced pressure. The residue was purified and concentrated by MPLC (Sift, EtOAc/hexane=0%~20%) to obtain desired compound 690 (0.060 g, 49.8%) as colorless oil.

$^1$H NMR (400 MHz, CDCl$_3$); δ 7.85-7.88 (m, 2H), 7.76 (d, 1H, J=13.4 Hz), 7.73 (s, 2H), 7.40-7.47 (m, 1H), 6.95 (s, 1H), 6.89 (s, 1H), 6.66 (s, 1H), 5.55-5.60 (m, 1H), 3.95-4.10 (m, 2H), 3.96 (s, 3H), 3.83 (s, 3H), 3.75-3.79 (m, 1H), 2.20-2.50 (m, 2H), 1.96 (s, 2H), 1.40-1.60 (m, 2H), 1.03 (d, 6H, J=12.8 Hz), 0.40 (d, 3H, J=6.8 Hz)

MS (ESI) m/z 694.2 (M$^+$+H).

Example 145

Compound 691

3'-(2-(((4S,5R)-5-(3,5-bis(trifluoromethyl)phenyl)-4-methyl-2-oxooxazolidin-3-yl)methyl)-4,4-dimethyl-cyclohex-1-enyl)-2-fluoro-5'-methoxybiphenyl-4-carboxylic acid Starting material 690 (0.062 g, 0.089 mmol) and anhydrous lithium hydroxide (0.011 g, 0.447 mmol) were dissolved in dioxane (1 mL)/water (0.25 mL) at 50° C., and the reaction mixture was stirred at the same temperature for 8 hours. Then, an aqueous solution of 1M hydrochloric acid was added to the reaction mixture, followed by extraction with ethyl acetate. The organic layer was washed with brine, dried with anhydrous magnesium sulfate, and then concentrated under reduced pressure. The residue was purified and concentrated by MPLC (Sift, EtOAc/hexane=0%~35%) to obtain desired compound 691 (0.010 g, 16.5%) as a brown foam solid.

$^1$H NMR (400 MHz, CDCl$_3$); δ 7.98 (s, 1H), 7.92 (s, 2H), 7.80 (d, 1H, J=9.1 Hz), 7.70 (d, 1H, J=11.9 Hz), 7.44 (t, 1H, J=7.9 Hz), 7.00 (s, 1H), 6.93 (s, 1H), 6.74 (s, 1H), 5.80 (d, 1H, J=8.2 Hz), 4.11-4.18 (m, 1H), 3.98 (d, 1H, J=14.8 Hz), 3.78-3.83 (m, 4H), 2.16-2.47 (m, 2H), 1.90-2.04 (m, 2H), 1.50-1.60 (m, 2H), 1.08, 1.03 (2s, 6H), 0.43 (d, 3H, J=6.5 Hz)

MS (ESI) m/z 680.2 (M$^+$+H).

Example 146

Compound 724 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2,4'-difluorobiphenyl-4-carboxylate Starting material 62c (0.240 g, 0.426 mmol), (2-fluoro-4-(methoxycarbonyl)phenyl)boronic acid (0.093 g, 0.468 mmol), Pd(dbpf)Cl$_2$ (0.014 g, 0.021 mmol) and sodium carbonate (0.099 g, 0.936 mmol) were added to dimethoxyethane/water (v/v=3/1, 2.0 mL) and stirred with microwave irradiation at 120° C. for 30 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (Sift, EtOAc/hexane=0%~20%) to obtain compound 724 (0.149 g, 51%) as a white foam solid.

$^1$H NMR (400 MHz, CDCl$_3$); δ 7.92-7.88 (m, 2H), 7.85-7.77 (m, 3H), 7.54-7.44 (m, 2H), 7.33 (dd, 1H, J=16.2, 7.0 Hz), 7.22-7.13 (m, 1H), 5.65-5.62 (m, 1H), 4.12-4.01 (m, 2H), 3.97 (s, 3H), 3.68-3.57 (m, 1H), 2.53-2.20 (m, 2H), 2.01 (s, 2H), 1.60-1.54 (m, 2H), 1.09-1.05 (m, 6H), 0.47-0.40 (m, 3H)

MS (ESI) m/z 682 (M$^+$+H).

Example 147

Compound 722

3'-(2-(((4S,5R)-5-(3,5-bis(trifluoromethyl)phenyl)-4-methyl-2-oxooxazolidin-3-yl)methyl)-4,4-dimethyl-cyclohex-1-enyl)-2,4'-difluorobiphenyl-4-carboxylic acid Starting material 724 (0.126 g, 0.185 mmol) and lithium hydroxide monohydrate (0.039 g, 0.926 mmol) were dissolved in dioxane/water (v/v=4:1, 2.0 mL), and then stirred at 50° C. for 2 hours. After completion of the reaction, the reaction mixture was cooled to room temperature, concentrated under reduced pressure to remove the solvent, and then diluted with ethyl acetate, and 1M HCl solution was added dropwise thereto until a pH of 2 was reached, followed by washing with water. The organic layer was dried with anhydrous magnesium sulfate, filtered, and then concentrated under reduced pressure to remove the solvent. The residue was purified by MPLC (Sift, EtOAc/hexane=0%~30%) to obtain compound 722 (0.093 g, 75%) as a white foam solid.

$^1$H NMR (400 MHz, CDCl$_3$); δ 8.00-7.96 (m, 1H), 7.92-7.86 (m, 2H), 7.78 (s, 2H), 7.59-7.46 (m, 2H), 7.38-7.32 (m, 1H), 7.24-7.15 (m, 1H), 5.67-5.63 (m, 1H), 4.12-3.96 (m, 2H), 3.69-3.58 (m, 1H), 2.53-2.22 (m, 2H), 2.01 (s, 2H), 1.60-1.52 (m, 2H), 1.10-1.05 (m, 6H), 0.49-0.42 (m, 3H)

MS (ESI) m/z 668.2 (M$^+$+H).

Example 148

Compound 725 methyl 5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-2-(trifluoromethyl)biphenyl-4-carboxylate Compound 62a (0.140 g, 0.248 mmol), methyl 4-(4,4,5,5-tetramethyl-1,3,2-dioxaborolan-2-yl)-3-(trifluoromethyl)benzoate (0.090 g, 0.273 mmol), Pd(dbpf)Cl$_2$ (0.008 g, 0.012 mmol) and sodium carbonate (0.058 g, 0.546 mmol) were added to dimethylformamide/water (v/v=2/1, 1.0 mL) and stirred with microwave irradiation at 120° C. for 5 minutes. After completion of the reaction, the reaction mixture was cooled to room temperature, diluted with ethyl acetate, and then washed with water and brine. The organic layer was dried with anhydrous magnesium sulfate, filtered, and then concentrated under reduced pressure to remove the solvent. The residue was purified by MPLC (Sift, EtOAc/hexane=0%~10%) to obtain compound 725 (0.086 g, 47%) as yellow oil.

$^1$H NMR (400 MHz, CDCl$_3$); δ 8.47 (d, 1H, J=7.1 Hz), 8.27 (t, 1H, J=8.6 Hz), 7.89 (d, 1H, J=4.7 Hz), 7.74 (d, 2H, J=9.4 Hz), 7.53 (t, 1H, J=7.9 Hz), 7.16-7.12 (m, 2H), 7.09-7.03 (m, 1H), 5.64-5.59 (m, 1H), 4.09-4.00 (m, 4H), 3.96-3.85 (m, 1H), 3.81-3.70 (m, 1H), 2.44-2.31 (m, 2H), 1.97 (s, 2H), 1.52-1.50 (m, 2H), 1.06-1.00 (m, 6H), 0.45-0.37 (m, 3H)

MS (ESI) m/z 732.1 (M$^+$+H).

Example 149

Compound 723

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-2'-fluoro-2-(trifluoromethyl)biphenyl-4-carboxylic acid Compound 725 (0.086 g, 0.118 mmol) and lithium hydroxide monohydrate (0.025 g, 0.588 mmol) were dissolved in dioxane/water (v/v=4:1, 1.0 mL), and then stirred at 50° C. for 4 hours. After completion of the reaction, the reaction mixture was cooled to room temperature, concentrated under reduced pressure to remove the solvent, and then diluted with ethyl acetate, and 1M HCl solution was added dropwise thereto until a pH of 2 was reached, followed by washing with water. The organic layer was dried with anhydrous magnesium sulfate, filtered, and then concentrated under reduced pressure to remove the solvent. The residue was purified by preparative TLC (SiO$_2$, CH$_3$OH/CH$_2$Cl$_2$=5%) to obtain compound 723 (0.027 g, 32%) as a white foam solid.

$^1$H NMR (400 MHz, CDCl$_3$); δ 8.55 (d, 1H, J=7.2 Hz), 8.35 (t, 1H, J=8.5 Hz), 7.89 (d, 1H, J=4.4 Hz), 7.75 (d, 2H, J=10.0 Hz), 7.58 (t, 1H, J=7.8 Hz), 7.26-7.12 (m, 2H), 7.10-7.04 (m, 1H), 5.66-5.62 (m, 1H), 4.11-4.07 (m, 1H), 3.98-3.87 (m, 1H), 3.82-3.71 (m, 1H), 2.44-2.28 (m, 2H), 1.98 (s, 2H), 1.53-1.52 (m, 2H), 1.06-1.01 (m, 6H), 0.46-0.41 (m, 3H)

MS (ESI) m/z 718.1 (M$^+$+H).

Example 150

Compound 743 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-methyl-5'-(trifluoromethyl)biphenyl-4-carboxylate Compound 63d (0.100 g, 0.163 mmol), methyl 6-methyl-5-(4,4,5,5-tetramethyl-1,3,2-dioxaborolan-2-yl)benzoate (0.090 g, 0.326 mmol), sodium carbonate (0.052 g, 0.489 mmol) and Pd(dbpf)Cl$_2$ (0.005 g, 0.008 mmol) were added to dimethylformamide (0.8 mL)/water (0.4 mL) and heated by microwave irradiation at 100° C. for 20 minutes. Then, the reaction mixture was cooled to room temperature, and water was added thereto, followed by extraction with ethyl acetate. The organic layer was dried with anhydrous magnesium sulfate, and then concentrated under reduced pressure. The residue was purified by MPLC (SiO$_2$, EtOAc/hexane=0%~20%) to obtain desired compound 743 (0.075 g, 63.3%) as a white foam solid.

$^1$H NMR (400 MHz, CDCl$_3$); δ 7.98 (s, 1H), 7.93 (dd, 1H, J=7.7, 1.5 Hz), 7.89 (s, 1H), 7.74 (s, 2H), 7.50 (s, 1H), 7.38 (s, 1H), 7.27-7.25 (m, 2H), 5.63 (d, 1H, J=8.1 Hz), 4.11-3.92 (m, 5H), 3.67 (d, 1H, J=14.9 Hz), 2.53-2.29 (m, 5H), 1.99 (m, 2H), 1.29 (m, 2H), 1.05 (m, 6H), 0.42 (d, 3H, J=6.6 Hz)

MS (ESI) m/z 728.2 (M$^+$+H).

Example 151

Compound 744

3'-(2-(((4S,5R)-5-(3,5-bis(trifluoromethyl)phenyl)-4-methyl-2-oxooxazolidin-3-yl)methyl)-4,4-dimethyl-cyclohex-1-enyl)-2-methyl-5'-(trifluoromethyl)biphenyl-4-carboxylic acid Starting material 743 (0.070 g, 0.096 mmol) and lithium hydroxide monohydrate (0.040 g, 0.962 mmol) were dissolved in 1,4-dioxane (8 mL)/water (2 mL) at room temperature, and the reaction mixture was stirred at the same temperature for 16 hours. Water was added to the reaction mixture, followed by extraction with ethyl acetate. The organic layer was dried with anhydrous magnesium sulfate to remove water, after which it was filtered and concentrated under reduced pressure. The residue was purified by MPLC (SiO$_2$, EtOAc/hexane=10%~50%) to obtain desired compound 744 (0.046 g, 67.0%) as colorless oil.

$^1$H NMR (400 MHz, CDCl$_3$); δ 8.06 (s, 1H), 8.01 (dd, 1H, J=7.9, 1.5 Hz), 7.89 (s, 1H), 7.75 (s, 2H), 7.51 (s, 1H), 7.40 (s, 1H), 7.32-7.29 (m, 2H), 5.64 (d, 1H, J=7.9 Hz), 4.11 (d, 1H, J=14.9 Hz), 3.96 (t, 1H, J=7.2 Hz), 3.68 (d, 1H, J=14.9 Hz), 2.50-2.31 (m, 5H), 1.99 (s, 2H), 1.56 (t, 2H, J=6.4 Hz), 1.06 (d, 6H, J=15.5 Hz), 0.44 (d, 3H, J=6.5 Hz)

MS (ESI) m/z 714.1 (M$^+$+H).

Example 152

Compound 745 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-(trifluoromethyl)biphenyl-4-carboxylate Starting material 6d (0.050 g, 0.081 mmol), methyl-4-(4,4,5,5-tetramethyl-1,3,2-dioxaborolan-2-yl)benzoate (0.043 g, 0.163 mmol), sodium carbonate (0.026 g, 0.244 mmol) and Pd(dbpf)Cl$_2$ (0.003 g, 0.004 mmol) were added to dimethylformamide (0.8 mL)/water (0.4 mL) and stirred with microwave irradiation at 100° C. for 20 minutes. Then, the reaction mixture was cooled to room temperature, and water was added thereto, followed by extraction with ethyl acetate. The organic layer was dried with anhydrous magnesium sulfate to remove water, and then concentrated under reduced pressure. The residue was purified by MPLC (SiO$_2$, EtOAc/hexane=0%~20%) to obtain desired compound 745 (0.050 g, 86.0%) as a white foam solid.

$^1$H NMR (400 MHz, CDCl$_3$); δ 8.13 (m, 2H), 7.88 (m, 1H), 7.77-7.74 (m, 3H), 7.67-7.63 (m, 2H), 7.56 (s, 1H), 7.28 (m, 1H), 5.63 (d, 1H, J=7.7 Hz), 4.13 (m, 1H), 3.97 (m, 4H), 3.66 (d, 1H, J=14.9 Hz), 2.47-2.33 (m, 2H), 2.00 (s, 2H), 1.57 (t, 2H, J=6.2 Hz), 1.07 (d, 6H, J=14.6 Hz), 0.44 (d, 3H, J=6.3 Hz)

MS (ESI) m/z 714.2 (M$^+$+H).

Example 153

Compound 746

3'-(2-(((4S,5R)-5-(3,5-bis(trifluoromethyl)phenyl)-4-methyl-2-oxooxazolidin-3-yl)methyl)-4,4-dimethyl-cyclohex-1-enyl)-5'-(trifluoromethyl)biphenyl-4-carboxylic acid Starting material 745 (0.045 g, 0.063 mmol) and lithium hydroxide monohydrate (0.026 g, 0.631 mmol) were dissolved in 1,4-dioxane (8 mL)/water (2 mL) at room temperature, and the reaction mixture was stirred at the same temperature for 16 hours. Water was added to the reaction mixture, followed by extraction with ethyl acetate. The organic layer was dried with anhydrous magnesium sulfate to remove water, after which it was filtered and concentrated under reduced pressure. The residue was purified and concentrated by MPLC (SiO$_2$, EtOAc/hexane=10%~50%) to obtain desired compound 746 (0.021 g, 47.6%) as colorless oil.

$^1$H NMR (400 MHz, CDCl$_3$); δ 8.23 (dd, 2H, J=6.7, 1.8 Hz), 7.88 (s, 1H), 7.79 (s, 1H), 7.74 (s, 2H), 7.71 (dd, 2H, J=6.7, 1.8 Hz), 7.57 (s, 1H), 7.41 (s, 1H), 5.62 (d, 1H, J=8.1 Hz), 4.14-3.93 (m, 2H), 3.67-3.63 (m, 1H), 2.48-2.34 (m, 2H), 2.00 (s, 2H), 1.57 (t, 2H, J=6.4 Hz), 1.08 (d, 6H, J=14.1 Hz), 0.44 (m, 3H)

MS (ESI) m/z 700.1 (M$^+$+H).

Example 154

Compound 747 methyl 3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-5'-(trifluoromethyl)biphenyl-4-carboxylate Starting material 63d (0.050 g, 0.081 mmol), methyl 6-fluoro-4-(4,4,5,5-tetramethyl-1,3,2-dioxaborolan-2-yl)benzoate (0.046 g, 0.163 mmol), sodium carbonate (0.026 g, 0.244 mmol) and Pd(dbpf)Cl$_2$ (0.003 g, 0.004 mmol) were added to dimethylformamide (0.8 mL)/water (0.4 mL) and heated by microwave irradiation at 100° C. for 20 minutes. Then, the reaction mixture was cooled to room temperature, and water was added thereto, followed by extraction with ethyl acetate. The organic layer was dried with anhydrous magnesium sulfate, and then concentrated under reduced pressure. The residue was purified by MPLC (SiO$_2$, EtOAc/hexane=0%~20%) to obtain desired compound 747 (0.058 g, 97.3%) as a white foam solid.

$^1$H NMR (400 MHz, CDCl$_3$); δ 7.95-7.82 (m, 3H), 7.75-7.71 (m, 3H), 7.55-7.51 (m, 2H), 7.42 (s, 1H), 5.59 (d, 1H, J=20.0 Hz), 4.09 (d, 1H, J=14.9 Hz), 3.97 (s, 4H), 3.68 (d, 1H, J=14.9 Hz), 2.42-2.36 (m, 2H), 2.00 (s, 2H), 1.55 (t, 2H, J=6.4 Hz), 1.08-1.04 (m, 6H), 0.41 (d, 3H, J=6.4 Hz)

MS (ESI) m/z 732.1 (M$^+$+H).

Example 155

Compound 748

3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-5'-(trifluoromethyl)biphenyl-4-carboxylic acid Starting material 747 (0.044 g, 0.060 mmol) and lithium hydroxide monohydrate (0.025 g, 0.601 mmol) were dissolved in 1,4-dioxane (8 mL)/water (2 mL) at room temperature, and the reaction mixture was stirred at the same temperature for 16 hours. Water was added to the reaction mixture, followed by extraction with ethyl acetate. The organic layer was dried with anhydrous magnesium sulfate, after which it was filtered and concentrated under reduced pressure. The residue was purified and concentrated by MPLC (SiO$_2$, EtOAc/hexane=10%~50%) to obtain desired compound 748 (0.030 g, 69.5%) as colorless oil.

$^1$H NMR (400 MHz, CDCl$_3$); δ 8.02 (dd, 1H, J=8.0, 1.5 Hz), 7.92 (dd, 1H, J=10.8, 1.4 Hz), 7.88 (s, 1H), 7.76-7.73 (m, 3H), 7.60-7.54 (m, 2H), 7.44 (s, 1H), 5.63 (d, 1H, J=7.8 Hz), 4.12-3.93 (m, 2H), 3.70 (m, 1H), 2.47-2.33 (m, 2H), 2.01 (s, 2H), 1.56 (t, 2H, J=6.3 Hz), 1.07 (d, 6H, J=14.0 Hz), 0.41 (m, 3H)

MS (ESI) m/z 718.1 (M$^+$+H).

Preparation of Novel Compounds According to Reaction Scheme 16

Example 156

Compound 682

3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2-methylbiphenyl-4-carboxamide Starting material 554 (1.370 g, 2.028 mmol), thionyl chloride (0.221 mL, 3.041 mmol) and dimethylformamide (0.156 mL, 2.028 mmol) were added to dichloromethane (30 ml), and the reaction mixture was heated under reflux for 4 hours, after which it was cooled to room temperature, and then concentrated under reduced pressure. The reaction mixture was dissolved in tetrahydrofuran (30 ml), and 2-3 drops of ammonia water was added thereto, followed by stirring for 5 minutes. Water was added to the reaction mixture, followed by extraction with ethyl acetate. The organic layer was washed with saturated brine and dried with anhydrous magnesium sulfate, followed by concentration under reduced pressure. The residue was purified by MPLC (SiO$_2$, CH$_3$OH/CH$_2$Cl$_2$=0%~5%) to obtain compound 682 (1.180 g, 86.3%) as a white solid.

$^1$H NMR (400 MHz, CDCl$_3$); 1:1.40 atropisomeric mixture; δ 7.85 (s, 1H), 7.73-7.70 (m, 3H), 7.64-7.61 (m, 1H), 7.27-7.15 (m, 2H), 6.94-6.87 (m, 2H), 6.10 (brs, 1H), 5.62 (brs, 1H), 5.61-5.57 (m, 1H), 4.01-3.92 (m, 2H), 3.82 (s, 1.3H), 3.79 (s, 1.7H), 3.64 (d, 0.6H, J=14.5 Hz), 3.51 (d, 0.4H, J=14.8 Hz), 2.56-2.06 (m, 5H), 1.98-1.86 (m, 2H), 1.56-1.46 (m, 2H), 1.05-1.00 (m, 6H), 0.42 (d, 1.3H, J=6.6 Hz), 0.35 (d, 1.7H, J=6.5 Hz)

MS (ESI) m/z 675.2 (M$^+$+H).

Example 157

Compound 740

3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-chloro-4'-methoxybiphenyl-4-carboxamide Starting material 643 (0.01 g, 0.014 mmol), thionyl chloride (0.002 mL, 0.022 mmol) and dimethylformamide (0.001 g, 0.007 mmol) were dissolved in methylene chloride (3 mL) at room temperature, and the reaction mixture was heated under reflux for 5 hours. Then, ammonia water was added to the reaction mixture at room temperature, followed by stirring at the same temperature for 16 hours. Water was added to the reaction mixture, followed by extraction with ethyl acetate. The organic layer was washed with brine and dried with anhydrous magnesium sulfate, after which it was filtered and concentrated under reduced pressure. The residue was purified and concentrated by MPLC (SiO₂, EtOAc/hexane=0%~50%) to obtain desired compound 740 (0.006 g, 60.1%) as colorless oil.

¹H NMR (400 MHz, CDCl₃); δ 7.95-7.91 (m, 1H), 7.87 (s, 1H), 7.80 (m, 3H), 7.44-7.31 (m, 2H), 7.13 (m, 1H), 6.95 (2d, 1H, J=8.6 Hz), 6.20-5.80 (m, 2H), 5.61 (2d, 1H, J=5.5 Hz), 4.10-3.90 (m, 2H), 3.84 (2s, 3H), 3.72-3.50 (m, 1H), 2.60-2.20 (m, 2H), 1.96 (m, 2H), 1.60-1.40 (m, 2H), 1.10-1.02 (m, 6H), 0.40 (2d, 3H, J=6.6 Hz)

MS (ESI) m/z 695.1 (M⁺+H).

Example 158

Compound 741

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-2'-fluoro-2-methylbiphenyl-4-carboxamide Starting material 681 (0.010 g, 0.014 mmol), thionyl chloride (0.002 mL, 0.022 mmol) and dimethylformamide (0.001 g, 0.007 mmol) were dissolved in methylene chloride (3 mL) at room temperature, and the reaction mixture was heated under reflux for 5 hours. Then, ammonia water was added to the reaction mixture at room temperature, followed by stiffing at the same temperature for 16 hours. Water was added to the reaction mixture, followed by extraction with ethyl acetate. The organic layer was washed with brine and dried with anhydrous magnesium sulfate, after which it was filtered and concentrated under reduced pressure. The residue was purified and concentrated by MPLC (SiO₂, EtOAc/hexane=0%~50%) to obtain desired compound 741 (0.007 g, 70.1%) as colorless oil.

¹H NMR (400 MHz, CDCl₃); δ 7.88 (s, 1H), 7.76 (m, 3H), 7.67 (m, 1H), 7.27 (m, 1H), 7.12 (m, 2H), 6.98 (m, 1H), 6.26-5.80 (m, 2H), 5.64 (d, 1H, J=8.1 Hz), 4.10-3.87 (m, 2H), 3.75 (d, 1H, J=14.7 Hz), 2.23-2.20 (m, 5H), 1.91 (m, 2H), 1.53 (t, 2H, J=6.5 Hz), 1.00 (m, 6H), 0.43 (d, 3H, J=6.5 Hz)

MS (ESI) m/z 663.2 (M⁺+H).

Example 159

Compound 742

3'-(2-(((4S,5R)-5-(3,5-bis(trifluoromethyl)phenyl)-4-methyl-2-oxooxazolidin-3-yl)methyl)-4,4-dimethyl-cyclohex-1-enyl)-4'-fluoro-2-(trifluoromethyl)biphenyl-4-carboxamide Starting material 695 (0.010 g, 0.014 mmol), thionyl chloride (0.002 mL, 0.021 mmol) and dimethylformamide (0.001 g, 0.007 mmol) were dissolved in methylene chloride (3 mL) at room temperature, and the reaction mixture was heated under reflux for 5 hours. Then, ammonia water was added to the reaction mixture at room temperature, followed by stiffing at the same temperature for 16 hours. Water was added to the reaction mixture, followed by extraction with ethyl acetate. The organic layer was washed with brine and dried with anhydrous magnesium sulfate, after which it was filtered and concentrated under reduced pressure. The residue was purified and concentrated by MPLC (SiO₂, EtOAc/hexane=0%~50%) to obtain desired compound 742 (0.008 g, 80.1%) as colorless oil.

¹H NMR (400 MHz, CDCl₃); δ 8.21 (s, 1H), 8.03 (m, 1H), 7.88 (s, 1H), 7.78-7.74 (m, 1H), 7.47-7.40 (m, 2H), 7.21-7.05 (m, 3H), 6.98 (m, 1H), 6.30-5.75 (m, 2H), 5.64 (2d, 1H, J=7.9 Hz), 4.10-3.82 (m, 2H), 3.80 (m, 1H), 2.53-2.26 (m, 2H), 2.00 (m, 2H), 1.53 (m, 2H), 1.05 (m, 6H), 0.44 (2d, 1H, J=6.3 Hz)

MS (ESI) m/z 717.1 (M⁺+H).

Example 160

Compound 754

(4S,5R)-5-(3,5-bis(trifluoromethyl)phenyl)-3-((2-(4'-(3,3-difluoroazetidine-1-carbonyl)-4-fluoro-2'-(trifluoromethyl)biphenyl-3-yl)-4,4-dimethylcyclohex-1-enyl)methyl)-4-methyloxazolidin-2-one Compound 695 (0.072 g, 0.100 mmol), 3,3-difluoroazetidine hydrochloride (0.014 g, 0.110 mmol), EDC (0.038 g, 0.201 mmol) and HOBt (0.027 g, 0.201 mmol) were dissolved in methylene chloride (1 mL) at room temperature, and diisopropylethylamine (0.088 mL, 0.502 mmol) was added to the reaction mixture, followed by stiffing overnight at the same temperature. Water was added to the reaction mixture, which was then extracted with methylene chloride. The extract was filtered through a plastic filter to remove the solid residue and the aqueous layer, followed by concentration under reduced pressure. The residue was purified by preparative TLC (SiO₂, EtOAc/hexane=33%) to obtain compound 754 (0.062 g, 78%) as a white foam solid.

¹H NMR (400 MHz, CDCl₃); δ 8.04 (s, 1H), 7.89-7.82 (m, 2H), 7.78-7.74 (m, 2H), 7.47-7.41 (m, 1H), 7.23-7.20 (m, 1H), 7.18-7.05 (m, 2H), 5.68-5.60 (m, 1H), 4.65-4.59 (m, 4H), 4.13-3.90 (m, 2H), 3.66-3.60 (m, 1H), 2.55-2.19 (m, 2H), 2.04-1.94 (m, 2H), 1.56-1.51 (m, 2H), 1.08-1.03 (m, 6H), 0.49-0.41 (m, 3H)

MS (ESI) m/z 793.1 (M⁺+H).

Example 161

Compound 755

(4S,5R)-5-(3,5-bis(trifluoromethyl)phenyl)-3-((2-(4-fluoro-4'-(3-hydroxyazetidine-1-carbonyl)-2'-(trifluoromethyl)biphenyl-3-yl)-4,4-dimethylcyclohex-1-enyl)methyl)-4-methyloxazolidin-2-one Compound 695 (0.072 g, 0.100 mmol), azetion-3-ol hydrochloride (0.012 g, 0.110 mmol), EDC (0.038 g, 0.201 mmol) and HOBt (0.027 g, 0.201 mmol) were dissolved in methylene chloride (1 mL) at room temperature, and diisopropylethylamine (0.088 mL, 0.502 mmol) was added to the reaction mixture, followed by stirring overnight at the same temperature. Water was added to the reaction mixture, which was then extracted with methylene chloride. The extract was filtered through a plastic filter to remove the solid residue and the aqueous layer, followed by concentration under reduced pressure. The residue was purified by preparative TLC (SiO₂, EtOAc/hexane=33%) to obtain compound 755 (0.012 g, 16%) as a white foam solid.

¹H NMR (400 MHz, CDCl₃); δ 8.44-8.24 (m, 1H), 8.06-7.89 (m, 2H), 7.84-7.74 (m, 2H), 7.50-7.39 (m, 1H), 7.22-7.21 (m, 1H), 7.10-7.05 (m, 2H), 5.68-5.60 (m, 1H), 4.83-4.75 (m, 1H), 4.51-4.43 (m, 1H), 4.12-3.90 (m, 2H), 3.67-3.60 (m, 1H), 2.55-2.19 (m, 2H), 2.04-1.94 (m, 2H), 1.72-1.51 (m, 5H), 1.08-1.03 (m, 6H), 0.49-0.41 (m, 3H)

MS (ESI) m/z Not detected (M⁺+H).

Example 162

Compound 756

3'-(2-(((4S,5R)-5-(3,5-bis(trifluoromethyl)phenyl)-4-methyl-2-oxooxazolidin-3-yl)methyl)-4,4-dimethyl-cyclohex-1-enyl)-N-ethyl-4'-fluoro-2-(trifluoromethyl)biphenyl-4-carboxamide Compound 695 (0.072 g, 0.100 mmol), ethylamine (0.005 g, 0.110 mmol), EDC (0.038 g, 0.201 mmol) and HOBt (0.027 g, 0.201 mmol) were dissolved in methylene chloride (1 mL) at room temperature, and diisopropylethylamine (0.088 mL, 0.502 mmol) was added to the reaction mixture, followed by stirring overnight at the same temperature. Water was added to the reaction mixture, which was then extracted with methylene chloride. The extract was filtered through a plastic filter to remove the solid residue and the aqueous layer, followed by concentration under reduced pressure. The residue was purified by preparative TLC ($SiO_2$, EtOAc/hexane=33%) to obtain compound 756 (0.055 g, 74%) as a white foam solid.

$^1$H NMR (400 MHz, $CDCl_3$); δ 8.14 (s, 1H), 7.98 (dd, 1H, J=14.9, 7.9 Hz), 7.88 (s, 1H), 7.76 (d, 2H, J=14.2 Hz), 7.40 (dd, 1H, J=20.0, 8.0 Hz), 7.22-7.19 (m, 1H), 7.16-7.02 (m, 2H), 6.39-6.28 (m, 1H), 5.67-5.61 (m, 1H), 4.11-3.89 (m, 2H), 3.67-3.53 (m, 3H), 2.55-2.19 (m, 2H), 2.04-1.94 (m, 2H), 1.60-1.47 (m, 2H), 1.33-1.28 (m, 3H), 1.08-1.02 (m, 6H), 0.47-0.40 (m, 3H)

MS (ESI) m/z 745.1 ($M^+$+H).

Example 163

Compound 757

3'-(2-(((4S,5R)-5-(3,5-bis(trifluoromethyl)phenyl)-4-methyl-2-oxooxazolidin-3-yl)methyl)-4,4-dimethyl-cyclohex-1-enyl)-N-ethyl-4'-fluoro-N-methyl-2-(trifluoromethyl)biphenyl-4-carboxamide Compound 695 (0.072 g, 0.100 mmol), N-methylethylamine (0.009 mL, 0.110 mmol), EDC (0.038 g, 0.201 mmol) and HOBt (0.027 g, 0.201 mmol) were dissolved in methylene chloride (1 mL) at room temperature, and diisopropylethylamine (0.088 mL, 0.502 mmol) was added to the reaction mixture, followed by stirring overnight at the same temperature. Water was added to the reaction mixture, which was then extracted with methylene chloride. The extract was filtered through a plastic filter to remove the solid residue and the aqueous layer, followed by concentration under reduced pressure. The residue was purified by preparative TLC ($SiO_2$, EtOAc/hexane=33%) to obtain compound 757 (0.048 g, 64%) as a white foam solid.

$^1$H NMR (400 MHz, $CDCl_3$); δ 7.89 (s, 1H), 7.80-7.75 (m, 3H), 7.63-7.59 (m, 1H), 7.37 (dd, 1H, J=20.0, 7.7 Hz), 7.21-7.20 (m, 1H), 7.16-7.04 (m, 2H), 5.67-5.61 (m, 1H), 4.13-3.89 (m, 2H), 3.68-3.61 (m, 2H), 3.35-3.34 (m, 1H), 3.13-3.01 (m, 3H), 2.55-2.16 (m, 2H), 2.04-1.94 (m, 2H), 1.59-1.48 (m, 2H), 1.30-1.21 (m, 3H), 1.08-1.03 (m, 6H), 0.48-0.41 (m, 3H)

MS (ESI) m/z 759.2 ($M^+$+H).

Example 164

Compound 758

(4S,5R)-5-(3,5-bis(trifluoromethyl)phenyl)-3-((2-(4-fluoro-4'-(morpholine-4-carbonyl)-2'-(trifluoromethyl)biphenyl-3-yl)-4,4-dimethylcyclohex-1-enyl)methyl)-4-methyloxazolidin-2-one Compound 695 (0.072 g, 0.100 mmol), morpholine (0.010 mL, 0.110 mmol), EDC (0.038 g, 0.201 mmol) and HOBt (0.027 g, 0.201 mmol) were dissolved in methylene chloride (1 mL) at room temperature, and diisopropylethylamine (0.088 mL, 0.502 mmol) was added to the reaction mixture, followed by stirring overnight at the same temperature. Water was added to the reaction mixture, which was then extracted with methylene chloride. The extract was filtered through a plastic filter to remove the solid residue and the aqueous layer, followed by concentration under reduced pressure. The residue was purified by preparative TLC ($SiO_2$, EtOAc/hexane=33%) to obtain compound 758 (0.066 g, 83%) as a white foam solid.

$^1$H NMR (400 MHz, $CDCl_3$); δ 7.59 (s, 1H), 7.78 (t, 3H, J=14.9 Hz), 7.62 (t, 1H, J=9.0 Hz), 7.39 (dd, 1H, J=17.9, 7.8 Hz), 7.23-7.19 (m, 1H), 7.17-7.03 (m, 2H), 5.67-5.60 (m, 1H), 4.13-3.89 (m, 2H), 3.83-3.51 (m, 9H), 2.55-2.18 (m, 2H), 2.04-1.94 (m, 2H), 1.59-1.49 (m, 2H), 1.08-1.05 (m, 6H), 0.48-0.41 (m, 3H)

MS (ESI) m/z 787.2 ($M^+$+H).

Preparation of Novel Compounds According to Reaction Scheme 17

Intermediate Compound 66: (2-(5-chloro-2-methoxyphenyl)-5,5-dimethylcyclohex-1-enyl)methanol Starting material 65 (0.560 g, 2.009 mmol) was dissolved in THF (20 mL) at 0° C., and LAH (1.00M solution in THF, 4.018 mL, 4.018 mmol) was added to the reaction mixture at the same temperature, followed by stirring for 1 hour. Then, 1M hydrochloric acid was added to the reaction mixture, followed by extraction with ethyl acetate. The organic layer was dried with anhydrous magnesium sulfate, and then concentrated under reduced pressure. The residue was purified by MPLC ($SiO_2$, EtOAc/hexane=0%~20%) to obtain desired compound 66 (0.350 g, 62.1%) as colorless oil.

Intermediate Compound 67: methyl 3'-(2-(hydroxymethyl)-4,4-dimethylcyclohex-1-enyl)-4'-methoxy-2-methylbiphenyl-4-carboxylate Starting material 66 (0.500 g, 1.781 mmol), compound 57 (0.983 g, 3.561 mmol), sodium carbonate (0.566 g, 5.342 mmol) and Pd(dbpf)$Cl_2$ (0.058 g, 0.089 mmol) were added to dimethoxymethane (1.2 mL)/water (0.4 mL) and heated by microwave irradiation at 120° C. for 20 minutes. Then, the reaction mixture was cooled to room temperature, and water was added thereto, followed by extraction with ethyl acetate. The organic layer was dried with anhydrous magnesium sulfate, and then concentrated under reduced pressure. The residue was purified by MPLC ($SiO_2$, EtOAc/hexane=0%~20%) to obtain compound 67 (0.250 g, 35.6%) as colorless oil.

Intermediate Compound 68: methyl 3'-(2-(chloromethyl)-4,4-dimethylcyclohex-1-enyl)-4'-methoxy-2-methylbiphenyl-4-carboxylate Starting material 67 (0.250 g, 0.634 mmol) and thionyl chloride (0.069 mL, 0.951 mmol) were dissolved in dimethylformamide (10 mL) at 0° C., and the reaction mixture was stirred at the same temperature for 3 hours. Then, water was added to the reaction mixture, followed by extraction with ethyl acetate. The organic layer was dried with anhydrous magnesium sulfate, and then concentrated under reduced pressure. The residue was purified by MPLC (SiO$_2$, EtOAc/hexane=0%~100%) to obtain compound 68 (0.190 g, 72.6%) as colorless oil.

Intermediate Compound 70: methyl 3'-(2-(((4S,5S)-5-(3,5-bis(trifluoromethyl)phenyl)-4-methyl-2-oxooxazolidin-3-yl)methyl)-4,4-dimethylcyclohex-1-enyl)-4'-methoxyphenyl-2-methylbiphenyl-4-carboxylate Starting material 68 (0.044 g, 0.107 mmol) and compound 69 (0.033 g, 0.107 mmol) were dissolved in dimethylformamide (10 ml), and sodium hydride (0.003 g, 0.107 mmol) was added to the reaction mixture at 0° C., followed by stirring at the same temperature for 3 hours. Then, water was added to the reaction mixture, followed by extraction with ethyl acetate. The organic layer was dried with anhydrous magnesium sulfate, and then concentrated under reduced pressure. The residue was purified by MPLC (Sift, EtOAc/hexane=0%~100%) to obtain compound 70 (0.030 g, 40.8%) as a white foam solid.

Intermediate Compound 72: methyl 3'-(2-(((4R,5S)-5-(3,5-bis(trifluoromethyl)phenyl)-4-methyl-2-oxooxazolidin-3-yl)methyl)-4,4-dimethylcyclohex-1-enyl)-4'-methoxyphenyl-2-methylbiphenyl-4-carboxylate Starting material 68 (0.080 g, 0.194 mmol) and compound 71 (0.061 g, 0.194 mmol) were dissolved in dimethylformamide (10 mL), and sodium hydride (0.005 g, 0.194 mmol) was added to the reaction mixture at 0° C., followed by stirring at the same temperature for 3 hours. Then, water was added to the reaction mixture, followed by extraction with ethyl acetate. The organic layer was dried with anhydrous magnesium sulfate, and then concentrated under reduced pressure. The residue was purified by MPLC (SiO$_2$, EtOAc/hexane=0%~20%) to obtain compound 72 (0.030 g, 22.5%) as a white foam solid.

Intermediate Compound 74: methyl 3'-(2-(((4R,5R)-5-(3,5-bis(trifluoromethyl)phenyl)-4-methyl-2-oxooxazolidin-3-yl)methyl)-4,4-dimethylcyclohex-1-enyl)-4'-methoxyphenyl-2-methylbiphenyl-4-carboxylate Starting material 68 (0.090 g, 0.218 mmol) and compound 73 (0.048 g, 0.153 mmol) were dissolved in dimethylformamide (10 mL), and the reaction mixture was cooled to 0° C. Sodium hydride (0.005 g, 0.218 mmol) was added to the reaction mixture, followed by stirring room temperature for 2 hours. Then, water was added to the reaction mixture, followed by extraction with ethyl acetate. The organic layer was dried with anhydrous magnesium sulfate, and then concentrated under reduced pressure. The residue was purified by MPLC (SiO$_2$, EtOAc/hexane=0%-20%) to obtain compound 74 (0.035 g, 23.3%) as a white foam solid.

Example 165

Compound 718

3'-(2-(((4S,5S)-5-(3,5-bis(trifluoromethyl)phenyl)-4-methyl-2-oxooxazolidin-3-yl)methyl)-4,4-dimethylcyclohex-1-enyl)-4'-methoxy-2-methylbiphenyl-4-carboxylic acid Starting material 70 (0.030 g, 0.043 mmol) and lithium hydroxide monohydrate (0.037 g, 0.870 mmol) were dissolved in dioxane (8 mL)/water (2 mL) at room temperature, and the reaction mixture was stirred at the same temperature for 16 hours. Then, 1M hydrochloric acid was added to the reaction mixture, followed by extraction with ethyl acetate. The organic layer was dried with anhydrous magnesium sulfate, and then concentrated under reduced pressure. The residue was purified by MPLC (Sift, EtOAc/hexane=0%-100%) to obtain desired compound 718 (0.025 g, 85.1%) as a white foam solid.

$^1$H NMR (400 MHz, CDCl$_3$); δ 8.03-7.75 (m, 4H), 7.30-7.18 (m, 2H), 6.92 (m, 2H), 4.98 (2d, 1H, J=5.6 Hz), 4.00-3.88 (m, 1H), 3.80-3.74 (m, 3H), 3.70-3.31 (m, 2H), 2.45-2.12 (m, 4H), 2.32-2.29 (m, 3H), 2.22-2.12 (m, 1H), 2.00-1.83 (m, 2H), 1.57-1.23 (m, 4H), 1.09-1.00 (m, 3H), 0.98-0.60 (m, 6H)

MS (ESI) m/z 676.2 (M$^+$+H).

Example 166

Compound 719

3'-(2-(((4R,5S)-5-(3,5-bis(trifluoromethyl)phenyl)-4-methyl-2-oxooxazolidin-3-yl)methyl)-4,4-dimethylcyclohex-1-enyl)-4'-methoxy-2-methylbiphenyl-4-carboxylic acid Starting material 72 (0.030 g, 0.043 mmol) and lithium hydroxide monohydrate (0.037 g, 0.870 mmol) were dissolved in dioxane (8 mL)/water (2 mL) at room temperature, and the reaction mixture was stirred at the same temperature for 16 hours. Then, 1M hydrochloric acid was added to the reaction mixture, followed by extraction with ethyl acetate. The organic layer was dried with anhydrous magnesium sulfate, and then concentrated under reduced pressure. The residue was purified by MPLC (SiO$_2$, EtOAc/hexane=0%-100%) to obtain desired compound 719 (0.025 g, 85.1%) as a white foam solid.

$^1$H NMR (400 MHz, CDCl$_3$); δ 7.99-7.69 (m, 5H), 7.29-7.16 (m, 2H), 6.92 (m, 2H), 5.59 (m, 1H), 4.06-3.87 (m, 2H), 3.81-3.78 (m, 3H), 3.65-3.48 (m, 1H), 2.55-2.06 (m, 5H), 1.93 (m, 2H), 1.55-1.42 (m, 2H), 1.04-1.99 (m, 6H), 0.38 (2d, 3H, J=6.6 Hz)

MS (ESI) m/z 676.2 (M$^+$+H).

Example 167

Compound 720

3'-(2-(((4R,5R)-5-(3,5-bis(trifluoromethyl)phenyl)-4-methyl-2-oxooxazolidin-3-yl)methyl)-4,4-dimethylcyclohex-1-enyl)-4'-methoxy-2-methylbiphenyl-4-carboxylic acid Starting material 74 (0.030 g, 0.043 mmol) and lithium hydroxide monohydrate (0.037 g, 0.870 mmol) were dissolved in dioxane (8 mL)/water (2 mL) at room temperature, and the reaction mixture was stirred at the same temperature for 16 hours. Then, 1M hydrochloric acid was added to the reaction mixture, followed by extraction with ethyl acetate. The organic layer was dried with anhydrous magnesium sulfate, and then concentrated under reduced pressure. The residue was purified by MPLC (SiO$_2$, EtOAc/hexane=0%~100%) to obtain desired compound 720 (0.028 g, 95.3%) as a white foam solid.

$^1$H NMR (400 MHz, CDCl$_3$); δ 8.03-7.75 (m, 5H), 7.30-7.18 (m, 2H), 6.92 (m, 2H), 4.98 (2d, 1H, J=5.6 Hz), 4.00-3.88 (m, 1H), 3.80-3.74 (m, 3H), 3.70-3.31 (m, 2H), 2.45-2.12 (m, 4H), 2.00-1.83 (m, 2H), 1.57-1.23 (m, 4H), 1.09-1.00 (m, 3H), 0.98-0.60 (m, 6H)

MS (ESI) m/z 676.2 (M$^+$+H).

Preparation of Novel Compounds According to Reaction Scheme 18

Intermediate Compound 76: (1R,2S)-2-((2-(5-chloro-2-methoxyphenyl)-5,5-dimethylcyclohex-1-enyl)methylamino)-1-(3,5-difluorophenyl)propan-1-ol Starting material 3b (0.500 g, 1.794 mmol), compound 75 (0.353 g, 1.883 mmol), sodium cyanoborohydride (0.135 g, 2.152 mmol) and acetic acid (0.123 mL, 2.152 mmol) were dissolved in dichloromethane (10 ml) at room temperature, and the reaction mixture was stirred for 2 hours at room temperature. Then, an aqueous solution of saturated sodium bicarbonate was added to the reaction mixture, followed by extraction with ethyl acetate. The organic layer was washed with aqueous solution of saturated sodium bicarbonate and dried with anhydrous magnesium sulfate, followed by concentration under reduced pressure. The residue was purified by MPLC (SiO$_2$, EtOAc/hexane=5%~10%) to obtain compound 76 (0.182 g, 22.6%) as colorless oil.

MS (ESI) m/z 450.2 (M$^+$+H).

Intermediate Compound 77: (4S,5R)-3-((2-(5-chloro-2-methoxyphenyl)-5,5-dimethylcyclohex-1-enyl)methyl)-5-(3,5-difluorophenyl)-4-methyloxazolidin-2-one Starting material 76 (0.182 g, 0.331 mmol) and diisopropylethylamine (0.347 mL, 1.986 mmol) were dissolved in dichloromethane (5 ml), and triphosgene (0.118 g, 0.397 mmol) was added thereto at room temperature, followed by stirring at the same temperature for 30 minutes. Then, an aqueous solution of saturated sodium bicarbonate was added to the reaction mixture, followed by extraction with ethyl acetate. The organic layer was washed with aqueous solution of saturated sodium bicarbonate and dried with anhydrous magnesium sulfate, followed by concentration under reduced pressure. The residue was purified by MPLC (SiO$_2$, EtOAc/hexane=5%~10%) to obtain compound 77 (0.142 g, 90.2%) as a white solid.

MS (ESI) m/z 476.1 (M$^+$+H).

Example 168

Compound 705 methyl 3'-(2-(((4S,5R)-5-(3,5-difluorophenyl)-4-methyl-2-oxooxazolidin-3-yl)methyl)-4,4-di methyl-cyclohex-1-enyl)-4'-methoxy-2-methylbiphenyl-4-carboxylate Starting material 77 (0.138 g, 0.290 mmol), compound 57 (0.073 g, 0.377 mmol), Pd(dbpf)Cl$_2$ (0.009 g, 0.014 mmol) and sodium carbonate (0.092 g, 0.870 mmol) were added to dimethoxyethane/water (v/v=3:1, 2 ml) and heated by microwave irradiation at 120° C. for 30 minutes. Then, the reaction mixture was cooled to room temperature, and water was added thereto, followed by extraction with ethyl acetate. The organic layer was washed with aqueous solution of saturated sodium bicarbonate and dried with anhydrous magnesium sulfate, followed by concentration under reduced pressure. The residue was purified by MPLC (Sift, EtOAc/hexane=10%~20%) to obtain compound 705 (0.110 g, 64.6%) as a white solid.

$^1$H NMR (400 MHz, CDCl$_3$); 1:1.31 atropisomeric mixture; δ 7.93-7.82 (m, 2H), 7.26-7.15 (m, 2H), 6.93-6.87 (m, 2H), 6.82-6.74 (m, 3H), 5.46-5.41 (m, 1H), 3.98-3.84 (m, 5H), 3.81-3.79 (m, 3H), 3.61 (d, 0.6H, J=14.5 Hz), 3.47 (d, 0.4H, J=15.1 Hz), 2.56-2.04 (m, 5H), 1.97-1.84 (m, 2H), 1.52-1.42 (m, 2H), 1.06-0.99 (m, 6H), 0.45 (d, 1.3H, J=6.5 Hz), 0.39 (d, 1.7H, J=6.5 Hz)

MS (ESI) m/z 590.2 (M$^+$+H).

Example 169

Compound 706

3'-(2-(((4S,5R)-5-(3,5-difluorophenyl)-4-methyl-2-oxooxazolidin-3-yl)methyl)-4,4-dimethylcyclohex-1-enyl)-4'-methoxy-2-methylbiphenyl-4-carboxylic acid Starting material 705 (0.103 g, 0.175 mmol) and lithium hydroxide monohydrate (0.037 g, 0.874 mmol) were dissolved in dioxane/water (v/v=4:1, 2 ml) at 45° C., and the reaction mixture was stirred overnight at the same temperature. Then, the reaction mixture was concentrated, and water was added thereto, followed by extraction with ethyl acetate. The organic layer was washed with aqueous solution of 1M hydrochloric acid and dried with anhydrous magnesium sulfate, followed by concentration under reduced pressure. The residue was purified by MPLC (Sift, CH$_3$OH/CH$_2$Cl$_2$=5%) to obtain compound 706 (0.051 g, 50.7%) as a white solid.

$^1$H NMR (400 MHz, CDCl$_3$); 1:1.35 atropisomeric mixture; δ 8.05-7.91 (m, 2H), 7.31-7.17 (m, 2H), 6.94-6.89 (m, 2H), 6.81-6.74 (m, 3H), 5.47-5.42 (m, 1H), 4.03-3.80 (m, 5H), 3.62 (d, 0.6H, J=14.6 Hz), 3.47 (d, 0.4H, J=15.0 Hz), 2.56-2.09 (m, 5H), 1.99-1.84 (m, 2H), 1.53-1.44 (m, 2H), 1.04-0.87 (m, 6H), 0.46 (d, 1.3H, J=6.6 Hz), 0.40 (d, 1.7H, J=6.5 Hz)

MS (ESI) m/z 576.3 (M$^+$+H).

The structural formulas of compounds 553 to 764 prepared as described above are shown in Tables 1 to 29 below.

TABLE 1
| Compound | Structure |
|---|---|
| 553 | 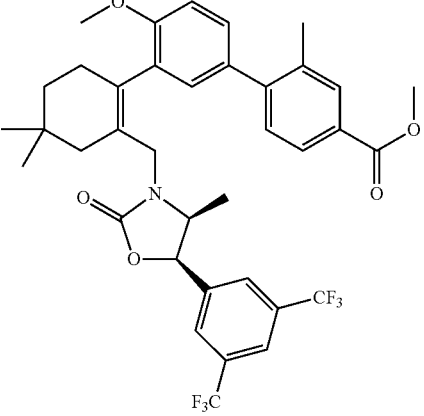 |
| 554 | 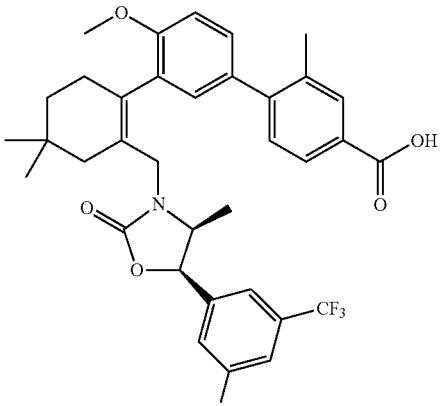 |
| 555 | 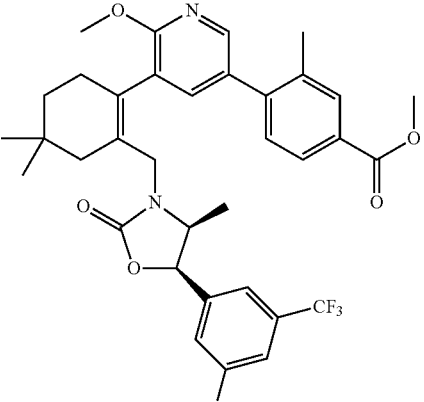 |
TABLE 1-continued
| Compound | Structure |
|---|---|
| 556 | 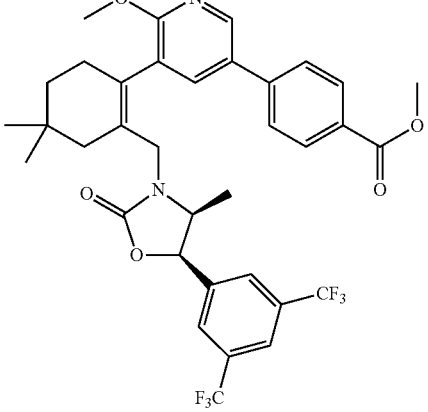 |
| 557 | 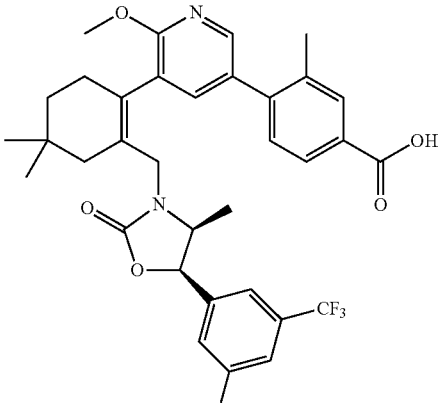 |
| 558 | 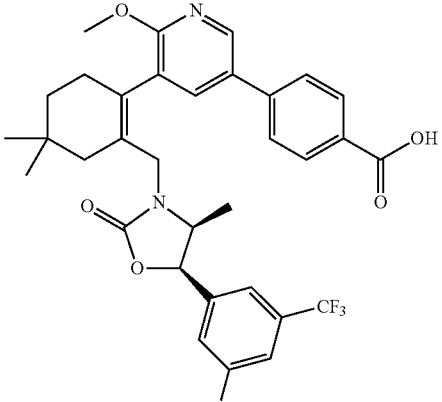 |

TABLE 2
| Compound | Structure |
|---|---|
| 559 | 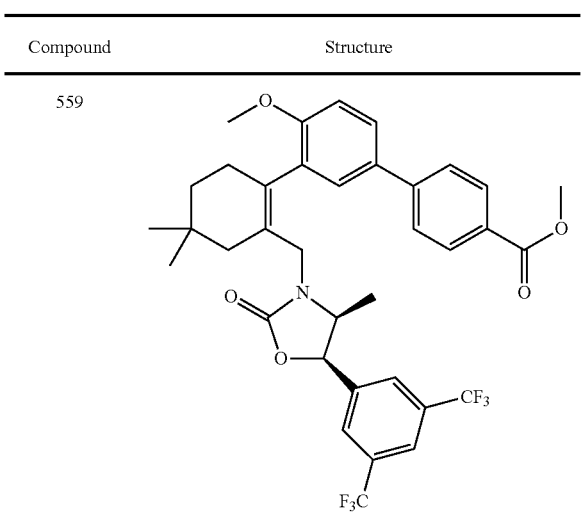 |
| 560 | 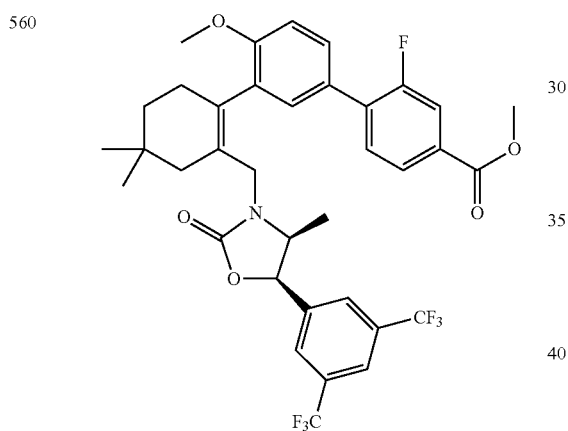 |
| 561 | 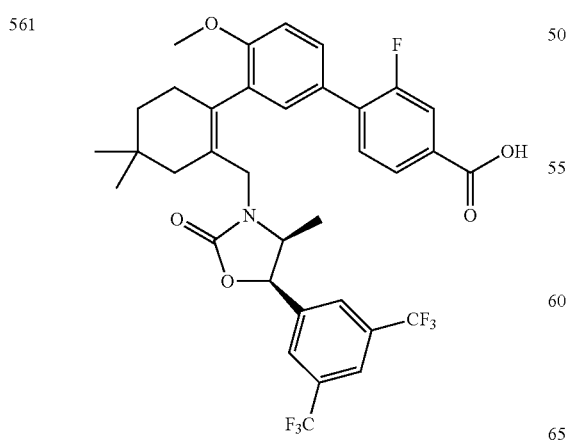 |
TABLE 2-continued
| Compound | Structure |
|---|---|
| 564 | 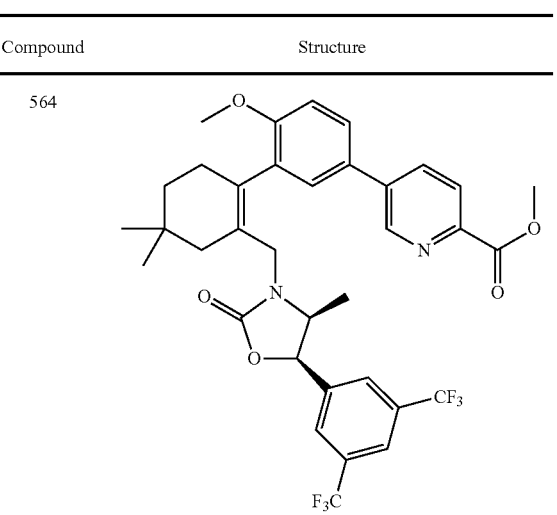 |
| 565 | 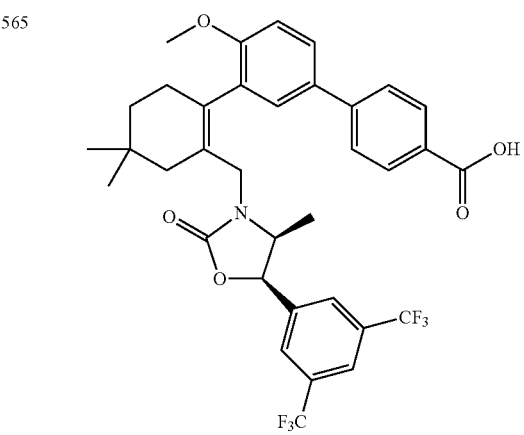 |
| 567 | 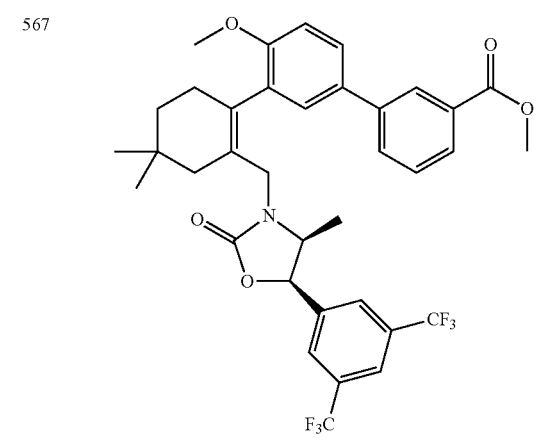 |

TABLE 3
| Compound | Structure |
|---|---|
| 568 | 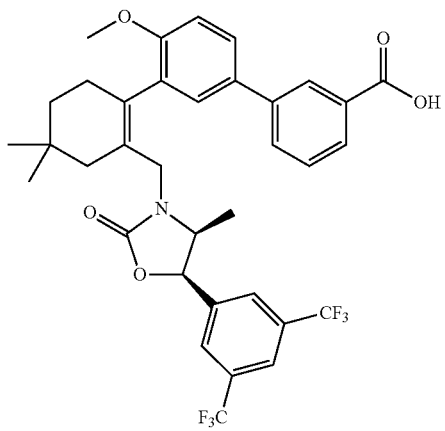 [SMILES: COc1ccc(-c2cccc(C(=O)O)c2)cc1C1=C(CN2C(=O)O[C@H](c3cc(C(F)(F)F)cc(C(F)(F)F)c3)[C@@H]2C)CC(C)(C)CC1] |
| 569 | 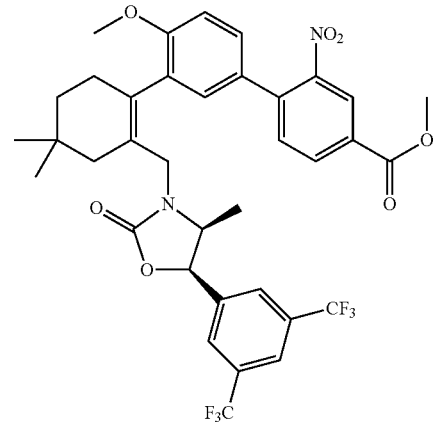 |
| 572 | 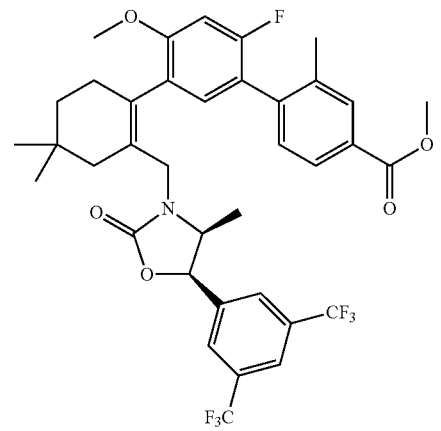 |
TABLE 3-continued
| Compound | Structure |
|---|---|
| 573 | 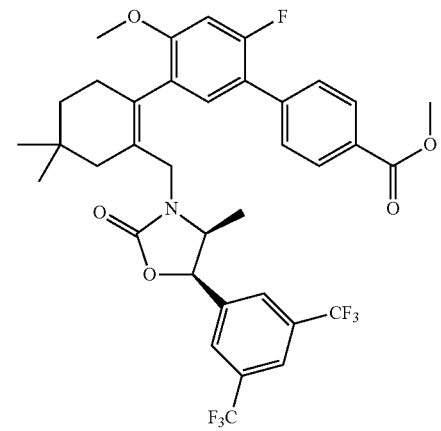 |
| 574 | 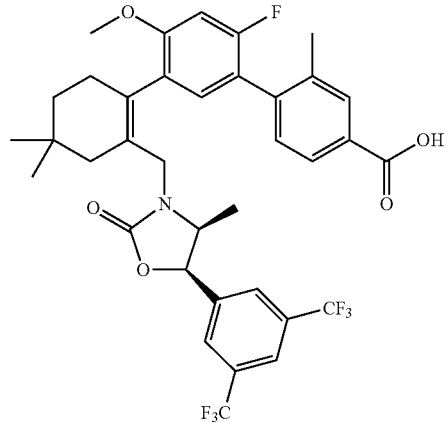 |
| 575 | 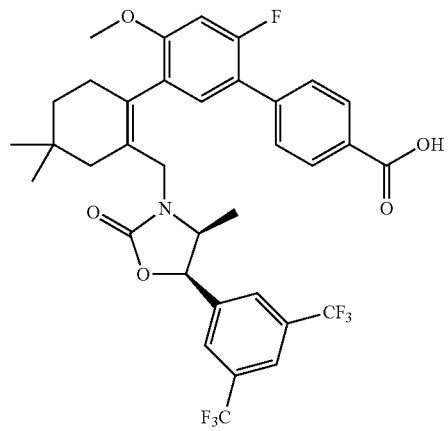 [SMILES: COc1cc(F)c(-c2ccc(C(=O)O)cc2)cc1C1=C(CN2C(=O)O[C@H](c3cc(C(F)(F)F)cc(C(F)(F)F)c3)[C@@H]2C)CC(C)(C)CC1] |

TABLE 4
| Compound | Structure |
|---|---|
| 577 | 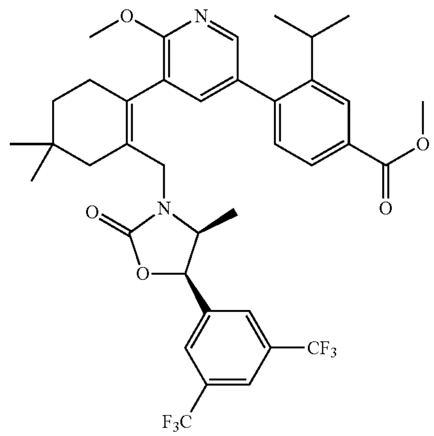 |
| 578 | 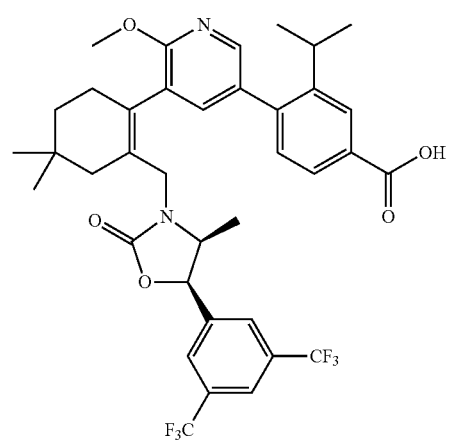 [SMILES: COc1ncc(-c2ccc(C(=O)O)cc2C(C)C)cc1C1=C(CN2C(=O)O[C@H](c3cc(C(F)(F)F)cc(C(F)(F)F)c3)[C@@H]2C)CC(C)(C)CC1] |
| 579 | 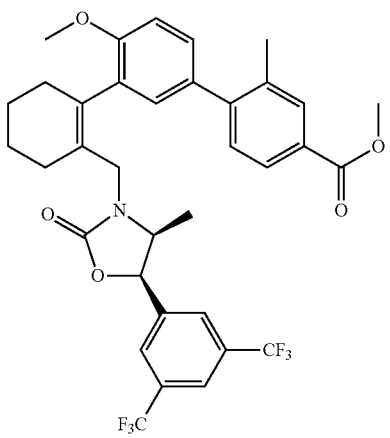 [SMILES: COC(=O)c1ccc(-c2ccc(OC)c(C3=C(CN4C(=O)O[C@H](c5cc(C(F)(F)F)cc(C(F)(F)F)c5)[C@@H]4C)CCCC3)c2)c(C)c1] |
TABLE 4-continued
| Compound | Structure |
|---|---|
| 580 | 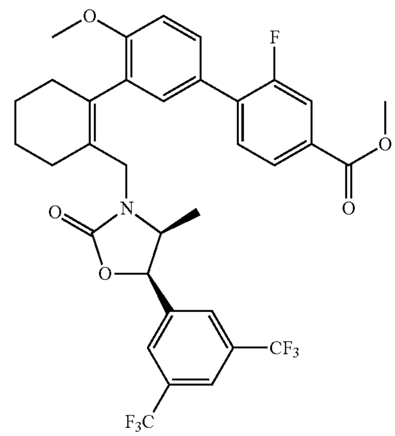 [SMILES: COC(=O)c1ccc(-c2ccc(OC)c(C3=C(CN4C(=O)O[C@H](c5cc(C(F)(F)F)cc(C(F)(F)F)c5)[C@@H]4C)CCCC3)c2)c(F)c1] |
| 581 | 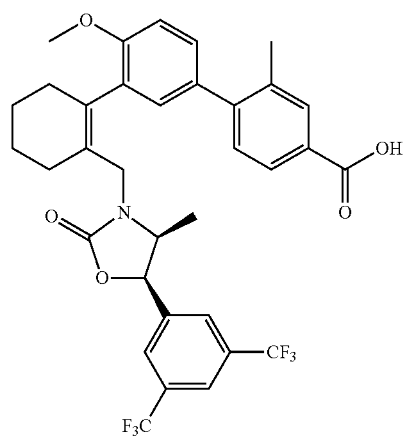 [SMILES: COc1ccc(-c2ccc(C(=O)O)cc2C)cc1C1=C(CN2C(=O)O[C@H](c3cc(C(F)(F)F)cc(C(F)(F)F)c3)[C@@H]2C)CCCC1] |
| 582 | 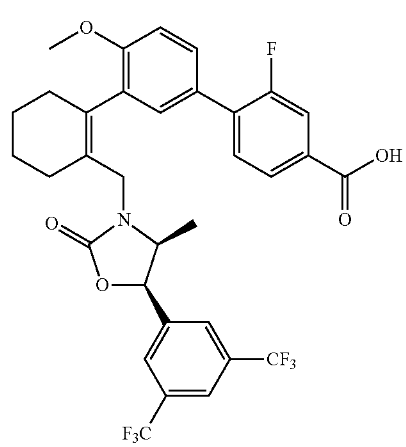 [SMILES: COc1ccc(-c2ccc(C(=O)O)cc2F)cc1C1=C(CN2C(=O)O[C@H](c3cc(C(F)(F)F)cc(C(F)(F)F)c3)[C@@H]2C)CCCC1] |

TABLE 5

| Compound | Structure |
|---|---|
| 583 | (structure) |
| 584 | (structure) |
| 585 | (structure) |

TABLE 5-continued

| Compound | Structure |
|---|---|
| 586 | (structure) |
| 587 | (structure) |
| 588 | (structure) |

TABLE 6
| Compound | Structure |
|---|---|
| 590 | 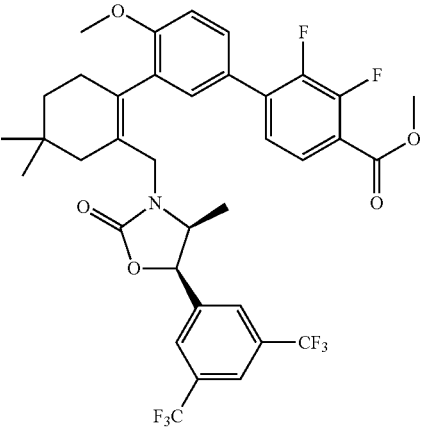 |
| 591 | 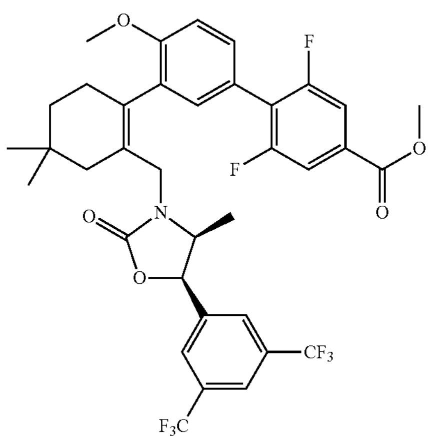 |
| 592 | 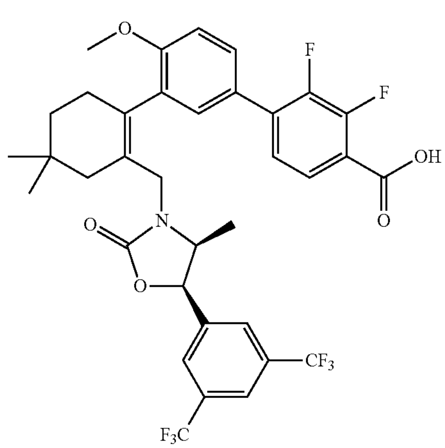 [SMILES: COc1ncc(-c2ccc(C(=O)O)c(F)c2F)cc1C1=C(CN2C(=O)O[C@H](c3cc(C(F)(F)F)cc(C(F)(F)F)c3)[C@@H]2C)CC(C)(C)CC1] |
| 593 | |
| 594 | |
| 595 | |

TABLE 7
| Compound | Structure |
|---|---|
| 596 | 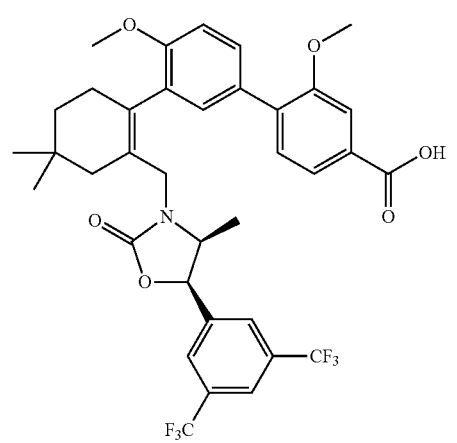 |
| 597 | 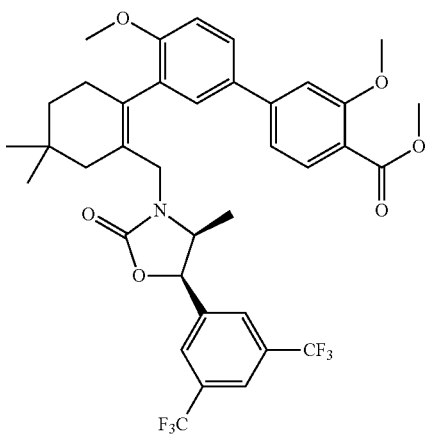 |
TABLE 7-continued
| Compound | Structure |
|---|---|
| 600 | 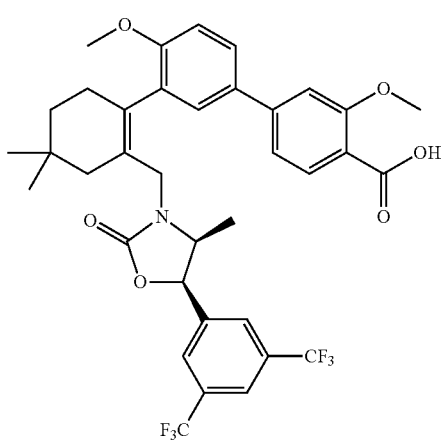 |
| 601 | 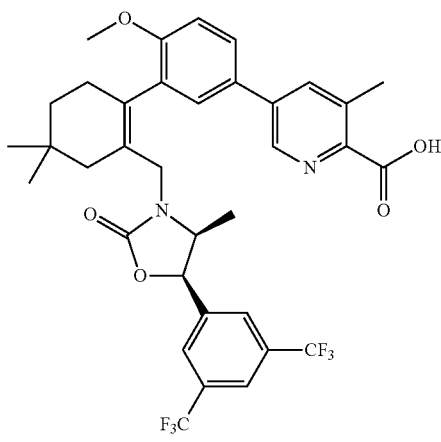 [SMILES: COc1ccc(-c2cnc(C(=O)O)c(C)c2)cc1C1=C(CN2C(=O)O[C@H](c3cc(C(F)(F)F)cc(C(F)(F)F)c3)[C@@H]2C)CC(C)(C)CC1] |

TABLE 8
| Compound | Structure |
|---|---|
| 603 | 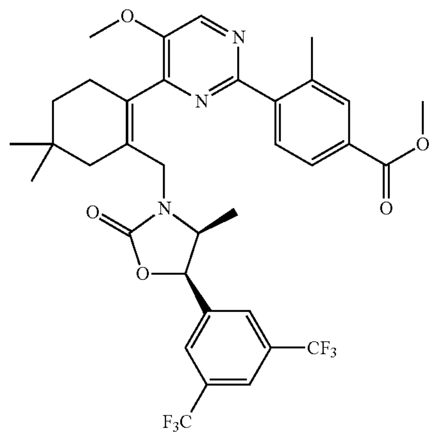 |
| 604 | 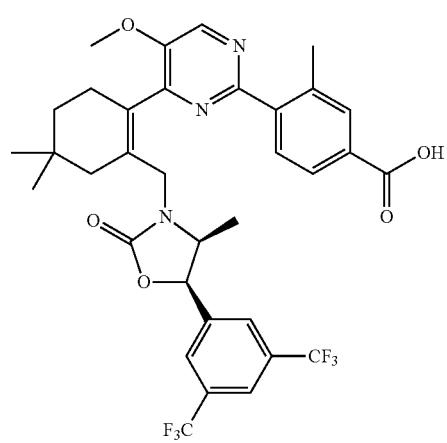 [SMILES: COc1cnc(-c2ccc(C(=O)O)cc2C)nc1C1=C(CN2C(=O)O[C@H](c3cc(C(F)(F)F)cc(C(F)(F)F)c3)[C@@H]2C)CC(C)(C)CC1] |
| 605 | 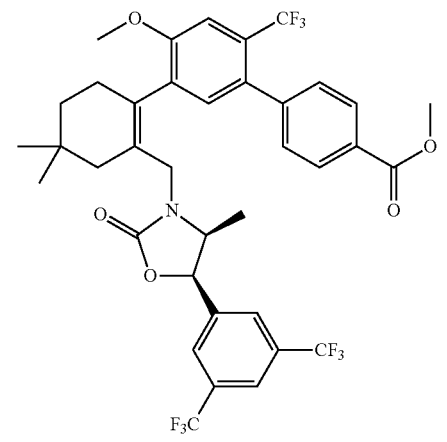 |
TABLE 8-continued
| Compound | Structure |
|---|---|
| 606 | 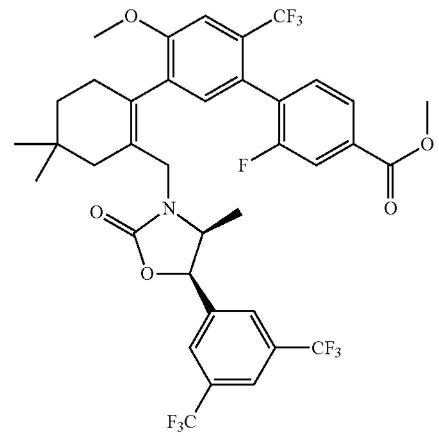 |
| 607 | 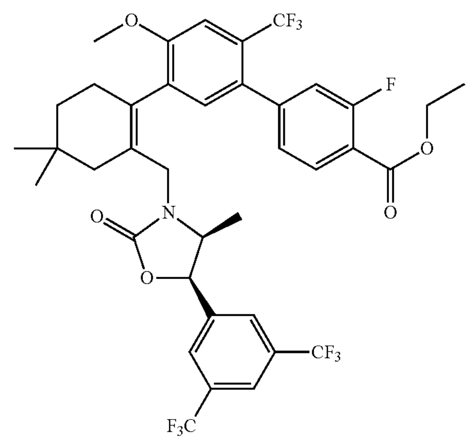 [SMILES: CCOC(=O)c1ccc(-c2cc(C3=C(CN4C(=O)O[C@H](c5cc(C(F)(F)F)cc(C(F)(F)F)c5)[C@@H]4C)CC(C)(C)CC3)c(OC)cc2C(F)(F)F)cc1F] |
| 608 | 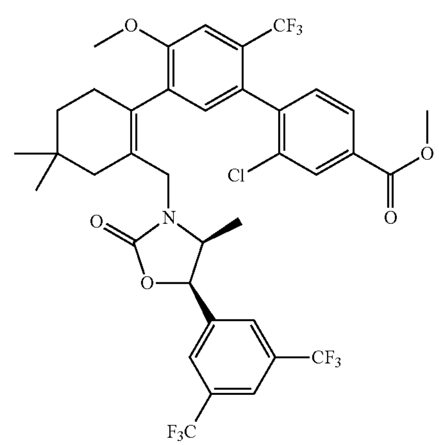 |

TABLE 9

| Compound | Structure |
|---|---|
| 609 | 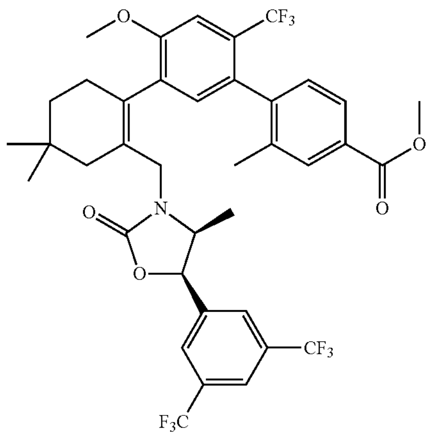 |
| 610 | 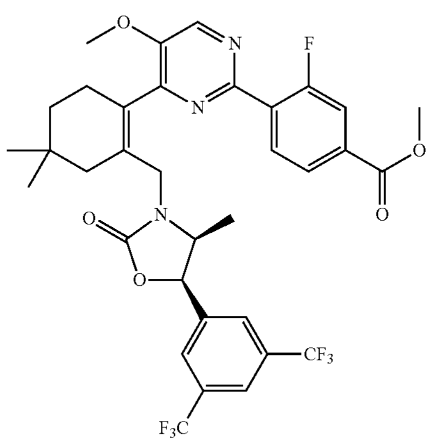 |
| 611 | 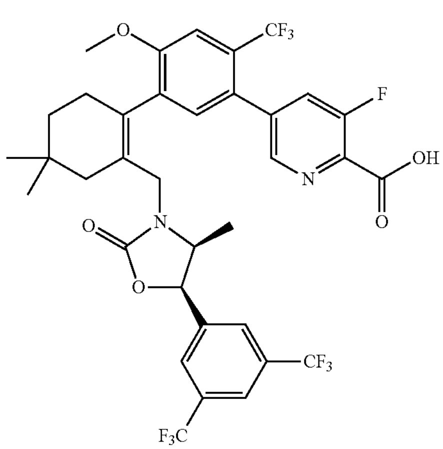 [SMILES: COc1cc(C(F)(F)F)c(-c2cnc(C(=O)O)c(F)c2)cc1C1=C(CN2C(=O)O[C@H](c3cc(C(F)(F)F)cc(C(F)(F)F)c3)[C@@H]2C)CC(C)(C)CC1] |
| 612 | |
| 613 | |
| 614 | |

TABLE 10

| Compound | Structure |
|---|---|
| 615 | 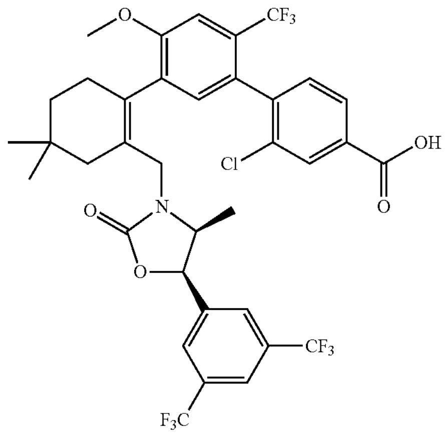 [SMILES: COc1cc(C(F)(F)F)c(-c2ccc(C(=O)O)cc2Cl)cc1C1=C(CN2C(=O)O[C@H](c3cc(C(F)(F)F)cc(C(F)(F)F)c3)[C@@H]2C)CC(C)(C)CC1] |
| 616 | 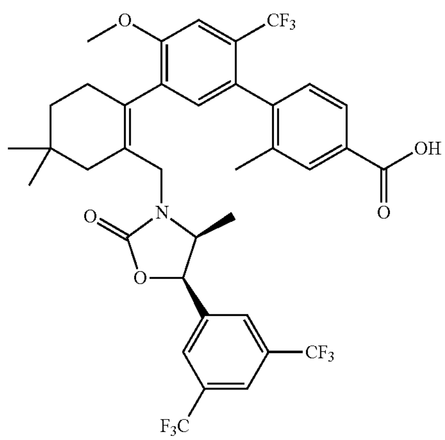 [SMILES: COc1cc(C(F)(F)F)c(-c2ccc(C(=O)O)cc2C)cc1C1=C(CN2C(=O)O[C@H](c3cc(C(F)(F)F)cc(C(F)(F)F)c3)[C@@H]2C)CC(C)(C)CC1] |
| 617 | 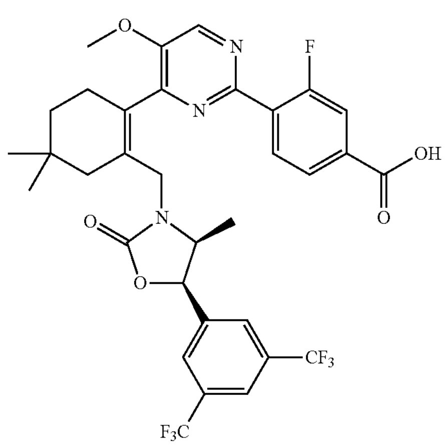 |

TABLE 10-continued

| Compound | Structure |
|---|---|
| 618 | 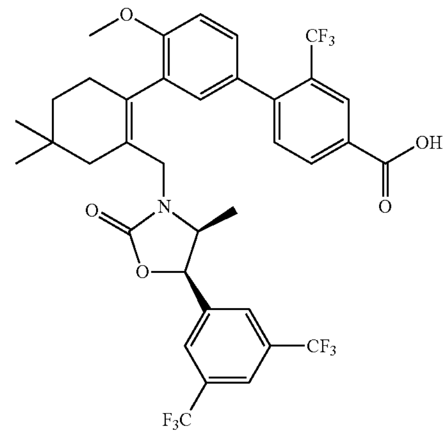 |
| 619 | 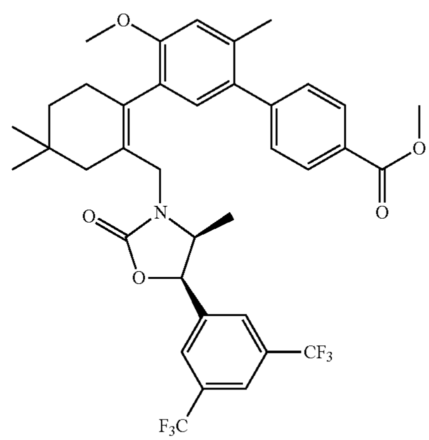 |
| 620 | 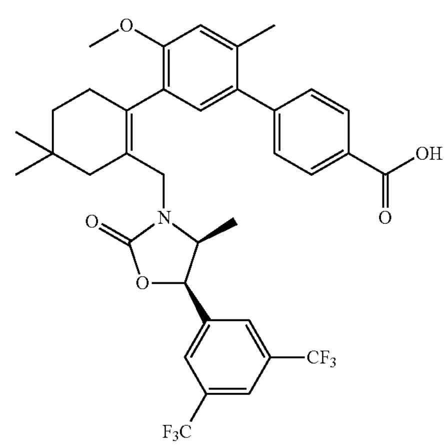 [SMILES: COc1cc(C)c(-c2ccc(C(=O)O)cc2)cc1C1=C(CN2C(=O)O[C@H](c3cc(C(F)(F)F)cc(C(F)(F)F)c3)[C@@H]2C)CC(C)(C)CC1] |

TABLE 11
| Compound | Structure |
|---|---|
| 621 | 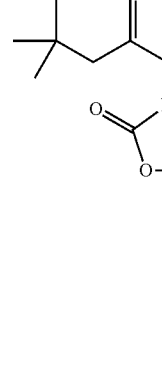 |
| 622 | 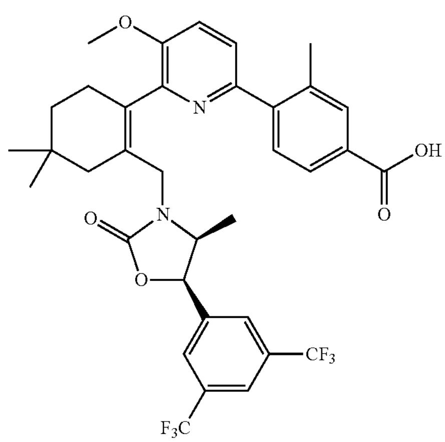 [SMILES: COc1ccc(-c2ccc(C(=O)O)cc2C)nc1C1=C(CN2C(=O)O[C@H](c3cc(C(F)(F)F)cc(C(F)(F)F)c3)[C@@H]2C)CC(C)(C)CC1] |
| 625 | 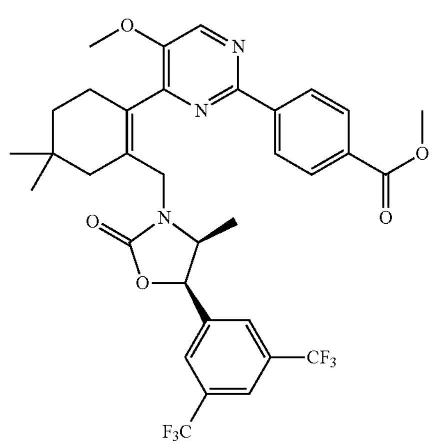 |
TABLE 11-continued
| Compound | Structure |
|---|---|
| 626 | 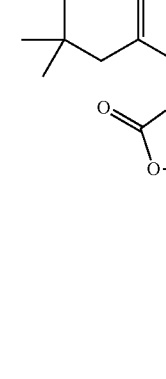 |
| 628 | 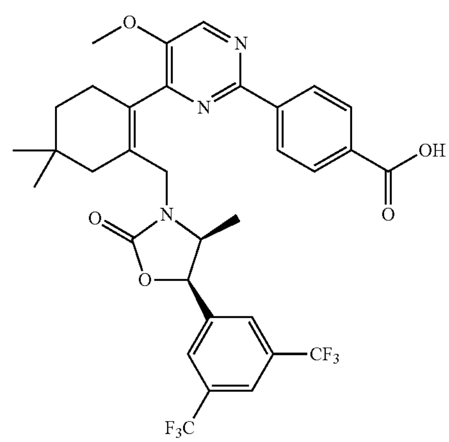 [SMILES: COc1cnc(-c2ccc(C(=O)O)cc2)nc1C1=C(CN2C(=O)O[C@H](c3cc(C(F)(F)F)cc(C(F)(F)F)c3)[C@@H]2C)CC(C)(C)CC1] |
| 629 | 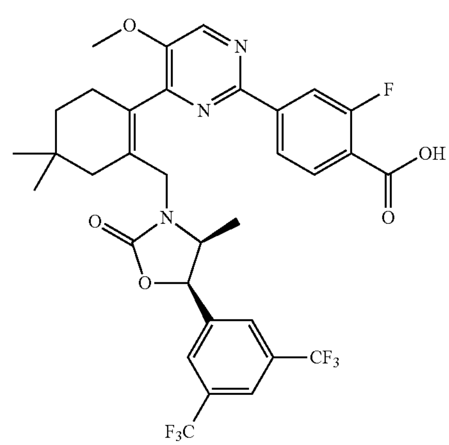 [SMILES: COc1cnc(-c2ccc(C(=O)O)c(F)c2)nc1C1=C(CN2C(=O)O[C@H](c3cc(C(F)(F)F)cc(C(F)(F)F)c3)[C@@H]2C)CC(C)(C)CC1] |

TABLE 12

| Compound | Structure |
|---|---|
| 630 | 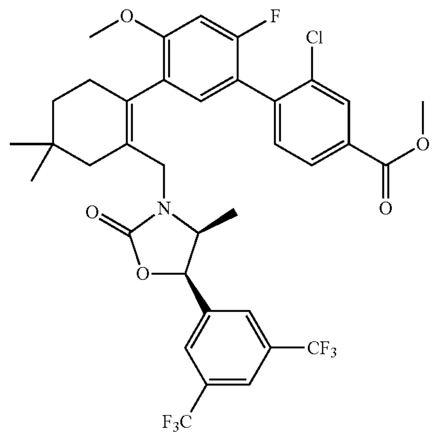 |
| 631 | 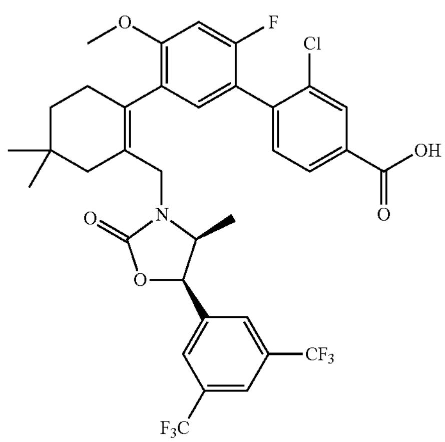 [SMILES: COc1cc(F)c(-c2ccc(C(=O)O)cc2Cl)cc1C1=C(CN2C(=O)O[C@H](c3cc(C(F)(F)F)cc(C(F)(F)F)c3)[C@@H]2C)CC(C)(C)CC1] |
| 632 | 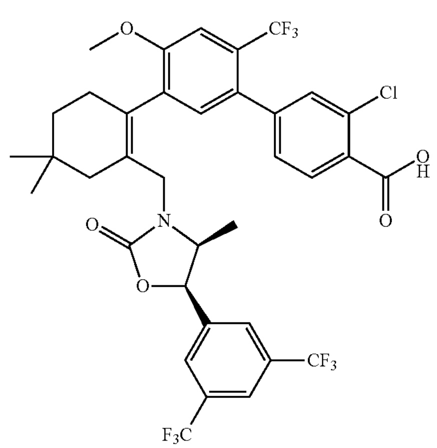 [SMILES: COc1cc(C(F)(F)F)c(-c2ccc(C(=O)O)c(Cl)c2)cc1C1=C(CN2C(=O)O[C@H](c3cc(C(F)(F)F)cc(C(F)(F)F)c3)[C@@H]2C)CC(C)(C)CC1] |
| 633 | |
| 636 | |
| 637 | |

TABLE 13
| Compound | Structure |
|---|---|
| 638 | 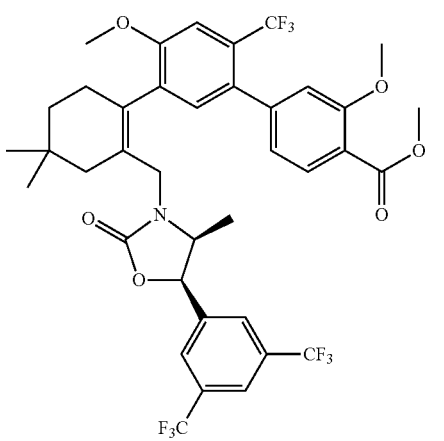 |
| 639 | 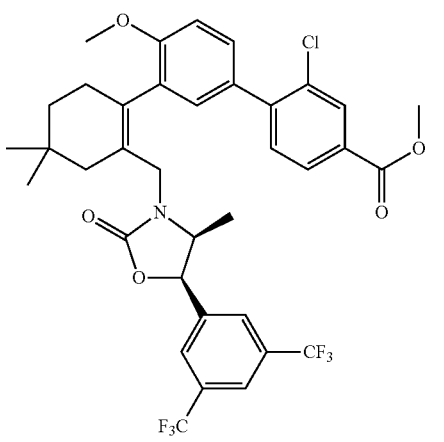 |
| 642 | 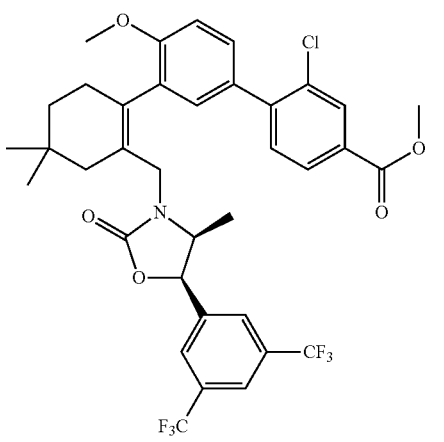 |
TABLE 13-continued
| Compound | Structure |
|---|---|
| 643 | 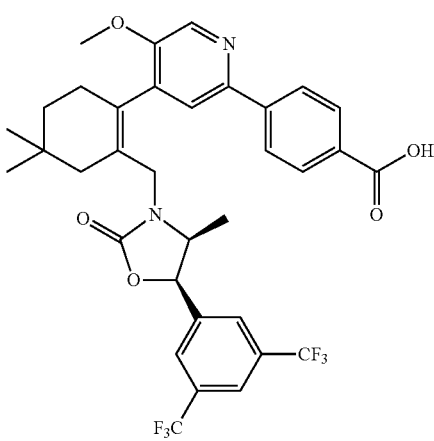 [SMILES: COc1cnc(-c2ccc(C(=O)O)cc2)cc1C1=C(CN2C(=O)O[C@H](c3cc(C(F)(F)F)cc(C(F)(F)F)c3)[C@@H]2C)CC(C)(C)CC1] |
| 644 | 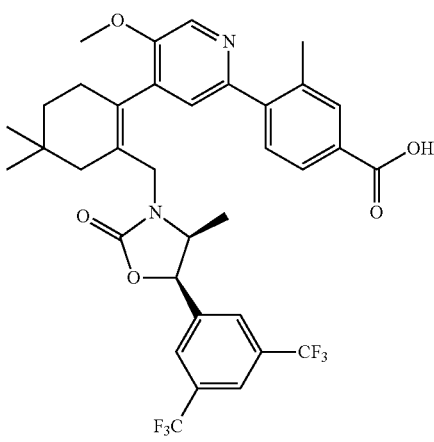 [SMILES: COc1cnc(-c2ccc(C(=O)O)cc2C)cc1C1=C(CN2C(=O)O[C@H](c3cc(C(F)(F)F)cc(C(F)(F)F)c3)[C@@H]2C)CC(C)(C)CC1] |
| 645 | 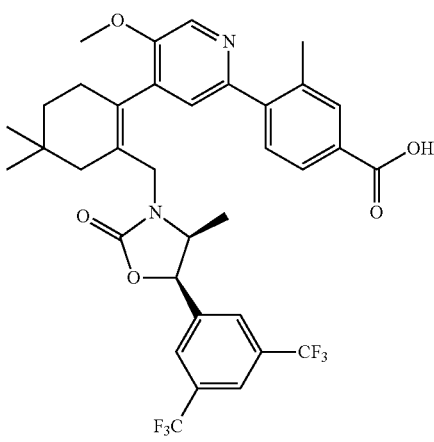 [SMILES: COc1cnc(-c2ccc(C(=O)O)cc2C)cc1C1=C(CN2C(=O)O[C@H](c3cc(C(F)(F)F)cc(C(F)(F)F)c3)[C@@H]2C)CC(C)(C)CC1] |

TABLE 14

| Compound | Structure |
|---|---|
| 646 | (structure) |
| 647 | (structure) |
| 648 | (structure) |

TABLE 14-continued

| Compound | Structure |
|---|---|
| 649 | (structure) |
| 650 | (structure) |
| 651 | (structure) |

TABLE 15
| Compound | Structure |
|---|---|
| 652 | 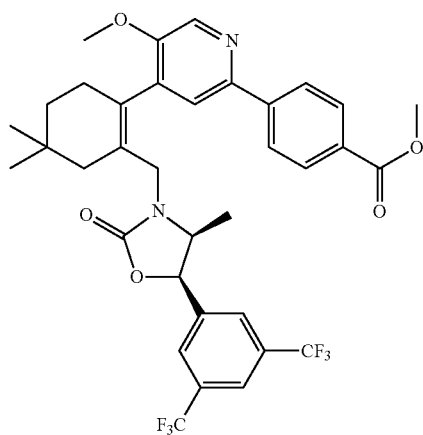 |
| 653 | 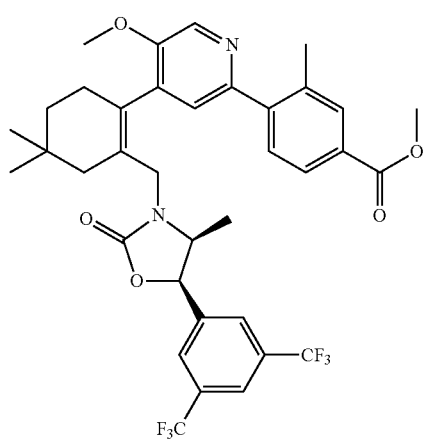 |
| 654 | 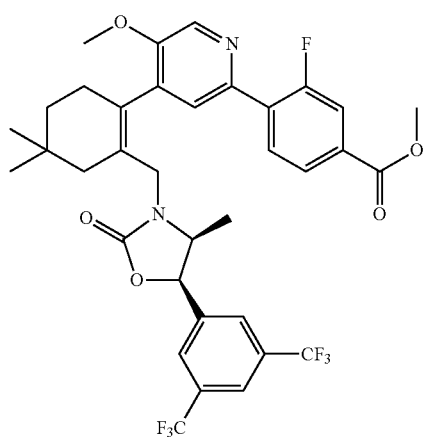 |
TABLE 15-continued
| Compound | Structure |
|---|---|
| 655 | 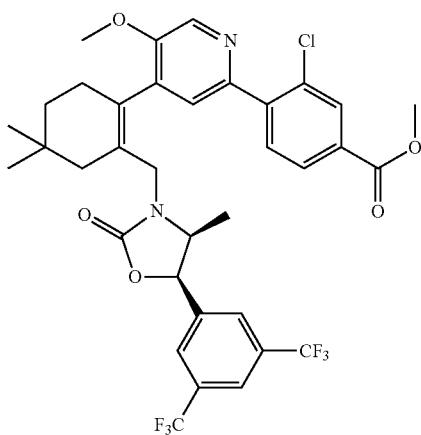 |
| 656 | 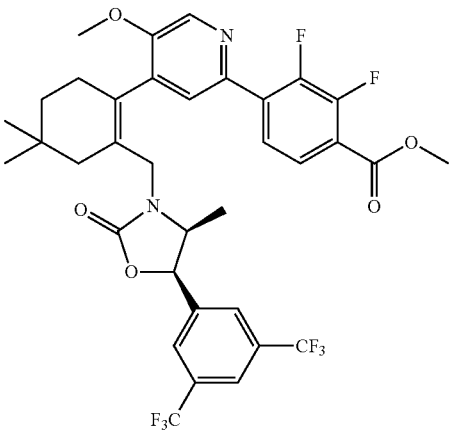 |
| 657 | 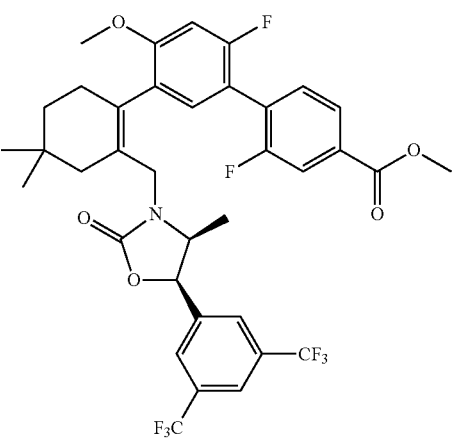 |

TABLE 16
| Compound | Structure |
|---|---|
| 658 | 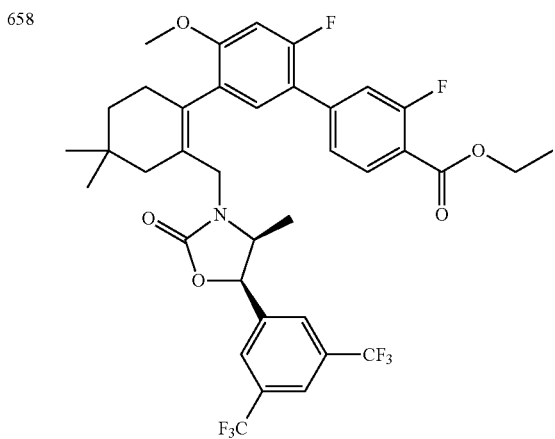 |
| 659 | 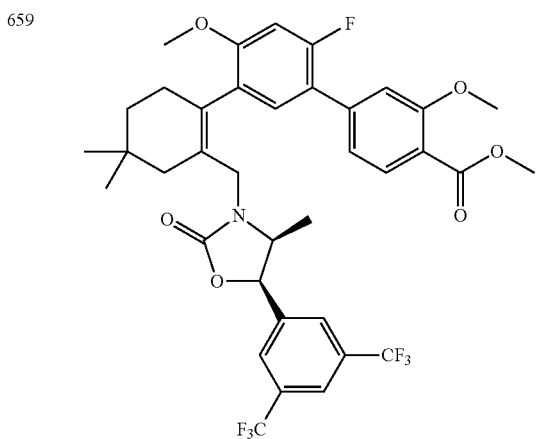 |
| 660 | 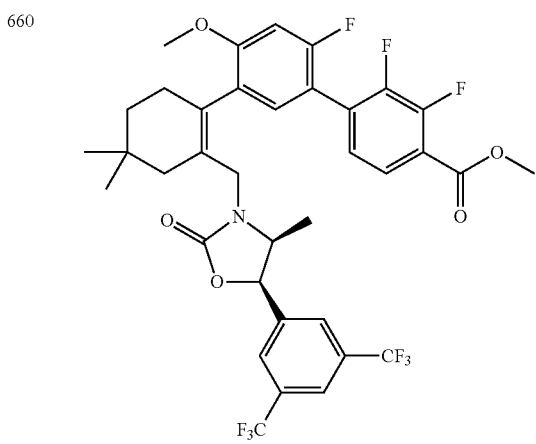 |
TABLE 16-continued
| Compound | Structure |
|---|---|
| 661 | 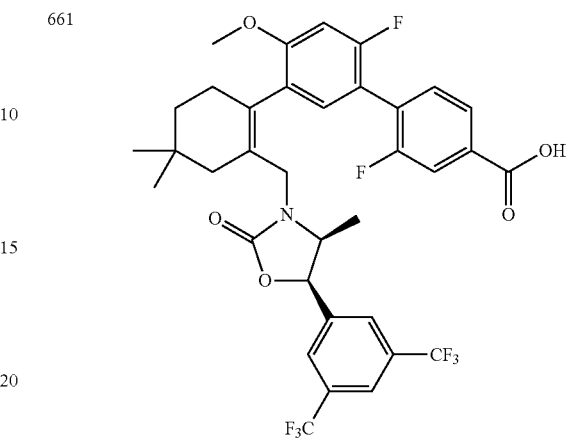 |
| 662 | 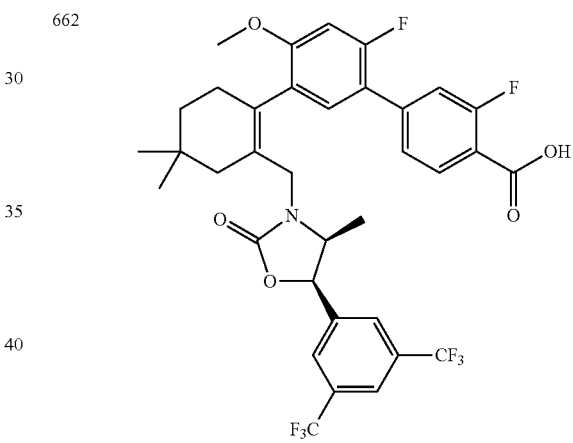 |
| 663 | 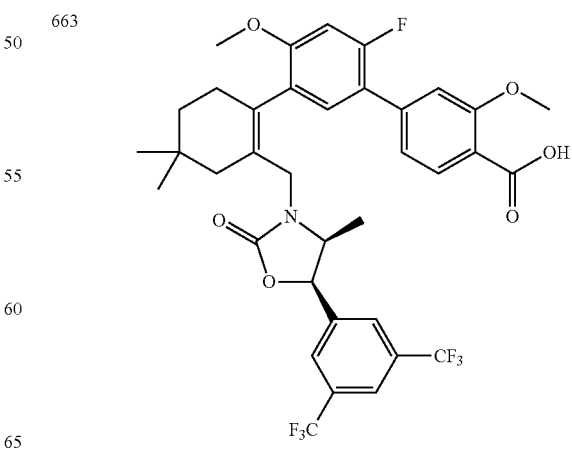 |

TABLE 17

| Compound | Structure |
|---|---|
| 664 | 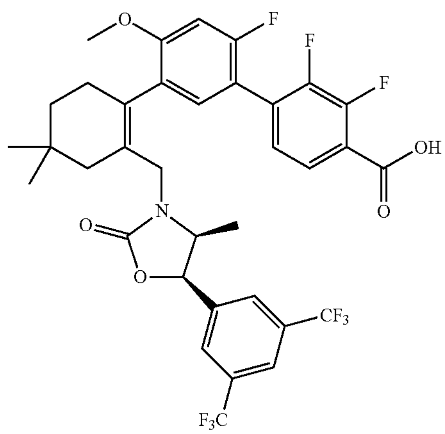 [SMILES: COc1cc(F)c(-c2ccc(C(=O)O)c(F)c2F)cc1C1=C(CN2C(=O)O[C@H](c3cc(C(F)(F)F)cc(C(F)(F)F)c3)[C@@H]2C)CC(C)(C)CC1] |
| 665 | 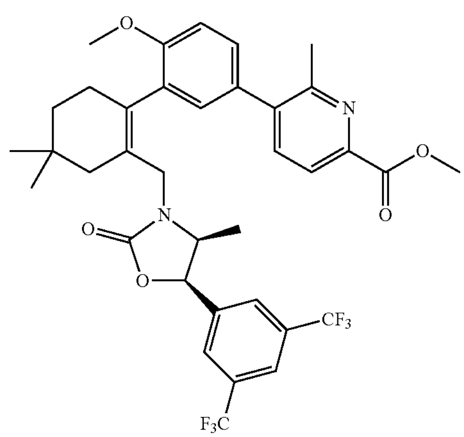 |
| 666 | 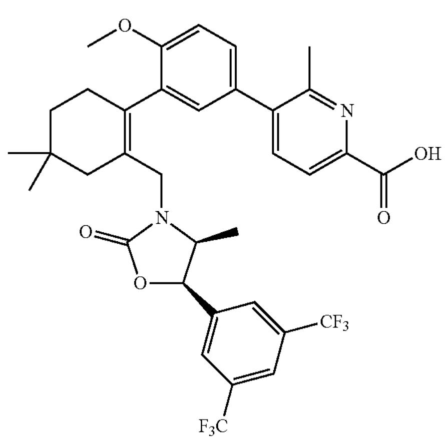 [SMILES: COc1ccc(-c2ccc(C(=O)O)nc2C)cc1C1=C(CN2C(=O)O[C@H](c3cc(C(F)(F)F)cc(C(F)(F)F)c3)[C@@H]2C)CC(C)(C)CC1] |

TABLE 17-continued

| Compound | Structure |
|---|---|
| 667 | 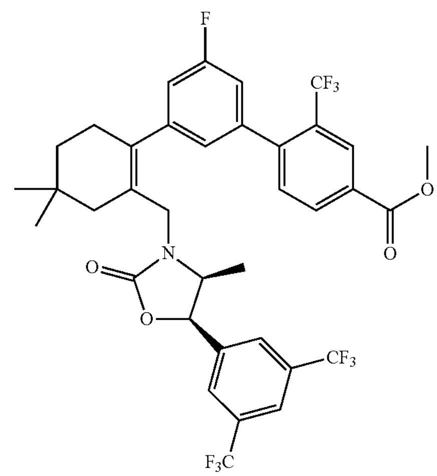 |
| 668 | 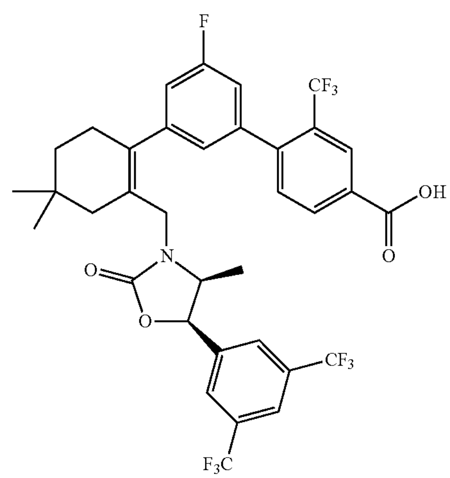 [SMILES: C[C@H]1[C@@H](c2cc(C(F)(F)F)cc(C(F)(F)F)c2)OC(=O)N1CC1=C(c2cc(F)cc(-c3ccc(C(=O)O)cc3C(F)(F)F)c2)CCC(C)(C)C1] |
| 670 | 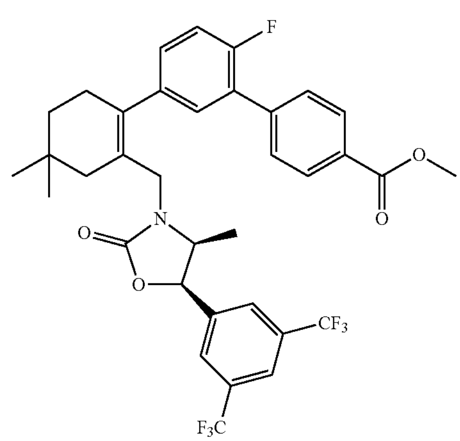 |

TABLE 18
| Compound | Structure |
|---|---|
| 671 | 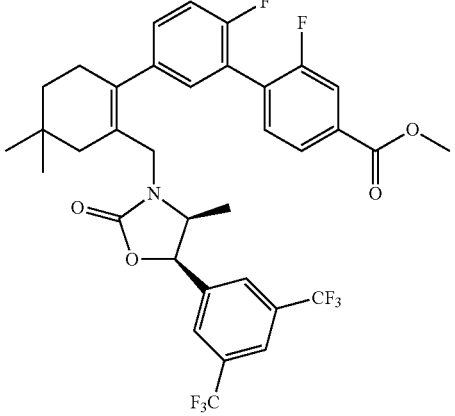 |
| 672 | 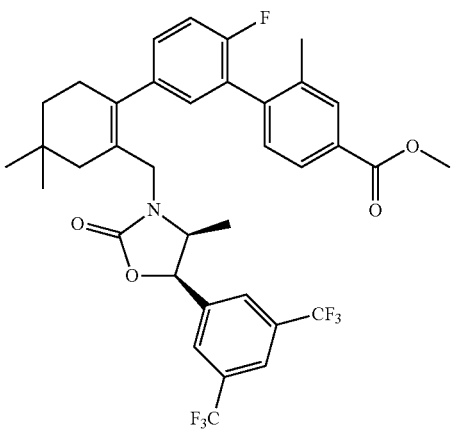 |
| 673 | 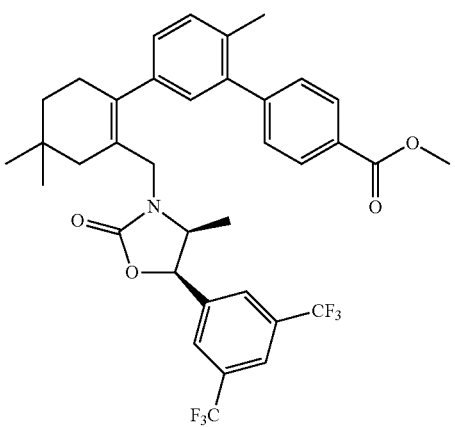 |
TABLE 18-continued
| Compound | Structure |
|---|---|
| 674 | 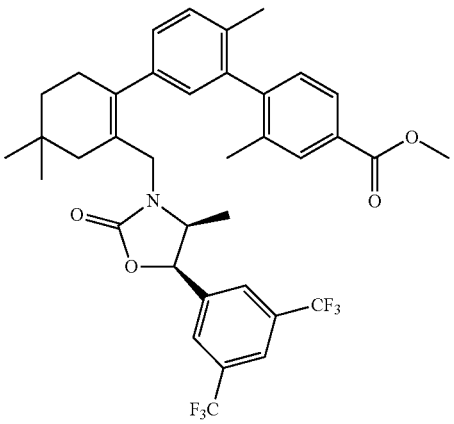 |
| 675 | 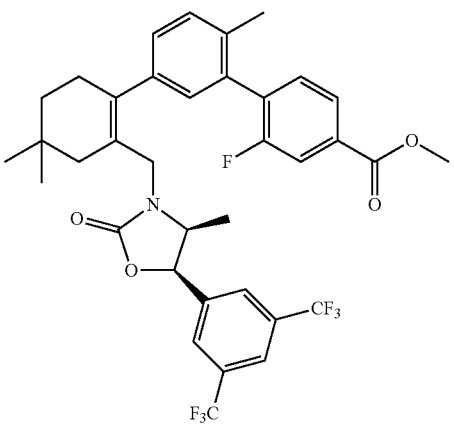 |
| 676 | 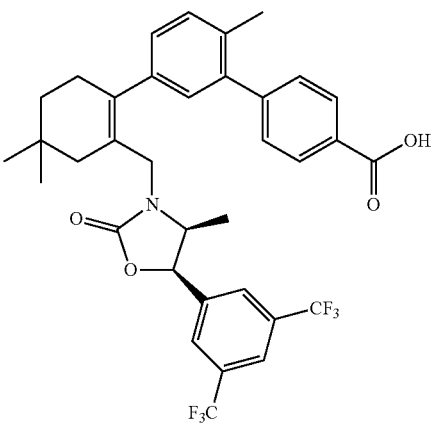 [SMILES: Cc1ccc(C2=C(CN3C(=O)O[C@H](c4cc(C(F)(F)F)cc(C(F)(F)F)c4)[C@@H]3C)CC(C)(C)CC2)cc1-c1ccc(C(=O)O)cc1] |

TABLE 19
| Compound | Structure |
|---|---|
| 677 | 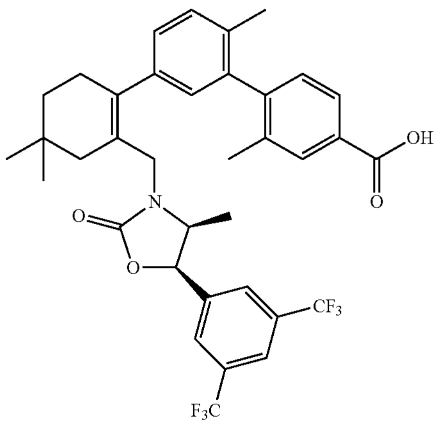 [SMILES: Cc1cc(C(=O)O)ccc1-c1cc(C2=C(CN3C(=O)O[C@H](c4cc(C(F)(F)F)cc(C(F)(F)F)c4)[C@@H]3C)CC(C)(C)CC2)ccc1C] |
| 678 | 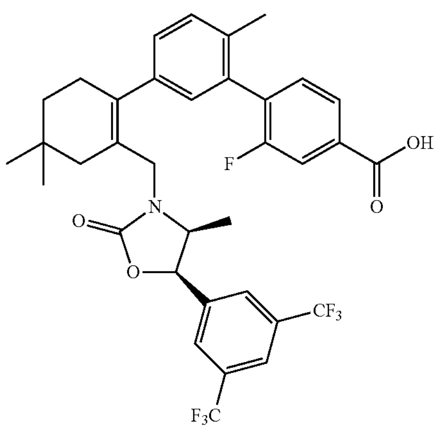 [SMILES: Cc1ccc(C2=C(CN3C(=O)O[C@H](c4cc(C(F)(F)F)cc(C(F)(F)F)c4)[C@@H]3C)CC(C)(C)CC2)cc1-c1ccc(C(=O)O)cc1F] |
| 679 | 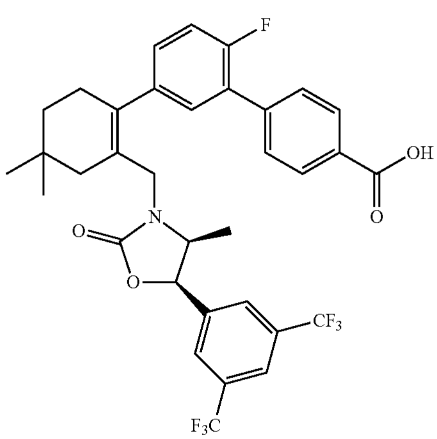 [SMILES: C[C@H]1[C@@H](c2cc(C(F)(F)F)cc(C(F)(F)F)c2)OC(=O)N1CC1=C(c2ccc(F)c(-c3ccc(C(=O)O)cc3)c2)CCC(C)(C)C1] |
| 680 | |
| 681 | |
| 682 | |
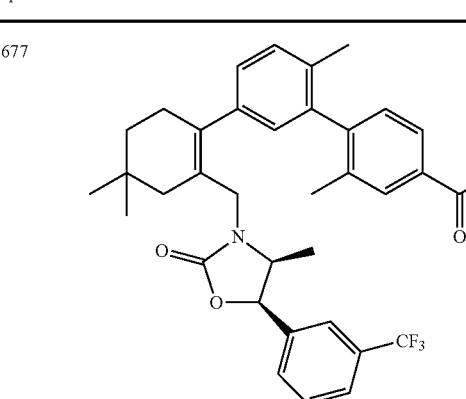

TABLE 20
| Compound | Structure |
|---|---|
| 683 | 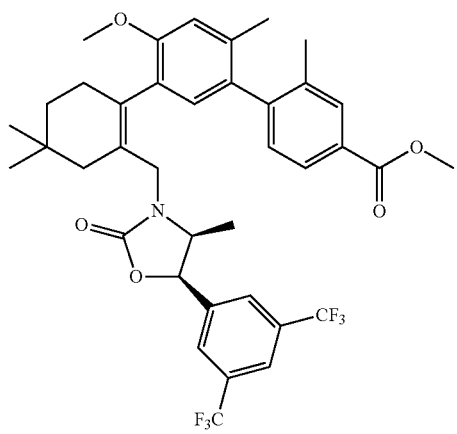 |
| 684 | 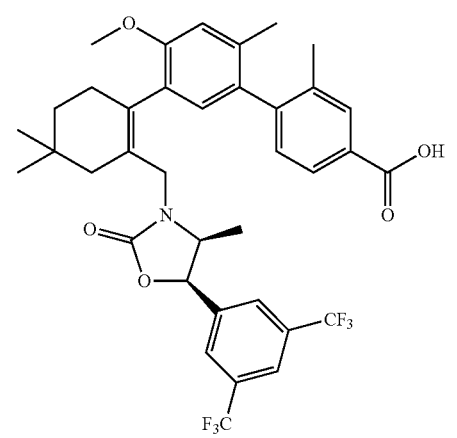 [SMILES: COc1cc(C)c(-c2ccc(C(=O)O)cc2C)cc1C1=C(CN2C(=O)O[C@H](c3cc(C(F)(F)F)cc(C(F)(F)F)c3)[C@@H]2C)CC(C)(C)CC1] |
| 686 | 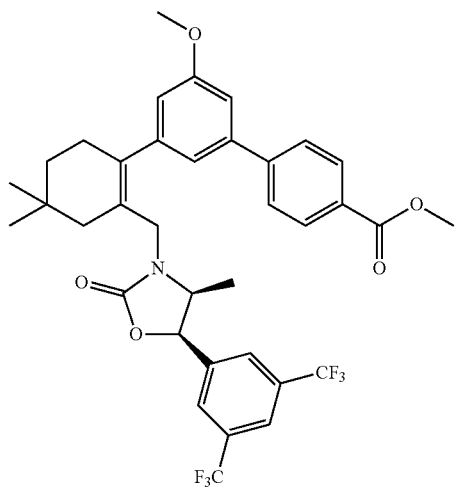 |
TABLE 20-continued
| Compound | Structure |
|---|---|
| 687 | 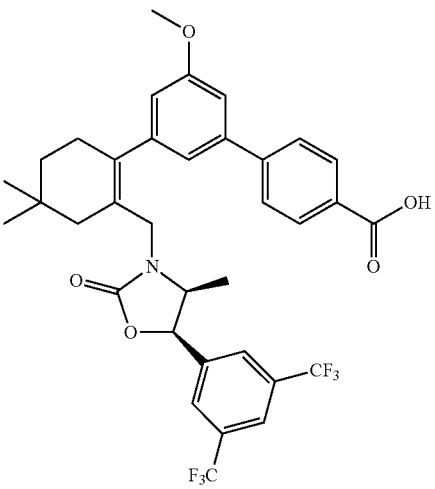 [SMILES: COc1cc(C2=C(CN3C(=O)O[C@H](c4cc(C(F)(F)F)cc(C(F)(F)F)c4)[C@@H]3C)CC(C)(C)CC2)cc(-c2ccc(C(=O)O)cc2)c1] |
| 688 | 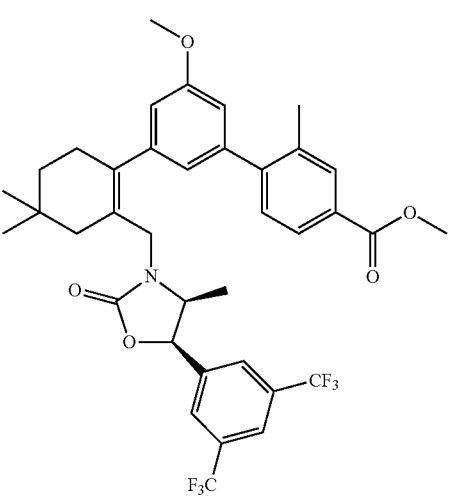 |
| 689 | 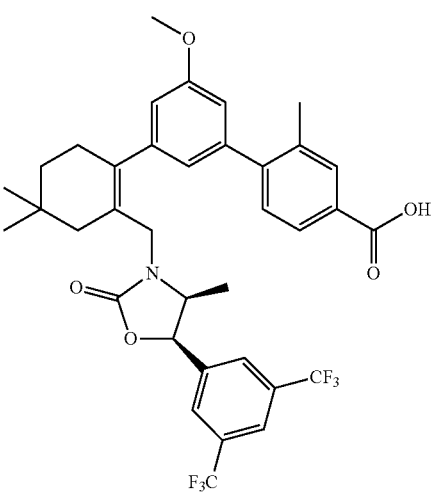 |

TABLE 21
| Compound | Structure |
|---|---|
| 690 | 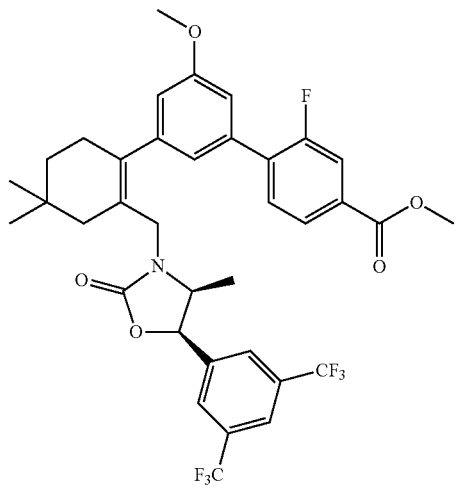 |
| 691 | 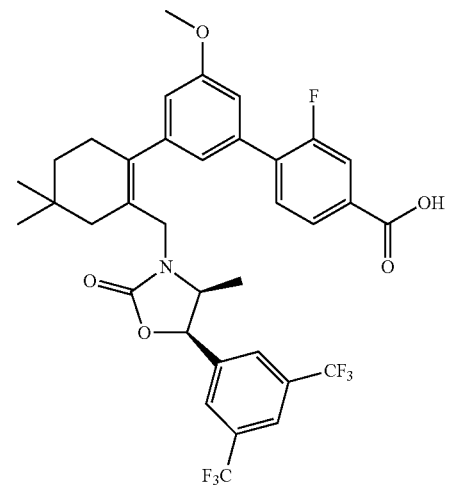 [SMILES: COc1cc(C2=C(CN3C(=O)O[C@H](c4cc(C(F)(F)F)cc(C(F)(F)F)c4)[C@@H]3C)CC(C)(C)CC2)cc(-c2ccc(C(=O)O)cc2F)c1] |
| 692 | 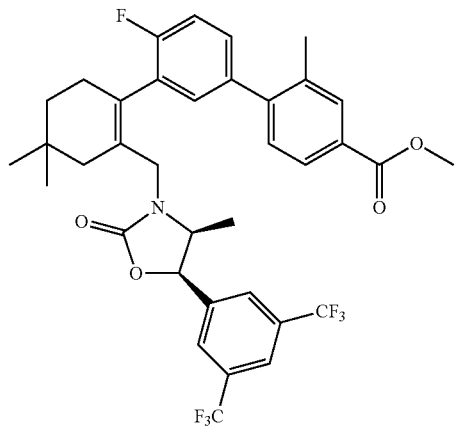 |
TABLE 21-continued
| Compound | Structure |
|---|---|
| 693 | 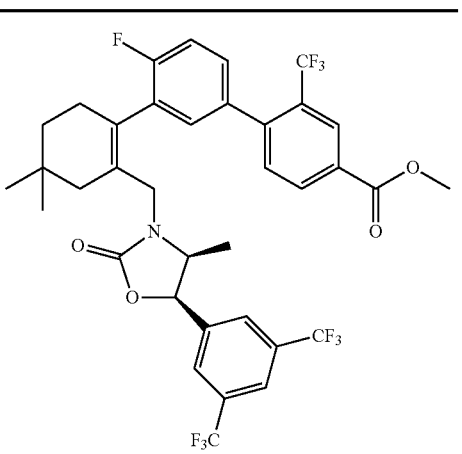 |
| 694 | 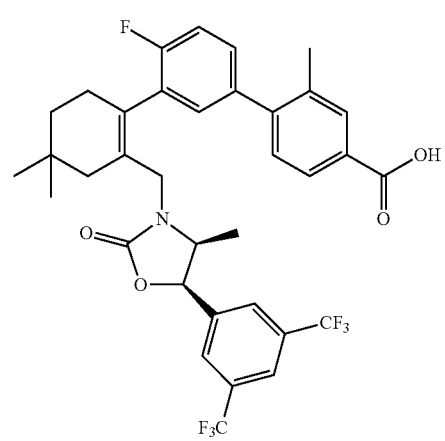 [SMILES: Cc1cc(C(=O)O)ccc1-c1ccc(F)c(C2=C(CN3C(=O)O[C@H](c4cc(C(F)(F)F)cc(C(F)(F)F)c4)[C@@H]3C)CC(C)(C)CC2)c1] |
| 695 | 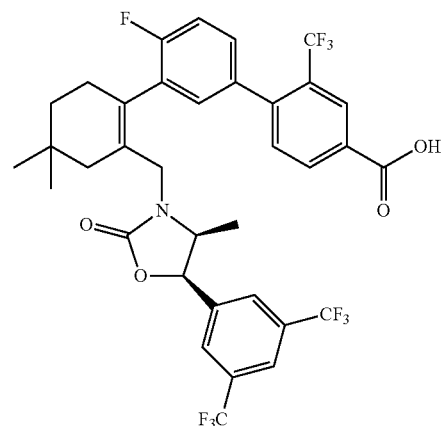 |

TABLE 22
| Compound | Structure |
|---|---|
| 696 | 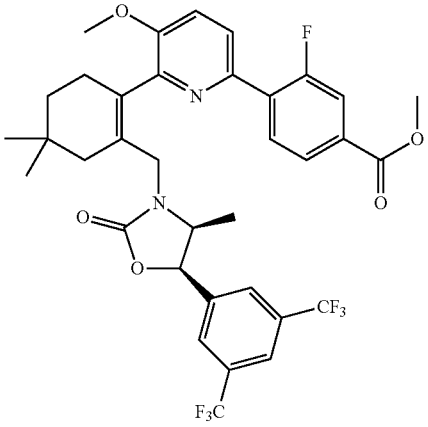 |
| 697 | 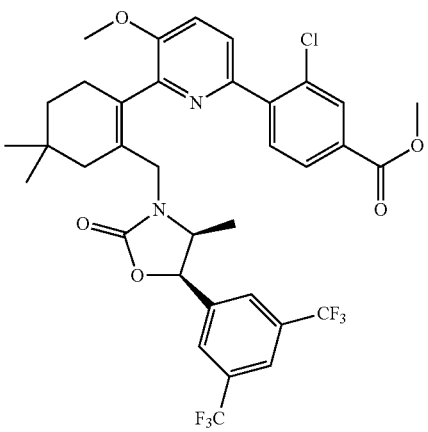 |
| 699 | 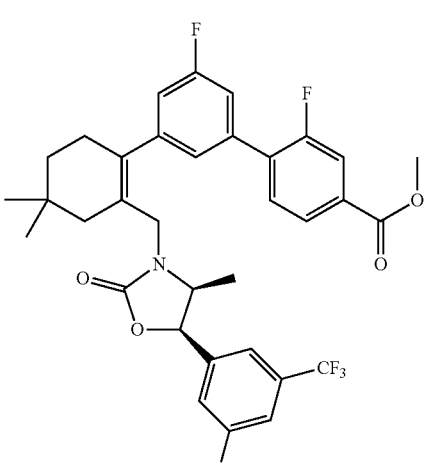 |
| 700 | 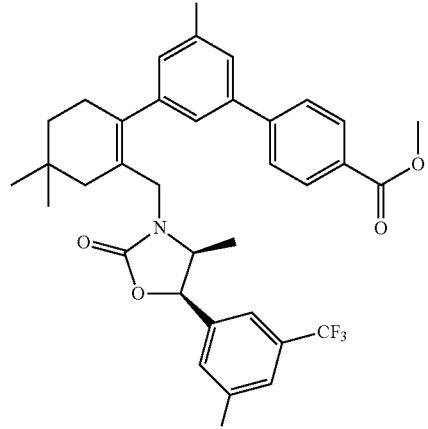 |
| 701 | 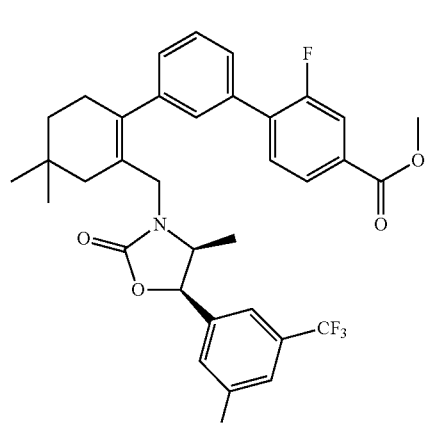 |
| 702 | 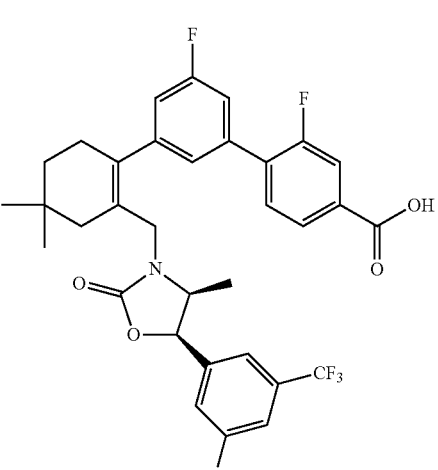 |

TABLE 23
| Compound | Structure |
|---|---|
| 703 | 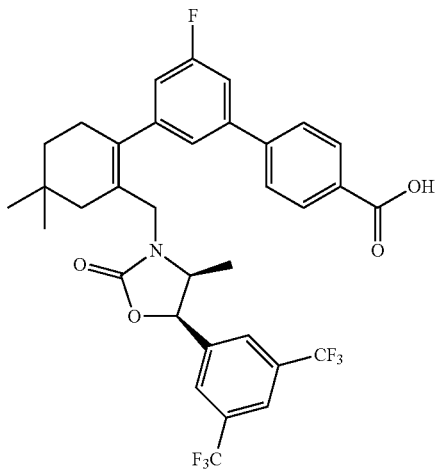 [SMILES: C[C@H]1[C@@H](c2cc(C(F)(F)F)cc(C(F)(F)F)c2)OC(=O)N1CC1=C(c2cc(F)cc(-c3ccc(C(=O)O)cc3)c2)CCC(C)(C)C1] |
| 704 | 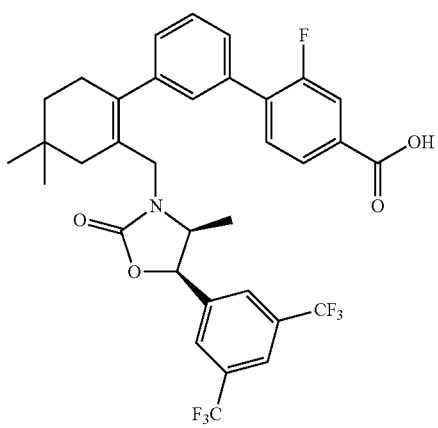 [SMILES: C[C@H]1[C@@H](c2cc(C(F)(F)F)cc(C(F)(F)F)c2)OC(=O)N1CC1=C(c2cccc(-c3ccc(C(=O)O)cc3F)c2)CCC(C)(C)C1] |
| 705 | 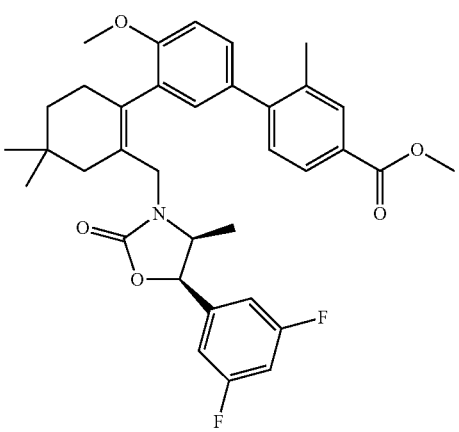 |
TABLE 23-continued
| Compound | Structure |
|---|---|
| 706 | 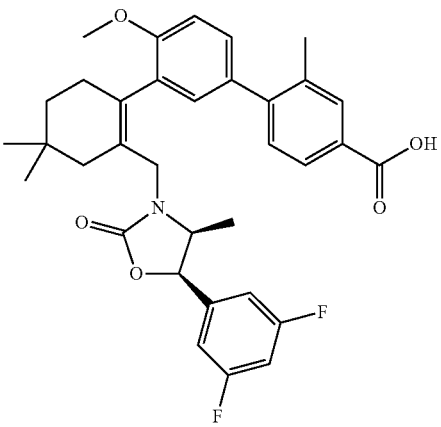 [SMILES: COc1ccc(-c2ccc(C(=O)O)cc2C)cc1C1=C(CN2C(=O)O[C@H](c3cc(F)cc(F)c3)[C@@H]2C)CC(C)(C)CC1] |
| 708 | 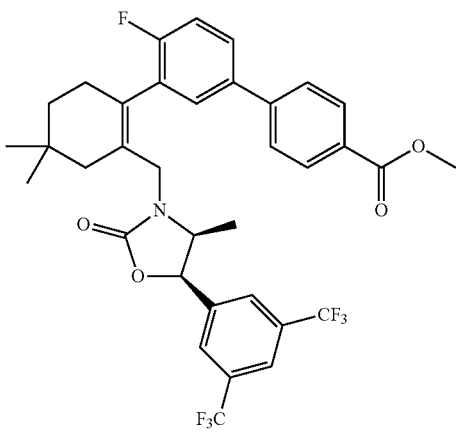 |
| 709 | 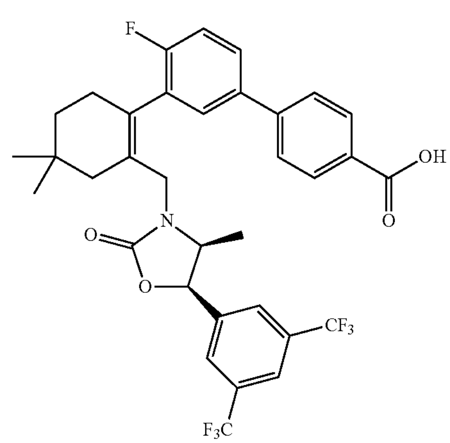 [SMILES: C[C@H]1[C@@H](c2cc(C(F)(F)F)cc(C(F)(F)F)c2)OC(=O)N1CC1=C(c2cc(-c3ccc(C(=O)O)cc3)ccc2F)CCC(C)(C)C1] |

TABLE 24
| Compound | Structure |
|---|---|
| 714 | 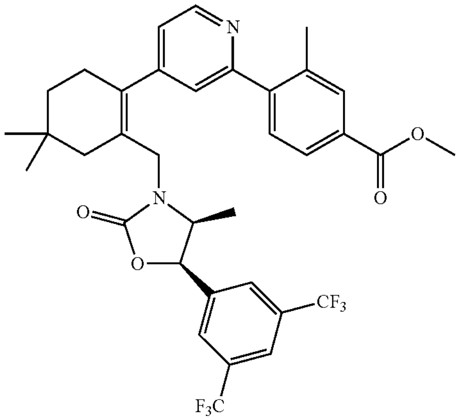 |
| 716 | 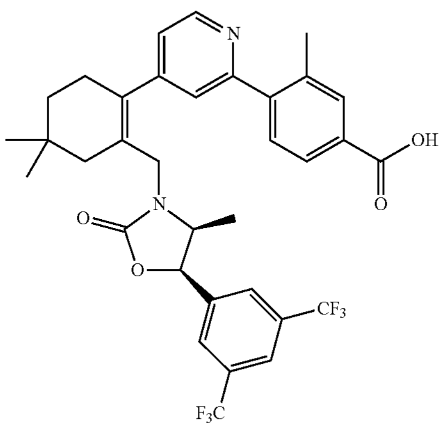 [SMILES: Cc1cc(C(=O)O)ccc1-c1cc(C2=C(CN3C(=O)O[C@H](c4cc(C(F)(F)F)cc(C(F)(F)F)c4)[C@@H]3C)CC(C)(C)CC2)ccn1] |
| 718 | 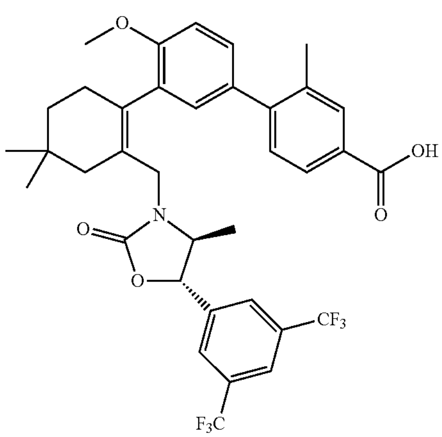 [SMILES: COc1ccc(-c2ccc(C(=O)O)cc2C)cc1C1=C(CN2C(=O)O[C@@H](c3cc(C(F)(F)F)cc(C(F)(F)F)c3)[C@@H]2C)CC(C)(C)CC1] |
TABLE 24-continued
| Compound | Structure |
|---|---|
| 719 | 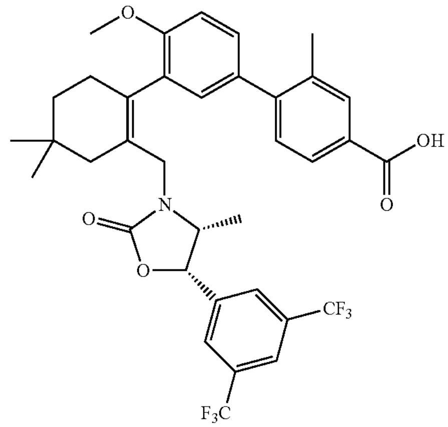 [SMILES: COc1ccc(-c2ccc(C(=O)O)cc2C)cc1C1=C(CN2C(=O)O[C@@H](c3cc(C(F)(F)F)cc(C(F)(F)F)c3)[C@H]2C)CC(C)(C)CC1] |
| 720 | 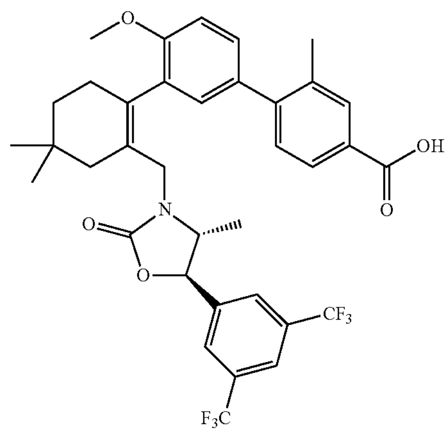 [SMILES: COc1ccc(-c2ccc(C(=O)O)cc2C)cc1C1=C(CN2C(=O)O[C@H](c3cc(C(F)(F)F)cc(C(F)(F)F)c3)[C@H]2C)CC(C)(C)CC1] |
| 722 | 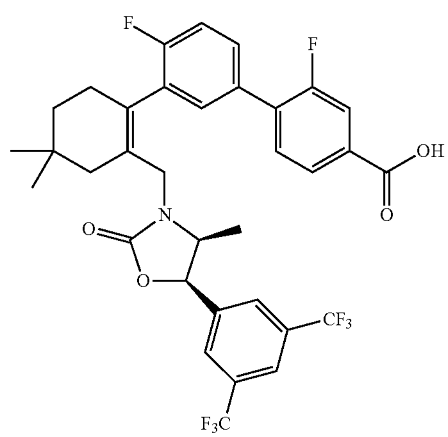 |
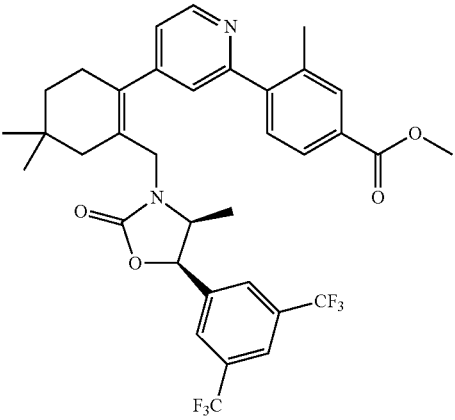

TABLE 25
| Compound | Structure |
|---|---|
| 723 | 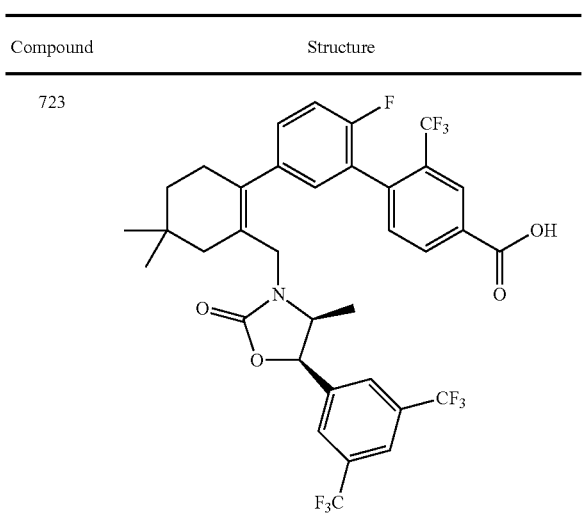 |
| 724 | 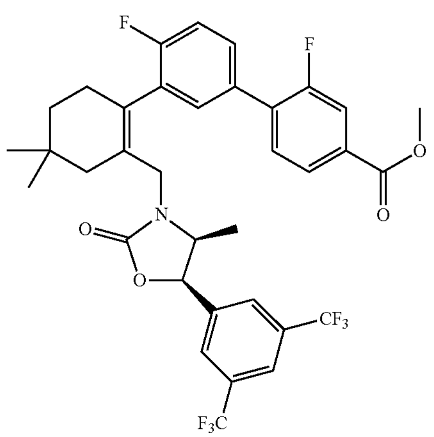 |
| 725 | 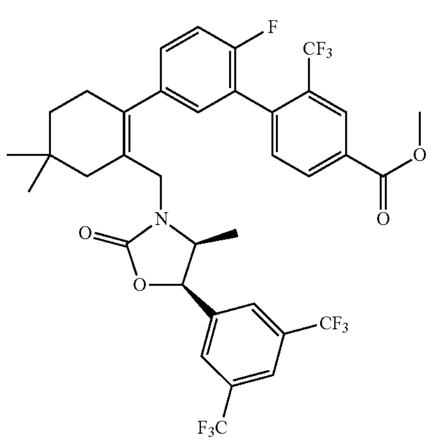 |
TABLE 25-continued
| Compound | Structure |
|---|---|
| 726 | 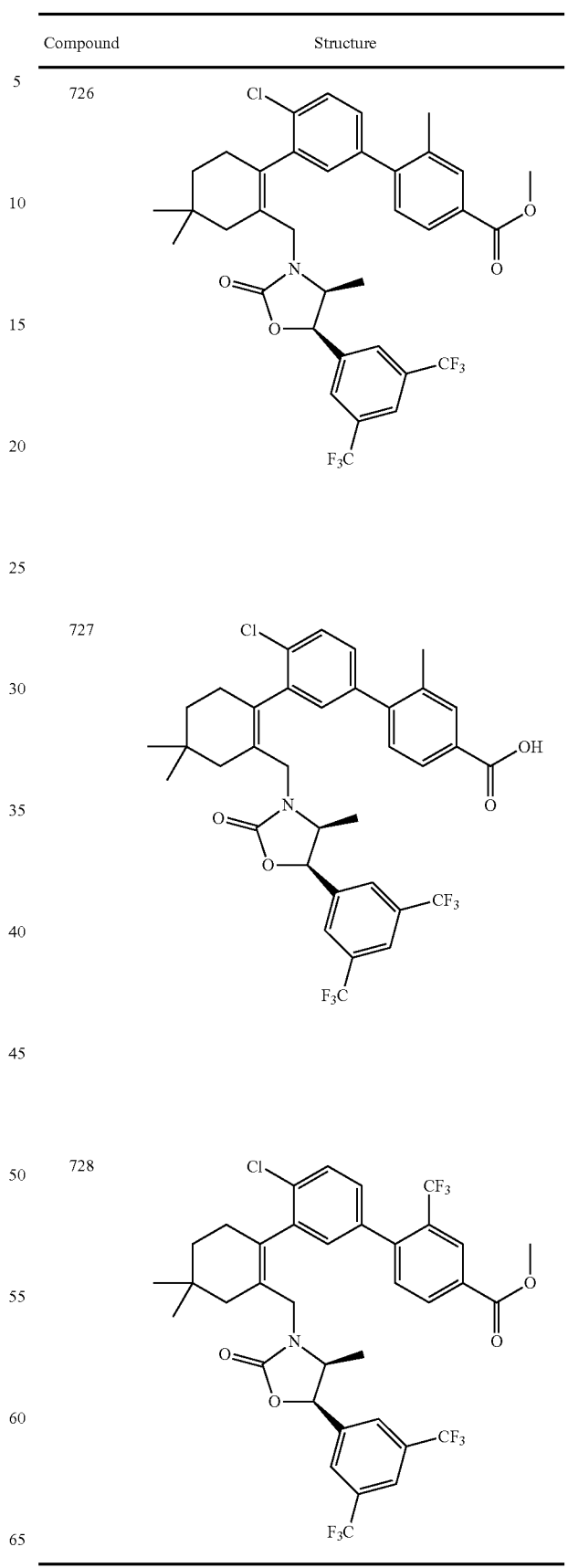 |
| 727 | 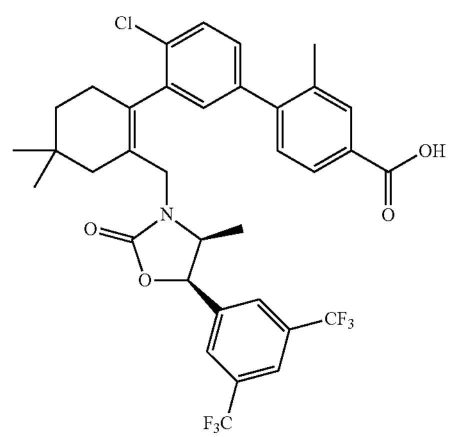 [SMILES: Cc1cc(C(=O)O)ccc1-c1ccc(Cl)c(C2=C(CN3C(=O)O[C@H](c4cc(C(F)(F)F)cc(C(F)(F)F)c4)[C@@H]3C)CC(C)(C)CC2)c1] |
| 728 | 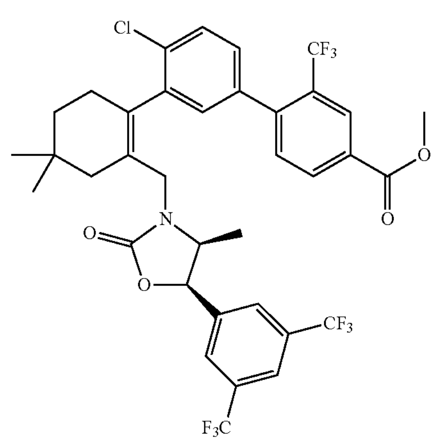 |

TABLE 26

| Compound | Structure |
|---|---|
| 729 | (structure) |
| 738 | (structure) |
| 739 | (structure) |

TABLE 26-continued

| Compound | Structure |
|---|---|
| 740 | (structure) |
| 741 | (structure) |
| 742 | (structure) |

TABLE 27

| Compound | Structure |
|---|---|
| 743 | (structure) |
| 744 | (structure) |
| 745 | (structure) |

TABLE 27-continued

| Compound | Structure |
|---|---|
| 746 | (structure) |
| 747 | (structure) |
| 748 | (structure) |

TABLE 28

| Compound | Structure |
|---|---|
| 754 | 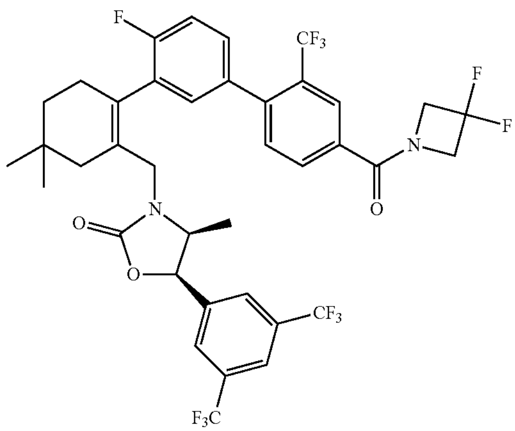 [SMILES: C[C@H]1[C@@H](c2cc(C(F)(F)F)cc(C(F)(F)F)c2)OC(=O)N1CC1=C(c2cc(-c3ccc(C(=O)N4CC(F)(F)C4)cc3C(F)(F)F)ccc2F)CCC(C)(C)C1] |
| 755 | 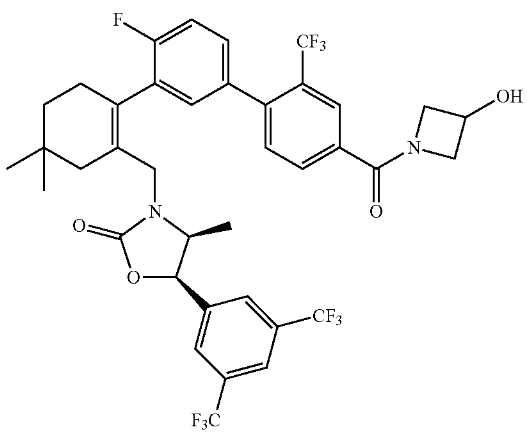 [SMILES: C[C@H]1[C@@H](c2cc(C(F)(F)F)cc(C(F)(F)F)c2)OC(=O)N1CC1=C(c2cc(-c3ccc(C(=O)N4CC(O)C4)cc3C(F)(F)F)ccc2F)CCC(C)(C)C1] |
| 756 | 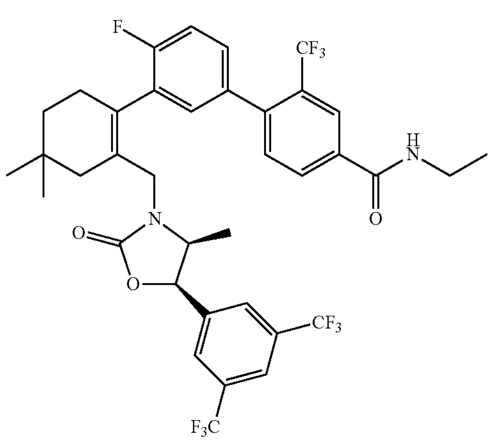 [SMILES: CCNC(=O)c1ccc(-c2ccc(F)c(C3=C(CN4C(=O)O[C@H](c5cc(C(F)(F)F)cc(C(F)(F)F)c5)[C@@H]4C)CC(C)(C)CC3)c2)c(C(F)(F)F)c1] |
| 757 | |
| 758 | |
| 763 | |

TABLE 29

| Compound | Structure |
|---|---|
| 764 | (structure: methoxy-pyridine with CF3-benzoic acid, dimethylcyclohexene, methyl-oxazolidinone, 3,5-bis(trifluoromethyl)phenyl) |

Measurement of Activities of Compounds According to the Present Invention—Test Protocols In the present invention, in order to test the preventive or therapeutic effects of the compounds of formula I against arteriosclerosis and hyperlipidemia and the safety of the compounds, comparative tests were performed using previously developed compounds as a control group.

Experimental Example 1

Test for Inhibition of Cholesteryl Ester Transfer (In Vitro)

1. Construction of Cholesteryl Ester Donor

To construct a cholesteryl ester donor to be used in the test, radiolabeled recombinant HDL containing [41]-cholesteryl oleate (GE healthcare, TRK886, 3.5 μCi/mg of apoA-1) and apoA-1 was synthesized. Then, rHDL-agarose having the recombinant HDL immobilized thereon by CNBr-activated Sepharose 4B (Amersham Biosciences, Sweden) resin was used in the test.

2. Cholesteryl Ester Transfer Test

As a protein source for cholesteryl ester transfer, plasma from healthy persons was used, and as a cholesteryl ester receptor, LDL from healthy persons was used. Samples were treated with each test compound to final concentrations of 16, 80, 400, 2000 and 10000 nM and analyzed in duplicate. For the cholesteryl ester transfer test, 20 μl of plasma, 50 μl of LDL (0.25 mg/ml) and 50 μl of rHDL-agarose (0.25 mg/ml) were added, and a solution containing a test compound was added, followed by reaction at 37° C. Then, centrifugation was performed at 4° C. for 3 minutes to stop the reaction, and 150 μl of the supernatant was taken and transferred to a 96-well plate for radioactivity measurement, and the radioactivity of the plate was measured with a beta-ray detector.

3. Statistical Processing

The ratio of [$^3$H]-cholesteryl oleate from HDL to LDL was calculated and used as a result value, and from the result value, $IC_{50}$ value was calculated using GraphPad Prism 5.0.

TABLE 30

Cholesteryl ester transfer test

| Compound | $IC_{50}$ (nM) |
|---|---|
| 554 | 5.8 |
| 555 | 28.4 |
| 557 | 5.4 |
| 561 | 23.2 |
| 567 | 56.6 |
| 572 | 15.0 |
| 574 | 3.9 |
| 575 | 14.6 |
| 578 | 12.6 |
| 584 | 5.3 |
| 586 | 13.0 |
| 592 | 8.4 |
| 593 | 1.5 |
| 596 | 17.9 |
| 597 | 50.2 |
| 612 | 6.9 |
| 613 | 9.1 |
| 614 | 27.0 |
| 615 | 12.3 |
| 616 | 7.6 |
| 618 | 1.6 |
| 620 | 11.6 |
| 631 | 1.9 |
| 643 | 7.3 |
| 650 | 11.9 |
| 651 | 10.7 |
| 661 | 2.5 |
| 668 | 5.0 |
| 677 | 15.9 |
| 681 | 6.6 |
| 684 | 1.9 |
| 689 | 24.3 |
| 695 | 6.4 |
| 723 | 9.6 |
| 727 | 11.4 |
| 729 | 7.5 |
| 739 | 20.3 |
| 748 | 15.9 |
| 756 | 5.9 |
| 758 | 7.1 |
| 764 | 8.9 |

As can be seen from the cholesteryl ester transfer test results in Table 30 above, the biaryl- or heterocyclic biaryl-substituted cyclohexene compounds show excellent abilities to inhibit cholesterol transfer.

Test Example 2

Test for Anti-Hyperlipidemic Effect in Hamsters (In Vivo)

1. Test Animals

In this test, 8-week-old male golden Syrian hamsters were used. The breeding room was maintained at constant temperature and constant humidity and a 12-hr light/12-hr dark cycle. The animals were allowed access to feed and water ad libitum.

2. Anti-Hyperlipidemic Test in Hamsters

The test animals were acclimated for 1 week before use in the test. The test animals were divided according to body weight into several groups, each consisting of 5-8 animals, and were then administered orally with a dose of 3 mg/kg. A solvent control and a CETP inhibitor were dissolved in imwitor 742: tween 80 (1:1) and administered orally for 5 days, and at 4 hours after the final administration, blood was collected from the heart. The collected blood was centrifuged at 3000 rpm for 15 minutes, and the separated serum was measured for HDL-Cholesterol (Biosystem) and LDL- Cholesterol (Biosystem) using a biochemical analysis instrument (ILab 300 plus, Instrumentation Laboratory).

3. Statistical Processing

All test results were expressed as Mean±SEM, and to evaluate the effect of each test group, each test group was compared with the control group using one-way ANOVA test (Dunnett's test, p<0.001).

TABLE 31

Measurement of increase in HDL-c and decrease in LDL-c in blood of hamsters

| Compound | Increase in HDL-c (%) | Decrease in LDL-c (%) |
| --- | --- | --- |
| 554 | 72 | 42 |
| 557 | 77 | 39 |
| 574 | 41 | 36 |
| 584 | 46 | 40 |
| 586 | 37 | 34 |
| 593 | 61 | 29 |
| 618 | 65 | 26 |
| 631 | 56 | 30 |
| 643 | 68 | 17 |
| 650 | 50 | 24 |
| 661 | 53 | 20 |
| 668 | 44 | 16 |
| 681 | 25 | 29 |
| 695 | 71 | 35 |

As can be seen from the measurement of the increase in the HDL-c in the blood of hamsters in Table 31 above, the biaryl- or heterocyclic biaryl-substituted cyclohexene compounds show excellent effects of increasing HDL-c and reducing LDL-c.

TEST EXAMPLE 3

Evaluation of the Ability of CETP Inhibitor to Secrete Blood Pressure-Hormone

1. Test Method

The results of ILLUMINATE regarding the results of phase III clinical trials for the first CETP inhibitor torcetrapib (Pfizer) indicated that morbidity rate and mortality rate in patients administered with a combination of torcetrapib and atorvastatin increase compared to those in patients administered with atorvastatin alone. Indeed, the secretion of hormones from human adrenal cortical tumor cells was evaluated using torcetrapib, and as a result, it was found that torcetrapib increased the secretion of aldosterone and cortisol that are blood pressure-increasing hormones (Endocrinology, 2009, 150(5), 2211-2219). Based on this, the secretion of blood pressure-increasing hormones from human adrenal cortical tumor cells was evaluated. The cell line H295R was purchased from ATCC (CRL-2128) and cultured in DMEM/F-12 medium (1% ITS, 2.5% Nu-serum). The H295R cell line was dispensed into a 24-well plate at a cell density of $1 \times 10^5$/well, and stabilized for 24 hours, after which the cells were starved for 24 hours using serum-free DMEM/F-12. Then, the cells were treated with each of 100 nM of torcetrapib and 1 µM of test compounds 554, 557, 574, 584, 586, 593, 618, 643, 650, 661, 681 and 695. At 24 hours after treatment with the drug or the compound, the supernatant was taken and stored at –20° C. The supernatant stored at –20° C. was thawed, and the amounts of aldosterone and cortisol secreted from the cells were measured using an aldosterone EIA kit (Cayman-10004377) and cortisol EIA kit (Cayman-500360).

2. Statistical Processing

All test results were expressed as Mean±SEM, and to evaluate the effect of each test group, each test group was compared with the control group using one-way ANOVA test (Dunnett's test, p<0.001).

TABLE 32

Evaluation of secretion of blood pressure-related hormones (treated with 1 µM of compound)

| Compound | Aldosterone (fold, vs con.) | Cortisol (fold, vs con.) |
| --- | --- | --- |
| 554 | 0.90 | 0.93 |
| 557 | 0.96 | 1.01 |
| 574 | 1.13 | 1.32 |
| 584 | 0.95 | 0.92 |
| 586 | 0.99 | 1.10 |
| 593 | 1.14 | 0.75 |
| 618 | 0.73 | 1.09 |
| 643 | 0.72 | 0.81 |
| 650 | 0.80 | 0.82 |
| 661 | 0.80 | 0.68 |
| 681 | 0.83 | 0.76 |
| 695 | 0.67 | 0.89 |
| Torcetrapib | 1.21~2.25 | 2.08~3.77 |

From the test results for the secretion of blood pressure-related hormones aldosterone and cortisol in Table 32 above, it can be seen that the control compound torcetrapib increased the secretion of the two hormones, but the biaryl- or heterocyclic biaryl-substituted cyclohexene compounds of the present invention did not influence the secretion of aldosterone and cortisol, which have a connection with blood pressure-related side effects. Thus, it can be seen that the compounds of the present invention does not cause increased blood pressure and side effects related to increased blood pressure.

The invention claimed is:
1. A compound of Formula I:

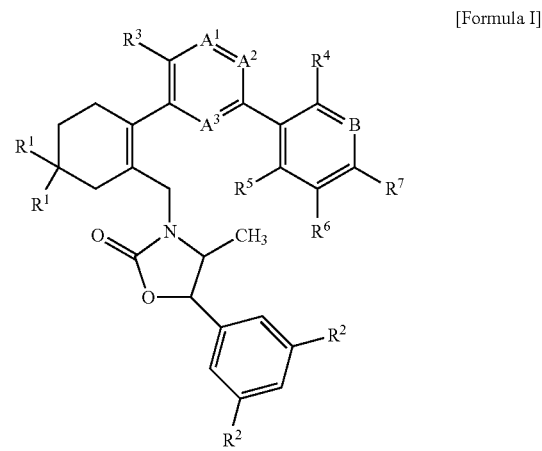

[Formula I]

or a stereoisomer or pharmaceutically acceptable salt thereof, wherein:
$R^1$ is —H or —$C_1$-$C_3$ alkyl;
$R^2$ is —H, halogen or —$C_1$-$C_3$ alkyl;
$R^3$, $R^4$, $R^5$ and $R^6$ are each independently —H, halogen, —$NO_2$, —$C_1$-$C_3$ alkyl, or —$OC_1$-$C_3$ alkyl;
$R^7$ is —H, —(C=O)$OR^8$, or

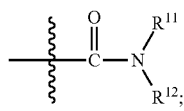

$R^8$ is —H or —$C_1$-$C_3$ alkyl;
$R^{11}$ and $R^{12}$ are each independently —H or —$C_1$-$C_3$ alkyl or may form a 4- to 6-membered non-aromatic ring, wherein the non-aromatic ring may contain 0 to 2 N or O heteroatoms, and one or more H in the non-aromatic ring may substituted with halogen or —OH;
$A^1$, $A^2$ and $A^3$ are each independently N or $CR^9$, wherein if $A^2$ or $A^3$ is N, $A^1$ is $CR^9$;
$R^9$ is —H, halogen, —$C_1$-$C_3$ alkyl or —$OC_1$-$C_3$ alkyl;
B is N or $CR^{10}$;
$R^{10}$ is H, halogen, —$C_1$-$C_3$ alkyl, —$OC_1$-$C_3$ alkyl, —(C=O)$OR^8$, or

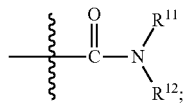

provided that one or more —H atoms in the —$C_1$-$C_3$ alkyl or the —$OC_1$-$C_3$ alkyl may be substituted with —F or —$CH_3$, and if $R^7$ is —H, B is $CR^{10}$, and $R^{10}$ is —(C=O)$OR^8$ or

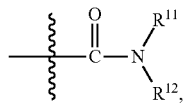

and if $R^7$ is not —H, $R^{10}$ cannot be —(C=O)$OR^8$ or

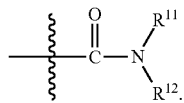

2. The compound of claim 1, wherein:
$R^1$ is —H or —$CH_3$;
$R^2$ is —F or —$CF_3$;
$R^3$, $R^4$, $R^5$ and $R^6$ are each independently —H, —F, —$NO_2$, —$CH_3$, —$CH(CH_3)_2$, —$CF_3$ or —$OCH_3$;
$R^7$ is —H, —(C=O)$OR^8$, or

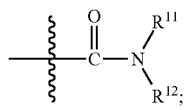

$R^8$ is —H, —$CH_3$ or —$CH_2CH_3$;
$R^{11}$ and $R^{12}$ are each independently —H, —$CH_3$ or —$CH_2CH_3$ or may form 4- to 6-membered non-aromatic ring, wherein the non-aromatic ring may contain 0 to 2 N or O heteroatoms, and one or more —H atoms in the non-aromatic ring may be substituted with —F or —OH;

$A^1$, $A^2$ and $A^3$ are each independently N or $CR^9$, wherein if $A^2$ or $A^3$ is N, $A^1$ is $CR^9$;
$R^9$ is —H, —F, —$CH_3$, —$CF_3$ or —$OCH_3$;
B is N or $CR^{10}$;
$R^{10}$ is —H, —F, —$CH_3$, —$OCH_3$, —$CO_2H$, —$CO_2CH_3$, —$CO_2CH_2CH_3$, or

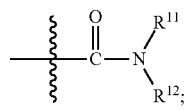

provided that if $R^7$ is —H, B is $CR^{10}$, and $R^{10}$ is —$CO_2H$, —$CO_2CH_3$, —$CO_2CH_2CH_3$, or

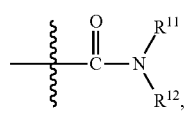

and if $R^7$ is not —H, $R^{10}$ is not —$CO_2H$, —$CO_2CH_3$, —$CO_2CH_2CH_3$, or

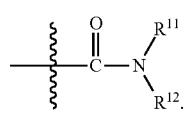

3. The compound of claim 2, wherein:
$R^1$ is —$CH_3$;
$R^2$ is —$CF_3$;
$R^3$ is —H, —F, —Cl or —$OCH_3$;
$R^4$ is —H, —F, —Cl, —$CH_3$, —$CH(CH_3)_2$, —$CF_3$ or —$OCH_3$;
$R^5$ is —H, —F or —Cl;
$R^6$ is —H;
$R^7$ is —H, —(C=O)OH,

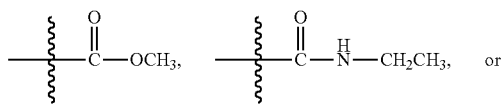 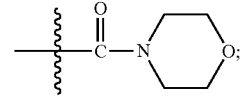

$A^1$, $A^2$ and $A^3$ are each independently N or $CR^9$, wherein if $A^2$ or $A^3$ is N, $A^1$ is $CR^9$;
$R^9$ is —H, —F, —$CH_3$, —$CF_3$ or —$OCH_3$;
B is $CR^{10}$;
$R^{10}$ is —H, —F or —$CO_2CH_3$;
provided that if $R^7$ is —H, B is $CR^{10}$, and $R^{10}$ is —$CO_2CH_3$, and if $R^7$ is not —H, $R^{10}$ is not —$CO_2CH_3$.

4. The compound of claim 3, wherein:
$R^3$ is —H, —F or —$OCH_3$;
$R^4$ is —H, —F, —Cl, —$CH_3$ or —$CF_3$;
$R^5$ is —H or —F;
$R^7$ is —(C=O)OH;
$A^1$ is N or $CR^9$;
$A^2$ and $A^3$ are each independently $CR^9$;
$R^9$ is —H or —F; and
B is CH.

5. The compound of claim 1, wherein the compound is selected from among the following compounds:

methyl 3'-(2-(((4S,5R)-5-(3,5-bis(trifluoromethyephenyl)-4-methyl-2-oxo-oxazolidin-3-yl)-methyl)-4,4-dimethylcyclohex-1-enyl)-4'-methoxy-2-methyl-biphenyl-4-carboxylate;

3'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-4'-methoxy-2-methyl-biphenyl-4-carboxylic acid;

methyl 4-(3-(2-(((4S,5R)-5-(3,5-bis(trifluoromethyl)phenyl)-4-methyl-2-oxo-oxazolidin-3-yl)methyl)-4,4-dimethylcyclohex-1-enyl)-2-methoxypyridin-5-yl)-3-methylbenzoate;

methyl 4-(3-(2-(((4S,5R)-5-(3,5-bis(trifluoromethyl)phenyl)-4-methyl-2-oxo-oxazolidin-3-yl)methyl)-4,4-dimethylcyclohex-1-enyl)-2-methoxypyridin-5-yl)-benzoate;

4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-3-methyl-benzoic acid;

4-(3-(2-(((4S,5R)-5-(3,5-bis(trifluoromethyl)phenyl)-4-methyl-2-oxooxazolidin-3-yl)-methyl)-4,4-dimethylcyclohex-1-enyl)-2-methoxypyridin-5-yl)benzoic acid;

methyl 3'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-4'-methoxybiphenyl-4-carboxylate;

methyl 3'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-2-fluoro-4'-methoxybiphenyl-4-carboxylate;

3'-(2-(((4S,5R)-5-(3,5-bis(trifluoromethyl)phenyl)-4-methyl-2-oxooxazolidin-3-yl)-methyl)-4,4-dimethylcyclohex-1-enyl)-2-fluoro-4'-methoxybiphenyl-4-carboxylic acid;

methyl 5-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-picolinate;

3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxybiphenyl-4-carboxylic acid;

methyl 3'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-4'-methoxybiphenyl-3-carboxylate;

3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxybiphenyl-3-carboxylic acid;

methyl 3'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-4'-methoxy-2-nitrobiphenyl-4-carboxylate;

methyl 5'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-2'-fluoro-4'-methoxy-2-methylbiphenyl-4-carboxylate;

methyl 5'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-2'-fluoro-4'-methoxy-biphenyl-4-carboxylate;

5'-(2-(((4S,5R)-5-(3,5-bis(trifluoromethyl)phenyl)-4-methyl-2-oxo-oxazolidin-3-yl)methyl)-4,4-dimethylcyclohex-1-enyl)-2'-fluoro-4'-methoxy-2-methylbiphenyl-4-carboxylic acid;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-4'-methoxybiphenyl-4-carboxylic acid;

methyl 4-(3-(2-(((4S,5R)-5-(3,5-bis(trifluoromethyl)phenyl)-4-methyl-2-oxo-oxazolidin-3-yl)methyl)-4,4-dimethylcyclohex-1-enyl)-2-methoxypyridin-5-yl)-3-isopropylbenzoate;

4-(3-(2-(((4S,5R)-5-(3,5-bis(trifluoromethyl)phenyl)-4-methyl-2-oxooxazolidin-3-yl)-methyl)-4,4-dimethylcyclohex-1-enyl)-2-methoxypyridin-5-yl)-3-isopropylbenzoic acid;

methyl 3'-(2-(((4S,5R)-5-(3,5-bis(trifluoromethyl)phenyl)-4-methyl-2-oxo-oxazolidin-3-yl)-methyl)cyclohex-1-enyl)-4'-methoxy-2-methylbiphenyl-4-carboxylate;

methyl 3'-(2-(((4S,5R)-5-(3,5-bis(trifluoromethyl)phenyl)-4-methyl-2-oxo-oxazolidin-3-yl)-methyl)cyclohex-1-enyl)-2-fluoro-4'-methoxybiphenyl-4-carboxylate;

3'-(2-(((4S,5R)-5-(3,5-bis(trifluoromethyl)phenyl)-4-methyl-2-oxooxazolidin-3-yl)-methyl)cyclohex-1-enyl)-4'-methoxy-2-methylbiphenyl-4-carboxylic acid;

3'-(2-(((4S,5R)-5-(3,5-bis(trifluoromethyl)phenyl)-4-methyl-2-oxooxazolidin-3-yl)-methyl)cyclohex-1-enyl)-2-fluoro-4'-methoxybiphenyl-4-carboxylic acid;

methyl 4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-3-chlorobenzoate;

4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-3-chlorobenzoic acid;

methyl 4-(3-(2-(((4S,5R)-5-(3,5-bis(trifluoromethyl)phenyl)-4-methyl-2-oxo-oxazolidin-3-yl)methyl)-4,4-dimethylcyclohex-1-enyl)-2-methoxypyridin-5-yl)-3-fluorobenzoate;

4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-3-fluorobenzoic acid;

methyl 3-(3-(2-(((4S,5R)-5-(3,5-bis(trifluoromethyl)phenyl)-4-methyl-2-oxo-oxazolidin-3-yl)methyl)-4,4-dimethylcyclohex-1-enyl)-2-methoxypyridin-5-yl)-benzoate;

3-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)benzoic acid;

methyl 3'-(2-(((4S,5R)-5-(3,5-bis(trifluoromethyl)phenyl)-4-methyl-2-oxo-oxazolidin-3-yl)methyl)-4,4-dimethylcyclohex-1-enyl)-2,3-difluoro-4'-methoxy-biphenyl-4-carboxylate;

methyl 3'-(2-(((4S,5R)-5-(3,5-bis(trifluoromethyl)phenyl)-4-methyl-2-oxo-oxazolidin-3-yl)methyl)-4,4-dimethylcyclohex-1-enyl)-2,6-difluoro-4'-methoxy-biphenyl-4-carboxylate;

3'-(2-(((4S,5R)-5-(3,5-bis(trifluoromethyl)phenyl)-4-methyl-2-oxooxazolidin-3-yl)-methyl)-4,4-dimethylcyclohex-1-enyl)-2,3-difluoro-4'-methoxybiphenyl-4-carboxylic acid;

3'-(2-(((4S,5R)-5-(3,5-bis(trifluoromethyl)phenyl)-4-methyl-2-oxooxazolidin-3-yl)-methyl)-4,4-dimethylcyclohex-1-enyl)-2,6-difluoro-4'-methoxybiphenyl-4-carboxylic acid;

methyl 3'-(2-(((4S,5R)-5-(3,5-bis(trifluoromethyl)phenyl)-4-methyl-2-oxo-oxazolidin-3-yl)methyl)-4,4-dimethylcyclohex-1-enyl)-2,4'-dimethoxybiphenyl-4-carboxylate;

methyl 4-(3-(2-(((4S,5R)-5-(3,5-bis(trifluoromethyl)phenyl)-4-methyl-2-oxo-oxazolidin-3-yl)methyl)-4,4-dimethylcyclohex-1-enyl)-2-methoxypyridin-5-yl)-2,3-difluorobenzoate;

4-(3-(2-(((4S,5R)-5-(3,5-bis(trifluoromethyl)phenyl)-4-methyl-2-oxooxazolidin-3-yl)methyl)-4,4-dimethylcyclohex-1-enyl)-2-methoxypyridin-5-yl)-2,3-difluorobenzoic acid;

3'-(2-(((4S,5R)-5-(3,5-bis(trifluoromethyl)phenyl)-4-methyl-2-oxooxazolidin-3-yl)methyl)-4,4-dimethylcyclohex-1-enyl)-2,4'-dimethoxybiphenyl-4-carboxylic acid;

methyl 3'-(2-(((4S,5R)-5-(3,5-bis(trifluoromethyephenyl)-4-methyl-2-oxo-oxazolidin-3-yl)-methyl)-4,4-dimethylcyclohex-1-enyl)-3,4'-dimethoxybiphenyl-4-carboxylate;

3'-(2-(((4S,5R)-5-(3,5-bis(trifluoromethyl)phenyl)-4-methyl-2-oxooxazolidin-3-yl)methyl)-4,4-dimethylcyclohex-1-enyl)-3,4'-dimethoxybiphenyl-4-carboxylic acid;

5-(3-(2-(((4S,5R)-5-(3,5-bis(trifluoromethyl)phenyl)-4-methyl-2-oxooxazolidin-3-yl)-methyl)-4,4-dimethylcyclohex-1-enyl)-4-methoxyphenyl)-3-methylpicolinic acid;

methyl 4-(4-(2-(((4S,5R)-5-(3,5-bis(trifluoromethyl)phenyl)-4-methyl-2-oxo-oxazolidin-3-yl)methyl)-4,4-dimethylcyclohex-1-enyl)-5-methoxypyrimidin-2-yl)-3-methylbenzoate;

4-(4-(2-(((4S,5R)-5-(3,5-bis(trifluoromethyl)phenyl)-4-methyl-2-oxooxazolidin-3-yl)-methyl)-4,4-dimethylcyclohex-1-enyl)-5-methoxypyrimidin-2-yl)-3-methylbenzoic acid;

methyl 5'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-4'-methoxy-2'-(trifluoromethyl)biphenyl-4-carboxylate;

methyl 5'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-2-fluoro-4'-methoxy-2'-(trifluoromethyl)biphenyl-4-carboxylate;

ethyl 5'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-3-fluoro-4'-methoxy-2'-(trifluoromethyl)biphenyl-4-carboxylate;

methyl 5'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-2-chloro-4'-methoxy-2'-(trifluoromethyl)biphenyl-4-carboxylate;

methyl 5'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-4'-methoxy-2-methyl-2'-(trifluoromethyl)biphenyl-4-carboxylate;

methyl 4-(4-(2-(((4S,5R)-5-(3,5-bis(trifluoromethyl)phenyl)-4-methyl-2-oxo-oxazolidin-3-yl methyl)-4,4-dimethylcyclohex-1-enyl)-5-methoxypyrimidin-2-yl)-3-fluorobenzoate;

5-(5-(2-(((4S,5R)-5-(3,5-bis(trifluoromethyl)phenyl)-4-methyl-2-oxooxazolidin-3-yl)-methyl)-4,4-dimethylcyclohex-1-enyl)-4-methoxy-2-(trifluoromethyl)phenyl)-3-fluoropicolinic acid;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2'-(trifluoromethyl)biphenyl-4-carboxylic acid;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-4'-methoxy-2'-(trifluoromethyl)-biphenyl-4-carboxylic acid;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-3-fluoro-4'-methoxy-T-(trifluoromethyl)-biphenyl-4-carboxylic acid;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-2-chloro-4'-methoxy-2'-(trifluoromethyl)-biphenyl-4-carboxylic acid;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2-methyl-2'-(trifluoromethyl)-biphenyl-4-carboxylic acid;

4-(4-(2-(((4S,5R)-5-(3,5-bis(trifluoromethyl)phenyl)-4-methyl-2-oxooxazolidin-3-yl)-methyl)-4,4-dimethylcyclohex-1-enyl)-5-methoxypyrimidin-2-yl)-3-fluorobenzoic acid;

3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2-(trifluoromethyl)biphenyl-4-carboxylic acid;

methyl 5'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-4'-methoxy-2'-methyl-biphenyl-4-carboxylate;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-T-methylbiphenyl-4-carboxylic acid;

methyl 4-(2-(2-(((4S,5R)-5-(3,5-bis(trifluoromethyl)phenyl)-4-methyl-2-oxo-oxazolidin-3-yl)methyl)-4,4-dimethylcyclohex-1-enyl)-3-methoxypyridin-6-yl)-3-methylbenzoate;

4-(2-(2-(((4S,5R)-5-(3,5-bis(trifluoromethyl)phenyl)-4-methyl-2-oxooxazolidin-3-yl)-methyl)-4,4-dimethylcyclohex-1-enyl)-3-methoxypyridin-6-yl)-3-methylbenzoic acid;

methyl 4-(4-(2-(((4S,5R)-5-(3,5-bis(trifluoromethyl)phenyl)-4-methyl-2-oxo-oxazolidin-3-yl)methyl)-4,4-dimethylcyclohex-1-enyl)-5-methoxypyrimidin-2-yl)-benzoate;

ethyl 4-(4-(2-(((4S,5R)-5-(3,5-bis(trifluoromethyl)phenyl)-4-methyl-2-oxo-oxazolidin-3-yl)-methyl)-4,4-dimethylcyclohex-1-enyl)-5-methoxypyrimidin-2-yl)-2-fluorobenzoate;

4-(4-(2-(((4S,5R)-5-(3,5-bis(trifluoromethyl)phenyl)-4-methyl-2-oxooxazolidin-3-yl)-methyl)-4,4-dimethylcyclohex-1-enyl)-5-methoxypyrimidin-2-yl)benzoic acid;

4-(4-(2-(((4S,5R)-5-(3,5-bis(trifluoromethyl)phenyl)-4-methyl-2-oxooxazolidin-3-yl)-methyl)-4,4-dimethylcyclohex-1-enyl)-5-methoxypyrimidin-2-yl)-2-fluorobenzoic acid;

methyl 5'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-2-chloro-2'-fluoro-4'-methoxybiphenyl-4-carboxylate;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-2-chloro-2'-fluoro-4'-methoxybiphenyl-4-carboxylic acid;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-3-chloro-4'-methoxy-T-(trifluoromethyl)-biphenyl-4-carboxylic acid;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-3,4'-dimethoxy-2'-(trifluoromethyl)-biphenyl-4-carboxylic acid;

4-(2-(2-(((4S,5R)-5-(3,5-bis(trifluoromethyl)phenyl)-4-methyl-2-oxooxazolidin-3-yl)-methyl)-4,4-dimethylcyclohex-1-enyl)-3-methoxypyridin-6-yl)-3-chlorobenzoic acid;

4-(2-(2-(((4S,5R)-5-(3,5-bis(trifluoromethyl)phenyl)-4-methyl-2-oxooxazolidin-3-yl)methyl)-4,4-dimethylcyclohex-1-enyl)-3-methoxypyridin-6-yl)-3-fluorobenzoic acid;

methyl 5'-(2-(((4S,5R)-5-(3,5-bis(trifluoromethyl)phenyl)-4-methyl-2-oxooxazolidin-3-yl)-methyl)-4,4-dimethylcyclohex-1-enyl)-3-chloro-4'-methoxy-2'-(trifluoromethyl)-biphenyl-4-carboxylate;

methyl 5'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-3,4'-dimethoxy-2'-(trifluoromethyl)-biphenyl-4-carboxylate;

methyl 3'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-2-chloro-4'-methoxy-biphenyl-4-carboxylate;

3'-(2-(((4S,5R)-5-(3,5-bis(trifluoromethyl)phenyl)-4-methyl-2-oxooxazolidin-3-yl)-methyl)-4,4-dimethylcyclohex-1-enyl)-2-chloro-4'-methoxybiphenyl-4-carboxylic acid;

4-(4-(2-(((4S,5R)-5-(3,5-bis(trifluoromethyl)phenyl)-4-methyl-2-oxooxazolidin-3-yl)-methyl)-4,4-dimethylcyclohex-1-enyl)-5-methoxypyridin-2-yl)benzoic acid;

4-(4-(2-(((4S,5R)-5-(3,5-bis(trifluoromethyl)phenyl)-4-methyl-2-oxooxazolidin-3-yl)methyl) 4,4-dimethylcyclohex-1-enyl)-5-methoxypyridin-2-yl)-3-methylbenzoic acid;

4-(4-(2-(((4S,5R)-5-(3,5-bis(trifluoromethyl)phenyl)-4-methyl-2-oxooxazolidin-3-yl)-methyl)-4,4-dimethylcyclohex-1-enyl)-5-methoxypyridin-2-yl)-3-fluorobenzoic acid;

4-(4-(2-(((4S,5R)-5-(3,5-bis(trifluoromethyl)phenyl)-4-methyl-2-oxooxazolidin-3-yl)methyl) 4,4-dimethylcyclohex-1-enyl)-5-methoxypyridin-2-yl)-3-chlorobenzoic acid;

methyl 3'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-5'-fluoro-2-methylbiphenyl-4-carboxylate;

methyl 3'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-2-methylbiphenyl-4-carboxylate;

3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-fluoro-2-methylbiphenyl-4-carboxylic acid;

3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-methylbiphenyl-4-carboxylic acid;

methyl 4-(4-(2-(((4S,5R)-5-(3,5-bis(trifluoromethyl)phenyl)-4-methyl-2-oxo-oxazolidin-3-yl)methyl)-4,4-dimethylcyclohex-1-enyl)-5-methoxypyridin-2-yl)-benzoate;

methyl 4-(4-(2-(((4S,5R)-5-(3,5-bis(trifluoromethyl)phenyl)-4-methyl-2-oxo-oxazolidin-3-yl)methyl)-4,4-dimethylcyclohex-1-enyl)-5-methoxypyridin-2-yl)-3-methylbenzoate;

methyl 4-(4-(2-(((4S,5R)-5-(3,5-bis(trifluoromethyl)phenyl)-4-methyl-2-oxo-oxazolidin-3-yl)methyl)-4,4-dimethylcyclohex-1-enyl)-5-methoxypyridin-2-yl)-3-fluorobenzoate;

methyl 4-(4-(2-(((4S,5R)-5-(3,5-bis(trifluoromethyl)phenyl)-4-methyl-2-oxo-oxazolidin-3-yl)methyl)-4,4-dimethylcyclohex-1-enyl)-5-methoxypyridin-2-yl)-3-chlorobenzoate;

methyl 4-(4-(2-(((4S,5R)-5-(3,5-bis(trifluoromethyl)phenyl)-4-methyl-2-oxo-oxazolidin-3-yl)methyl)-4,4-dimethylcyclohex-1-enyl)-5-methoxypyridin-2-yl)-2,3-difluorobenzoate;

methyl 5'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-2,2'-difluoro-4'-methoxy-biphenyl-4-carboxylate;

ethyl 5'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-2',3-difluoro-4'-methoxy-biphenyl-4-carboxylate;

methyl 5'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-2'-fluoro-3,4'-dimethoxy-biphenyl-4-carboxylate;

methyl 5'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-2,2',3-trifluoro-4'-methoxy-biphenyl-4-carboxylate;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-2,2'-difluoro-4'-methoxybiphenyl-4-carboxylic acid;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-2',3-difluoro-4'-methoxybiphenyl-4-carboxylic acid;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-3,4'-dimethoxybiphenyl-4-carboxylic acid;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-2,2',3-trifluoro-4'-methoxybiphenyl-4-carboxylic acid;

methyl 5-(3-(2-(((4S,5R)-5-(3,5-bis(trifluoromethyl)phenyl)-4-methyl-2-oxo-oxazolidin-3-yl)methyl)-4,4-dimethylcyclohex-1-enyl)-4-methoxyphenyl)-6-methyl-picolinate;

5-(3-(2-(((4S,5R)-5-(3,5-bis(trifluoromethyl)phenyl)-4-methyl-2-oxooxazolidin-3-yl)methyl)-4,4-dimethylcyclohex-1-enyl)-4-methoxyphenyl)-6-methylpicolinic acid;

methyl 3'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-5'-fluoro-2-(trifluoro-methyl)biphenyl-4-carboxylate;

3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-fluoro-2-(trifluoromethyl)biphenyl-4-carboxylic acid;

methyl 5'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-2'-fluorobiphenyl-4-carboxylate;

methyl 5'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-2,2'-difluorobiphenyl-4-carboxylate;

methyl 5'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-2'-fluoro-2-methylbiphenyl-4-carboxylate;

methyl 5'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-T-methylbiphenyl-4-carboxylate;

methyl 5'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-2,2'-dimethylbiphenyl-4-carboxylate;

methyl 5'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-2-fluoro-2'-methylbiphenyl-4-carboxylate;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-methylbiphenyl-4-carboxylic acid;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-2,2'-dimethylbiphenyl-4-carboxylic acid;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-2'-methylbiphenyl-4-carboxylic acid;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluorobiphenyl-4-carboxylic acid;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-2,2'-difluorobiphenyl-4-carboxylic acid;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-2-methylbiphenyl-4-carboxylic acid;

3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-methoxy-2-methylbiphenyl-4-carboxamide;

methyl 5'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-4'-methoxy-2,2'-dimethyl-biphenyl-4-carboxylate;

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-4'-methoxy-2,2'-dimethylbiphenyl-4-carboxylic acid;

methyl 3'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-5'-methoxybiphenyl-4-carboxylate;

3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-methoxybiphenyl-4-carboxylic acid;

methyl 3'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-5'-methoxy-2-methyl-biphenyl-4-carboxylate;

3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-methoxy-2-methylbiphenyl-4-carboxylic acid;

methyl 3'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-2-fluoro-5'-methoxybiphenyl-4-carboxylate;

3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-5'-methoxybiphenyl-4-carboxylic acid;

methyl 3'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-4'-fluoro-2-methylbiphenyl-4-carboxylate;

methyl 3'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-4'-fluoro-2-(trifluoromethyl)-biphenyl-4-carboxylate;

3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-fluoro-2-methylbiphenyl-4-carboxylic acid;

3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-fluoro-2-(trifluoromethyl)biphenyl-4-carboxylic acid;

methyl 4-(2-(2-(((4S,5R)-5-(3,5-bis(trifluoromethyl)phenyl)-4-methyl-2-oxo-oxazolidin-3-yl)methyl)-4,4-dimethylcyclohex-1-enyl)-3-methoxypyridin-6-yl)-3-fluorobenzoate;

methyl 4-(2-(2-(((4S,5R)-5-(3,5-bis(trifluoromethyl)phenyl)-4-methyl-2-oxo-oxazolidin-3-yl)methyl)-4,4-dimethylcyclohex-1-enyl)-3-methoxypyridin-6-yl)-3-chlorobenzoate;

methyl 3'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-2,5'-difluorobiphenyl-4-carboxylate;

methyl 3'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-5'-fluorobiphenyl-4-carboxylate;

methyl 3'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-2-fluorobiphenyl-4-carboxylate;

3'-(2-(((4S,5R)-5-(3,5-bis(trifluoromethyl)phenyl)-4-methyl-2-oxooxazolidin-3-yl)methyl)-4,4-dimethylcyclohex-1-enyl)-2,5'-difluorobiphenyl-4-carboxylic acid;

3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-fluorobiphenyl-4-carboxylic acid;

3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluorobiphenyl-4-carboxylic acid;

methyl 3'-(2-(((4S,5R)-5-(3,5-difluorophenyl)-4-methyl-2-oxooxazolidin-3-yl)-methyl)-4,4-dimethylcyclohex-1-enyl)-4'-methoxy-2-methylbiphenyl-4-carboxylate;
3'-(2-(((4S,5R)-5-(3,5-difluorophenyl)-4-methyl-2-oxooxazolidin-3-yl)methyl)-4,4-dimethylcyclohex-1-enyl)-4'-methoxy-2-methylbiphenyl-4-carboxylic acid;
methyl 3'-(2-(((4S,5R)-5-(3,5-bis(trifluoromethyl)phenyl)-4-methyl-2-oxo-oxazolidin-3-yl)-methyl)-4,4-dimethylcyclohex-1-enyl)-4'-fluorobiphenyl-4-carboxylate;
3'-(2-(((4S,5R)-5-(3,5-bis(trifluoromethyl)phenyl)-4-methyl-2-oxooxazolidin-3-yl)-methyl)-4,4-dimethylcyclohex-1-enyl)-4'-fluorobiphenyl-4-carboxylic acid;
methyl 4-(4-(2-(((4S,5R)-5-(3,5-bis(trifluoromethyl)phenyl)-4-methyl-2-oxo-oxazolidin-3-yl methyl)-4,4-dimethylcyclohex-1-enyl)pyridin-2-yl)-3-methylbenzoate;
4-(4-(2-(((4S,5R)-5-(3,5-bis(trifluoromethyl)phenyl)-4-methyl-2-oxooxazolidin-3-yl)methyl)-4,4-dimethylcyclohex-1-enyl)pyridin-2-yl)-3-methylbenzoic acid;
3'-(2-(((4S,5S)-5-(3,5-bis(trifluoromethyl)phenyl)-4-methyl-2-oxooxazolidin-3-yl)methyl)-4,4-dimethylcyclohex-1-enyl)-4'-methoxy-2-methylbiphenyl-4-carboxylic acid;
3'-(2-(((4R,5S)-5-(3,5-bis(trifluoromethyl)phenyl)-4-methyl-2-oxooxazolidin-3-yl)methyl)-4,4-dimethylcyclohex-1-enyl)-4'-methoxy-2-methylbiphenyl-4-carboxylic acid;
3'-(2-(((4R,5R)-5-(3,5-bis(trifluoromethyl)phenyl)-4-methyl-2-oxooxazolidin-3-yl)methyl)-4,4-dimethylcyclohex-1-enyl)-4'-methoxy-2-methylbiphenyl-4-carboxylic acid;
3'-(2-(((4S,5R)-5-(3,5-bis(trifluoromethyl)phenyl)-4-methyl-2-oxooxazolidin-3-yl)methyl)-4,4-dimethylcyclohex-1-enyl)-2,4'-difluorobiphenyl-4-carboxylic acid;
5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-2-(trifluoromethyl)biphenyl-4-carboxylic acid;
methyl 3'-(2-(((4S,5R)-5-(3,5-bis(trifluoromethyl)phenyl)-4-methyl-2-oxo-oxazolidin-3-yl)methyl)-4,4-dimethylcyclohex-1-enyl)-2,4'-difluorobiphenyl-4-carboxylate;
methyl 5'-(2-(((4S,5R)-5-(3,5-bis(trifluoromethyl)phenyl)-4-methyl-2-oxo-oxazolidin-3-yl)methyl)-4,4-dimethylcyclohex-1-enyl)-2'-fluoro-2-(trifluoromethyl)-biphenyl-4-carboxylate;
methyl 3'-(2-(((4S,5R)-5-(3,5-bis(trifluoromethyl)phenyl)-4-methyl-2-oxo-oxazolidin-3-yl)methyl)-4,4-dimethylcyclohex-1-enyl)-4'-chloro-2-methylbiphenyl-4-carboxylate;
3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-chloro-2-methylbiphenyl-4-carboxylic acid;
methyl 3'-(2-(((4S,5R)-5-(3,5-bis(trifluoromethyl)phenyl)-4-methyl-2-oxo-oxazolidin-3-yl)methyl)-4,4-dimethylcyclohex-1-enyl)-4'-chloro-2-(trifluoromethyl)-biphenyl-4-carboxylate;
3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-chloro-2-(trifluoromethyl)biphenyl-4-carboxylic acid;
methyl 3'-(2-(((4S,5R)-5-(3,5-bis(trifluoromethyl)phenyl)-4-methyl-2-oxo-oxazolidin-3-yl)methyl)-4,4-dimethylcyclohex-1-enyl)-2-chloro-4'-fluorobiphenyl-4-carboxylate;
3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-chloro-4'-fluorobiphenyl-4-carboxylic acid;
3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-chloro-4'-methoxybiphenyl-4-carboxamide;
5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-2-methylbiphenyl-4-carboxamide;
3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-fluoro-2-(trifluoromethyl)biphenyl-4-carboxamide;
methyl 3'-(2-(((4S,5R)-5-(3,5-bis(trifluoromethyl)phenyl)-4-methyl-2-oxo-oxazolidin-3-yl)methyl)-4,4-dimethylcyclohex-1-enyl)-2-methyl-5'-(trifluoromethyl)-biphenyl-4-carboxylate;
3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-methyl-5'-(trifluoromethyl)biphenyl-4-carboxylic acid;
methyl 3'-(2-(((4S,5R)-5-(3,5-bis(trifluoromethyl)phenyl)-4-methyl-2-oxo-oxazolidin-3-yl)methyl)-4,4-dimethylcyclohex-1-enyl)-5'-(trifluoromethyl)biphenyl-4-carboxylate;
3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-(trifluoromethyl)biphenyl-4-carboxylic acid;
methyl 3'-(2-(((4S,5R)-5-(3,5-bis(trifluoromethyl)phenyl)-4-methyl-2-oxo-oxazolidin-3-yl)methyl)-4,4-dimethylcyclohex-1-enyl)-2-fluoro-5'-(trifluoromethyl)-biphenyl-4-carboxylate;
3'-(2-(((4S,5R)-5-(3,5-bis(trifluoromethyl)phenyl)-4-methyl-2-oxooxazolidin-3-yl)methyl)-4,4-dimethylcyclohex-1-enyl)-2-fluoro-5'-(trifluoromethyl)biphenyl-4-carboxylic acid;
(4S,5R)-5-(3,5-bis(trifluoromethyl)phenyl)-3-((2-(4'-(3,3-difluoroazetidine-1-carbonyl)-4-fluoro-2'-(trifluoromethyl)biphenyl-3-yl)-4,4-dimethylcyclohex-1-enyl)methyl)-4-methyl-oxazolidin-2-one;
(4S,5R)-5-(3,5-bis(trifluoromethyl)phenyl)-3-((2-(4-fluoro-4'-(3-hydroxy-azetidine-1-carbonyl)-2'-(trifluoromethyl)biphenyl-3-yl)-4,4-dimethylcyclohex-1-enyl)methyl)-4-methyloxazolidin-2-one;
3'-(2-(((4S,5R)-5-(3,5-bis(trifluoromethyl)phenyl)-4-methyl-2-oxooxazolidin-3-yl)methyl)-4,4-dimethylcyclohex-1-enyl)-N-ethyl-4'-fluoro-2-(trifluoromethyl)-biphenyl-4-carboxamide;
3'-(2-(((4S,5R)-5-(3,5-bis(trifluoromethyl)phenyl)-4-methyl-2-oxooxazolidin-3-yl)methyl)-4,4-dimethylcyclohex-1-enyl)-N-ethyl-4'-fluoro-N-methyl-2-(trifluoro-methyl)biphenyl-4-carboxamide;
(4S,5R)-5-(3,5-bis(trifluoromethyl)phenyl)-3-((2-(4-fluoro-4'-(morpholine-4-carbonyl)-2'-(trifluoromethyl)biphenyl-3-yl)-4,4-dimethylcyclohex-1-enyl)methyl)-4-methyloxazolidin-2-one;
methyl 4-(2-(2-(((4S,5R)-5-(3,5-bis(trifluoromethyl)phenyl)-4-methyl-2-oxo-oxazolidin-3-yl)methyl)-4,4-dimethylcyclohex-1-enyl)-3-methoxypyridin-6-yl)-3-(trifluoromethyl)benzoate; and 4-(2-(2-(((4S,5R)-5-(3,5-bis(trifluoromethyl)phenyl)-4-methyl-2-oxooxazolidin-3-yl)methyl)-4,4-dimethylcyclohex-1-enyl)-3-methoxypyridin-6-yl)-3-(trifluoromethyl)-benzoic acid.

6. The compound of claim 5, wherein the compound is selected from among the following compounds:

3'-(2-(((4S,5R)-5-(3,5-bis(trifluoromethyl)phenyl)-4-methyl-2-oxo-oxazolidin-3-yl)-methyl)-4,4-dimethyl-cyclohex-1-enyl)-4'-methoxy-2-methyl-biphenyl-4-carboxylic acid;

methyl 4-(3-(2-(((4S,5R)-5-(3,5-bis(trifluoromethyl)phenyl)-4-methyl-2-oxo-oxazolidin-3-yl)methyl)-4,4-dimethylcyclohex-1-enyl)-2-methoxypyridin-5-yl)-3-methylbenzoate;

4-(3-(2-(((4S,5R)-5-(3,5-bis(trifluoromethyl)phenyl)-4-methyl-2-oxo-oxazolidin-3-yl)methyl)-4,4-dimethyl-cyclohex-1-enyl)-2-methoxypyridin-5-yl)-3-methyl-benzoic acid;

3'-(2-(((4S,5R)-5-(3,5-bis(trifluoromethyl)phenyl)-4-methyl-2-oxooxazolidin-3-yl)-methyl) 4,4-dimethylcyclohex-1-enyl)-2-fluoro-4'-methoxybiphenyl-4-carboxylic acid;

methyl 3'-(2-(((4S,5R)-5-(3,5-bis(trifluoromethyl)phenyl)-4-methyl-2-oxo-oxazolidin-3-yl)methyl)-4,4-dimethylcyclohex-1-enyl)-4'-methoxybiphenyl-3-carboxylate;

methyl 5'-(2-(((4S,5R)-5-(3,5-bis(trifluoromethyl)phenyl)-4-methyl-2-oxo-oxazolidin-3-yl)methyl)-4,4-dimethylcyclohex-1-enyl)-2'-fluoro-4'-methoxy-2-methyl-biphenyl-4-carboxylate;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-4'-methoxy-2-methylbiphenyl-4-carboxylic acid;

5'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-2'-fluoro-4'-methoxybiphenyl-4-carboxylic acid;

4-(3-(2-(((4S,5R)-5-(3,5-bis(trifluoromethyl)phenyl)-4-methyl-2-oxo-oxazolidin-3-yl)-methyl)-4,4-dimethyl-cyclohex-1-enyl)-2-methoxypyridin-5-yl)-3-isopropyl-benzoic acid;

4-(3-(2-(((4S,5R)-5-(3,5-bis(trifluoromethyl)phenyl)-4-methyl-2-oxooxazolidin-3-yl)-methyl)-4,4-dimethyl-cyclohex-1-enyl)-2-methoxypyridin-5-yl)-3-chlorobenzoic acid;

4-(3-(2-(((4S,5R)-5-(3,5-bis(trifluoromethyl)phenyl)-4-methyl-2-oxooxazolidin-3-yl)-methyl)-4,4-dimethyl-cyclohex-1-enyl)-2-methoxypyridin-5-yl)-3-fluorobenzoic acid;

3'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-2,3-difluoro-4'-methoxybiphenyl-4-carboxylic acid;

3'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-2,6-difluoro-4'-methoxybiphenyl-4-carboxylic acid;

4-(3-(2-(((4S,5R)-5-(3,5-bis(trifluoromethyl)phenyl)-4-methyl-2-oxooxazolidin-3-yl)-methyl)-4,4-dimethyl-cyclohex-1-enyl)-2-methoxypyridin-5-yl)-2,3-difluorobenzoic acid;

3'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-2,4'-dimethoxybiphenyl-4-carboxylic acid;

5'-(2-(((4S,5R)-5-(3,5-bis(trifluoromethyl)phenyl)-4-methyl-2-oxooxazolidin-3-yl)methyl)-4,4-dimethyl-cyclohex-1-enyl)-4'-methoxy-2'-(trifluoromethyl)biphenyl-4-carboxylic acid;

5'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-2-fluoro-4'-methoxy-2'-(trifluoromethyl)biphenyl-4-carboxylic acid;

5'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-3-fluoro-4'-methoxy-2'-(trifluoromethyl)biphenyl-4-carboxylic acid;

5'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-2-chloro-4'-methoxy-2'-(trifluoromethyl)biphenyl-4-carboxylic acid;

5'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-4'-methoxy-2-methyl-2'-(trifluoromethyl)biphenyl-4-carboxylic acid;

3'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-4'-methoxy-2-(trifluoromethyl)biphenyl-4-carboxylic acid;

5'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-4'-methoxy-2'-methylbiphenyl-4-carboxylic acid;

5'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-2-chloro-2'-fluoro-4'-methoxybiphenyl-4-carboxylic acid;

3'-(2-(((4 S,5R)-5-(3,5-bis(trifluoromethyl)phenyl)-4-methyl-2-oxooxazolidin-3-yl)-methyl)-4,4-dimethyl-cyclohex-1-enyl)-2-chloro-4'-methoxybiphenyl-4-carboxylic acid;

3'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-5'-fluoro-2-methylbiphenyl-4-carboxylic acid;

3'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-2-methylbiphenyl-4-carboxylic acid;

5'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-2,2'-difluoro-4'-methoxybiphenyl-4-carboxylic acid;

3'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-5'-fluoro-2-(trifluoromethyl)biphenyl-4-carboxylic acid;

5'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-2,2'-dimethylbiphenyl-4-carboxylic acid;

5'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-2'-fluoro-2-methylbiphenyl-4-carboxylic acid;

5'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-4'-methoxy-2,2'-dimethylbiphenyl-4-carboxylic acid;

3'-(2-(((4S,5R)-5-(3,5-bis(trifluoromethyl)phenyl)-4-methyl-2-oxooxazolidin-3-yl)methyl)-4,4-dimethylcyclohex-1-enyl)-5'-methoxy-2-methylbiphenyl-4-carboxylic acid;

3'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-4'-fluoro-2-(trifluoromethyl)biphenyl-4-carboxylic acid;

5'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-2'-fluoro-2-(trifluoromethyl)biphenyl-4-carboxylic acid;

3'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-4'-chloro-2-methylbiphenyl-4-carboxylic acid;

3'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-4'-chloro-2-(trifluoromethyl)biphenyl-4-carboxylic acid;

3'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-2-chloro-4'-fluorobiphenyl-4-carboxylic acid;

3'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-2-fluoro-5'-(trifluoromethyl)biphenyl-4-carboxylic acid;

3'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-N-ethyl-4'-fluoro-2-(trifluoromethyl)biphenyl-4-carboxamide;

(4S,5R)-5-(3,5-bis(trifluoromethyl)phenyl)-3-((2-(4-fluoro-4'-(morpholine-4-carbonyl)-2'-(trifluoromethyl)biphenyl-3-yl)-4,4-dimethylcyclohex-1-enyl)methyl)-4-methyloxazolidin-2-one; and 4-(2-(2-(((4S,5R)-5-(3,5-bis(trifluoromethyl)phenyl)-4-methyl-2-oxooxazolidin-3-yl)-methyl)-4,4-dimethyl-cyclohex-1-enyl)-3-methoxypyridin-6-yl)-3-(trifluoromethyl)benzoic acid.

7. The compound of claim 6, wherein compound is selected from among the following compounds:

3'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-4'-methoxy-2-methylbiphenyl-4-carboxylic acid;

4-(3-(2-(((4S,5R)-5-(3,5-bis(trifluoromethyl)phenyl)-4-methyl-2-oxo-oxazolidin-3-yl)methyl)-4,4-dimethyl-cyclohex-1-enyl)-2-methoxypyridin-5-yl)-3-methylbenzoic acid;

5'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-2'-fluoro-4'-methoxy-2-methyl-biphenyl-4-carboxylic acid;

4-(3-(2-(((4 S,5R)-5-(3,5-bis(trifluoromethyl)phenyl)-4-methyl-2-oxo-oxazolidin-3-yl)methyl)-4,4-dimethyl-cyclohex-1-enyl)-2-methoxypyridin-5-yl)-3-chlorobenzoic acid;

4-(3-(2-(((4S,5R)-5-(3,5-bis(trifluoromethyl)phenyl)-4-methyl-2-oxo-oxazolidin-3-yl)methyl)-4,4-dimethyl-cyclohex-1-enyl)-2-methoxypyridin-5-yl)-3-fluorobenzoic acid;

3'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-2,6-difluoro-4'-methoxybiphenyl-4-carboxylic acid;

3'-(2-(((4 S,5R)-5-(3,5-bis(trifluoromethyl)phenyl)-4-methyl-2-oxooxazolidin-3-yl)methyl)-4,4-dimethylcyclohex-1-enyl)-4'-methoxy-2-(trifluoromethyl)-biphenyl-4-carboxylic acid;

5'-(2-(((4 S,5R)-5-(3,5-bis(trifluoromethyl)phenyl)-4-methyl-2-oxooxazolidin-3-yl)-methyl)-4,4-dimethyl-cyclohex-1-enyl)-2-chloro-2'-fluoro-4'-methoxy-biphenyl-4-carboxylic acid;

3'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-2-chloro-4'-methoxybiphenyl-4-carboxylic acid;

3'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-5'-fluoro-2-methylbiphenyl-4-carboxylic acid;

5'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-2,2'-difluoro-4'-methoxybiphenyl-4-carboxylic acid;

3'-(2-(((4S,5R)-5-(3,5-bis(trifluoromethyl)phenyl)-4-methyl-2-oxooxazolidin-3-yl)-methyl)-4,4-dimethyl-cyclohex-1-enyl)-5'-fluoro-2-(trifluoromethyl)biphenyl-4-carboxylic acid;

5'-(2-(((4S,5R)-5-(3,5-bis(trifluoromethyl)phenyl)-4-methyl-2-oxooxazolidin-3-yl)methyl)-4,4-dimethylcyclohex-1-enyl)-2'-fluoro-2-methylbiphenyl-4-carboxylic acid; and 3'-(2-(((4S,5R)-5-(3,5-bis(trifluoromethyl)phenyl)-4-methyl-2-oxooxazolidin-3-yl)methyl)-4,4-dimethylcyclohex-1-enyl)-4'-fluoro-2-(trifluoromethyl)-biphenyl-4-carboxylic acid.

8. A pharmaceutical composition, comprising:
a compound of formula I of claim 1; and
a pharmaceutically acceptable carrier.

9. A method for treatment of dyslipidemia or a dyslipidemia-related disease, the method comprising administering to a mammal in need thereof a composition comprising, as an active ingredient, a compound of formula I of claim 1, wherein the dyslipidemia-related disease is angina pectoris, myocardial infarction or arteriosclerosis.

10. The method of claim 9, wherein the mammal is a human.

* * * * *